(12) United States Patent
Guckian et al.

(10) Patent No.: US 9,555,050 B2
(45) Date of Patent: Jan. 31, 2017

(54) ATX MODULATING AGENTS

(71) Applicant: BIOGEN MA INC., Cambridge, MA (US)

(72) Inventors: Kevin Guckian, Northborough, MA (US); Gnanasambandam Kumaravel, Lexington, MA (US); Bin Ma, Arlington, MA (US); Sha Mi, Belmont, MA (US); Zhaohui Shao, Brookline, MA (US); Lihong Sun, Lexington, MA (US); Arthur Taveras, Boston, MA (US); Deping Wang, Furlong, PA (US); Zhili Xin, Lexington, MA (US); Lei Zhang, Westford, MA (US)

(73) Assignee: BIOGEN MA INC., Cambridge, MA (US)

( * ) Notice: Subject to any disclaimer, the term of this patent is extended or adjusted under 35 U.S.C. 154(b) by 0 days.

(21) Appl. No.: 14/417,353

(22) PCT Filed: Jul. 26, 2013

(86) PCT No.: PCT/US2013/052325
§ 371 (c)(1),
(2) Date: Jan. 26, 2015

(87) PCT Pub. No.: WO2014/018887
PCT Pub. Date: Jan. 30, 2014

(65) Prior Publication Data
US 2015/0246063 A1    Sep. 3, 2015

Related U.S. Application Data

(60) Provisional application No. 61/676,698, filed on Jul. 27, 2012.

(51) Int. Cl.
| | | |
|---|---|---|
| *C07D 215/20* | (2006.01) |
| *A61K 31/662* | (2006.01) |
| *A61K 45/06* | (2006.01) |
| *C07D 401/04* | (2006.01) |
| *C07D 401/06* | (2006.01) |
| *C07C 229/48* | (2006.01) |
| *C07D 265/30* | (2006.01) |
| *C07D 211/34* | (2006.01) |
| *C07D 211/62* | (2006.01) |
| *C07D 213/79* | (2006.01) |
| *C07D 223/06* | (2006.01) |
| *C07C 233/47* | (2006.01) |
| *C07D 205/04* | (2006.01) |
| *C07D 207/08* | (2006.01) |
| *C07D 207/16* | (2006.01) |
| *C07C 229/46* | (2006.01) |
| *C07F 9/38* | (2006.01) |
| *A61K 31/196* | (2006.01) |
| *A61K 31/397* | (2006.01) |
| *A61K 31/435* | (2006.01) |
| *A61K 31/445* | (2006.01) |

(Continued)

(52) U.S. Cl.
CPC .......... *A61K 31/662* (2013.01); *A61K 31/196* (2013.01); *A61K 31/397* (2013.01); *A61K 31/435* (2013.01); *A61K 31/445* (2013.01); *A61K 31/454* (2013.01); *A61K 31/47* (2013.01); *A61K 31/5375* (2013.01); *A61K 31/505* (2013.01); *A61K 31/55* (2013.01); *A61K 45/06* (2013.01); *C07C 229/46* (2013.01); *C07C 229/48* (2013.01); *C07C 233/47* (2013.01); *C07D 205/04* (2013.01); *C07D 207/08* (2013.01); *C07D 207/16* (2013.01); *C07D 211/34* (2013.01); *C07D 211/62* (2013.01); *C07D 213/79* (2013.01); *C07D 213/80* (2013.01); *C07D 215/20* (2013.01); *C07D 223/06* (2013.01); *C07D 265/30* (2013.01); *C07D 401/04* (2013.01); *C07D 401/06* (2013.01); *C07F 9/38* (2013.01); *C07F 9/3808* (2013.01); *C07B 2200/07* (2013.01); *C07C 2101/02* (2013.01); *C07C 2101/04* (2013.01); *C07C 2101/14* (2013.01); *C07C 2102/26* (2013.01)

(58) Field of Classification Search
CPC ... C07D 215/20; C07D 401/04; C07D 401/06; C07D 265/30; C07D 211/34; C07D 211/62; C07D 213/79; C07D 213/80; C07D 223/06; C07D 205/04; C07D 207/08; C07D 207/16; A61K 31/662; A61K 31/196; A61K 31/397; A61K 31/435; A61K 31/445; A61K 31/454; A61K 31/47; A61K 45/06
See application file for complete search history.

(56) References Cited

U.S. PATENT DOCUMENTS 8,269,043 B2 * 9/2012 Caldwell .............. A61K 31/135
564/316
8,349,849 B2 * 1/2013 Caldwell .............. C07C 217/52
514/266.1

(Continued)

FOREIGN PATENT DOCUMENTS

| WO | WO-2011/017561 A1 | 2/2011 |
| WO | WO-2012/109108 A1 | 8/2012 |
| WO | WO-2014/018891 A1 | 1/2014 |

OTHER PUBLICATIONS

Sevastou, Biochimica et Biophysica Acta, 1831, 42-60, 2013.*

(Continued)

*Primary Examiner* — D M Seaman
(74) *Attorney, Agent, or Firm* — McCarter & English, LLP; Steven G. Davis; Xin Zhang

(57) ABSTRACT

Compounds of formula (I) can modulate the activity of autotaxin (ATX).

24 Claims, No Drawings

(51) Int. Cl.
*A61K 31/454* (2006.01)
*A61K 31/47* (2006.01)
*A61K 31/5375* (2006.01)
*A61K 31/55* (2006.01)
*C07D 213/80* (2006.01)

(56) References Cited

U.S. PATENT DOCUMENTS

| | | | |
|---|---|---|---|
| 8,546,359 B2* | 10/2013 | Caldwell | A61K 31/135 |
| | | | 514/114 |
| 8,802,659 B2* | 8/2014 | Thomas | C07C 229/14 |
| | | | 514/114 |
| 2006/0009449 A1 | 1/2006 | McArthur et al. | |
| 2012/0190649 A1* | 7/2012 | Thomas | C07C 229/14 |
| | | | 514/114 |
| 2015/0183741 A1 | 7/2015 | Guckian et al. | |
| 2015/0203493 A1 | 7/2015 | Guckian et al. | |
| 2015/0203515 A1 | 7/2015 | Guckian et al. | |
| 2015/0210647 A1 | 7/2015 | Guckian et al. | |
| 2015/0361029 A1 | 12/2015 | Guckian et al. | |

OTHER PUBLICATIONS

Hozumi, Lab Invest, 93(5), 508-519, 2013.*
Benesch, PEBS Letters, 583, 2712-2727, 2014.*
Oikonomou, American Journal of Respiratory Cell and Molecular Biology, vol. 47, 2012, 566-574.*
Chu, Int J Clin Exp Med, 8(10), 17117-17122, 2015.*

* cited by examiner

ATX MODULATING AGENTS

RELATED APPLICATIONS

This application is a 35 U.S.C. §371 national stage filing of International Application No. PCT/US2013/052325, filed on July 26, 2013, which claims the benefit of the filing date of U.S. Provisional Application No. 61/676,698, filed on July 27, 2012, the entire contents of which are incorporated herein by reference.

TECHNICAL FIELD

This invention relates to compounds that are ATX modulating agents, especially ATX inhibitors, and methods of making and using such compounds.

BACKGROUND

Autotaxin (ATX, ENPP2) is a secreted glycoprotein widely present in biological fluids, including blood, cancer ascites, synovial, pleural and cerebrospinal fluids, originally isolated from the supernatant of melanoma cells as an autocrine motility stimulation factor (Stracke, M. L., et al. Identification, purification, and partial sequence analysis of autotaxin, a novel motility-stimulating protein. J Biol Chem 267, 2524-2529 (1992), which is incorporated by reference in its entirety). ATX is encoded by a single gene on human chromosome 8 (mouse chromosome 15) whose transcription, regulated by diverse transcription factors (Hoxa13, NFAT-1 and v-jun), results in four alternatively spliced isoforms (α, β, γ and δ). See, for example, Giganti, A., et al Murine and Human Autotaxin alpha, beta, and gamma Isoforms: Gene organization, tissue distribution and biochemical characterization. J Biol Chem 283, 7776-7789 (2008); and van Meeteren, L. A. & Moolenaar, W. H. Regulation and biological activities of the autotaxin-LPA axis. Prog Lipid Res 46, 145-160 (2007); Hashimoto, et al, "Identification and Biochemical Characterization of a Novel Autotaxin Isoform, ATXδ," J. of Biochemistry Advance Access (Oct. 11, 2011); each of which is incorporated by reference in its entirety.

ATX is synthesized as a prepro-enzyme, secreted into the extracellular space after the proteolytic removal of its N-terminal signal peptide (Jansen, S., el al Proteolytic maturation and activation of autotaxin (NPP2), a secreted metastasis-enhancing lysophospho lipase D. J Cell Sci 118, 3081-3089 (2005), which is incorporated by reference in its entirety). ATX is a member of the ectonucleotide pyrophosphatase/phosphodiesterase family of ectoenzymes (E-NPP) that hydrolyze phosphodiesterase (PDE) bonds of various nucleotides and derivatives (Stefan, C, Jansen, S. & Bollen, M. NPP-type ectophosphodiesterases: unity in diversity. Trends Biochem Sci 30, 542-550 (2005), which is incorporated by reference in its entirety). The enzymatic activity of ATX was enigmatic, until it was shown to be identical to lysophospholipase D (lysoPLD) (Umezu-Goto, M., et al. Autotaxin has lysophospholipase D activity leading to tumor cell growth and motility by lysophosphatidic acid production. J Cell Biol 158, 227-233 (2002), which is incorporated by reference in its entirety), which is widely present in biological fluids. Since ATX is a constitutively active enzyme, the biological outcome of ATX action will largely depend on its expression levels and the local availability of its substrates. The major lysophospholipid substrate for ATX, lysophosphatidylcholine (LPC), is secreted by the liver and is abundantly present in plasma (at about 100 µM) as a predominantly albumin bound form (Croset, M., Brossard, N., Polette, A. & Lagarde, M. Characterization of plasma unsaturated lysophosphatidylcholines in human and rat Biochem J 345 Pt 1, 61-67 (2000), which is incorporated by reference in its entirety). LPC is also detected in tumor-cell conditioned media (Umezu-Goto, M., et al.), presumably as a constituent of shed microvesicles. ATX, through its lysoPLD activity converts LPC to lysophosphatidic acid (LPA).

LPC is an important inflammatory mediator with recognized effects in multiple cell types and pathophysiological processes. It is a major component of oxidized low density lipoprotein (oxLDL) and it can exist in several other forms including free, micellar, bound to hydrophobic proteins such as albumin and incorporated in plasma membranes. It is produced by the hydrolysis of phosphatidylcholine (PC) by PLA2 with concurrent release of arachidonic acid and in turn of other pro-inflammatory mediators (prostaglandins and leukotrienes). Moreover, LPC externalization constitutes a chemotactic signal to phagocytic cells, while interaction with its receptors can also stimulate lymphocytic responses. LPC has been shown to have therapeutic effects in experimental sepsis, possibly by suppressing endotoxin-induced HMGB1 release from macrophages/monocytes.

LPA, the product of ATX action on LPC, is a bioactive phospholipid with diverse functions in almost every mammalian cell line (Moolenaar, W. H., van Meeteren, L. A. & Giepmans, B. N. The ins and outs of lysophosphatidic acid signaling. Bioessays 28, 870-881 (2004), which is incorporated by reference in its entirety). LPA is a major constituent of serum bound tightly to albumin, gelsolin and possibly other as yet unidentified proteins. (See, e.g., Goetzl, E. J., et al Gelsolin binding and. cellular presentation of lysophosphatidic acid. J Biol Chem 275, 14573-14578 (2000); and Tigyi, G. & Miledi, R, Lysophosphatidates bound to serum albumin activate membrane currents in *Xenopus* oocytes and neurite retraction in PC12 pheochromocytoma cells. J Biol Chem 267, 21360-21367 (1992); each of which is incorporated by reference in its entirety.)

LPA is also found in other biofluids, such as saliva and follicular fluid, and has been implicated in a wide array of functions, such as wound healing, tumor invasion and metastasis, neurogenesis, myelination, astrocytes outgrowth and neurite retraction. The long list of LPA functions was also explained with the discovery that it signals through G-protein coupled receptors (GPCRs), via classical second messenger pathways. Five mammalian cell-surface LPA receptors have been identified so far. The best known are LPA1-3 (namely Edg-2, Edg-4 and Edg7) which are all members of the so-called 'endothelial differentiation gene' (EDG) family of GPCRs (Contos, J. J., Ishii, I. & Chun, J. Lysophosphatidic acid receptors. Mol Pharmacol 58, 1188-1196 (2000), which is incorporated by reference in its entirety). LPA receptors can couple to at least three distinct G proteins ($G_q$, $G_i$ and $G_{12/13}$), which, in turn, feed into multiple effector systems. LPA activates $G_q$ and thereby stimulates phospholipase C (PLC), with subsequent phosphatidylinositol-bisphosphate hydrolysis and generation of multiple second messengers leading to protein kinase C activation and changes in cytosolic calcium. LPA also activates $G_i$, which leads to at least three distinct signaling routes: inhibition of adenylyl cyclase with inhibition of cyclic AMP accumulation; stimulation of the mitogenic RAS-MAPK (mitogen-activated protein kinase) cascade; and activation of phosphatidylinositol 3-kinase (PI3K), leading to activation of the guanosine diphosphate/guanosine triphosphate (GDP/GTP) exchange factor TIAM1 and the downstream RAC GTPase, as well as to activation of the AKT/PKB antiapoptotic pathway. Finally, LPA activates $G_{12/13}$, leading to activation of the small GTPase RhoA, which drives cytoskeletal contraction and cell rounding. So, LPA not only signals via classic second messengers such as calcium, diacylglycerol and cAMP, but it also activates RAS- and RHO-family GTPases, the master switches that control cell proliferation, migration and morphogenesis.

LPA signaling through the RhoA-Rho kinase pathway mediates neurite retraction and inhibition of axon growth. Interfering with LPA signaling has been shown to promote axonal regeneration and functional recovery after CNS injury or cerebral ischemia. (See Broggini, et al., *Molecular Biology of the Cell* (2010), 21:521-537.) It has been reported that addition of LPA to dorsal root fibers in ex vivo culture causes demyelination, whereas LPC fails to cause significant demyelination of nerve fibers in ex vivo cultures without further addition of recombinant ATX to the culture which when added caused significant demyelination at equivalent levels to LPA presumable due to conversion of LPC to LPA through the enzymatic activity of ATX. Moreover, injury induced demyelination was attenuated by about 50% in $atx^{+/-}$ mice (Nagai, et al., *Molecular Pain* (2010), 6:78).

A number of diseases or disorders involve demyelination of the central or peripheral nervous system which can occur for a number of reasons such as immune dysfunction as in multiple sclerosis, encephalomyelitis, Guillain-Barre Syndrome, chronic inflammatory demyelinating polyneuropathy (CIDP), transverse myelitis, and optic neuritis; demyelination due to injury such as spinal cord injury, traumatic brain injury, stroke, acute ischemic optic neuropathy, or other ischemia, cerebral palsy, neuropathy (e.g. neuropathy due to diabetes, chronic renal failure, hypothyroidism, liver failure, or compression of the nerve (e.g. in Bell's palsy)), post radiation injury, and central pontine myelolysis (CPM); inherited conditions such as Charcot-Marie-Tooth disease (CMT), Sjogren-Larsson syndrome, Refsum disease, Krabbe disease, Canavan disease, Alexander disease, Friedreich's ataxia, Pelizaeus-Merzbacher disease, Bassen-Kornzweig syndrome, metachromatic leukodystrophy (MLD), adrenoleukodystrophy, and nerve damage due to pernicious anemia; viral infection such as progressive multifocal leukoencephalopathy (PML), Lyme disease, or tabes dorsalis due to untreated syphilis; toxic exposure due to chronic alcoholism (which is a possible cause of Marchiafava-Bignami disease), chemotherapy, or exposure to chemicals such as organophosphates; or dietary deficiencies such as vitamin B12 deficiency, vitamin E deficiency and copper deficiency. Other demyelination disorders may have unknown causes or multiple causes such as trigeminal neuralgia, Marchiafava-Bignami disease and Bell's palsy. One particularly successful approach to treating demyelination disorders which are caused by autoimmune dysfunction has been to attempt to limit the extent of demyelination by treating the patient with immunoregulatory drugs. However, typically this approach has merely postponed but not avoided the onset of disability in these patients. Patients with demyelination due to other causes have even fewer treatment options. Therefore, the need exists to develop new treatments for patients with demyelination diseases or disorders.

SUMMARY

The present invention relates to compounds which inhibit ATX. Without wishing to be bound by any theory, it is believed that LPA inhibits remyelination of neurons that have suffered demyelination due to injury or disease and that inhibition of ATX will prevent the conversion of LPC to LPA and thus allow remyelination to occur. In addition, activation of PLC, ERK and Rho via LPA receptors results in cell proliferation, cell survival and changes in cell morphology. Therefore, inhibition of ATX is expected to be useful for treating demyelination due to injury or disease, as well as for treating proliferative disorders such as cancer.

Thus, in one aspect, the invention relates to a compound of formula (I), or a pharmaceutically acceptable salt thereof, represented by formula (I):

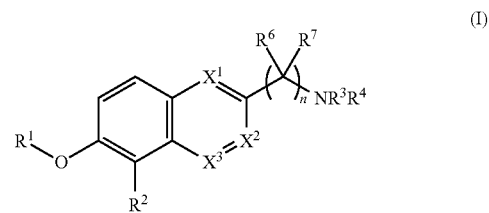

In formula (I), $X^1$, $X^2$, and $X^3$ can be CH; or one of $X^1$, $X^2$, or $X^3$ can be N and the other two can be CH.

$R^1$ can be

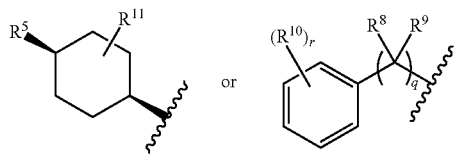

$R^2$ can be a $C_{1-4}$haloalkyl or cyano.

$R^3$ can be $-L^1-J-L^2-R^{12}$; and $R^4$ can be hydrogen or a $C_{1-6}$alkyl; or $R^3$ and $R^4$ together with the nitrogen to which they are attached can be a 3- to 8-membered heterocyclyl which can be substituted with $-L^2-R^{12}$, and is optionally substituted with a halo, hydroxyl, amino, or a $C_{1-6}$alkyl.

$R^5$ can be a halo, a $C_{1-6}$alkyl or a $C_{1-6}$haloalkyl.

$R^6$ and $R^7$ can each be independently hydrogen or $C_{1-6}$alkyl; or $R^6$ and $R^7$ together with the carbon to which they are attached can be —C(=O)—, a $C_{3-8}$spirocycloalkyl, or a 3- to 8-membered spiroheterocyclalkyl.

$R^8$ and $R^9$ can each be independently hydrogen or a $C_{1-6}$alkyl; or $R^8$ and $R^9$ taken together with the carbon to which they are attached can be —C(=O)—.

$R^{10}$, for each occurrence, can be halo.

$R^{11}$ can be hydrogen, halo, or $C_{1-4}$alkyl.

$R^{12}$ can be —COOR$^{13}$ or —P(O)(OR$^{13}$)$_2$.

Each $R^{13}$, independently, can be H, $C_{1-4}$alkyl, aryl, or aryl-$C_{1-4}$-alkyl.

J can be a $C_{1-6}$alkylene, a $C_{3-8}$cycloalkylene, a 3- to 8-membered divalent monocyclic heterocyclyl, a phenylene, or a 5- to 6-membered heteroarylene, wherein J can be optionally substituted with one or two substituents independently selected from a halo and a $C_{1-6}$alkyl.

$L^1$ and $L^2$ can each be independently, a $C_{1-3}$alkylene or a direct bond.

n can be 1, 2 or 3.

q can be 1 or 2.

r can be 0, 1, or 2.

In some embodiments, $R^{12}$ can be —P(O)(OH)$_2$. n can be 1. $R^6$ and $R^7$ together with the carbon to which they are attached can be —C(=O)—. $L^1$ can be a direct bond; J can be a $C_{1-6}$alkylene or a phenylene, wherein J can be optionally substituted with one or two substituents independently selected from a halo and a $C_{1-6}$alkyl; $L^2$ can be a $C_{1-3}$alkylene; and $R^{12}$ can be —P(O)(OR$^{13}$)$_2$.

$R^3$ and $R^4$ together with the nitrogen to which they are attached can be a 4- to 7-membered heterocyclyl which is substituted with -L$^2$-R$^{12}$, and can be optionally substituted with a halo, hydroxyl, amino, or a $C_{1-6}$alkyl; $L^2$ can be a direct bond or —CH$_2$—; and $R^{12}$ can be —COOR$^{13}$. $R^2$ can be —CHF$_2$ or —CF$_3$.

In some embodiments, $R^1$ can be

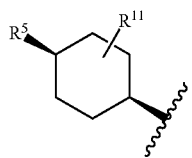

wherein $R^5$ can be a halo, a $C_1$alkyl, or a $C_1$haloalkyl.

In some embodiments, $R^1$ can be

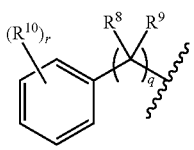

wherein q can be 1, $R^8$ and $R^9$ can each be independently H, and each $R^{10}$ can be independently H or a halo.

In another aspect, the invention relates to a compound of formula (Ia), or a pharmaceutically acceptable salt thereof, represented by formula (Ia):

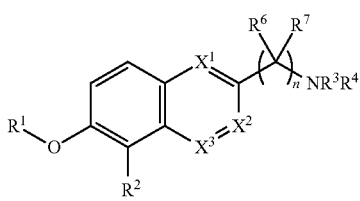

(Ia)

or a pharmaceutically acceptable salt thereof.

In formula (Ia), $X^1$, $X^2$, and $X^3$ can be CH; or one of $X^1$, $X^2$, or $X^3$ can be N and the other two can be CH.

$R^1$ can be

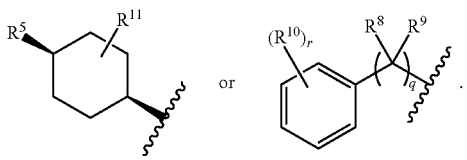

$R^2$ can be a $C_{1-4}$haloalkyl or cyano.

$R^3$ can be -L$^1$-J-L$^2$-R$^{12}$; and $R^4$ can be hydrogen or a $C_{1-6}$alkyl; or $R^3$ and $R^4$ together with the nitrogen to which they are attached can be a 3- to 8-membered heterocyclyl which can be substituted with -L$^2$-R$^{12}$, and is optionally substituted with a halo, hydroxyl, amino, or a $C_{1-6}$alkyl.

$R^5$ can be a halo, a $C_{1-6}$alkyl or a $C_{1-6}$haloalkyl.

$R^6$ and $R^7$ can each be independently hydrogen, $C_{1-6}$alkyl, a $C_{1-6}$haloalkyl, $C_{3-7}$cycloalkyl, or COOH; or $R^6$ and $R^7$ together with the carbon to which they are attached can be —C(=O)—, a $C_{3-8}$spirocycloalkyl, or a 3- to 8-membered spiroheterocyclalkyl.

$R^8$ and $R^9$ can each be independently hydrogen or a $C_{1-6}$alkyl; or $R^8$ and $R^9$ taken together with the carbon to which they are attached can be —C(=O)—.

$R^{10}$, for each occurrence, can be halo.

$R^{11}$ can be hydrogen, halo, or $C_{1-4}$alkyl.

$R^{12}$ can be —COOR$^{13}$, —P(O)(OR$^{13}$)$_2$, or tetrazolyl.

Each $R^{13}$, independently, can be H, $C_{1-4}$alkyl, aryl, or aryl-$C_{1-4}$-alkyl.

J can be a $C_{1-6}$alkylene, a $C_{3-8}$cycloalkylene, a 3- to 8-membered divalent monocyclic heterocyclyl, a phenylene, or a 5- to 6-membered heteroarylene, wherein J can be optionally substituted with one or two substituents independently selected from a halo and a $C_{1-6}$alkyl.

$L^1$ and $L^2$ can each be independently, a $C_{1-3}$alkylene or a direct bond.

n can be 1, 2 or 3.

q can be 1 or 2.

r can be 0, 1, or 2.

In another aspect, a compound can be selected from the group consisting of:

2,2-dimethyl-3-(((5-(trifluoromethyl)-6-((cis-4-(trifluoromethyl)cyclohexyl)oxy)naphthalen-2-yl)methyl)amino)cyclobutanecarboxylic acid;

1-((5-(trifluoromethyl)-6-((cis-4-(trifluoromethyl)cyclohexyl)oxy)-naphthalen-2-yl)methyl)piperidine-4-carboxylic acid;

3-(((5-(trifluoromethyl)-6-((cis-4-(trifluoromethyl)cyclohexyl)oxy)-naphthalen-2-yl)methyl)amino)cyclopentanecarboxylic acid;

(R)-2-(1-((6-((4,4-difluorocyclohexyl)oxy)-5-(trifluoromethyl)naphthalen-2-yl)methyl)piperidin-3-yl)acetic acid;

4-(2H-tetrazol-5-yl)-1-((5-(trifluoromethyl)-6-((cis-4-(trifluoromethyl)cyclohexyl)oxy)naphthalen-2-yl)methyl)piperidine;

2-((3R)-1-(1-(6-((cis-4-ethylcyclohexyl)oxy)-5-(trifluoromethyl)naphthalen-2-yl)ethyl)piperidin-3-yl)acetic acid;

2-((3R)-1-(1-(6-((cis-4-ethylcyclohexyl)oxy)-5-(trifluoromethyl)naphthalen-2-yl)propyl)piperidin-3-yl)acetic acid;

2-(4-((6-((cis-4-Methylcyclohexyl)oxy)-5-(trifluoromethyl)naphthalen-2-yl)methyl)morpholin-2-yl)acetic acid;

2-(1-((6-((cis-4-methylcyclohexyl)oxy)-5-(trifluoromethyl)naphthalen-2-yl)methyl)piperidin-3-yl)acetic acid;

2-((3R)-1-(1-(6-((cis-4-Methylcyclohexyl)oxy)-5-(trifluoromethyl)naphthalen-2-yl)propyl)piperidin-3-yl)acetic acid;

1-(Carboxy(6-((cis-4-methylcyclohexyl)oxy)-5-(trifluoromethyl)naphthalen-2-yl)methyl)piperidine-4-carboxylic acid;

1-(2,2,2-Trifluoro-1-(6-((cis-4-methylcyclohexyl)oxy)-5-(trifluoromethyl)naphthalen-2-yl)ethyl)piperidine-4-carboxylic acid;

1-((5-(Difluoromethyl)-6-((cis-4-methylcyclohexyl)oxy)naphthalen-2-yl)methyl)piperidine-4-carboxylic acid;

2-((R)-1-(((5-(trifluoromethyl)-6-(cis-4-(trifluoromethyl)cyclohexyl)oxy)quinolin-2-yl)methyl)piperidin-3-yl)acetic acid; and 2,2-dimethyl-3-(((1-(5-(trifluoromethyl)-6-(cis-4-(trifluoromethyl)cyclo-hexyl)oxy)quinolin-2-yl)ethyl)amino)cyclobutanecarboxylic acid.

2,2-dimethyl-3-((1-(6-(cis-4-methylcyclohexyl)oxy)-5-(trifluoromethyl)naphthalen-2-yl)cyclopropyl)amino)cyclobutanecarboxylic acid;
4-Acetamido-4-(5-(trifluoromethyl)-6-(cis-4-(trifluoromethyl)cyclo-hexyl)oxy)naphthalen-2-yl)pentanoic acid;
(3-(6-((3,5-dichlorobenzyl)oxy)-5-(trifluoromethyl)-2-naphthamido)propyl)phosphonic acid;
(3-(5-(trifluoromethyl)-6-((cis-4-(trifluoromethyl)cyclohexyl)oxy)-2-naphthamido)propyl)phosphonic acid;
1-((5-cyano-6-((cis-4-(trifluoromethyl)cyclohexyl)oxy)naphthalen-2-yl)methyl)piperidine-4-carboxylic acid;
1-((5-(difluoromethyl)-6-((cis-4-(trifluoromethyl)cyclohexyl)oxy)naphthalen-2-yl)methyl)piperidine-4-carboxylic acid;
1-((5-(trifluoromethyl)-6-((cis-4-(trifluoromethyl)cyclohexyl)amino)naphthalen-2-yl)methyl)piperidine-4-carboxylic acid;
6-((5-(trifluoromethyl)-6-((cis-4-(trifluoromethyl)cyclohexyloxy)-2-naphthamido)methyl)nicotinic acid;
(R)-1-((5-(trifluoromethyl)-6-((cis-4-(trifluoromethyl)cyclohexyloxy)naphthalen-2-yl)methyl)piperidine-3-carboxylic acid;
(trans)-4-(((5-(trifluoromethyl)-6-((cis-4-(trifluoromethyl)cyclohexyloxy)naphthalen-2-yl)methylamino)methyl)cyclohexanecarboxylic acid;
(S)-1-((5-(trifluoromethyl)-6-((cis-4-(trifluoromethyl)cyclohexyloxy)naphthalen-2-yl)methyl)piperidine-3-carboxylic acid;
2-(1-((5-(trifluoromethyl)-6-((cis-4-(trifluoromethyl)cyclohexyloxy)naphthalen-2-yl)methyl)piperidin-2-yl)acetic acid;
(trans)-4-((methyl((5-(trifluoromethyl)-6-((cis-4-(trifluoromethyl)cyclohexyloxy)naphthalen-2-yl)methyl)amino)methyl)cyclohexanecarboxylic acid;
1-((5-(trifluoromethyl)-6-((cis-4-(trifluoromethyl)cyclohexyloxy)naphthalen-2-yl)methyl)piperidine-2-carboxylic acid;
4-methyl-1-((5-(trifluoromethyl)-6-((cis-4-(trifluoromethyl)cyclohexyloxy)naphthalen-2-yl)methyl)piperidine-4-carboxylic acid;
1-(5-(trifluoromethyl)-6-((cis-4-(trifluoromethyl)cyclohexyloxy)-2-naphthoyl)azepane-4-carboxylic acid;
2-(4-((5-(difluoromethyl)-6-((cis-4-(trifluoromethyl)cyclohexyloxy)naphthalen-2-yl)methyl)morpholin-2-yl)acetic acid;
3-((5-(difluoromethyl)-6-((cis-4-(trifluoromethyl)cyclohexyloxy)naphthalen-2-yl)methylamino)-2,2-dimethylcyclobutanecarboxylic acid;
(trans)-4-(((5-(difluoromethyl)-6-((cis-4-(trifluoromethyl)cyclohexyloxy)naphthalen-2-yl)methylamino)methyl)cyclohexanecarboxylic acid;
4-hydroxy-1-((5-(trifluoromethyl)-6-((cis-4-(trifluoromethyl)cyclohexyloxy)naphthalen-2-yl)methyl)piperidine-3-carboxylic acid;
2,2-dimethyl-3-(1-(6-((cis)-4-methylcyclohexyloxy)-5-(trifluoromethyl)naphthalen-2-yl)propylamino)cyclobutanecarboxylic acid;
2,2-dimethyl-3-(1-(5-(trifluoromethyl)-6-((cis)-4-(trifluoromethyl)cyclohexyloxy)naphthalen-2-yl)ethylamino)cyclobutanecarboxylic acid;
3-(cyclopropyl(6-((cis)-4-methylcyclohexyloxy)-5-(trifluoromethyl)naphthalen-2-yl)methylamino)-2,2-dimethylcyclobutanecarboxylic acid;
2,2-dimethyl-3-(2-methyl-1-(5-(trifluoromethyl)-6-((cis)-4-(trifluoromethyl)cyclohexyloxy)naphthalen-2-yl)propylamino)cyclobutanecarboxylic acid;
2,2-dimethyl-3-(3-methyl-1-(5-(trifluoromethyl)-6-((cis)-4-(trifluoromethyl)cyclohexyloxy)naphthalen-2-yl)butylamino)cyclobutanecarboxylic acid;
4-(1-((5-(trifluoromethyl)-6-((cis)-4-(trifluoromethyl)cyclohexyloxy)naphthalen-2-yl)methylamino)ethyl)cyclohexanecarboxylic acid;
3-(cyclohexyl(6-((cis)-4-methylcyclohexyloxy)-5-(trifluoromethyl)naphthalen-2-yl)methylamino)-2,2-dimethylcyclobutanecarboxylic acid;
3-(cyclohexyl(5-(trifluoromethyl)-6-((cis)-4-(trifluoromethyl)cyclohexyloxy)naphthalen-2-yl)methylamino)-2,2-dimethylcyclobutanecarboxylic acid;
3-(cyclopropyl(5-(trifluoromethyl)-6-((cis)-4-(trifluoromethyl)cyclohexyloxy)naphthalen-2-yl)methylamino)-2,2-dimethylcyclobutanecarboxylic acid;
1-(1-(5-trifluoromethyl-6-(cis-4-methylcyclohexyloxy)naphthalene-2-yl)ethyl)-piperidine-4-carboxylic acid;
1-((5-trifluoromethyl-6-(cis-4-methylcyclohexyloxy)naphthalene-2-yl)methyl)-pyrrolidine-3-acetic acid;
1-((5-trifluoromethyl-6-(cis-4-methylcyclohexyloxy)naphthalene-2-yl)methyl)-azetidine-3-acetic acid;
1-((5-trifluoromethyl-6-(cis-4-methylcyclohexyloxy)naphthalene-2-yl)methyl)-azepane-3-carboxylic acid;
2-((3R)-1-((6-((cis-4-Methylcyclohexyl)oxy)-5-(trifluoromethyl)naphthalen-2-yl)methyl)piperidin-3-yl)acetic acid;
1-(1-(6-((cis-4-Methylcyclohexyl)oxy)-5-(trifluoromethyl)naphthalen-2-yl)propyl)piperidine-4-carboxylic acid;
2-((3R)-1-(1-(6-((cis-4-Methylcyclohexyl)oxy)-5-(trifluoromethyl)naphthalen-2-yl)ethyl)piperidin-3-yl)acetic acid;
2-((3S)-1-(1-(6-((cis-4-Methylcyclohexyl)oxy)-5-(trifluoromethyl)naphthalen-2-yl)propyl)piperidin-3-yl)acetic acid;
2-((3R)-1-(1-(6-((cis-4-Methylcyclohexyl)oxy)-5-(difluoromethyl)naphthalen-2-yl)ethyl)piperidin-3-yl)acetic acid;
2-((3S)-1-(1-(6-((cis-4-Methylcyclohexyl)oxy)-5-(difluoromethyl)naphthalen-2-yl)ethyl)piperidin-3-yl)acetic acid;
1-(1-(6-((cis-4-Methylcyclohexyl)oxy)-5-(difluoromethyl)naphthalen-2-yl)ethyl)piperidine-4-carboxylic acid;
2-((3R)-1-((6-((cis-4-Methylcyclohexyl)oxy)-5-(difluoromethyl)naphthalen-2-yl)methyl)piperidin-3-yl)acetic acid;
2-((3R)-1-(1-(6-((cis-4-Methylcyclohexyl)oxy)-5-(difluoromethyl)naphthalen-2-yl)propyl)piperidin-3-yl)acetic acid;
1-(1-(6-((cis-4-Methylcyclohexyl)oxy)-5-(difluoromethyl)naphthalen-2-yl)propyl)piperidine-4-carboxylic acid;
2-((3R)-1-((S)-1-(6-((cis-4-Methylcyclohexyl)oxy)-5-(trifluoromethyl)naphthalen-2-yl)propyl)piperidin-3-yl)acetic acid;
2-((3R)-1-((R)-1-(6-((cis-4-Methylcyclohexyl)oxy)-5-(trifluoromethyl)naphthalen-2-yl)propyl)piperidin-3-yl)acetic acid;
1-((S)-1-(6-((cis-4-Methylcyclohexyl)oxy)-5-(difluoromethyl)naphthalen-2-yl)ethyl)piperidine-4-carboxylic acid;
2-(1-((5-(trifluoromethyl)-6-(4-cis-(trifluoromethyl)cyclohexyloxy)naphthalene-2-yl)methyl)azetidine-3-yl)acetic acid;
3-(((5-(trifluoromethyl)-6-(cis-4-(trifluoromethyl)cyclohexyloxy)naphthalene-2-yl)methyl)amino)propylphosphonic acid;
1-((5-(trifluoromethyl)-6-((cis-4-(trifluoromethyl)cyclohexyl)oxy)-naphthalen-2-yl)methyl)pyrrolidine-3-acetic acid;

1-((5-(trifluoromethyl)-6-((cis-4-(trifluoromethyl)cyclo-hexyl)oxy)-naphthalen-2-yl)methyl)piperidine-4-acetic acid;

1-((5-(trifluoromethyl)-6-((cis-4-(trifluoromethyl)cyclo-hexyl)oxy)-naphthalen-2-yl)methyl)aminocyclopentane-3-carboxylic acid;

1-((5-(trifluoromethyl)-6-((cis-4-(trifluoromethyl)cyclo-hexyl)oxy)-naphthalen-2-yl)methyl)piperidine-3-acetic acid;

(4-((5-(trifluoromethyl)-6-(cis-4-(trifluoromethyl)cyclo-hexyloxy)naphthalene-2-yl)methyl)aminophenyl)methyl-phosphonic acid;

6-((((5-(trifluoromethyl)-6-((cis)-4-(trifluoromethyl)cyclo-hexyloxy)naphthalene-2-yl)methyl)amino)methyl)nico-tinic acid;

cis-4-(((5-(trifluoromethyl)-6-((cis)-4-(trifluoromethyl)cy-clohexyloxy)naphthalene-2-yl)methyl)amino)cyclo-hexane-1-carboxylic acid;

(S)-1-((5-(trifluoromethyl)-6-((cis)-4-(trifluoromethyl)cy-clohexyloxy)naphthalene-2-yl)methyl)pyrrolidine-3-ace-tic acid;

(R)-1-((5-(trifluoromethyl)-6-((cis)-4-(trifluoromethyl)cy-clohexyloxy)naphthalene-2-yl)methyl)pyrrolidine-3-ace-tic acid;

3-((4-((5-(trifluoromethyl)-6-(cis-4-(trifluoromethyl)cyclo-hexyloxy)naphthalene-2-yl)methyl)amino)cyclohexyl) propionic acid;

1-((5-(trifluoromethyl)-6-((cis-4-(trifluoromethyl)cyclo-hexyl)oxy)-naphthalen-2-yl)methyl)-3-methylpiperidine-4-carboxylic acid;

5-((((5-(trifluoromethyl)-6-((cis-4-(trifluoromethyl)cyclo-hexyl)oxy)-naphthalen-2-yl)methyl)amino)methyl)pyri-dine-2-carboxylic acid;

1-((5-(trifluoromethyl)-6-((cis-4-(trifluoromethyl)cyclo-hexyl)oxy)-naphthalen-2-yl)methyl)azepane-4-carbox-ylic acid;

4-((5-(trifluoromethyl)-6-((cis-4-(trifluoromethyl)cyclo-hexyl)oxy)-naphthalen-2-yl)methyl)morpholine-2-car-boxylic acid;

1-((5-(trifluoromethyl)-6-((cis-4-(trifluoromethyl)cyclo-hexyl)oxy)-naphthalen-2-yl)methyl)-3-aminopyrrolidine-3-carboxylic acid;

N-methyl-cis-4-(((5-(trifluoromethyl)-6-(cis-4-(trifluorom-ethyl)cyclohexyloxy)naphthalene-2-yl)methyl)amino)cy-clohexane-1-carboxylic acid;

2-((R)-1-((2-(cis-4-(trifluoromethyl)cyclohexyloxy)-1-(trif-luoromethyl)naphthalen-6-yl)methyl)piperidin-3-yl)ace-tic acid;

1-((5-(trifluoromethyl)-6-(cis-4-(trifluoromethyl)cyclo-hexyloxy)naphthalene-2-yl)methyl)-5-hydroxypiperi-dine-3-carboxylic acid;

2-((S)-4-((2-(cis-4-(trifluoromethyl)cyclohexyloxy)-1-(trif-luoromethyl)naphthalen-6-yl)methyl)morpholin-2-yl) acetic acid;

3-(1-((2-(cis-4-(trifluoromethyl)cyclohexyloxy)-1-(trifluo-romethyl)naphthalen-6-yl)methyl)piperidine-4-yl)propi-onic acid;

2-((R)-1-((2-(cis-4-(ethyl)cyclohexyloxy)-1-(trifluorom-ethyl)naphthalen-6-yl)methyl)piperidin-3-yl)acetic acid;

2,2-dimethyl-3-((((S)-1-(5-(trifluoromethyl)-6-(cis-4-(trif-luoromethyl)cyclo-hexyl)oxy)naphthalene-2-yl)ethyl) amino)cyclobutanecarboxylic acid;

2,2-dimethyl-3-((((R)-1-(5-(trifluoromethyl)-6-(cis-4-(trif-luoromethyl)cyclo-hexyl)oxy)naphthalene-2-yl)ethyl) amino)cyclobutanecarboxylic acid;

2,2-dimethyl-3-((((5-(trifluoromethyl)-6-(cis-4-(trifluorom-ethyl)cyclo-hexyl)oxy)quinolin-2-yl)methyl)amino)cy-clobutanecarboxylic acid;

2-((S)-1-(((5-(trifluoromethyl)-6-(cis-4-(trifluoromethyl)cy-clohexyl)oxy)quinolin-2-yl)methyl)piperidin-3-yl)acetic acid;

2-((S)-1-(1-(2-(cis-4-(trifluoromethyl)cyclohexyloxy)-1-(trifluoromethyl)naphthalen-6-yl)propyl)piperidin-3-yl) acetic acid;

2,2-dimethyl-3-(1-(6-((cis)-4-methylcyclohexyloxy)-5-(trif-luoromethyl)naphthalen-2-yl)-3-methylbutylamino)cy-clobutanecarboxylic acid;

2-((3R)-1-((S)-1-(6-((cis-4-Methylcyclohexyl)oxy)-5-(dif-luoromethyl)naphthalen-2-yl)ethyl)piperidin-3-yl)acetic acid;

2-((3R)-1-((R)-1-(6-((cis-4-Methylcyclohexyl)oxy)-5-(dif-luoromethyl)naphthalen-2-yl)ethyl)piperidin-3-yl)acetic acid;

2-((3R)-1-((S)-1-(6-((cis-4-Methylcyclohexyl)oxy)-5-(dif-luoromethyl)naphthalen-2-yl)propyl)piperidin-3-yl)ace-tic acid;

2-((3R)-1-((R)-1-(6-((cis-4-Methylcyclohexyl)oxy)-5-(dif-luoromethyl)naphthalen-2-yl)propyl)piperidin-3-yl)ace-tic acid;

2-((3R)-1-((S)-1-(6-((cis-4-Methylcyclohexyl)oxy)-5-(trif-luoromethyl)naphthalen-2-yl)ethyl)piperidin-3-yl)acetic acid;

2-((3R)-1-((R)-1-(6-((cis-4-Methylcyclohexyl)oxy)-5-(trif-luoromethyl)naphthalen-2-yl)ethyl)piperidin-3-yl)acetic acid;

1-((5-(Difluoromethyl)-6-((cis-4-methylcyclohexyl)oxy) naphthalen-2-yl)methyl)azetidine-3-acetic acid;

1-(1-(5-(Difluoromethyl)-6-((cis-4-methylcyclohexyl)oxy) naphthalen-2-yl)ethyl)azetidine-3-acetic acid;

1-(1-(5-(Difluoromethyl)-6-((cis-4-methylcyclohexyl)oxy) naphthalen-2-yl)propyl)azetidine-3-acetic acid;

2-((S)-1-((S)-1-(2-(cis-4-methylcyclohexyloxy)-1-(difluo-romethyl)naphthalen-6-yl)ethyl)piperidin-3-yl)acetic acid;

2-((R)-1-((S)-1-(2-(cis-4-methylcyclohexyloxy)-1-(difluo-romethyl)naphthalen-6-yl)ethyl)piperidin-3-yl)acetic acid;

(S)-2-((R)-1-((5-(trifluoromethyl)-6-((cis-4-(trifluorom-ethyl)cyclohexyl)oxy)naphthalen-2-yl)methyl)piperidin-3-yl)propanoic acid;

2-((R)-1-((R)-1-(5-(trifluoromethyl)-6-((cis-4-(trifluorom-ethyl)cyclohexyl)oxy)naphthalen-2-yl)propyl)piperidin-3-yl)acetic acid; and 2-((R)-1-((S)-1-(5-(trifluoromethyl)-6-((cis-4-(trifluorom-ethyl)cyclohexyl)oxy)naphthalen-2-yl)propyl)piperidin-3-yl)acetic acid, or a pharmaceutically acceptable salt thereof.

In another aspect, a pharmaceutical composition includes a pharmaceutically acceptable carrier or excipient and a compound represented by formula (I):

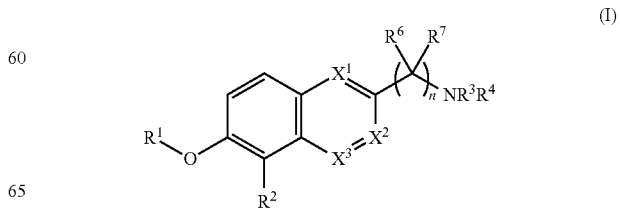

or a pharmaceutically acceptable salt thereof.

In formula (I), $X^1$, $X^2$, and $X^3$ can be CH; or one of $X^1$, $X^2$, or $X^3$ can be N and the other two can be CH.

$R^1$ can be

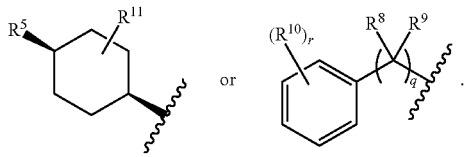

$R^2$ can be a $C_{1-4}$haloalkyl or cyano.

$R^3$ can be $-L^1-J-L^2-R^{12}$; and $R^4$ can be hydrogen or a $C_{1-6}$alkyl; or $R^3$ and $R^4$ together with the nitrogen to which they are attached can be a 3- to 8-membered heterocyclyl which can be substituted with $-L^2-R^{12}$, and is optionally substituted with a halo, hydroxyl, amino, or a $C_{1-6}$alkyl.

$R^5$ can be a halo, a $C_{1-6}$alkyl or a $C_{1-6}$haloalkyl.

$R^6$ and $R^7$ can each be independently hydrogen or $C_{1-6}$alkyl; or $R^6$ and $R^7$ together with the carbon to which they are attached can be $-C(=O)-$, a $C_{3-8}$spirocycloalkyl, or a 3- to 8-membered spiroheterocyclalkyl.

$R^8$ and $R^9$ can each be independently hydrogen or a $C_{1-6}$alkyl; or $R^8$ and $R^9$ taken together with the carbon to which they are attached can be $-C(=O)-$.

$R^{10}$, for each occurrence, can be halo.

$R^{11}$ can be hydrogen, halo, or $C_{1-4}$alkyl.

$R^{12}$ can be $-COOR^{13}$ or $-P(O)(OR^{13})_2$.

Each $R^{13}$, independently, can be H, $C_{1-4}$alkyl, aryl, or aryl-$C_{1-4}$-alkyl.

J can be a $C_{1-6}$alkylene, a $C_{3-8}$cycloalkylene, a 3- to 8-membered divalent monocyclic heterocyclyl, a phenylene, or a 5- to 6-membered heteroarylene, wherein J can be optionally substituted with one or two substituents independently selected from a halo and a $C_{1-6}$alkyl.

$L^1$ and $L^2$ can each be independently, a $C_{1-3}$alkylene or a direct bond.

n can be 1, 2 or 3.

q can be 1 or 2.

r can be 0, 1, or 2.

In another aspect, a pharmaceutical composition includes a pharmaceutically acceptable carrier or excipient and a compound represented by formula (Ia):

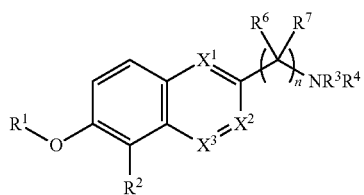

or a pharmaceutically acceptable salt thereof.

In formula (Ia), $X^1$, $X^2$, and $X^3$ can be CH; or one of $X^1$, $X^2$, or $X^3$ can be N and the other two can be CH.

$R^1$ can be

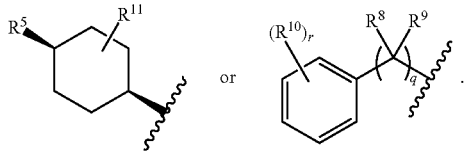

$R^2$ can be a $C_{1-4}$haloalkyl or cyano.

$R^3$ can be $-L^1-J-L^2-R^{12}$; and $R^4$ can be hydrogen or a $C_{1-6}$alkyl; or $R^3$ and $R^4$ together with the nitrogen to which they are attached can be a 3- to 8-membered heterocyclyl which can be substituted with $-L^2-R^{12}$, and is optionally substituted with a halo, hydroxyl, amino, or a $C_{1-6}$alkyl.

$R^5$ can be a halo, a $C_{1-6}$alkyl or a $C_{1-6}$haloalkyl.

$R^6$ and $R^7$ can each be independently hydrogen, $C_{1-6}$alkyl, a $C_{1-6}$haloalkyl, $C_{3-7}$cycloalkyl, or COOH; or $R^6$ and $R^7$ together with the carbon to which they are attached can be $-C(=O)-$, a $C_{3-8}$spirocycloalkyl, or a 3- to 8-membered spiroheterocyclalkyl.

$R^8$ and $R^9$ can each be independently hydrogen or a $C_{1-6}$alkyl; or $R^8$ and $R^9$ taken together with the carbon to which they are attached can be $-C(=O)-$.

$R^{10}$, for each occurrence, can be halo.

$R^{11}$ can be hydrogen, halo, or $C_{1-4}$alkyl.

$R^{12}$ can be $-COOR^{13}$, $-P(O)(OR^{13})_2$, or tetrazolyl.

Each $R^{13}$, independently, can be H, $C_{1-4}$alkyl, aryl, or aryl-$C_{1-4}$-alkyl.

J can be a $C_{1-6}$alkylene, a $C_{3-8}$cycloalkylene, a 3- to 8-membered divalent monocyclic heterocyclyl, a phenylene, or a 5- to 6-membered heteroarylene, wherein J can be optionally substituted with one or two substituents independently selected from a halo and a $C_{1-6}$alkyl.

$L^1$ and $L^2$ can each be independently, a $C_{1-3}$alkylene or a direct bond.

n can be 1, 2 or 3.

q can be 1 or 2.

r can be 0, 1, or 2.

In another aspect, a method of preventing, treating, or reducing symptoms of a condition mediated by ATX activity in a mammal includes administering to said mammal an effective amount of a compound, or a pharmaceutically acceptable salt thereof, represented by formula (I):

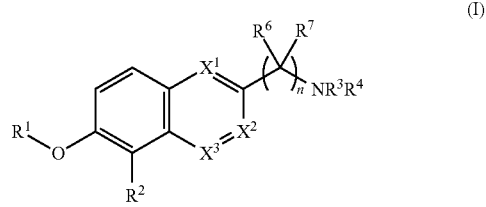

In formula (I), $X^1$, $X^2$, and $X^3$ can be CH; or one of $X^1$, $X^2$, or $X^3$ can be N and the other two can be CH.

$R^1$ can be

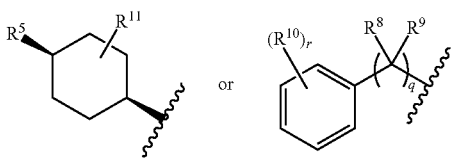

$R^2$ can be a $C_{1-4}$haloalkyl or cyano.

$R^3$ can be $-L^1-J-L^2-R^{12}$; and $R^4$ can be hydrogen or a $C_{1-6}$alkyl; or $R^3$ and $R^4$ together with the nitrogen to which they are attached can be a 3- to 8-membered heterocyclyl which can be substituted with $-L^2-R^{12}$, and is optionally substituted with a halo, hydroxyl, amino, or a $C_{1-6}$alkyl.

$R^5$ can be a halo, a $C_{1-6}$alkyl or a $C_{1-6}$haloalkyl.

$R^6$ and $R^7$ can each be independently hydrogen or $C_{1-6}$alkyl; or $R^6$ and $R^7$ together with the carbon to which they are attached can be $-C(=O)-$, a $C_{3-8}$spirocycloalkyl, or a 3- to 8-membered spiroheterocyclalkyl.

$R^8$ and $R^9$ can each be independently hydrogen or a $C_{1-6}$alkyl; or $R^8$ and $R^9$ taken together with the carbon to which they are attached can be $-C(=O)-$.

$R^{10}$, for each occurrence, can be halo.

$R^{11}$ can be hydrogen, halo, or $C_{1-4}$alkyl.

$R^{12}$ can be —COOR$^{13}$ or —P(O)(OR$^{13}$)$_2$.

Each $R^{13}$, independently, can be H, $C_{1-4}$alkyl, aryl, or aryl-$C_{1-4}$-alkyl.

J can be a $C_{1-6}$alkylene, a $C_{3-8}$cycloalkylene, a 3- to 8-membered divalent monocyclic heterocyclyl, a phenylene, or a 5- to 6-membered heteroarylene, wherein J can be optionally substituted with one or two substituents independently selected from a halo and a $C_{1-6}$alkyl.

$L^1$ and $L^2$ can each be independently, a $C_{1-3}$alkylene or a direct bond.

n can be 1, 2 or 3.

q can be 1 or 2.

r can be 0, 1, or 2.

In another aspect, a method of preventing, treating, or reducing symptoms of a condition mediated by ATX activity in a mammal includes administering to said mammal an effective amount of a compound, or a pharmaceutically acceptable salt thereof, represented by formula (Ia):

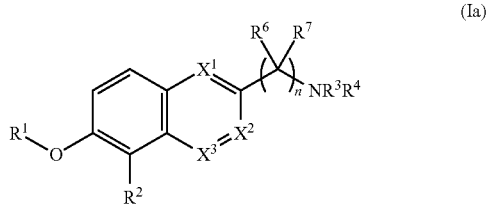

(Ia)

or a pharmaceutically acceptable salt thereof.

In formula (Ia), $X^1$, $X^2$, and $X^3$ can be CH; or one of $X^1$, $X^2$, or $X^3$ can be N and the other two can be CH.

$R^1$ can be

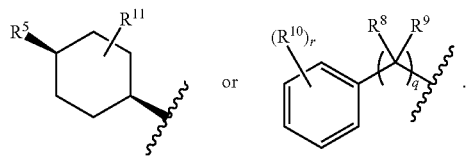

$R^2$ can be a $C_{1-4}$haloalkyl or cyano.

$R^3$ can be -$L^1$-J-$L^2$-$R^{12}$; and $R^4$ can be hydrogen or a $C_{1-6}$alkyl; or $R^3$ and $R^4$ together with the nitrogen to which they are attached can be a 3- to 8-membered heterocyclyl which can be substituted with -$L^2$-$R^{12}$, and is optionally substituted with a halo, hydroxyl, amino, or a $C_{1-6}$alkyl.

$R^5$ can be a halo, a $C_{1-6}$alkyl or a $C_{1-6}$haloalkyl.

$R^6$ and $R^7$ can each be independently hydrogen, $C_{1-6}$alkyl, a $C_{1-6}$haloalkyl, $C_{3-7}$cycloalkyl, or COOH; or $R^6$ and $R^7$ together with the carbon to which they are attached can be —C(=O)—, a $C_{3-8}$spirocycloalkyl, or a 3- to 8-membered spiroheterocyclalkyl.

$R^8$ and $R^9$ can each be independently hydrogen or a $C_{1-6}$alkyl; or $R^8$ and $R^9$ taken together with the carbon to which they are attached can be —C(=O)—.

$R^{10}$, for each occurrence, can be halo.

$R^{11}$ can be hydrogen, halo, or $C_{1-4}$alkyl.

$R^{12}$ can be —COOR$^{13}$, —P(O)(OR$^{13}$)$_2$, or tetrazolyl.

Each $R^{13}$, independently, can be H, $C_{1-4}$alkyl, aryl, or aryl-$C_{1-4}$-alkyl.

J can be a $C_{1-6}$alkylene, a $C_{3-8}$cycloalkylene, a 3- to 8-membered divalent monocyclic heterocyclyl, a phenylene, or a 5- to 6-membered heteroarylene, wherein J can be optionally substituted with one or two substituents independently selected from a halo and a $C_{1-6}$alkyl.

$L^1$ and $L^2$ can each be independently, a $C_{1-3}$alkylene or a direct bond.

n can be 1, 2 or 3.

q can be 1 or 2.

r can be 0, 1, or 2.

The condition can be selected from the group consisting of an inflammatory disorder, an autoimmune disorder, a fibrosis of the lung, or a malignancy of the lung. The inflammatory disorder can be rheumatoid arthritis. The autoimmune disorder can be multiple sclerosis.

The method can further include administering to said mammal an effective amount of one or more drugs selected from the group consisting of: a corticosteroid, a bronchodilator, an antiasthmatic, an antiinflammatory, an antirheumatic, an immunosuppressant, an antimetabolite, an immunomodulator, an antipsoriatic, and an antidiabetic.

In another aspect, the invention provides a method of treating or preventing an inflammatory disorder, an autoimmune disorder, a fibrosis of the lung, or a malignancy of the lung in a mammal in need of such treatment, comprising treat the mammal with an effective amount of a compound, or a pharmaceutically acceptable salt thereof, represented by formula (I):

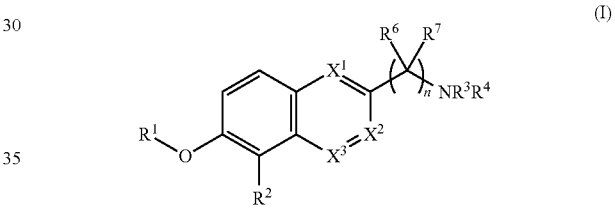

(I)

In formula (I), $X^1$, $X^2$, and $X^3$ can be CH; or one of $X^1$, $X^2$, or $X^3$ can be N and the other two can be CH.

$R^1$ can be

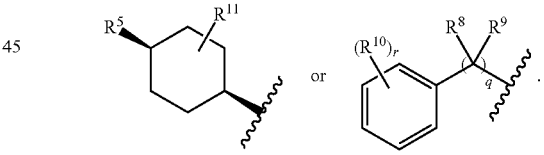

$R^2$ can be a $C_{1-4}$haloalkyl or cyano.

$R^3$ can be -$L^1$-J-$L^2$-$R^{12}$; and $R^4$ can be hydrogen or a $C_{1-6}$alkyl; or $R^3$ and $R^4$ together with the nitrogen to which they are attached can be a 3- to 8-membered heterocyclyl which can be substituted with -$L^2$-$R^{12}$, and is optionally substituted with a halo, hydroxyl, amino, or a $C_{1-6}$alkyl.

$R^5$ can be a halo, a $C_{1-6}$alkyl or a $C_{1-6}$haloalkyl.

$R^6$ and $R^7$ can each be independently hydrogen or $C_{1-6}$alkyl; or $R^6$ and $R^7$ together with the carbon to which they are attached can be —C(=O)—, a $C_{3-8}$spirocycloalkyl, or a 3- to 8-membered spiroheterocyclalkyl.

$R^8$ and $R^9$ can each be independently hydrogen or a $C_{1-6}$alkyl; or $R^8$ and $R^9$ taken together with the carbon to which they are attached can be —C(=O)—.

$R^{10}$, for each occurrence, can be halo.

$R^{11}$ can be hydrogen, halo, or $C_{1-4}$alkyl.

$R^{12}$ can be —COOR$^{13}$ or —P(O)(OR$^{13}$)$_2$.

Each $R^{13}$, independently, can be H, $C_{1-4}$alkyl, aryl, or aryl-$C_{1-4}$-alkyl.

J can be a $C_{1-6}$alkylene, a $C_{3-8}$cycloalkylene, a 3- to 8-membered divalent monocyclic heterocyclyl, a phenylene, or a 5- to 6-membered heteroarylene, wherein J can be optionally substituted with one or two substituents independently selected from a halo and a $C_{1-6}$alkyl.

$L^1$ and $L^2$ can each be independently, a $C_{1-3}$alkylene or a direct bond.

n can be 1, 2 or 3.

q can be 1 or 2.

r can be 0, 1, or 2.

In another aspect, the invention provides a method of treating an inflammatory disorder, an autoimmune disorder, a fibrosis of the lung, or a malignancy of the lung in a mammal in need of such treatment, comprising administering to the mammal an effective amount of a compound, or a pharmaceutically acceptable salt thereof, represented by formula (Ia):

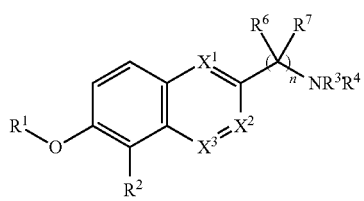

(Ia)

or a pharmaceutically acceptable salt thereof.

In formula (Ia), $X^1$, $X^2$, and $X^3$ can be CH; or one of $X^1$, $X^2$, or $X^3$ can be N and the other two can be CH.

$R^1$ can be

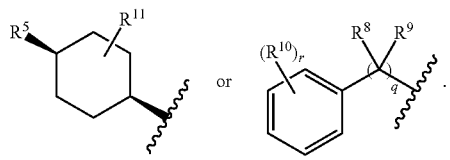

$R^2$ can be a $C_{1-4}$haloalkyl or cyano.

$R^3$ can be -$L^1$-J-$L^2$-$R^{12}$; and $R^4$ can be hydrogen or a $C_{1-6}$alkyl; or $R^3$ and $R^4$ together with the nitrogen to which they are attached can be a 3- to 8-membered heterocyclyl which can be substituted with -$L^2$-$R^{12}$, and is optionally substituted with a halo, hydroxyl, amino, or a $C_{1-6}$alkyl.

$R^5$ can be a halo, a $C_{1-6}$alkyl or a $C_{1-6}$haloalkyl.

$R^6$ and $R^7$ can each be independently hydrogen, $C_{1-6}$alkyl, a $C_{1-6}$haloalkyl, $C_{3-7}$cycloalkyl, or COOH; or $R^6$ and $R^7$ together with the carbon to which they are attached can be —C(=O)—, a $C_{3-8}$spirocycloalkyl, or a 3- to 8-membered spiroheterocyclalkyl.

$R^8$ and $R^9$ can each be independently hydrogen or a $C_{1-6}$alkyl; or $R^8$ and $R^9$ taken together with the carbon to which they are attached can be —C(=O)—.

$R^{10}$, for each occurrence, can be halo.

$R^{11}$ can be hydrogen, halo, or $C_{1-4}$alkyl.

$R^{12}$ can be —COOR$^{13}$, —P(O)(OR$^{13}$)$_2$, or tetrazolyl.

Each $R^{13}$, independently, can be H, $C_{1-4}$alkyl, aryl, or aryl-$C_{1-4}$-alkyl.

J can be a $C_{1-6}$alkylene, a $C_{3-8}$cycloalkylene, a 3- to 8-membered divalent monocyclic heterocyclyl, a phenylene, or a 5- to 6-membered heteroarylene, wherein J can be optionally substituted with one or two substituents independently selected from a halo and a $C_{1-6}$alkyl.

$L^1$ and $L^2$ can each be independently, a $C_{1-3}$alkylene or a direct bond.

n can be 1, 2 or 3.

q can be 1 or 2.

r can be 0, 1, or 2.

In another aspect, a method of preventing, treating, or reducing chronic pain in a mammal includes administering to said mammal an effective amount of a compound, or a pharmaceutically acceptable salt thereof, represented by formula (I):

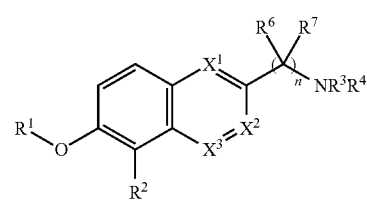

(I)

In formula (I), $X^1$, $X^2$, and $X^3$ can be CH; or one of $X^1$, $X^2$, or $X^3$ can be N and the other two can be CH.

$R^1$ can be

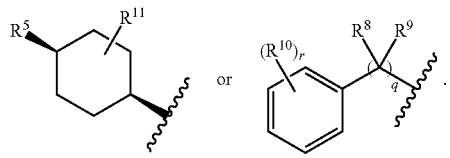

$R^2$ can be a $C_{1-4}$haloalkyl or cyano.

$R^3$ can be -$L^1$-J-$L^2$-$R^{12}$; and $R^4$ can be hydrogen or a $C_{1-6}$alkyl; or $R^3$ and $R^4$ together with the nitrogen to which they are attached can be a 3- to 8-membered heterocyclyl which can be substituted with -$L^2$-$R^{12}$, and is optionally substituted with a halo, hydroxyl, amino, or a $C_{1-6}$alkyl.

$R^5$ can be a halo, a $C_{1-6}$alkyl or a $C_{1-6}$haloalkyl.

$R^6$ and $R^7$ can each be independently hydrogen or $C_{1-6}$alkyl; or $R^6$ and $R^7$ together with the carbon to which they are attached can be —C(=O)—, a $C_{3-8}$spirocycloalkyl, or a 3- to 8-membered spiroheterocyclalkyl.

$R^8$ and $R^9$ can each be independently hydrogen or a $C_{1-6}$alkyl; or $R^8$ and $R^9$ taken together with the carbon to which they are attached can be —C(=O)—.

$R^{10}$, for each occurrence, can be halo.

$R^{11}$ can be hydrogen, halo, or $C_{1-4}$alkyl.

$R^{12}$ can be —COOR$^{13}$ or —P(O)(OR$^{13}$)$_2$.

Each $R^{13}$, independently, can be H, $C_{1-4}$alkyl, aryl, or aryl-$C_{1-4}$-alkyl.

J can be a $C_{1-6}$alkylene, a $C_{3-8}$cycloalkylene, a 3- to 8-membered divalent monocyclic heterocyclyl, a phenylene, or a 5- to 6-membered heteroarylene, wherein J can be optionally substituted with one or two substituents independently selected from a halo and a $C_{1-6}$alkyl.

$L^1$ and $L^2$ can each be independently, a $C_{1-3}$alkylene or a direct bond.

n can be 1, 2 or 3.

q can be 1 or 2.

r can be 0, 1, or 2.

In some embodiments, the chronic pain can be inflammatory pain or neuropathic pain.

Other features or advantages will be apparent from the following detailed description of several embodiments, and also from the appended claims.

DETAILED DESCRIPTION

The disclosed compounds can have activity as ATX modulators. In particular, the compounds can be ATX inhibitors.

A compound represented by formula (I):

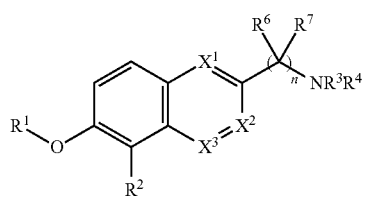

or a pharmaceutically acceptable salt thereof, can be an ATX modulating agent.

In formula (I), $X^1$, $X^2$, and $X^3$ can be CH; or one of $X^1$, $X^2$, or $X^3$ can be N and the other two can be CH.

$R^1$ can be

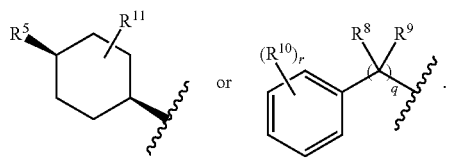

$R^2$ can be a $C_{1-4}$haloalkyl or cyano.

$R^3$ can be -$L^1$-J-$L^2$-$R^{12}$; and $R^4$ can be hydrogen or a $C_{1-6}$alkyl; or $R^3$ and $R^4$ together with the nitrogen to which they are attached can be a 3- to 8-membered heterocyclyl which can be substituted with -$L^2$-$R^{12}$, and can be optionally substituted with a halo, hydroxyl, amino, or a $C_{1-6}$alkyl.

$R^5$ can be a halo, a $C_{1-6}$alkyl or a $C_{1-6}$haloalkyl.

$R^6$ and $R^7$ can be each independently hydrogen or $C_{1-6}$alkyl; or $R^6$ and $R^7$ together with the carbon to which they are attached can be —C(=O)—, a $C_{3-8}$spirocycloalkyl, or a 3- to 8-membered spiroheterocyclalkyl.

$R^8$ and $R^9$ can be each independently hydrogen or a $C_{1-6}$alkyl; or $R^8$ and $R^9$ taken together with the carbon to which they are attached can be —C(=O)—.

$R^{10}$, for each occurrence, can be halo.

$R^{11}$ can be hydrogen, halo, or $C_{1-4}$alkyl.

$R^{12}$ can be —COOR$^{13}$ or —P(O)(OR$^{13})_2$.

Each $R^{13}$, independently, can be H, $C_{1-4}$alkyl, aryl, or aryl-$C_{1-4}$-alkyl.

J can be a $C_{1-6}$alkylene, a $C_{3-8}$cycloalkylene, a 3- to 8-membered divalent monocyclic heterocyclyl, a phenylene, or a 5- to 6-membered heteroarylene, wherein J can be optionally substituted with one or two substituents independently selected from a halo and a $C_{1-6}$alkyl;

$L^1$ and $L^2$ can be each independently, a $C_{1-3}$alkylene or a direct bond.

n can be 1, 2 or 3. q can be 1 or 2. r can be 0, 1, or 2.

In some embodiments, $R^{12}$ can be —P(O)(OH)$_2$. n can be 1.

In some embodiments of formula (I) or (Ia), n is 1 and $R^6$ and $R^7$ together with the carbon to which they are attached can be —C(=O)—.

In some embodiments of formula (I) or (Ia), n is 1 and $R^6$ and $R^7$ are both hydrogen.

In some embodiments of formula (I) or (Ia), n is 1 and $R^6$ is H and $R^7$ is methyl, ethyl, isopropyl, or isobutyl.

In some embodiments of formula (Ia), n is 1 and $R^6$ is H and $R^7$ is methyl, trifluoromethyl, ethyl, isopropyl, isobutyl, or cyclopropyl.

In some embodiments, $L^1$ can be a direct bond; J can be a $C_{1-6}$alkylene or a phenylene, wherein J can be optionally substituted with one or two substituents independently selected from a halo and a $C_{1-6}$alkyl; $L^2$ can be a $C_{1-3}$alkylene; and $R^{12}$ can be —P(O)(OR$^{13})_2$.

In some embodiments, $R^3$ and $R^4$ together with the nitrogen to which they are attached can be a 4- to 7-membered heterocyclyl which can be substituted with $L^2$-$R^{12}$, and can be optionally substituted with a halo, hydroxyl, amino, or a $C_{1-6}$alkyl; $L^2$ can be a direct bond or —CH$_2$—; and $R^{12}$ can be —COOR$^{13}$.

In some embodiments, $R^2$ can be —CHF$_2$ or —CF$_3$. $R^1$ can be

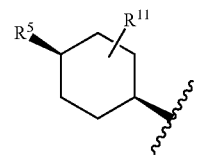

wherein $R^5$ can be a halo, a $C_1$alkyl, or a $C_1$haloalkyl.

$R^1$ can be

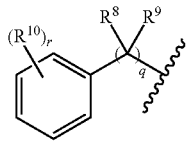

wherein q can be 1, $R^8$ and $R^9$ can be each independently H, and each $R^{10}$ can be independently H or a halo.

Each of the following compounds can be an ATX modulating agent:

2,2-dimethyl-3-(((5-(trifluoromethyl)-6-((cis-4-(trifluoromethyl)cyclo-hexyl)oxy)naphthalen-2-yl)methyl)amino)cyclobutanecarboxylic acid;

1-((5-(trifluoromethyl)-6-((cis-4-(trifluoromethyl)cyclohexyl)oxy)-naphthalen-2-yl)methyl)piperidine-4-carboxylic acid;

3-(((5-(trifluoromethyl)-6-((cis-4-(trifluoromethyl)cyclohexyl)oxy)-naphthalen-2-yl)methyl)amino)cyclopentanecarboxylic acid;

(R)-2-(1-(((6-((4,4-difluorocyclohexyl)oxy)-5-(trifluoromethyl)naphthalen-2-yl)methyl)piperidin-3-yl)acetic acid;

4-(2H-tetrazol-5-yl)-1-((5-(trifluoromethyl)-6-((cis-4-(trifluoromethyl)cyclohexyl)oxy)naphthalen-2-yl)methyl)piperidine;

2-((3R)-1-(1-(6-((cis-4-ethylcyclohexyl)oxy)-5-(trifluoromethyl)naphthalen-2-yl)ethyl)piperidin-3-yl)acetic acid;

2-((3R)-1-(1-(6-((cis-4-ethylcyclohexyl)oxy)-5-(trifluoromethyl)naphthalen-2-yl)propyl)piperidin-3-yl)acetic acid;

2-(4-((6-((cis-4-Methylcyclohexyl)oxy)-5-(trifluoromethyl)naphthalen-2-yl)methyl)morpholin-2-yl)acetic acid;

2-(1-((6-((cis-4-methylcyclohexyl)oxy)-5-(trifluoromethyl)naphthalen-2-yl)methyl)piperidin-3-yl)acetic acid;

2-((3R)-1-(1-(6-((cis-4-Methylcyclohexyl)oxy)-5-(trifluoromethyl)naphthalen-2-yl)propyl)piperidin-3-yl)acetic acid;

1-(Carboxy(6-((cis-4-methylcyclohexyl)oxy)-5-(trifluoromethyl)naphthalen-2-yl)methyl)piperidine-4-carboxylic acid;

1-(2,2,2-Trifluoro-1-(6-((cis-4-methylcyclohexyl)oxy)-5-(trifluoromethyl)naphthalen-2-yl)ethyl)piperidine-4-carboxylic acid;

1-((5-(Difluoromethyl)-6-((cis-4-methylcyclohexyl)oxy)naphthalen-2-yl)methyl)piperidine-4-carboxylic acid;

2-((R)-1-(((5-(trifluoromethyl)-6-(cis-4-(trifluoromethyl)cyclohexyl)oxy)quinolin-2-yl)methyl)piperidin-3-yl)acetic acid; and 2,2-dimethyl-3-(((1-(5-(trifluoromethyl)-6-(cis-4-(trifluoromethyl)cyclo-hexyl)oxy)quinolin-2-yl)ethyl)amino)cyclobutanecarboxylic acid.

2,2-dimethyl-3-((1-(6-(cis-4-methylcyclohexyl)oxy)-5-(trifluoromethyl)naphthalen-2-yl)cyclopropyl)amino)cyclobutanecarboxylic acid;

4-Acetamido-4-(5-(trifluoromethyl)-6-(cis-4-(trifluoromethyl)cyclo-hexyl)oxy)naphthalen-2-yl)pentanoic acid;

(3-(6-((3,5-dichlorobenzyl)oxy)-5-(trifluoromethyl)-2-naphthamido)propyl)phosphonic acid;

(3-(5-(trifluoromethyl)-6-((cis-4-(trifluoromethyl)cyclohexyl)oxy)-2-naphthamido)propyl)phosphonic acid;

1-((5-cyano-6-((cis-4-(trifluoromethyl)cyclohexyl)oxy)naphthalen-2-yl)methyl)piperidine-4-carboxylic acid;

1-((5-(difluoromethyl)-6-((cis-4-(trifluoromethyl)cyclohexyl)oxy)naphthalen-2-yl)methyl)piperidine-4-carboxylic acid;

1-((5-(trifluoromethyl)-6-((cis-4-(trifluoromethyl)cyclohexyl)amino)naphthalen-2-yl)methyl)piperidine-4-carboxylic acid;

6-((5-(trifluoromethyl)-6-((cis)-4-(trifluoromethyl)cyclohexyloxy)-2-naphthamido)methyl)nicotinic acid;

(R)-1-((5-(trifluoromethyl)-6-((cis)-4-(trifluoromethyl)cyclohexyloxy)naphthalen-2-yl)methyl)piperidine-3-carboxylic acid;

(trans)-4-(((5-(trifluoromethyl)-6-((cis)-4-(trifluoromethyl)cyclohexyloxy)naphthalen-2-yl)methylamino)methyl)cyclohexanecarboxylic acid;

(S)-1-((5-(trifluoromethyl)-6-((cis)-4-(trifluoromethyl)cyclohexyloxy)naphthalen-2-yl)methyl)piperidine-3-carboxylic acid;

2-(1-((5-(trifluoromethyl)-6-((cis)-4-(trifluoromethyl)cyclohexyloxy)naphthalen-2-yl)methyl)piperidin-2-yl)acetic acid;

(trans)-4-((methyl((5-(trifluoromethyl)-6-((cis)-4-(trifluoromethyl)cyclohexyloxy)naphthalen-2-yl)methyl)amino)methyl)cyclohexanecarboxylic acid;

1-((5-(trifluoromethyl)-6-((cis)-4-(trifluoromethyl)cyclohexyloxy)naphthalen-2-yl)methyl)piperidine-2-carboxylic acid;

4-methyl-1-((5-(trifluoromethyl)-6-((cis)-4-(trifluoromethyl)cyclohexyloxy)naphthalen-2-yl)methyl)piperidine-4-carboxylic acid;

1-(5-(trifluoromethyl)-6-((cis)-4-(trifluoromethyl)cyclohexyloxy)-2-naphthoyl)azepane-4-carboxylic acid;

2-(4-((5-(difluoromethyl)-6-((cis)-4-(trifluoromethyl)cyclohexyloxy)naphthalen-2-yl)methyl)morpholin-2-yl)acetic acid;

3-((5-(difluoromethyl)-6-((cis)-4-(trifluoromethyl)cyclohexyloxy)naphthalen-2-yl)methylamino)-2,2-dimethylcyclobutanecarboxylic acid;

(trans)-4-(((5-(difluoromethyl)-6-((cis)-4-(trifluoromethyl)cyclohexyloxy)naphthalen-2-yl)methylamino)methyl)cyclohexanecarboxylic acid;

4-hydroxy-1-((5-(trifluoromethyl)-6-((cis)-4-(trifluoromethyl)cyclohexyloxy)naphthalen-2-yl)methyl)piperidine-3-carboxylic acid;

2,2-dimethyl-3-(1-(6-((cis)-4-methylcyclohexyloxy)-5-(trifluoromethyl)naphthalen-2-yl)propylamino)cyclobutanecarboxylic acid;

2,2-dimethyl-3-(1-(5-(trifluoromethyl)-6-((cis)-4-(trifluoromethyl)cyclohexyloxy)naphthalen-2-yl)ethylamino)cyclobutanecarboxylic acid;

3-(cyclopropyl(6-((cis)-4-methylcyclohexyloxy)-5-(trifluoromethyl)naphthalen-2-yl)methylamino)-2,2-dimethylcyclobutanecarboxylic acid;

2,2-dimethyl-3-(2-methyl-1-(5-(trifluoromethyl)-6-((cis)-4-(trifluoromethyl)cyclohexyloxy)naphthalen-2-yl)propylamino)cyclobutanecarboxylic acid;

2,2-dimethyl-3-(3-methyl-1-(5-(trifluoromethyl)-6-((cis)-4-(trifluoromethyl)cyclohexyloxy)naphthalen-2-yl)butylamino)cyclobutanecarboxylic acid;

4-(1-((5-(trifluoromethyl)-6-((cis)-4-(trifluoromethyl)cyclohexyloxy)naphthalen-2-yl)methylamino)ethyl)cyclohexanecarboxylic acid;

3-(cyclohexyl(6-((cis)-4-methylcyclohexyloxy)-5-(trifluoromethyl)naphthalen-2-yl)methylamino)-2,2-dimethylcyclobutanecarboxylic acid;

3-(cyclohexyl(5-(trifluoromethyl)-6-((cis)-4-(trifluoromethyl)cyclohexyloxy)naphthalen-2-yl)methylamino)-2,2-dimethylcyclobutanecarboxylic acid;

3-(cyclopropyl(5-(trifluoromethyl)-6-((cis)-4-(trifluoromethyl)cyclohexyloxy)naphthalen-2-yl)methylamino)-2,2-dimethylcyclobutanecarboxylic acid;

1-(1-(5-trifluoromethyl-6-(cis-4-methylcyclohexyloxy)naphthalene-2-yl)ethyl)-piperidine-4-carboxylic acid;

1-((5-trifluoromethyl-6-(cis-4-methylcyclohexyloxy)naphthalene-2-yl)methyl)-pyrrolidine-3-acetic acid;

1-((5-trifluoromethyl-6-(cis-4-methylcyclohexyloxy)naphthalene-2-yl)methyl)-azetidine-3-acetic acid;

1-((5-trifluoromethyl-6-(cis-4-methylcyclohexyloxy)naphthalene-2-yl)methyl)-azepane-3-carboxylic acid;

2-((3R)-1-((6-((cis-4-Methylcyclohexyl)oxy)-5-(trifluoromethyl)naphthalen-2-yl)methyl)piperidin-3-yl)acetic acid;

1-(1-(6-((cis-4-Methylcyclohexyl)oxy)-5-(trifluoromethyl)naphthalen-2-yl)propyl)piperidine-4-carboxylic acid;

2-((3R)-1-(1-(6-((cis-4-Methylcyclohexyl)oxy)-5-(trifluoromethyl)naphthalen-2-yl)ethyl)piperidin-3-yl)acetic acid;

2-((3S)-1-(1-(6-((cis-4-Methylcyclohexyl)oxy)-5-(trifluoromethyl)naphthalen-2-yl)propyl)piperidin-3-yl)acetic acid;

2-((3R)-1-(1-(6-((cis-4-Methylcyclohexyl)oxy)-5-(difluoromethyl)naphthalen-2-yl)ethyl)piperidin-3-yl)acetic acid;

2-((3S)-1-(1-(6-((cis-4-Methylcyclohexyl)oxy)-5-(difluoromethyl)naphthalen-2-yl)ethyl)piperidin-3-yl)acetic acid;

1-(1-(6-((cis-4-Methylcyclohexyl)oxy)-5-(difluoromethyl)naphthalen-2-yl)ethyl)piperidine-4-carboxylic acid;

2-((3R)-1-((6-((cis-4-Methylcyclohexyl)oxy)-5-(difluoromethyl)naphthalen-2-yl)methyl)piperidin-3-yl)acetic acid;

2-((3R)-1-(1-(6-((cis-4-Methylcyclohexyl)oxy)-5-(difluoromethyl)naphthalen-2-yl)propyl)piperidin-3-yl)acetic acid;

1-(1-(6-((cis-4-Methylcyclohexyl)oxy)-5-(difluoromethyl)naphthalen-2-yl)propyl)piperidine-4-carboxylic acid;

2-((3R)-1-((S)-1-(6-((cis-4-Methylcyclohexyl)oxy)-5-(trifluoromethyl)naphthalen-2-yl)propyl)piperidin-3-yl)acetic acid;

2-((3R)-1-((R)-1-(6-((cis-4-Methylcyclohexyl)oxy)-5-(trifluoromethyl)naphthalen-2-yl)propyl)piperidin-3-yl)acetic acid;

1-((S)-1-(6-((cis-4-Methylcyclohexyl)oxy)-5-(difluoromethyl)naphthalen-2-yl)ethyl)piperidine-4-carboxylic acid;

2-(1-((5-(trifluoromethyl)-6-(4-cis-(trifluoromethyl)cyclohexyloxy)naphthalene-2-yl)methyl)azetidine-3-yl)acetic acid;

3-(((5-(trifluoromethyl)-6-(cis-4-(trifluoromethyl)cyclohexyloxy)naphthalene-2-yl)methyl)amino)propylphosphonic acid;

1-((5-(trifluoromethyl)-6-((cis-4-(trifluoromethyl)cyclohexyl)oxy)-naphthalen-2-yl)methyl)pyrrolidine-3-acetic acid;

1-((5-(trifluoromethyl)-6-((cis-4-(trifluoromethyl)cyclohexyl)oxy)-naphthalen-2-yl)methyl)piperidine-4-acetic acid;

1-((5-(trifluoromethyl)-6-((cis-4-(trifluoromethyl)cyclohexyl)oxy)-naphthalen-2-yl)methyl)aminocyclopentane-3-carboxylic acid;

1-((5-(trifluoromethyl)-6-((cis-4-(trifluoromethyl)cyclohexyl)oxy)-naphthalen-2-yl)methyl)piperidine-3-acetic acid;

(4-((5-(trifluoromethyl)-6-(cis-4-(trifluoromethyl)cyclohexyloxy)naphthalene-2-yl)methyl)aminophenyl)methylphosphonic acid;

6-((((5-(trifluoromethyl)-6-((cis)-4-(trifluoromethyl)cyclohexyloxy)naphthalene-2-yl)methyl)amino)methyl)nicotinic acid;

cis-4-(((5-(trifluoromethyl)-6-((cis)-4-(trifluoromethyl)cyclohexyloxy)naphthalene-2-yl)methyl)amino)cyclohexane-1-carboxylic acid;

(S)-1-((5-(trifluoromethyl)-6-((cis)-4-(trifluoromethyl)cyclohexyloxy)naphthalene-2-yl)methyl)pyrrolidine-3-acetic acid;

(R)-1-((5-(trifluoromethyl)-6-((cis)-4-(trifluoromethyl)cyclohexyloxy)naphthalene-2-yl)methyl)pyrrolidine-3-acetic acid;

3-((4-((5-(trifluoromethyl)-6-(cis-4-(trifluoromethyl)cyclohexyloxy)naphthalene-2-yl)methyl)amino)cyclohexyl)propionic acid;

1-((5-(trifluoromethyl)-6-((cis-4-(trifluoromethyl)cyclohexyl)oxy)-naphthalen-2-yl)methyl)-3-methylpiperidine-4-carboxylic acid;

5-(((5-(trifluoromethyl)-6-((cis-4-(trifluoromethyl)cyclohexyl)oxy)-naphthalen-2-yl)methyl)amino)methyl)pyridine-2-carboxylic acid;

1-((5-(trifluoromethyl)-6-((cis-4-(trifluoromethyl)cyclohexyl)oxy)-naphthalen-2-yl)methyl)azepane-4-carboxylic acid;

4-((5-(trifluoromethyl)-6-((cis-4-(trifluoromethyl)cyclohexyl)oxy)-naphthalen-2-yl)methyl)morpholine-2-carboxylic acid;

1-((5-(trifluoromethyl)-6-((cis-4-(trifluoromethyl)cyclohexyl)oxy)-naphthalen-2-yl)methyl)-3-aminopyrrolidine-3-carboxylic acid;

N-methyl-cis-4-(((5-(trifluoromethyl)-6-(cis-4-(trifluoromethyl)cyclohexyloxy)naphthalene-2-yl)methyl)amino)cyclohexane-1-carboxylic acid;

2-((R)-1-((2-(cis-4-(trifluoromethyl)cyclohexyloxy)-1-(trifluoromethyl)naphthalen-6-yl)methyl)piperidin-3-yl)acetic acid;

1-((5-(trifluoromethyl)-6-(cis-4-(trifluoromethyl)cyclohexyloxy)naphthalene-2-yl)methyl)-5-hydroxypiperidine-3-carboxylic acid;

2-((S)-4-((2-(cis-4-(trifluoromethyl)cyclohexyloxy)-1-(trifluoromethyl)naphthalen-6-yl)methyl)morpholin-2-yl) acetic acid;

3-(1-((2-(cis-4-(trifluoromethyl)cyclohexyloxy)-1-(trifluoromethyl)naphthalen-6-yl)methyl)piperidine-4-yl)propionic acid;

2-((R)-1-((2-(cis-4-(ethyl)cyclohexyloxy)-1-(trifluoromethyl)naphthalen-6-yl)methyl)piperidin-3-yl)acetic acid;

2,2-dimethyl-3-((((S)-1-(5-(trifluoromethyl)-6-(cis-4-(trifluoromethyl)cyclo-hexyl)oxy)naphthalene-2-yl)ethyl)amino)cyclobutanecarboxylic acid;

2,2-dimethyl-3-((((R)-1-(5-(trifluoromethyl)-6-(cis-4-(trifluoromethyl)cyclo-hexyl)oxy)naphthalene-2-yl)ethyl)amino)cyclobutanecarboxylic acid;

2,2-dimethyl-3-((((5-(trifluoromethyl)-6-(cis-4-(trifluoromethyl)cyclo-hexyl)oxy)quinolin-2-yl)methyl)amino)cyclobutanecarboxylic acid;

2-((S)-1-(((5-(trifluoromethyl)-6-(cis-4-(trifluoromethyl)cyclohexyl)oxy)quinolin-2-yl)methyl)piperidin-3-yl)acetic acid;

2-((S)-1-(1-(2-(cis-4-(trifluoromethyl)cyclohexyloxy)-1-(trifluoromethyl)naphthalen-6-yl)propyl)piperidin-3-yl) acetic acid;

2,2-dimethyl-3-(1-(6-((cis)-4-methylcyclohexyloxy)-5-(trifluoromethyl)naphthalen-2-yl)-3-methylbutylamino)cyclobutanecarboxylic acid;

2-((3R)-1-((S)-1-(6-((cis-4-Methylcyclohexyl)oxy)-5-(difluoromethyl)naphthalen-2-yl)ethyl)piperidin-3-yl)acetic acid;

2-((3R)-1-((R)-1-(6-((cis-4-Methylcyclohexyl)oxy)-5-(difluoromethyl)naphthalen-2-yl)ethyl)piperidin-3-yl)acetic acid;

2-((3R)-1-((S)-1-(6-((cis-4-Methylcyclohexyl)oxy)-5-(difluoromethyl)naphthalen-2-yl)propyl)piperidin-3-yl)acetic acid;

2-((3R)-1-((R)-1-(6-((cis-4-Methylcyclohexyl)oxy)-5-(difluoromethyl)naphthalen-2-yl)propyl)piperidin-3-yl)acetic acid;

2-((3R)-1-((S)-1-(6-((cis-4-Methylcyclohexyl)oxy)-5-(trifluoromethyl)naphthalen-2-yl)ethyl)piperidin-3-yl)acetic acid;

2-((3R)-1-((R)-1-(6-((cis-4-Methylcyclohexyl)oxy)-5-(trifluoromethyl)naphthalen-2-yl)ethyl)piperidin-3-yl)acetic acid;

1-((5-(Difluoromethyl)-6-((cis-4-methylcyclohexyl)oxy)naphthalen-2-yl)methyl)azetidine-3-acetic acid;

1-(1-(5-(Difluoromethyl)-6-((cis-4-methylcyclohexyl)oxy)naphthalen-2-yl)ethyl)azetidine-3-acetic acid;

1-(1-(5-(Difluoromethyl)-6-((cis-4-methylcyclohexyl)oxy)naphthalen-2-yl)propyl)azetidine-3-acetic acid;

2-((S)-1-((S)-1-(2-(cis-4-methylcyclohexyloxy)-1-(difluoromethyl)naphthalen-6-yl)ethyl)piperidin-3-yl)acetic acid; and 2-((R)-1-((S)-1-(2-(cis-4-methylcyclohexyloxy)-1-(difluoromethyl)naphthalen-6-yl)ethyl)piperidin-3-yl)acetic acid;

or a pharmaceutically acceptable salt thereof.

As used herein, the term "alkyl" refers to a fully saturated branched or unbranched hydrocarbon moiety. Preferably the alkyl comprises 1 to 20 carbon atoms, more preferably 1 to 16 carbon atoms, 1 to 10 carbon atoms, 1 to 6 carbon atoms, or 1 to 4 carbon atoms. In some embodiments, an alkyl comprises from 6 to 20 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, or n-decyl.

"Alkylene" refers to a divalent alkyl group. Examples of alkylene groups include methylene, ethylene, propylene, n-butylene, and the like. The alkylene is attached to the rest of the molecule through a single bond and to the radical group through a single bond. The points of attachment of the alkylene to the rest of the molecule and to the radical group can be through one carbon or any two carbons within the carbon chain.

As used herein, the term "haloalkyl" refers to an alkyl, as defined herein, that is substituted by one or more halo groups as defined herein. A haloalkyl can be monohaloalkyl, dihaloalkyl or polyhaloalkyl including perhaloalkyl. A monohaloalkyl can have one iodo, bromo, chloro or fluoro substituent. Dihaloalkyl and polyhaloalkyl groups can be substituted with two or more of the same halo atoms or a combination of different halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms. Preferred haloalkyl groups are trifluoromethyl and difluoromethyl.

"Halogen" or "halo" may be fluoro, chloro, bromo or iodo.

As used herein, the term "carbocyclyl" refers to saturated or partially unsaturated (but not aromatic) monocyclic, bicyclic or tricyclic hydrocarbon groups of 3-14 carbon atoms, preferably 3-9, or more preferably 3-7 carbon atoms. Carbocyclyls include fused or bridged ring systems. The term "carbocyclyl" encompasses cycloalkyl groups. The term "cycloalkyl" refers to completely saturated monocyclic, bicyclic or tricyclic hydrocarbon groups of 3-12 carbon atoms, preferably 3-9, or more preferably 3-8 carbon atoms. Exemplary monocyclic carbocyclyl groups include, but are not limited to, cyclopropyl, cyclobutyl, cyclopentyl, cyclopentenyl, cyclohexyl or cyclohexenyl. Exemplary bicyclic carbocyclyl groups include bornyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethyl-bicyclo[3.1.1]heptyl, or bicyclo[2.2.2]octyl. Exemplary tricyclic carbocyclyl groups include adamantyl.

The term "spirocycloalkyl," as used herein, is a cycloalkyl that has one ring atom in common with the group to which it is attached. Spirocycloalkyl groups may have from 3 to 14 ring members. In a preferred embodiment, the spirocycloalkyl has from 3 to 8 ring carbon atoms and is monocyclic.

The term "cycloalkylene," as used herein, refers to a divalent cycloalkyl group.

The term "aryl" refers to monocyclic, bicyclic or tricyclic aromatic hydrocarbon groups having from 6 to 14 carbon atoms in the ring portion. In one embodiment, the term aryl refers to monocyclic and bicyclic aromatic hydrocarbon groups having from 6 to 10 carbon atoms. Representative examples of aryl groups include phenyl, naphthyl, fluorenyl, and anthracenyl.

The term "aryl" also refers to a bicyclic or tricyclic group in which at least one ring is aromatic and is fused to one or two non-aromatic hydrocarbon ring(s). Nonlimiting examples include tetrahydronaphthalene, dihydronaphthalenyl and indanyl.

The term "arylalkyl" refers to an alkyl group substituted with an aryl group. Representative examples of arylalkyl groups include, for example, benzyl, picolyl, and the like.

The term "phenylene" refers to a divalent phenyl.

As used herein, the term "heterocyclyl" refers to a saturated or unsaturated, non-aromatic monocyclic, bicyclic or tricyclic ring system which has from 3- to 15-ring members at least one of which is a heteroatom, and up to 10 of which may be heteroatoms, wherein the heteroatoms are independently selected from O, S and N, and wherein N and S can be optionally oxidized to various oxidation states. In one embodiment, a heterocyclyl is a 3-7-membered monocyclic. In another embodiment, a heterocyclyl is a 6-12-membered bicyclic. In yet another embodiment, a heterocyclycyl is a 10-15-membered tricyclic ring system. The heterocyclyl group can be attached at a heteroatom or a carbon atom. Heterocyclyls include fused or bridged ring systems. The term "heterocyclyl" encompasses heterocycloalkyl groups. The term "heterocycloalkyl" refers to completely saturated monocyclic, bicyclic or tricyclic heterocyclyl comprising 3-15 ring members, at least one of which is a heteroatom, and up to 10 of which may be heteroatoms, wherein the heteroatoms are independently selected from O, S and N, and wherein N and S can be optionally oxidized to various oxidation states. Examples of heterocyclyls include dihydrofuranyl, [1,3]dioxolane, 1,4-dioxane, 1,4-dithiane, piperazinyl, 1,3-dioxolane, imidazolidinyl, imidazolinyl, pyrrolidine, dihydropyran, oxathiolane, dithiolane, 1,3-dioxane, 1,3-dithianyl, oxathianyl, thiomorpholinyl, oxiranyl, aziridinyl, oxetanyl, azetidinyl, tetrahydrofuranyl, pyrrolidinyl, tetrahydropyranyl, piperidinyl, morpholinyl, piperazinyl, azepinyl, oxapinyl, oxazepinyl and diazepinyl.

The term "spiroheterocycloalkyl" as used herein, is a heterocycloalkyl that has one ring atom in common with the group to which it is attached. Spiroheterocycloalkyl groups may have from 3 to 15 ring members. In a preferred embodiment, the spiroheterocycloalkyl has from 3 to 8 ring atoms selected from carbon, nitrogen, sulfur and oxygen and is monocyclic.

As used herein, the term "heteroaryl" refers to a 5-14 membered monocyclic-, bicyclic-, or tricyclic-ring system, having 1 to 10 heteroatoms independently selected from N, O or S, wherein N and S can be optionally oxidized to various oxidation states, and wherein at least one ring in the ring system is aromatic. In one embodiment, the heteroaryl is monocyclic and has 5 or 6 ring members. Examples of monocyclic heteroaryl groups include pyridyl, thienyl, furanyl, pyrrolyl, pyrazolyl, imidazoyl, oxazolyl, isoxazolyl, thiazolyl, isothiazolyl, triazolyl, oxadiazolyl, thiadiazolyl and tetrazolyl. In another embodiment, the heteroaryl is bicyclic and has from 8 to 10 ring members. Examples of bicyclic heteroaryl groups include indolyl, benzofuranyl, quinolyl, isoquinolyl indazolyl, indolinyl, isoindolyl, indolizinyl, benzamidazolyl, quinolinyl, 5,6,7,8-tetrahydroquinoline and 6,7-dihydro-5H-pyrrolo[3,2-d]pyrimidine.

The term "heteroarylene," as used herein refers to a divalent heteroaryl.

An amino is a group having the formula $NH_2$—. The term N-alkylamino is an amino group in which one of the hydrogen atoms is replaced with an alkyl group. The term N,N-dialkylamino is an amino group in which each hydrogen atoms is replaced with an alkyl group which may be the same or different.

The number of carbon atoms in a group is specified herein by the prefix "$C_{x-xx}$", wherein x and xx are integers. For example, "$C_{1-4}$alkyl" is an alkyl group which has from 1 to 4 carbon atoms; $C_{1-6}$alkoxy is an alkoxy group having from 1 to 6 carbon atoms; $C_{6-10}$aryl is an aryl group which has from 6 to 10 carbon atoms; $C_{1-4}$haloalkyl is a haloalkyl group which has from 1 to 4 carbon atoms; and N,N-di-$C_{1-6}$alkylamino is a N,N-dialkylamino group in which the nitrogen is substituted with two alkyl groups each of which is independently from 1 to 6 carbon atoms.

The phrase "compound of the invention," as used herein, refers to compounds represented by formulae I and Ia, and any of the specific examples disclosed herein.

The disclosed compounds can contain one or more asymmetric centers in the molecule. In accordance with the present disclosure any structure that does not designate the stereochemistry is to be understood as embracing all the various optical isomers (e.g., diastereomers and enantiomers) in pure or substantially pure form, as well as mixtures thereof (such as a racemic mixture, or an enantiomerically enriched mixture). It is well known in the art how to prepare such optically active forms (for example, resolution of the racemic form by recrystallization techniques, synthesis from optically-active starting materials, by chiral synthesis, or chromatographic separation using a chiral stationary phase). The compounds can be isotopically-labeled compounds, for example, compounds including various isotopes of hydrogen, carbon, nitrogen, oxygen, phosphorous, fluorine, iodine, or chlorine. The disclosed compounds may exist in tautomeric forms and mixtures and separate individual tautomers are contemplated. In addition, some compounds may exhibit polymorphism.

By way of clarity, compounds of the invention included all isotopes of the atoms present in formulae (I) or (Ia), and any of the examples or embodiments disclosed herein. For example, H (or hydrogen) represents any isotopic form of hydrogen including $^1$H, $^2$H (D), and $^3$H (T); C represents any isotopic form of carbon including $^{12}$C, $^{13}$C, and $^{14}$C; O represents any isotopic form of oxygen including $^{16}$O, $^{17}$O and $^{18}$O; N represents any isotopic form of nitrogen including $^{13}$N, $^{14}$N and $^{15}$N; P represents any isotopic form of phosphorous including $^{31}$P and $^{32}$P; S represents any isotopic form of sulfur including $^{32}$S and $^{35}$S; F represents any isotopic form of fluorine including $^{19}$F and $^{18}$F; Cl represents any isotopic form of chlorine including $^{35}$Cl, $^{37}$Cl and $^{36}$Cl; and the like. In a preferred embodiment, compounds represented by formulae (I) or (Ia), and any of the examples or embodiments disclosed herein comprises isotopes of the atoms therein in their naturally occurring abundance. However, in certain instances, it is desirable to enrich one or more atom in a particular isotope which would normally be present in less abundance. For example, $^1$H would normally be present in greater than 99.98% abundance; however, a compound of the invention can be enriched in $^2$H or $^3$H at one or more positions where H is present. In particular embodiments of the compounds of formulae (I) or (Ia), when, for example, hydrogen is enriched in the deuterium isotope, the symbol "D" may be used to represent the enrichment in deuterium. In one embodiment, when a compound of the invention is enriched in a radioactive isotope, for example $^3$H and $^{14}$C, they may be useful in drug and/or substrate tissue distribution assays. It is to be understood that the invention encompasses all such isotopic forms which modulate ATX activity.

Compounds of the invention are ATX modulators, i.e., they modulate the activity of ATX. For example, a compound of the invention can be an ATX inhibitor. The compound can be a selective ATX modulator. Being selective can mean that the compound binds to ATX preferentially when exposed to a variety of potential binding partners. The compound can have a greater affinity for the ATX, by at by at least 100-fold, by at least 50-fold, by at least 10-fold, by at least 5-fold or by at least 2-fold, than for other binding partners. Affinity can be measured, for example, as a dissociation constant ($K_d$), as an inhibition constant (such as $IC_{50}$), or another measure; provided that affinity is measured in a consistent fashion between ATX and the other binding partners it is compared to.

An inhibitor of ATX mediated activity can block interaction of ATX with its native substrate(s), such as LPC. For example, the inhibitor can show an $IC_{50}$ value of less than 1 µM, less than 750 nM, less than 500 nM, less than 250 nM, less than 100 nM, less than 50 nM, less than 25 nM, or less than 10 nM, when measured in a FRET-based assay using FS-3 substrate (see, e.g., Ferguson, C. G., et al., Org Lett. 2006 May 11; 8(10): 2023-2026, which is incorporated by reference in its entirety).

Some substrates and inhibitors of ATX are described in WO 2011/151461, which is incorporated by reference in its entirety.

Potential uses of an ATX modulating agent include, but are not limited to, prevention or treatment of a pathological condition or symptom mediated by ATX activity in a mammal. The pathological disorder can be an inflammatory disorder, an autoimmune disorder, a fibrosis of the lung, or a malignancy of the lung. Prevention or treatment of the pathological condition or symptom can include administering to the mammal an effective amount of an ATX modulating agent, e.g., an ATX inhibitor, to prevent, treat or reduce symptoms of the inflammatory disorder, autoimmune disorder, the fibrosis of the lung, or the malignancy of the lung. In one embodiment, the inflammatory disorder is rheumatoid arthritis (RA). In another embodiment, the autoimmune disorder is multiple sclerosis (MS). A particular example of lung fibrosis is an interstitial lung disease, for instance, pulmonary fibrosis. See, for example, WO 2011/151461, which is incorporated by reference in its entirety.

In a preferred embodiment, an ATX inhibitor of the present invention can be used to treat or prevent a demyelinating disease or disorder. Demyelinating diseases or disorders include multiple sclerosis, Guillain-Barre Syndrome, chronic inflammatory demyelinating polyneuropathy (CIDP), transverse myelitis, and optic neuritis, spinal cord injury, stroke or other ischemia, cerebral palsy, Charcot-Marie-Tooth disease (CMT), Sjogren-Larsson syndrome, Refsum disease, Krabbe disease, Canavan disease, Alexander disease, nerve damage due to pernicious anemia, progressive multifocal leukoencephalopathy (PML), Lyme disease, tabes dorsalis due to untreated syphilis, demyelination due to exposure to an organophosphates, demyelination due to vitamin B12 deficiency or copper deficiency.

Neurological Disorders

A number of studies have shown that ATX is expressed in non-pathological conditions, throughout development, with high expression levels in the CNS among other tissues. ATX mRNA was identified as highly upregulated during oligodendrocyte differentiation and ATX protein expression is also apparent in maturing ODCs, temporally correlated with the process of myelination. Finally, in the adult brain ATX is expressed in secretory epithelial cells, such as the choroid plexus, ciliary, iris pigment, and retinal pigment epithelial cells, whereas there is evidence for ATX expression in leptomenigneal cells and cells of the CNS vasculature. See, for example, Fuss, B., et al., J Neurosci 17, 9095-9103 (1997); Kawagoe, H., et al. Genomics 30, 380-384 (1995); Lee, H. Y., et al. J Biol Chem 271, 24408-24412 (1996); Narita, M., et al., J Biol Chem 269, 28235-28242 (1994); Bachner, D., et al., Mechanisms of Development 84, 121-

125 (1999); Awatramani, R., et al., Nat Genet 35, 70-75 (2003); Li, Y., et al., J Neurol Sci 193, 137-146 (2002); Dugas, J. C., et al., J Neurosci 26, 10967-10983 (2006); Fox, M. A., et al., Molecular and Cellular Neuroscience 27, 140-150 (2004); Hoelzinger, D. B., et al., Neoplasia 7, 7-16 (2005); and Sato, K., et al., J Neurochem 92, 904-914 (2005); each of which is incorporated by reference in its entirety.

Although neurons and astrocytes do not seem to express ATX under physiological conditions, ATX is highly upregulated in astrocytes following brain lesion. Two hallmarks of reactive astrogliosis can be induced by LPA itself: hypertrophy of astrocytes and stress fiber formation. This may indicate an autoregulation loop of astrocytic activation, in which astrocytes upregulate the LPA-generating enzyme ATX and become activated by its metabolite LPA, while increased amounts of the metabolite inhibit the catalytic activity of ATX. See, e.g., Savaskan, N. E., et al., Cell Mol Life Sci 64, 230-243 (2007); Ramakers, G. J, & Moolenaar, W. H., Exp Cell Res 245, 252-262 (1998); and van Meeteren, L. A., et al., J Biol Chem 280, 21155-21161 (2005); each of which is incorporated by reference in its entirety.

ATX expression levels were shown to be elevated in glioblastoma multiform samples, and ATX was shown to augment invasiveness of cells transformed with ras, a key signaling molecule that promotes gliomagenesis. ATX expression was also detected in primary tumor tissues from neuroblastoma patients and retinoic acid induced expression of ATX in N-myc-amplified neuroblastoma cells.

There is significant evidence for ATX signaling in demyelination processes and in other neurodegenerative conditions. As noted above, it has been reported that addition of LPA to dorsal root fibers in ex vivo culture causes demyelination, whereas LPC fails to cause significant demyelination of nerve fibers in ex vivo cultures without further addition of recombinant ATX to the culture. Addition of recombinant ATX caused significant demyelination at equivalent levels to LPA presumable due to conversion of LPC to LPA through the enzymatic activity of ATX. In addition, injury induced demyelination was attenuated by about 50% in atx$^{+/-}$ mice over their wild type counterparts (Nagai, et al., *Molecular Pain* (2010), 6:78).

ATX protein levels were found deregulated in an animal model of MS (experimental autoimmune encephalitis; EAE) at the onset of clinical symptoms. See, e.g., Hoelzinger, D. B., et al. Neoplasia 7, 7-16 (2005); Nam, S. W., et al., Oncogene 19, 241-247 (2000); Kawagoe, H., et al., Cancer Res 57, 2516-2521 (1997); Dufner-Beattie, J., et al., Mol Carcinog 30, 181-189 (2001); Umemura, K., et al., Neuroscience Letters 400, 97-100 (2006); and Fuss, B., et al., J Neurosci 17, 9095-9103 (1997); each of which is incorporated by reference in its entirety. Moreover, significant ATX expression was detected in the cerebrospinal fluid of patients suffering with multiple sclerosis (MS), while completely lacking from the control samples, suggesting a role for ATX in maintenance of cerebrospinal fluid homeostasis during pathological/demyelinating conditions. Hammack, B. N., et al. Proteomic analysis of multiple sclerosis cerebrospinal fluid. Mult Scler 10, 245-260 (2004); and Dennis, J., et al., J Neurosci Res 82, 737-742 (2005); each of which is incorporated by reference in its entirety. Interestingly, ATX mRNA expression was found to be elevated in the frontal cortex of Alzheimer-type dementia patients indicating a potential involvement for ATX signaling in neurodegenerative diseases. LPA receptors are enriched in the CNS and their expression patterns suggest their potential involvement in developmental process including neurogenesis, neuronal migration, axon extension and myelination. Noteworthy, only two receptors have the same spatiotemporal expression as ATX in the CNS (Contos, J. J., et al., Mol Cell Biol 22, 6921-6929 (2002); Jaillard, C, et al, Edg8/S1 P5: an oligodendroglial receptor with dual function on process retraction and cell survival. J Neurosci 25, 1459-1469 (2005); and Saba, J. D. Journal of cellular biochemistry 92, 967-992 (2004); each of which is incorporated by reference in its entirety). LPAi and SIPS are specific for ODCs, and their expression highly correlates with the process of myelination. LPA1 is expressed in restricted fashion within the neuroblasts of the neuroproliferatve Ventricular Zone (VZ) of the developing cortex, in the dorsal olfactory bulb, along the pial cells of neural crest origin, and in developing facial bone tissue. Expression is observed during E11-E18, corresponding to a time period during which neurogenesis occurs. LPA1 expression is undetectable in the VZ after this point, to reappear during the first postnatal week within ODCs. Notably, Schwann cells (the myelinating cells of the Peripheral Nervous System; PNS) express high levels of LPA1 early in development and persistently throughout life, suggesting an influence of LPA on myelinating processes (Weiner. J. A. & Chun, J., Proc Natl Acad Sci USA 96, 5233-5238 (1999), which is incorporated by reference in its entirety).

The above data strongly support a critical role for ATX and LPA signaling in neuronal development, oligodendrocyte differentiation and myelination, as well as possibly in the autoregulation of astrocyte activation. Moreover, the regulation of ATX and thus LPA production at local sites of CNS injury, inflammatory or autoimmune, could contribute to tissue homeostasis through the numerous effects of LPA. As demyelination and deregulated cerebrospinal fluid homeostasis are the hallmarks of multiple sclerosis, a role of ATX and LPA signaling in the pathophysiology of multiple sclerosis seems very likely.

The ATX inhibitors of the invention can be used to various forms of MS including relapsing-remitting, secondary-progressive, primary-progressive, and progressive-relapsing. In addition, ATX inhibitors of the invention can be used alone or in conjunction with other agents to treat or prevent MS. In a preferred embodiment, the compounds of the invention can be used to treat or prevent MS in combination with an immunomodulating therapy such as corticosteroids, beta interferon-1a (such as Avonex® or Rebif®), beta interferon-1b (Betaseron®), natalizumab (Tysabri®), glatiramer, and mitoxantrone.

Pain Mediation

Pain experienced by mammals can be divided into two main categories: acute pain (or nociceptive) and chronic pain which can be subdivided into chronic inflammatory pain and chronic neuropathic pain. Acute pain is a response to stimulus that causes tissue injury and is a signal to move away from the stimulus to minimize tissue damage. Chronic pain, on the other hand, serves no biological function and develops as a result of inflammation caused by tissue damage (inflammatory pain) or by damage to the nervous system such as demyelination (neuropathic pain). Chronic pain is generally characterized by stimulus-independent, persistent pain or by abnormal pain perception triggered by innocuous stimuli.

LPA has been found to be a mediator of both inflammatory pain and neuropathic pain. The transient receptor potential channel TRPV1 is known to be the originator of inflammatory pain. LPA has been shown to directly activate TRPV1 thereby creating pain stimulus by binding to its intracellular C-terminus (Tigyi, Nature Chemical Biology (January 2012), 8:22-23). Thus, compounds which inhibit the formation of LPA by inhibiting the action of ATX would be useful in treating inflammatory pain.

LPA has also been shown to play a role in neuropathic pain. For example, sciatic nerve injury has been shown to induce demyelination, down-regulation of myelin-associated glycoprotein (MAG) and damage to Schwann cell partitioning of C-fiber-containing Remak bundles in the sciatic nerve and dorsal root. However, demyelination, MAG down-regulation and Remak bundle damage in the dorsal root were abolished in $LPA_1$ receptor-deficient ($Lpar1^{-/-}$) mice (Nagai, et al., Molecular Pain (2010), 6:78). These results indicate that compounds that inhibit the formation of LPA by inhibiting the action of ATX would decrease dorsal root demyelination following nerve injury and decrease or eliminate neuropathic pain.

Thus the compounds of the invention are useful in treating or preventing chronic pain such as inflammatory pain and neuropathic pain in mammals.

Rheumatoid Arthritis (RA)

Studies in human and animal models of RA suggest that ATX plays a role in the development and progress of the disease. For example, increased ATX mRNA expression was detected in synovial fibroblasts (SFs) from animal models of RA during differential expression profiling, and human RA SFs were shown to express mRNA for both ATX and LPARs (Aidinis, V., et al., PLoS genetics 1, e48 (2005); Zhao, C, et al., Molecular pharmacology 73, 587-600 (2008); each of which is incorporated by reference in its entirety). ATX is overexpressed from activated SFs in arthritic joints, both in animal models and human patients (see WO 2011/151461). ATX expression was shown to be induced from TNF, the major pro-inflammatory factor driving RA.

Disease development was assessed in well established animal models of RA. When ATX expression was conditionally ablated specifically in SFs, the lack of ATX expression in the joints resulted in marked decreased inflammation and synovial hyperplasia. This suggested an active involvement of the ATX-LPA axis in the pathogenesis of the disease. Similar results were also obtained with pharmacologic inhibition of ATX enzymatic activity and LPA signaling. A series of ex vivo experiments on primary SFs revealed that ATX, through LPA production, stimulates rearrangements of the actin cytoskeleton, proliferation and migration to the extracellular matrix (ECM), as well as the secretion of proinflammatory cytokines and matrix metalloproteinases (MMPs). Moreover, the LPA effect was shown to be synergistic with TNF and dependent on the activation of MAPK cellular signaling pathways. See, e.g., Armaka, M., et al., The Journal of experimental medicine 205, 331-337 (2008); which is incorporated by reference in its entirety.

In one embodiment, a method for treating an individual with RA or the individual at risk of suffering thereof comprises administering to said individual an ATX inhibitor of the invention in combination with an anti-TNF antibody for use in the treatment of RA. Examples of suitable anti-TNF antibodies are adalimumab, etanercept, golimumab, and infliximab (Taylor P C, Feldmann M. Anti-TNF biologic agents: still the therapy of choice for rheumatoid arthritis. Nat Rev Rheumatol. 2009 October; 5(10):578-82).

Pulmonary Fibrosis

Evidence also suggests a role for ATX in pulmonary fibrosis. Mice lacking lysophosphatidic acid (LPA) receptor 1 (LPAR1) were protected from Bleomycin (BLM)-induced pulmonary fibrosis and mortality, suggesting a major role for LPA in disease pathophysiology. The majority of circulating LPA is produced by the phospholipase D activity of Autotaxin (ATX) and the hydrolysis of lysophosphatidylcholine (LPC). Increased ATX expression has been previously reported in the hyperplastic epithelium of fibrotic lungs of human patients and animal models.

Therefore, we hypothesized that genetic or pharmacologic inhibition of ATX activity would reduce local or circulating LPA levels and hence attenuate disease pathogenesis.

Lung Cancer

Increased ATX expression has been detected in a large number of malignancies, including mammary, thyroid, hepatocellular and renal cell carcinomas, glioblastoma and neuroblastoma, as well as NSCLC. Strikingly, transgenic overexpression of ATX was shown to induce spontaneous mammary carcinogenesis. In accordance, in vitro ATX overexpression in various cell types promotes proliferation and metastasis while inhibiting apoptosis. LPA's actions are concordant with many of the "hallmarks of cancer", indicating a role for LPA in the initiation or progression of malignant disease. Indeed LPA levels are significantly increased in malignant effusions, and its receptors are aberrantly expressed in several human cancers.

See, for example: Euer, N., et al., Anticancer Res 22, 733-740 (2002); Liu, S., et al., Cancer Cell 15, 539-550 (2009); Zhang, G., et al., Chin Med J (Engl) 112, 330-332 (1999); Stassar, M. J., et al., Br J Cancer 85. 1372-1382 (2001); Kishi, Y., et al., J Biol Chem 281, 17492-17500 (2006); Kawagoe, H., et al., Cancer Res 57, 2516-2521 (1997); Yang, Y., et al., Am J Respir Cell Mol Biol 21, 216-222 (1999); and Toews, M. L., et al. Biochim Biophys Acta 1582, 240-250 (2002); each of which is incorporated by reference in its entirety.

LPA has been shown to be involved in lymphocyte trafficking and helps promote entry of lymphocytes into secondary lymphoid organs (see Kanda, et al., Nat. Immunology (2008), 9:415-423). Therefore the disclosed compounds are expected to be useful for altering lymphocyte trafficking as a method for prolonging allograft survival, for example transplantation including solid organ transplants, treatment of graft vs. host disease, bone marrow transplantation, and the like.

Pharmaceutical compositions can include a compound of the invention, or a pharmaceutically acceptable salt thereof. More particularly, such compounds can be formulated as pharmaceutical compositions using standard pharmaceutically acceptable carriers, fillers, solubilizing agents and stabilizers known to those skilled in the art. For example, a pharmaceutical composition including a compound of the invention, or a salt, analog, derivative, or modification thereof, as described herein, is used to administer the appropriate compound to a subject.

The compounds of the invention, or a pharmaceutically acceptable salt thereof, are useful for treating a disease or disorder associated with ATX activity. In one embodiment, a therapeutically acceptable amount of a compound of the invention, or a pharmaceutically acceptable salt thereof, is administered to a subject in need thereof. In another embodiment, a pharmaceutical composition comprising a therapeutically effective amount of a compound of the invention, or a pharmaceutically acceptable salt thereof, and a pharmaceutically-acceptable carrier is administered to a subject in need thereof.

The compounds of the invention can be used in combination with at least one further active ingredient, such as a medicament used in the treatment of multiple sclerosis such as Tysabri®, dimethyl fumarate, an interferon (such as pegylated or non-pegylated interferons, preferably interferon β-1a or pegylated interferon β-1a), glatiramer acetate, a compound improving vascular function, an immunomodulating agent (such as Fingolimod, cyclosporins, rapamycins or ascomycins, or their immunosuppressive analogs, e.g. cyclosporine A, cyclosporine G, FK-506, ABT-281, ASM981, rapamycin, 40-O-(2-hydroxyl)ethyl-rapamycin etc.); corticosteroids; cyclophosphamide; azathioprine; mitoxanthrone, methotrexate; leflunomide; mizoribine; mycophenolic add; mycophenolate mofetil; 15-deoxyspergualine; diflucortolone valerate; difluprednate; Alclometasone dipropionate; amcinonide; amsacrine; asparaginase; azathioprine; basiliximab; beclometasone dipropionate; betamethasone; betamethasone dipropionate; betamethasone phosphate sodique; betamethasone valerate; budesonide; captopril; chlormethine chlorhydrate; clobetasol propionate; cortisone acetate; cortivazol; cyclophosphamide; cytarabine; daclizumab; dactinomycine; desonide; desoximetasone; dexamethasone; dexamethasone acetate; dexamethasone isonicotinate; dexamethasone metasulfobenzoate sodique; dexamethasonephosphate; dexamethasone tebutate; dichlorisone acetate; doxorubicinee chlorhydrate; epirubicine chlorhydrate; fluclorolone acetonide; fludrocortisone acetate; fludroxycortide; flumetasone pivalate; flunisolide; fluocinolone acetonide; fluocinonide; fluocortolone; fluocortolone hexanoate; fluocortolone pivalate; fluorometholone; fluprednidene acetate; fluticasone propionate; gemcitabine chlorhydrate; halcinonide; hydrocortisone; hydrocortisone acetate; hydrocortisone butyrate; hydrocortisone hemisuccinate; melphalan; meprednisone; mercaptopurine; methylprednisolone; methylprednisolone acetate; methylprednisolone hemisuccinate; misoprostol; muromonab-cd3; mycophenolate mofetil; paramethansone acetate; prednazoline, prednisolone; prednisolone acetate; prednisolone caproate; prednisolone metasulfobenzoate sodique; prednisolone phosphate sodique; prednisone; prednylidene; rifampicine; rifampicine sodique; tacrolimus; teriflunomide; thalidomide; thiotepa; tixocortol pivalate; triamcinolone; triamcinolone acetonide hemisuccinate; triamcinolone benetonide; triamcinolone diacetate; triamcinolone hexacetonide; immunosuppressive monoclonal antibodies, e.g., monoclonal antibodies to leukocyte receptors, e.g., MHC, CD2, CD3, CD4, CD7, CD20 (e.g., rituximab and ocrelizumab), CD25, CD28, B7, CD40, CD45, CD56 (e.g., daclizumab), or CD58 or their ligands; or other immunomodulatory compounds, e.g. CTLA41g, or other adhesion molecule inhibitors, e.g. mAbs or low molecular weight inhibitors including Selectin antagonists and VLA-4 antagonists (such as Tysabri®); remyelinating agents such as BIIB033. Compounds of the invention can also be used in combination with agents which treat the symptoms of multiple sclerosis such as fampridine.

Axons and dendrites can extend from neurons. The distal tip of an extending axon or neurite can include a specialized region, known as the growth cone. Growth cones can sense the local environment and can guide axonal growth toward a neuron's target cell. Growth cones can respond to environmental cues, for example, surface adhesiveness, growth factors, neurotransmitters and electric fields. The growth cones can advance at a rate of one to two millimeters per day. The growth cone can explore the area ahead of it and on either side, by means of elongations classified as lamellipodia and filopodia. When an elongation contacts an unfavorable surface, it can withdraw. When an elongation contacts a favorable growth surface, it can continue to extend and guides the growth cone in that direction. When the growth cone reaches an appropriate target cell a synaptic connection can be created.

Nerve cell function can be influenced by contact between neurons and other cells in their immediate environment (Rutishauser, et al., 1988, Physiol. Rev. 68:819, which is incorporated by reference in its entirety). These cells can include specialized glial cells, oligodendrocytes in the central nervous system (CNS), and Schwann cells in the peripheral nervous system (PNS), which can sheathe the neuronal axon with myelin (Lemke, 1992, in An Introduction to Molecular Neurobiology, Z. Hall, Ed., p. 281, Sinauer, each of which is incorporated by reference in its entirety). LPA causes the collapse of the neuron growth cone and tends to inhibit or reverse the morphological differentiation of many neuronal cell lines (see Gendaszewska-Darmach, Acta Biochimica Polonica (2008), 55(2):227-240). Since ATX activity is involved in the generation of LPA, inhibitors of ATX should increase the ability of the nervous system to make synaptic connections. Thus, ATX inhibitors may be useful in treating neurodegenerative disorders such as Alzheimer's disease, Huntington's disease, Parkinson's disease (including Parkinson's dementia), Lewy Body Dementia, amylotrophic lateral sclerosis (ALS), Friedreich's ataxia, spinal muscular atrophy.

CNS neurons can have the inherent potential to regenerate after injury, but they can be inhibited from doing so by inhibitory proteins present in myelin (Brittis et al., 2001, Neuron 30:11-14; Jones et al., 2002, J. Neurosci. 22:2792-2803; Grimpe et al., 2002, J. Neurosci.: 22:3144-3160, each of which is incorporated by reference in its entirety). Such diseases, disorders or injuries can include, but are not limited to, multiple sclerosis (MS), progressive multifocal leukoencephalopathy (PML), encephalomyelitis (EPL), central pontine myelolysis (CPM), adrenoleukodystrophy, Alexander's disease, Pelizaeus Merzbacher disease (PMZ), Globoid cell Leucodystrophy (Krabbe's disease) and Wallerian Degeneration, optic neuritis, transverse myelitis, amylotrophic lateral sclerosis (ALS), Huntington's disease, Alzheimer's disease, Parkinson's disease, spinal cord injury, traumatic brain injury, post radiation injury, neurologic complications of chemotherapy, stroke, acute ischemic optic neuropathy, vitamin E deficiency, isolated vitamin E deficiency syndrome, AR, Bassen-Kornzweig syndrome, Marchiafava-Bignami syndrome, metachromatic leukodystrophy, trigeminal neuralgia, or Bell's palsy. Among these diseases, MS may the most widespread, affecting approximately 2.5 million people worldwide.

MS can begin with a relapsing-remitting pattern of neurologic involvement, which then can progress to a chronic phase with increasing neurological damage. MS can be associated with the destruction of myelin, oligodendrocytes or axons localized to chronic lesions. The demyelination observed in MS may not always permanent and remyelination has been documented in early stages of the disease. Remyelination of neurons can require oligodendrocytes.

Various disease-modifying treatments may be available for MS, including the use of corticosteroids and immunomodulators such as interferon beta or Tysabri®. In addition, because of the central role of oligodendrocytes and myelination in MS, there have been efforts to develop therapies to increase oligodendrocyte numbers or enhance myelination. See, e.g., Cohen et al., U.S. Pat. No. 5,574,009; Chang et al., N. Engl. J. Med. 346: 165-73 (2002), each of which is incorporated by reference in its entirety. However, there remains an urgent need to devise additional therapies for MS and other demyelination and dismyelination disorders.

A compound of the invention, or a pharmaceutically acceptable salt thereof, can promote myelination or remyelination. A method can include administering a compound of the invention, or a pharmaceutically acceptable salt thereof, to cells. A method of promoting oligodendrocyte progenitor cell differentiation can include administering a compound of the invention, or a pharmaceutically acceptable salt thereof, to cells. A method of treating multiple sclerosis can include administering a compound of the invention, or a pharmaceutically acceptable salt thereof, to a subject.

The dose of a compound of the invention, or a pharmaceutically acceptable salt thereof, administered to a subject can be less than 10 µg, less than 25 µg, less than 50 µg, less than 75 µg, less than 0.10 mg, less than 0.25 mg, less than 0.5 mg, less than 1 mg, less than 2.5 mg, less than 5 mg, less than 10 mg, less than 15 mg, less than 20 mg, less than 50 mg, less than 75 mg, less than 100 mg, or less than 500 mg.

Administering can include administering by topical, enteral, parenteral, transdermal, transmucosal, inhalational, intracisternal, epidural, intravaginal, intravenous, intramuscular, subcutaneous, intradermal or intravitreal administration.

The duration of administering can be less than 30 seconds, less than 1 minute, about 1 minute, between 1 minute and 5 minutes, between 5 minutes and 10 minutes, between 10 minutes and 20 minutes, between 20 minutes and 30 minutes, between 30 minutes and 1 hour, between 1 hour and 3 hours, between 3 hours and 6 hours, between 6 hours and 12 hours, between 12 hours and 24 hours or for more than 24 hours.

Administering the inhibitor or compound can include multiple administrations. The duration between administrations can be less than 30 seconds, less than 1 minute, about 1 minute, between 1 minute and 5 minutes, between 5 minutes and 10 minutes, between 10 minutes and 20 minutes, between 20 minutes and 30 minutes, between 30 minutes and 1 hour, between 1 hour and 3 hours, between 3 hours and 6 hours, between 6 hours and 12 hours, between 12 hours and 24 hours or for more than 24 hours.

The duration between successive administrations can be less than 30 seconds, less than 1 minute, about 1 minute, between 1 minute and 5 minutes, between 5 minutes and 10 minutes, between 10 minutes and 20 minutes, between 20 minutes and 30 minutes, between 30 minutes and 1 hour, between 1 hour and 3 hours, between 3 hours and 6 hours, between 6 hours and 12 hours, between 12 hours and 24 hours, between 24 hours and 48 hours, between 48 hours and 72 hours, between 72 hours and 1 week or between 1 week and 2 weeks.

Administering an inhibitor or compound to cells can include cells of an in vitro or in vivo system or model. The cells can be part of a cell line. The cell line can be a primary or secondary cell line. The cell line can be an immortal cell line. The cells can be ruptured and be in the form of a cell lysate. The cells can be part of a living organism, i.e., a subject, for example, a mammal. A mammal can include a rat, a mouse, a gerbil, a hamster, a rabbit or a human. The human can be a subject or a patient.

A method can further include monitoring a property of a sample or a subject. A sample can be removed from a subject. For instance, a sample can include a sample of cells or a tissue from a subject. A sample can include blood, plasma, or neuronal tissue including neurons or glial cells. A sample can also remain in the subject. For example, a sample can be a tissue or cells that are observed within the patient.

A method can further include providing untreated control cells, sample or subject and measuring a property of a sample of the untreated control cells, sample or subject.

A property can include the presence or absence of a molecule, the concentration of a molecule, for example myelin basic protein, myelin associated glycoprotein or myelin oligodendrocyte glycoprotein. In some embodiments, determining the presence of a molecule can include determining the concentration of the molecule, determining the purity of the molecule or determining the quantity of the molecule.

A property can be the conductivity of a tissue or cell. A property can be an emission, for example, electromagnetic radiation.

Monitoring a property can include observing the property of the sample or subject alone. Monitoring a property can include monitoring the property before the sample or subject has been administered a compound of the invention, or a pharmaceutically acceptable salt thereof. Monitoring a property can include monitoring the property after the sample or subject has been administered a compound. Monitoring a property can include monitoring a property after the sample or subject has been administered a known concentration of a compound.

Monitoring a property of a sample or subject can include observing the property through a microscope. Monitoring a property of the composition can include measuring the property using a microscope. Monitoring a property of the composition can include monitoring the property using still photography or movies. The photography or movies can be on film media or digital form. Monitoring a property can include taking a scan, for example, an MRI or CT scan.

Promoting myelination, remyelination or oligodendrocyte progenitor cell differentiation can prevent or can treat a pathological condition or symptom in a mammal. A number of diseases or disorders involve demyelination of the central or peripheral nervous system which can occur for a number of reasons such as immune dysfunction as in multiple sclerosis, encephalomyelitis, Guillain-Barre Syndrome, chronic inflammatory demyelinating polyneuropathy (CIDP), transverse myelitis, and optic neuritis; demyelination due to injury such as spinal cord injury, traumatic brain injury, stroke, acute ischemic optic neuropathy, or other ischemia, cerebral palsy, neuropathy (e.g. neuropathy due to diabetes, chronic renal failure, hypothyroidism, liver failure, or compression of the nerve), post radiation injury, and central pontine myelolysis (CPM); inherited conditions such as Charcot-Marie-Tooth disease (CMT), Sjogren-Larsson syndrome, Refsum disease, Krabbe disease, Canavan disease, Alexander disease, Friedreich's ataxia, Pelizaeus-Merzbacher disease, Bassen-Kornzweig syndrome, metachromatic leukodystrophy (MLD), adrenoleukodystrophy, and nerve damage due to pernicious anemia; viral infection such as progressive multifocal leukoencephalopathy (PML), Lyme disease, or tabes dorsalis due to untreated syphilis; toxic exposure due to chronic alcoholism (which is a possible cause of Marchiafava-Bignami disease), chemotherapy, or exposure to chemicals such as organophosphates; or dietary deficiencies such as vitamin B12 deficiency, vitamin E deficiency, and copper deficiency. Some demyelination disorders can have unknown or multiple causes such as trigeminal neuralgia, Marchiafava-Bignami disease and Bell's palsy. In addition, demyelination can contribute to neuropathic pain. Compounds of the invention are expected to be useful in treating demyelination disorders.

Since LPA is a proinflammatory factor reducing the amount of LPA producted by inhibiting ATX is useful for treating inflammatory disorders such as asthma, allergies, arthritis, inflammatory neuropathies, transplantation rejection, Crohn's disease, ulcerative colitis, lupus erythematosis, psoriasis, an inflammatory bowel condition, and diabetes.

LPA has been shown to be involved in wound healing and stimulates the proliferation and migration of endothelial cells promoting processes such as angiogenesis. However, these same processes when deregulated can promote tumor growth and metastasis, and LPA is thought to contribute to the development, progression, and metastasis of several types of cancer including ovarian, prostate, melanoma, breast, head and neck cancers (see Gendaszewska-Darmach, Acta Biochimica Polonica (2008), 55(2):227-240). In addition, since ATX is located outside the cell in circulation, ATX inhibitors are expected to be of most benefit outside the cell. Therefore, ATX inhibitors are expected to be useful in treating cancer, particularly multidrug resistant (MDR) cancers where drug efflux mechanisms are the largest contributor to the drug resistance.

The compound can be administered as a pharmaceutical composition. A pharmaceutical composition can include a compound of the invention, or a pharmaceutically acceptable salt thereof. More particularly, a compound of the invention, or a pharmaceutically acceptable salt thereof can be formulated as pharmaceutical compositions using standard pharmaceutically acceptable carriers, fillers, solubilizing agents and stabilizers known to those skilled in the art. For example, a pharmaceutical composition including a compound of the invention, or a salt, analog, derivative, or modification thereof, as described herein, can be used to administer the appropriate compound to a subject.

A compound of the invention, or a pharmaceutically acceptable salt thereof, can be useful for treating a disease or disorder, for example, in a method including administering to a subject in need thereof of a therapeutically acceptable amount of compound of the invention, or a pharmaceutically acceptable salt thereof, or a pharmaceutical composition comprising a therapeutically effective amount of a compound of the invention, or a pharmaceutically acceptable salt thereof, and a pharmaceutically-acceptable carrier.

In cases where a compound of the invention can be sufficiently basic or acidic to form stable nontoxic acid or base salts, preparation and administration of the compounds as pharmaceutically acceptable salts may be appropriate. Examples of pharmaceutically acceptable salts can be organic acid addition salts formed with acids which form a physiological acceptable anion, for example, tosylate, methanesulfonate, acetate, citrate, malonate, tartarate, succinate, benzoate, ascorbate, α-ketoglutarate, or α-glycerophosphate. Inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Pharmaceutically-acceptable base addition salts can be prepared from inorganic and organic bases. Salts from inorganic bases, can include but are not limited to, sodium, potassium, lithium, ammonium, calcium or magnesium salts. Salts derived from organic bases can include, but are not limited to, salts of primary, secondary or tertiary amines, such as alkyl amines, dialkyl amines, trialkyl amines, substituted alkyl amines, di(substituted alkyl)amines, tri(substituted alkyl)amines, alkenyl amines, dialkenyl amines, trialkenyl amines, substituted alkenyl amines, di(substituted alkenyl)amines, tri(substituted alkenyl)amines, cycloalkyl amines, di(cycloalkyl)amines, tri(cycloalkyl)amines, substituted cycloalkyl amines, disubstituted cycloalkyl amine, trisubstituted cycloalkyl amines, cycloalkenyl amines, di(cycloalkenyl)amines, tri(cycloalkenyl)amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, or mixed di- and tri-amines where at least two of the substituents on the amine can be different and can be alkyl, substituted alkyl, alkenyl, substituted alkenyl, cycloalkyl, substituted cycloalkyl, cycloalkenyl, substituted cycloalkenyl, aryl, heteroaryl, or heterocyclic and the like. Also included can be amines where the two or three substituents, together with the amino nitrogen, form a heterocyclic or heteroaryl group. Non-limiting examples of amines can include, isopropylamine, trimethyl amine, diethyl amine, tri(iso-propyl)amine, tri(n-propyl)amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, or N-ethylpiperidine, and the like. Other carboxylic acid derivatives can be useful, for example, carboxylic acid amides, including carboxamides, lower alkyl carboxamides, or dialkyl carboxamides, and the like.

A compound of the invention, or a pharmaceutically acceptable salt thereof, formulated as a pharmaceutical composition and administered to a mammalian host, such as a human patient in a variety of forms adapted to the chosen route of administration, e.g., orally or parenterally, as eyedrops, by intravenous, intramuscular, topical or subcutaneous routes. In addition, the term "administer" or "administering" encompasses delivering a compound of the invention as a prodrug which is converted or metabolized in the body of the mammal into a compound of the invention. In one embodiment, a compound of the invention is administered in a non-prodrug form. In another embodiment, the compound is administered as a prodrug which is metabolized to a compound of the invention in the body of a mammal.

Thus, compound of the invention, or a pharmaceutically acceptable salt thereof, may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, or wafers, and the like. Such compositions and preparations should contain at least about 0.1% of active compound. The percentage of the compositions and preparations may, of course, be varied and may conveniently be between about 2 to about 60% of the weight of a given unit dosage form. The amount of active compound in such therapeutically useful compositions can be such that an effective dosage level will be obtained.

The tablets, troches, pills, capsules, and the like can include the following: binders such as gum tragacanth, acacia, corn starch or gelatin; excipients such as dicalcium phosphate; a disintegrating agent such as corn starch, potato starch, alginic acid and the like; a lubricant such as magnesium stearate; or a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl or propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

Exemplary pharmaceutical dosage forms for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, or nontoxic glyceryl esters, and mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, or thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate or gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation can be vacuum drying and the freeze drying techniques, which can yield a powder of the active ingredient plus any additional desired ingredient present in the previously sterile-filtered solutions.

For topical administration, a compound of the invention may be applied in pure form, e.g., when they are liquids. However, it can be generally be desirable to administer them to the skin as compositions or formulations, in combination with a dermatologically acceptable carrier, which may be a solid or a liquid.

Exemplary solid carriers can include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts or esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of the invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508), each of which is incorporated by reference in its entirety.

Useful dosages of the compounds of the invention can be determined by comparing their in vitro activity, and in vivo activity in animal models. Methods for the extrapolation of effective dosages in mice, and other animals, to humans are known to the art; for example, see U.S. Pat. No. 4,938,949, which is incorporated by reference in its entirety.

Generally, the concentration of the compound(s) of the invention in a liquid composition, such as a lotion, can be from about 0.1 to about 25 weight percent, preferably from about 0.5-10 weight percent. The concentration in a semi-solid or solid composition such as a gel or a powder can be about 0.1-5 wt-%, preferably about 0.5-2.5 weight percent based on the total weight of the composition.

The amount of the compound, or an active salt or derivative thereof, required for use in treatment can vary not only with the particular salt selected but also with the route of administration, the nature of the condition being treated and the age and condition of the patient and can be ultimately at the discretion of the attendant physician or clinician. In general, however, a dose can be in the range of from about 0.1 to about 10 mg/kg of body weight per day.

The compound can be conveniently administered in unit dosage form; for example, containing 0.01 to 10 mg, or 0.05 to 1 mg, of active ingredient per unit dosage form. In some embodiments, a dose of 5 mg/kg or less can be suitable.

The active ingredient can be administered so as to achieve a desired peak plasma concentration of the active compound. The desired peak plasma concentration can be from about 0.5 $\mu$M to about 75 $\mu$M, preferably, about 1 $\mu$M to 50 $\mu$M, or about 2 $\mu$M to about 30 $\mu$M. This may be achieved, for example, by the intravenous injection of a 0.05 to 5% solution of the active ingredient, optionally in saline, or orally administered as a bolus containing between about 1 mg to about 100 mg of the active ingredient.

The desired dose may conveniently be presented in a single dose or as divided doses administered at appropriate intervals, for example, as two, three, four, or more sub-doses per day. The sub-dose itself may be further divided, e.g., into a number of discrete loosely spaced administrations; such as multiple inhalations from an insufflator or by application of a plurality of drops into the eye.

The disclosed method can include a kit comprising a compound of the invention and instructional material which can describe administering the compound or a composition comprising the compound to a cell or a subject. This should be construed to include other embodiments of kits that are known to those skilled in the art, such as a kit comprising a (preferably sterile) solvent for dissolving or suspending the compound or composition prior to administering the compound or composition to a cell or a subject. Preferably, the subject can be a human.

In accordance with the disclosed methods, as described above or as discussed in the Examples below, there can be employed conventional chemical, cellular, histochemical, biochemical, molecular biology, microbiology, and in vivo techniques which are known to those of skill in the art. Such techniques are explained fully in the literature.

EXAMPLES

In general, a compound of the invention, or a pharmaceutically acceptable salt thereof, can be prepared according to Scheme 1.

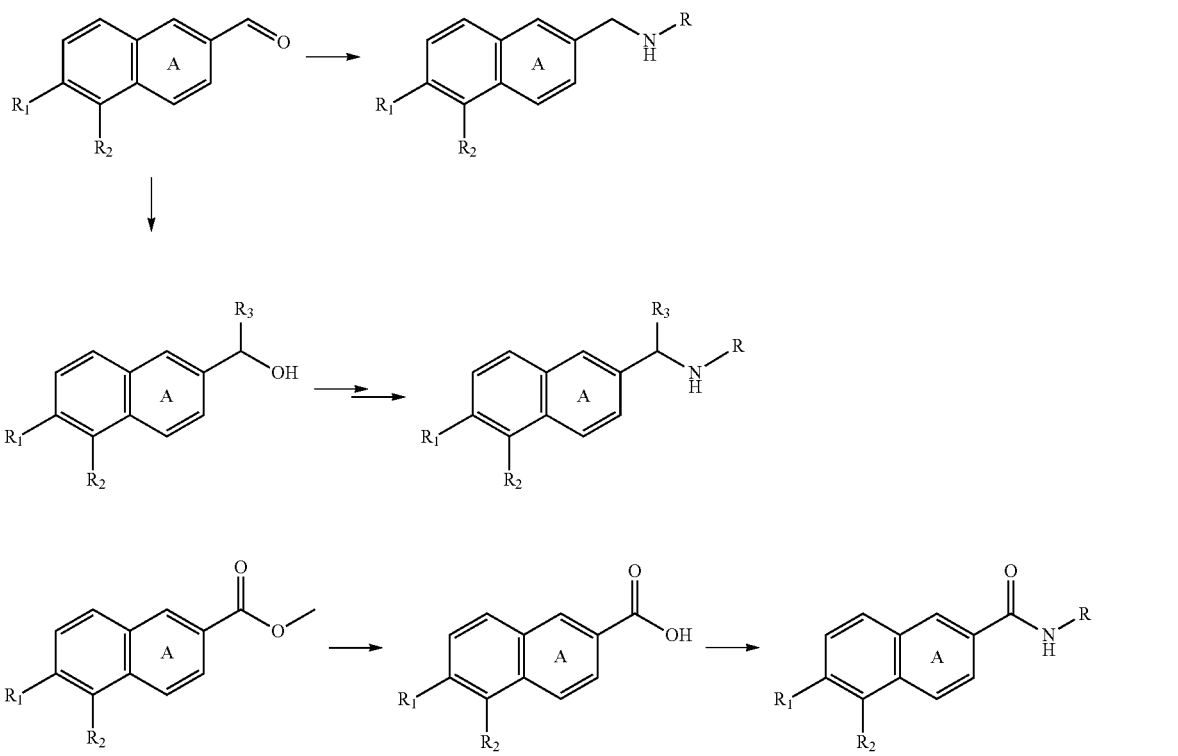
Example 1
2,2-dimethyl-3-(((5-(trifluoromethyl)-6-((cis-4-(trifluoromethyl)cyclo-hexyl)oxy)naphthalen-2-yl)methyl)amino)cyclobutanecarboxylic acid
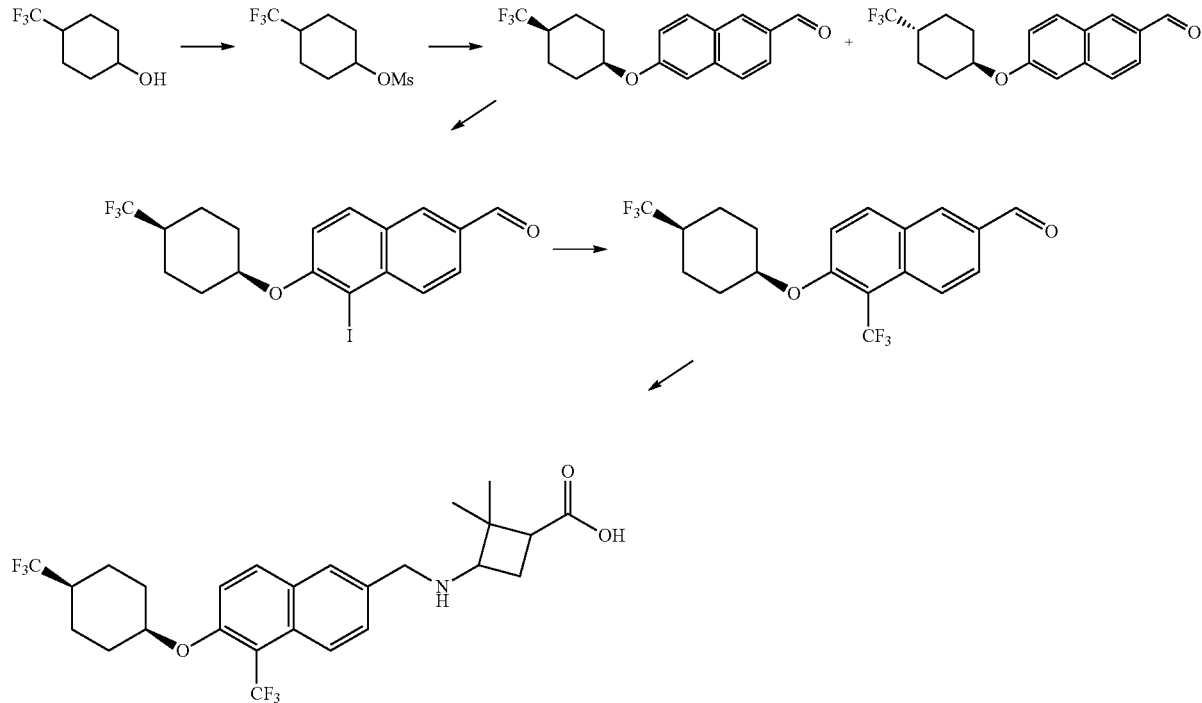

Step 1: 4-(trifluoromethyl)cyclohexyl methanesulfonate (1.1)

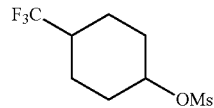

To a solution of 4-trifluoromethyl-cyclohexanol (20.0 g, 119 mmol, mixture of cis/trans, ~20/80, Youchemicals), and triethylamine (22 mL, 155 mmol) in methylene chloride (300.0 mL) was added methanesulfonyl chloride (12 mL, 155 mmol) dropwise at 0° C. A white precipitate formed. The reaction mixture was stirred from 0° C. to RT overnight. The mixture was diluted with dichloromethane and washed with citric acid (5% in water), sodium bicarbonate aqueous solution and water, dried over sulfate, filtered, concentrated and dried overnight on the lyophilizer and collected to give the title compound 1.1 as a white solid (23.9 g, 82%, a mixture of cis & trans, ratio is ~20/80 based on the NMR); $^1$H NMR (400 MHz, CHLOROFORM-d) δ 4.50-5.13 (m, 1H), 3.05 (s, 3H), 1.94-2.37 (m, 4H), 1.35-1.91 (m, 5H).

Step 2: 6-((cis-4-(trifluoromethyl)cyclohexyl)oxy)-2-naphthaldehyde (1.2) and 6-((trans-4-(trifluoromethyl)cyclohexyl)oxy)-2-naphthaldehyde (1.3)

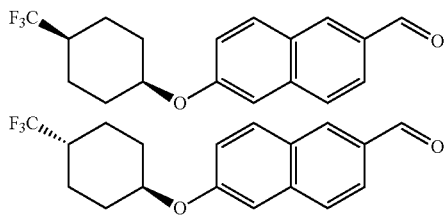

To a mixture of 6-hydroxy-naphthalene-2-carbaldehyde (4.0 g, 23 mmol) and cesium carbonate (15.14 g, 46 mmol) in N,N-dimethylformamide (100 mL) was added methanesulfonic acid 4-trifluoromethyl-cyclohexyl ester (1.1) (11 g, 46 mmol) in two portions (the 2$^{nd}$ portion was added after heating for 4 h). The resulting mixture was heated at 85° C. overnight. Diluted with ethyl acetate, washed with water, brine and dried over sodium sulfate. The crude mixture was then purified by ISCO column chromatography (ethyl acetate/heptane gradient 0% to 30%) to give two isomers (2.95 g, 39% of cis-isomer 1.2 and 1.23 g, 16% of trans-isomer 1.3). For cis-isomer: LCMS: RT 2.01, MH+323.1, $^1$H NMR (400 MHz, CHLOROFORM-d) δ 10.10 (s, 1H), 8.26 (s, 1H), 7.93 (d, J=8.78 Hz, 2H), 7.78 (d, J=8.53 Hz, 1H), 7.25-7.30 (m, 1H), 7.20 (d, J=2.01 Hz, 1H), 4.76-4.86 (m, 1H), 2.28 (d, J=14.81 Hz, 2H), 2.07-2.22 (m, 1H), 1.75-1.92 (m, 4H), 1.61-1.72 (m, 2H); For trans-isomer: LCMS: RT 2.00 min; MH+323.1; $^1$H NMR (400 MHz, CHLOROFORM-d) δ 10.10 (s, 1H), 8.26 (s, 1H), 7.86-7.97 (m, 2H), 7.79 (d, J=8.53 Hz, 1H), 7.14-7.24 (m, 2H), 4.32-4.50 (m, 1H), 2.37 (d, J=5.77 Hz, 2H), 2.12 (d, J=6.02 Hz, 3H), 1.47-1.58 (m, 4H).

Step 3: 5-Iodo-6-(cis-4-(trifluoromethyl)cyclohexyl)oxy)-2-naphthaldehyde (1.4)

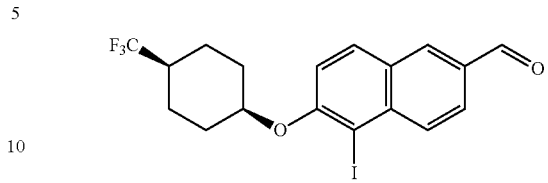

To a mixture of 6-((cis-4-(trifluoromethyl)cyclohexyl)oxy)-2-naphthaldehyde (1.2) (3.0 g, 9.31 mmol) and zirconium chloride (0.30 g, 1.86 mmol) in methylene chloride (60 mL) was added N-iodosuccinimide (2.51 g, 11.2 mmol). The reaction was then stirred at RT overnight. LC-MS showed complete conversion and the formation of the desired product. Worked up with aqueous sodium thiosulfate and ethyl acetate, the organic extracts were washed with sodium bicarbonate and dried over magnesium sulfate, and concentrated. The product was recrystallized from methanol to give the title compound as a light yellow solid (4.06 g, 97%). LCMS: RT: 2.18 min., MH+449.0; $^1$H NMR (400 MHz, CHLOROFORM-d) δ 10.15 (s, 1H), 8.20-8.31 (m, 2H), 7.92-8.02 (m, 2H), 7.24 (d, J=9.04 Hz, 1H), 4.94 (br. s., 1H), 1.98-2.30 (m, 5H), 1.76-1.89 (m, 2H), 1.64 (t, J=14.06 Hz, 2H).

Step 4: 5-(trifluoromethyl)-6-((cis-4-(trifluoromethyl)cyclohexyl)oxy)-2-naphthaldehyde (1.5)

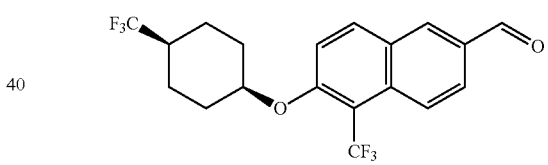

According to the procedure reported in WO2006057869, 2006, by Aicher, Thomas. D. et al., which is incorporated by reference in its entirety, a solution of 5-iodo-6-(4-trifluoromethyl-cyclohexyloxy)-naphthalene-2-carbaldehyde (1.4) (4.0 g, 8.9 mmol), hexamethylphosphoramide (7.8 mL, 44.6 mmol) in N,N-dimethylformamide (40 mL) was degassed with Ar. To this was added copper(I) iodide (3.06 g, 16.1 mmol) and methyl fluorosulphonyldifluoroacetate (5.8 mL, 44.6 mmol) and the reaction was stirred at 85° C. under an atmosphere of argon. After stirring for 5 hours, LCMS showed no starting material left and the formation of the desired product. The reaction mixture was diluted with ethyl acetate, and washed with water (5×). The organic layer was then dried over MgSO4, concentrated. The solid was then crystallized from methanol to give the product as a white powder (1.88 g, 54%).

$^1$H NMR (400 MHz, DMSO-d$_6$) δ 10.12 (s, 1H), 8.63 (d, J=1.51 Hz, 1H), 8.45 (d, J=9.29 Hz, 1H), 8.21 (d, J=8.28 Hz, 1H), 8.02 (dd, J=1.76, 9.04 Hz, 1H), 7.79 (d, J=9.29 Hz, 1H), 5.17 (br. s., 1H), 2.35-2.47 (m, 1H), 2.07 (d, J=13.55 Hz, 2H), 1.53-1.85 (m, 6H). ESI-MS (M+H)$^+$: 391.10

Step 5: 2,2-dimethyl-3-(((5-(trifluoromethyl)-6-((cis-4-(trifluoromethyl)cyclohexyl)oxy)naphthalen-2-yl)methyl)amino)cyclobutanecarboxylic acid

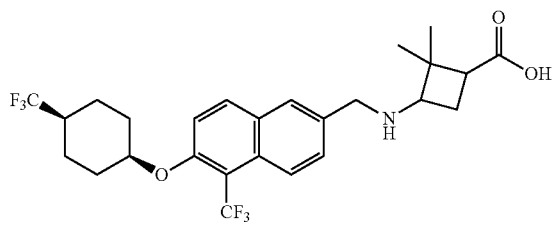 [SMILES: CC1(C)C(NCc2ccc3c(C(F)(F)F)c(O[C@H]4CC[C@@H](C(F)(F)F)CC4)ccc3c2)CC1C(=O)O]

A mixture of 5-trifluoromethyl-6-(cis-4-trifluoromethyl-cyclohexyloxy)-naphthalene-2-carbaldehyde (1.5) (50 mg, 0.13 mmol), 3-Amino-2,2-dimethyl-cyclobutanecarboxylic acid (37 mg, 0.26 mmol) in methanol (2.0 mL) and 1,2-dichloroethane (2.0 mL) was heated with microwave at 90° C. for 50 min. Cooled down. To the reaction mixture was added acetic acid (7.3 uL, 0.13 mmol), followed by sodium triacetoxyborohydride (54 mg, 0.26 mmol). Stirred at rt overnight. Removed the solvent under vacuo. The residue was diluted with ethyl acetate, washed with water, dried and concentrated. The crude was purified by HPLC to give the title compound as a white powder (33.6 mg). LCMS: RT 1.45 min.; MH+518.2; $^1$H NMR (400 MHz, METHANOL-$d_4$) δ 8.27 (d, J=8.78 Hz, 1H), 8.15 (d, J=9.29 Hz, 1H), 8.04 (d, J=1.25 Hz, 1H), 7.67 (dd, J=1.76, 9.04 Hz, 1H), 7.59 (d, J=9.29 Hz, 1H), 5.02 (br. s., 1H), 4.24-4.41 (m, 2H), 3.55 (t, J=8.91 Hz, 1H), 2.77 (t, J=9.16 Hz, 1H), 2.11-2.39 (m, 5H), 1.67-1.90 (m, 6H), 1.28-1.46 (m, 3H), 1.16-1.27 (m, 3H).

Example 2

1-((5-(trifluoromethyl)-6-((cis-4-(trifluoromethyl)cyclohexyl)oxy)-naphthalen-2-yl)methyl)piperidine-4-carboxylic acid

Step 1: Methyl 1-((5-(trifluoromethyl)-6-((cis-4-(trifluoromethyl)cyclohexyl)-oxy)naphthalen-2-yl)methyl)piperidine-4-carboxylate (2.1)

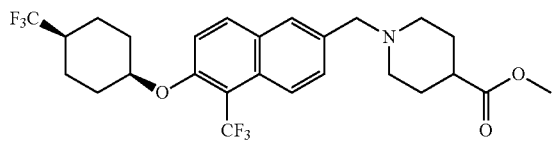 [SMILES: COC(=O)C1CCN(Cc2ccc3c(C(F)(F)F)c(O[C@H]4CC[C@@H](C(F)(F)F)CC4)ccc3c2)CC1]

A mixture of 5-trifluoromethyl-6-(cis-4-trifluoromethyl-cyclohexyloxy)-naphthalene-2-carbaldehyde (1.5, 1.1 g, 2.8 mmol), ethyl piperidine-4-carboxylate (0.61 mL, 3.9 mmol) and acetic acid (0.16 mL, 2.8 mmol) in 1,2-dichloroethane (20 mL, 200 mmol) was stirred at 50° C. for 1 h, cooled down, sodium triacetoxyborohydride (0.96 g, 4.5 mmol) was added, and the reaction was stirred at RT overnight. The reaction was diluted with ethyl acetate and washed with brine, dried over sulfate, and concentrated to give the desired product as a colorless oil which was used directly in the next step without further purifications. LCMS: RT 1.54 min.; MH+532.2.

Step 2: 1-((5-(trifluoromethyl)-6-((cis-4-(trifluoromethyl)cyclohexyl)oxy)-naphthalen-2-yl)methyl)piperidine-4-carboxylic acid

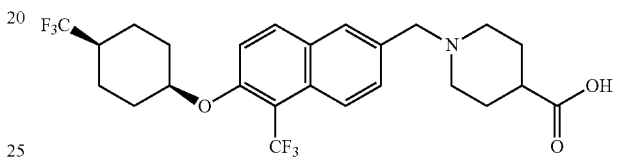

To a solution of methyl 1-((5-(trifluoromethyl)-6-((cis-4-(trifluoromethyl)cyclo-hexyl)oxy)naphthalen-2-yl)methyl)piperidine-4-carboxylate (80.0 mg, 0.15 mmol) in tetrahydrofuran (2.0 mL, 25 mmol) was added 1.0 M of aqueous lithium hydroxide (2.0 mL, 2.0 mmol) at RT. The reaction mixture was stirred at 35° C. for 3 h. The reaction mixture was neutralized with conc. HCl. Removed the solvent, the crude was purified by HPLC to give the title product as a white powder (65 mg, TFA salt). LCMS: RT 1.41 min; MH+504.20; $^1$H NMR (400 MHz, DMSO-$d_6$) δ 9.62 (br. s., 1H), 8.24 (d, J=9.29 Hz, 1H), 8.05-8.17 (m, 2H), 7.67-7.78 (m, 2H), 5.13 (br. s., 1H), 4.37-4.56 (m, 2H), 3.25-3.53 (m, 2H), 2.91-3.13 (m, 2H), 2.44 (br. s., 1H), 1.82-2.18 (m, 5H), 1.54-1.81 (m, 8H).

Example 3

3-(((5-(trifluoromethyl)-6-((cis-4-(trifluoromethyl)cyclohexyl)oxy)-naphthalen-2-yl)methyl)amino)cyclopentanecarboxylic acid

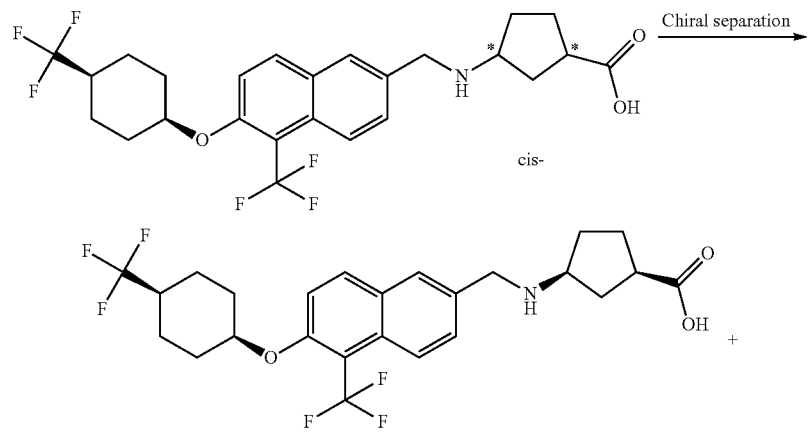

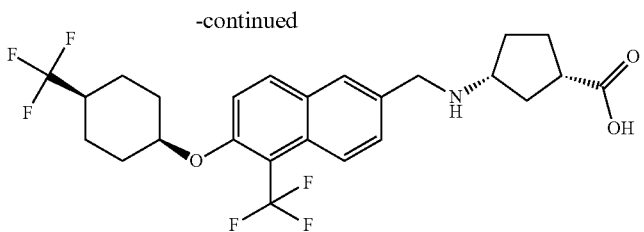

3-(((5-(trifluoromethyl)-6-((cis-4-(trifluoromethyl)cyclohexyl)oxy)-naphthalen-2-yl)methyl)amino)cyclopentanecarboxylic acid was prepared from corresponding cis-amino acid ethyl ester using the same method for Example 2, followed by chiral separation to give each single enantiomer as Example 3a and Example 3b.

Chiral Separation method: IC (2×15 cm), 30% methanol (0.1% DEA) CO2, 100 bar, 65 ml/min., 220 nm, inj vol.: 0.5 ml, 5 mg/ml methanol. Chiral separation the two title compounds which were randomly assigned as Example 3a and Example 3b.

Example 3a

LCMS: RT 1.42 min.; MH+504.2; 1H NMR (400 MHz, METHANOL-d4) d 8.23 (d, J=8.53 Hz, 1H), 8.14 (d, J=9.29 Hz, 1H), 8.02 (s, 1H), 7.67 (dd, J=1.63, 9.16 Hz, 1H), 7.55 (d, J=9.29 Hz, 1H), 5.00 (br. s., 1H), 4.38 (d, J=13.05 Hz, 1H), 4.19-4.30 (m, 1H), 3.74 (br. s., 1H), 2.94 (br. s., 1H), 1.94-2.38 (m, 10H), 1.65-1.90 (m, 7H).

Example 3b

LCMS: RT 1.44 min.; MH+504.2; 1H NMR (400 MHz, METHANOL-$d_4$) δ 8.24 (d, J=8.28 Hz, 1H), 8.14 (d, J=9.29 Hz, 1H), 8.02 (s, 1H), 7.67 (dd, J=1.26, 9.04 Hz, 1H), 7.56 (d, J=9.29 Hz, 1H), 5.01 (br. s., 1H), 4.39 (d, J=13.30 Hz, 1H), 4.19-4.30 (m, 1H), 3.74 (br. s., 1H), 2.95 (br. s., 1H), 1.95-2.37 (m, 10H), 1.66-1.91 (m, 7H).

Example 4

(R)-2-(1-((6-((4,4-difluorocyclohexyl)oxy)-5-(trifluoromethyl)naphthalen-2-yl)methyl)piperidin-3-yl)acetic acid

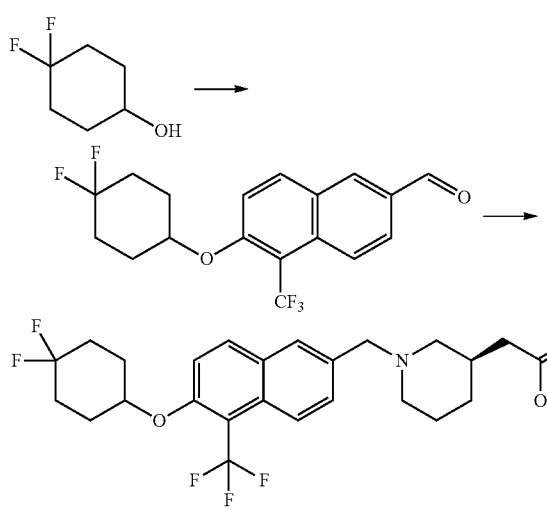

Step 1: 6-((4,4-difluorocyclohexyl)oxy)-5-(trifluoromethyl)-2-naphthaldehyde (4.1)

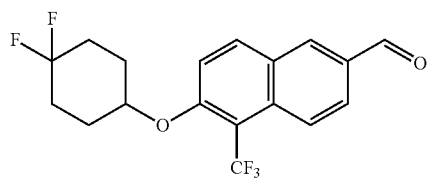 [SMILES: O=Cc1ccc2c(C(F)(F)F)c(OC3CCC(F)(F)CC3)ccc2c1]

A solution of 6-(4,4-Difluoro-cyclohexyloxy)-5-iodo-naphthalene-2-carbaldehyde (3.0 g, 7.2 mmol), hexamethylphosphoramide (6.02 mL, 34.3 mmol) in N,N-dimethylformamide (30 mL, 400 mmol) was degassed with argon. To this was added copper(I) iodide (2.34 g, 12.3 mmol) and methyl fluorosulphonyldifluoroacetate (4.49 mL, 34.3 mmol) and the reaction was stirred at 85° C. under an atmosphere of argon. After stirring for 3 hours, LCMS showed no starting material left and confirms the identity of the product (RT=2.01 min, MH+359.10). The reaction was diluted with EtOAc, filtered off the solid, and the filtrate was washed with brine, and water. The organic layer was then separated, dried, concentrated. The crude was recrystallized from methanol to give the title product as a white powder (1.95 g). LCMS: RT 2.01 min; MH+359.1; $^1$H NMR (400 MHz, CHLOROFORM-d) δ 10.15 (s, 1H), 8.28-8.40 (m, 2H), 8.14 (d, J=9.29 Hz, 1H), 8.03 (dd, J=1.63, 9.16 Hz, 1H), 7.40 (d, J=9.04 Hz, 1H), 4.86 (br. s., 1H), 2.11-2.37 (m, 4H), 1.93-2.08 (m, 4H).

Step 2: (R)-2-(1-((6-((4,4-difluorocyclohexyl)oxy)-5-(trifluoromethyl)naphthalen-2-yl)methyl)piperidin-3-yl)acetic acid

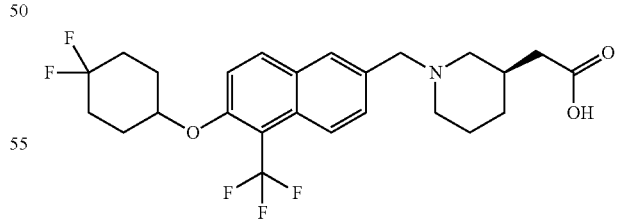

The title compound was prepared using similar method described for Example 1 from compound 4.1 and (R)-methyl 2-(piperidin-3-yl)acetate. LCMS: RT 1.34 min.; MH+486.2; 1H NMR (400 MHz, METHANOL-$d_4$) δ 8.28 (d, J=8.53 Hz, 1H), 8.18 (d, J=9.29 Hz, 1H), 8.06 (s, 1H), 7.59-7.74 (m, 2H), 4.97 (d, J=2.01 Hz, 1H), 4.47 (s, 2H), 3.44-3.67 (m, 2H), 2.90-3.03 (m, 1H), 2.80 (t, J=11.92 Hz, 1H), 1.87-2.47 (m, 13H), 1.68-1.86 (m, 1H), 1.19-1.38 (m, 1H).

Example 5

4-(2H-tetrazol-5-yl)-1-((5-(trifluoromethyl)-6-((cis-4-(trifluoromethyl)cyclohexyl)oxy)naphthalen-2-yl)methyl)piperidine

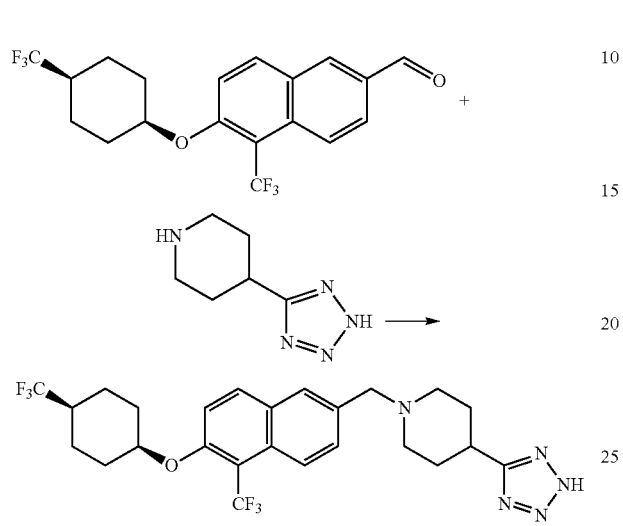

A solution of 5-trifluoromethyl-6-(4-trifluoromethyl-cyclohexyloxy)-naphthalene-2-carbaldehyde (200 mg, 0.512 mmol) and 4-(2H-tetrazol-5-yl)-piperidine (78.5 mg, 0.512 mmol) in ethanol (1 mL) was heated to reflux for 2 h. The yellow solution was cooled to rt and sodium cyanoborohydride (38.6 mg, 0.615 mmol) was added and was heated to reflux for 3 d. After cooled down to rt, and concentrated down. The solid was suspended in citric acid and EtOAc, The organic layer was washed with brine and dry and concentrated. The residue was chromatographed with preparative HPLC (ACN/H2O, 0.1% TFA) to give a solid as the product (90 mg, 33%). LCMS: Rt=1.50 min, m/z=528.00 [M+1]. $^{1}$H NMR (400 MHz, METHANOL-$d_4$) δ 8.30 (d, J=8.85 Hz, 1H), 8.17 (d, J=9.04 Hz, 1H), 8.08 (s, 1H), 7.69 (d, J=8.91 Hz, 1H), 7.61 (d, J=9.22 Hz, 1H), 5.03 (br. s., 1H), 4.53 (s, 2H), 3.20-3.77 (m, 4H), 1.49-2.86 (m, 14H).

Example 6

2-((3R)-1-(1-(6-((cis-4-ethylcyclohexyl)oxy)-5-(trifluoromethyl)naphthalen-2-yl)ethyl)piperidin-3-yl)acetic acid

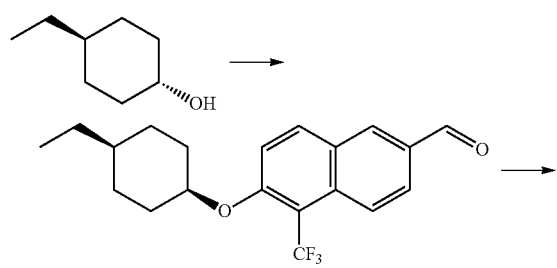

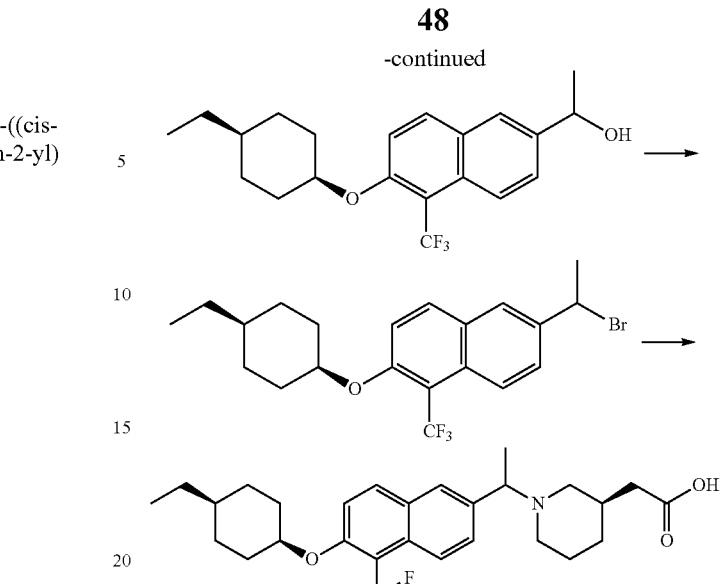

Step 1: 6-((cis-4-ethylcyclohexyl)oxy)-5-(trifluoromethyl)-2-naphthaldehyde (6.1)

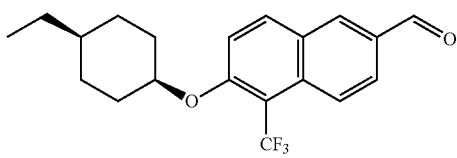 [SMILES: CC[C@H]1CC[C@@H](Oc2ccc3cc(C=O)ccc3c2C(F)(F)F)CC1]

The title compound (6.1) was prepared according to the method described for compound (1.5) from trans-4-ethylcyclohexanol. 1H NMR (400 MHz, CHLOROFORM-d) δ 10.13 (s, 1H), 8.23-8.39 (m, 2H), 8.09 (d, J=9.04 Hz, 1H), 8.00 (dd, J=1.63, 9.16 Hz, 1H), 7.39 (d, J=9.29 Hz, 1H), 4.86 (br. s., 1H), 2.02-2.18 (m, 2H), 1.54-1.71 (m, 4H), 1.39-1.53 (m, 2H), 1.22-1.38 (m, 3H), 0.92 (t, J=7.15 Hz, 3H); ESI-MS (M+H)$^{+}$: 351.0.

Step 2: 1-(6-((cis-4-ethylcyclohexyl)oxy)-5-(trifluoromethyl)naphthalen-2-yl)ethanol (6.2)

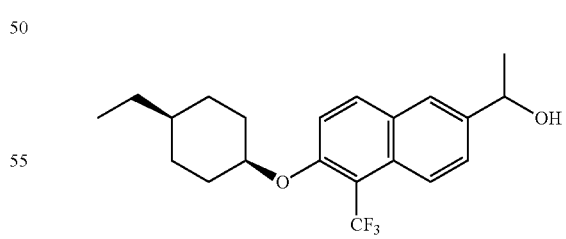

To a solution of 6-(cis-4-ethyl-cyclohexyloxy)-5-trifluoromethyl-naphthalene-2-carbaldehyde (6.1, 0.90 g, 2.56 mmol) in dry tetrahydrofuran (20 mL, 200 mmol) at −78° C. (acetone/dry ice bath) under argon was dropwise added 1.4 M of methyl bromide in toluene/THF (mixture of 75/25 (2.7 mL, 3.8 mmol) over 10 min. After stirred at −78° C. for 1 h, allowed the reaction to warm up a little before quenched with sat.ammonium chloride, extracted with ethyl acetate.

The organic phase was separated, dried, filtered and concentrated. The crude was purified by ISCO column chromatography (EtOAc/heptane gradient from 0/100 to 60/40) to give the title compound 6.2 as a colorless oil (0.84 g). LC-MS: RT 2.23 min.; ESI-MS: 349.1 (M-OH) and 389.0 (M+Na).

Step 3: 6-(1-bromoethyl)-2-((cis-4-ethylcyclohexyl)oxy)-1-(trifluoromethyl)Naphthalene (6.3)

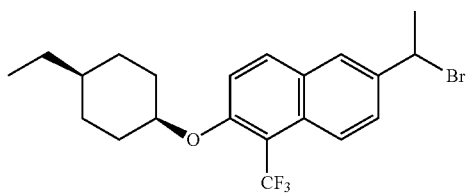 [SMILES: CC[C@H]1CC[C@@H](Oc2ccc3cc(C(C)Br)ccc3c2C(F)(F)F)CC1]

To a solution of 1-[6-(cis-4-Ethyl-cyclohexyloxy)-5-trifluoromethyl-naphthalen-2-yl]-ethanol (6.2, 0.84 g, 1.1 mmol) in tetrahydrofuran (5.0 mL, 62 mmol) was added 1.0 M of phosphorus tribromide in methylene chloride (1.15 mL, 1.15 mmol). The mixture was stirred at RT for 5 min. The reaction was diluted with ethyl acetate, washed with water. The organic layer was then dried over MgSO4 and concentrated to give the title product 6.3 as a colorless oil (0.70 g) which was used in the next step without further purifications. LCMS: RT 2.62 min.; ESI-MS: 349.0 (M-Br).

Step 4: 2-((3R)-1-(1-(6-((cis-4-ethylcyclohexyl)oxy)-5-(trifluoromethyl)naphthalen-2-yl)ethyl)piperidin-3-yl)acetic acid

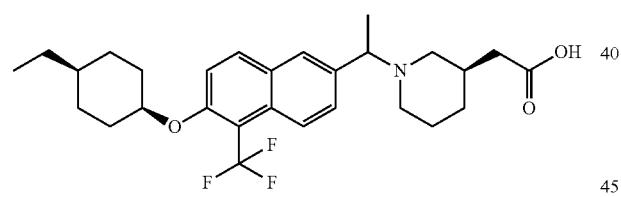

To a mixture of potassium carbonate (35.4 mg, 0.256 mmol) and (R)-Piperidin-3-yl-acetic acid ethyl ester hydrochloride (62.9 mg, 0.303 mmol) in N,N-dimethylformamide (2.0 mL, 26 mmol) was added a solution of 6-(1-bromoethyl)-2-(cis-4-ethyl-cyclohexyl-oxy)-1-trifluoromethyl-naphthalene (6.3, 0.15 g, 0.17 mmol) in N,N-dimethylformamide (5 ml). The reaction mixture was stirred at RT overnight. The mixture partitioned between ethyl acetate and saturated aqueous sodium bicarbonate. The organic phase was washed with brine, dried, filtered and concentrated. The crude was purified by HPLC to give desired intermediate as a colorless oil (LC-MS: RT 1.77 min., MH+520.1) which was then dissolved in tetrahydrofuran (1.0 mL, 12 mmol) and methanol (1.0 mL, 25 mmol). 3.0 M of aqueous sodium hydroxide (1.0 mL, 3.0 mmol) was added, and the reaction mixture was heated in microwave at 100° C. for 10 min. The reaction mixture was diluted with ethyl acetate, and then neutralized with 2N HCl (aq). The organic layer was separated, dried and concentrated. The crude was then purified by HPLC to give the title product as a white powder (46 mg, TFA salt). LC-MS: RT 1.67 min., MH+492.1; 1H NMR (400 MHz, METHANOL-d$_4$) δ 8.28 (d, J=8.78 Hz, 1H), 8.14 (d, J=9.29 Hz, 1H), 8.02 (d, J=1.25 Hz, 1H), 7.67 (dd, J=1.88, 9.16 Hz, 1H), 7.58 (d, J=9.29 Hz, 1H), 4.95 (br. s., 1H), 4.63 (q, J=6.86 Hz, 1H), 3.68-3.87 (m, 1H), 3.36-3.53 (m, 1H), 2.52-2.93 (m, 2H), 2.14-2.42 (m, 3H), 1.53-2.13 (m, 12H), 1.11-1.52 (m, 6H), 0.93 (t, J=7.15 Hz, 3H).

Example 7

2-((3R)-1-(1-(6-((cis-4-ethylcyclohexyl)oxy)-5-(trifluoromethyl)naphthalen-2-yl)propyl)piperidin-3-yl)acetic acid

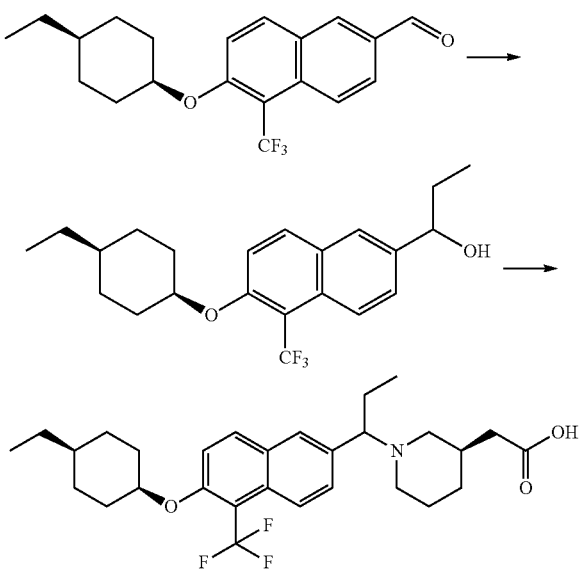

Step 1: 1-(6-((cis-4-ethylcyclohexyl)oxy)-5-(trifluoromethyl)naphthalen-2-yl)-propan-1-ol (7.1)

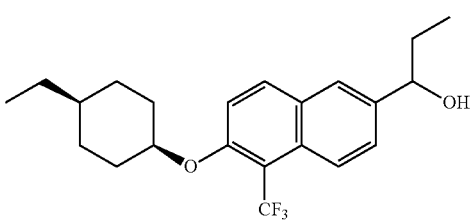 [SMILES: CCC(O)c1ccc2c(C(F)(F)F)c(O[C@H]3CC[C@@H](CC)CC3)ccc2c1]

The title compound was prepared from 6-(4-ethyl-cyclohexyloxy)-5-trifluoromethyl-naphthalene-2-carbalde-hyde (6.1) and ethyl bromide according to the method described in the preparation of 1-(6-((cis-4-ethylcyclohexyl)oxy)-5-(trifluoromethyl)naphthalen-2-yl)ethanol (6.2). LC-MS: RT 2.37 min.; ESI+: 363.0 (M-OH) and 403 (M+Na).

Step 2: 6-(1-bromopropyl)-2-((cis-4-ethylcyclo-hexyl)oxy)-1-(trifluoromethyl)-naphthalene (7.2)

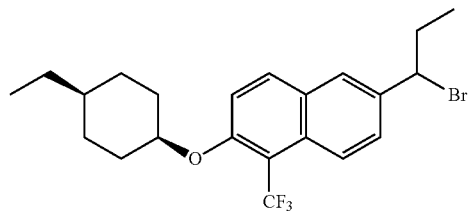 [SMILES: CCC(Br)c1ccc2c(C(F)(F)F)c(O[C@H]3CC[C@@H](CC)CC3)ccc2c1]

The title compound was prepared according to the method described for compound (6.3). The compound was used in the next step without further purifications.

Step 3: 2-((3R)-1-(1-(6-((cis-4-ethylcyclohexyl)oxy)-5-(trifluoromethyl)naphthalen-2-yl)propyl)piperidin-3-yl)acetic acid

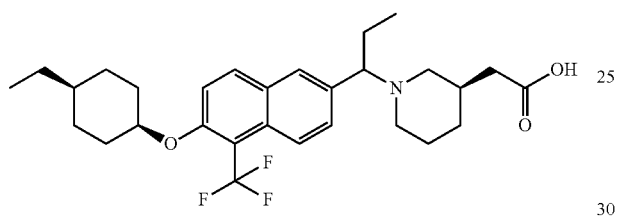

To a mixture of potassium carbonate (35.8 mg, 0.259 mmol) and (R)-piperidin-3-yl-acetic acid ethyl ester hydrochloride (28.1 mg, 0.135 mmol) in N,N-dimethylformamide (1.0 mL, 13 mmol) was added a solution of 6-(1-bromopropyl)-2-(-cis-4-ethyl-cyclohexyloxy)-1-trifluoromethyl-naphthalene (50.0 mg, 0.113 mmol) in DMF (5 ml). The reaction mixture was stirred at RT overnight. The reaction mixture was diluted with ethyl acetate, and washed with brine, dried, filtered and concentrated. The crude was purified by HPLC to give desired intermediate as a colorless oil (RT 1.85 min., MH+534.1) which was then dissolved in tetrahydrofuran (1.0 mL, 12 mmol) and methanol (0.5 mL, 10 mmol), treated with 3.0 M of aqueous sodium hydroxide (1.0 mL, 3.0 mmol). The reaction was heated in microwave at 100° C. for 10 min. Cooled down, the reaction was neutralized with 2N HCl. The organic phase was then separated, dried and concentrated. The crude was purified by HPLC to give the title product as a white powder (22 mg). LC-MS: RT 1.69 min., MH+506.1; 1H NMR (400 MHz, METHANOL-d4) δ 8.30 (d, J=8.53 Hz, 1H), 8.14 (d, J=9.29 Hz, 1H), 8.02 (s, 1H), 7.54-7.70 (m, 2H), 4.96 (br. s., 1H), 4.31-4.62 (m, 1H), 3.69-4.15 (m, 1H), 3.38-3.58 (m, 1H), 2.69-2.84 (m, 1H), 2.59 (dt, J=6.15, 11.61 Hz, 1H), 2.15-2.45 (m, 5H), 1.53-2.13 (m, 9H), 1.38-1.53 (m, 2H), 1.24-1.37 (m, 3H), 1.08-1.23 (m, 1H), 0.93 (t, J=7.15 Hz, 3H), 0.74-0.87 (m, 3H).

Example 8

2-(4-(((6-((cis-4-Methylcyclohexyl)oxy)-5-(trifluoromethyl)naphthalen-2-yl)methyl)morpholin-2-yl)acetic acid

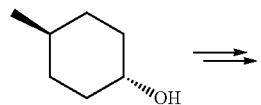

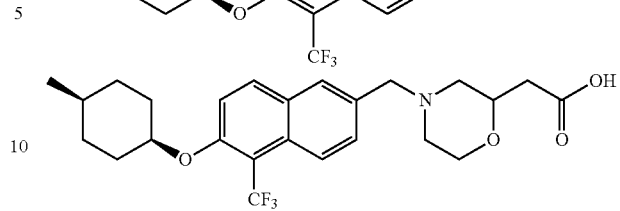

Step 1: 6-((cis-4-methylcyclohexyl)oxy)-5-(trifluoromethyl)-2-naphthaldehyde (8.1)

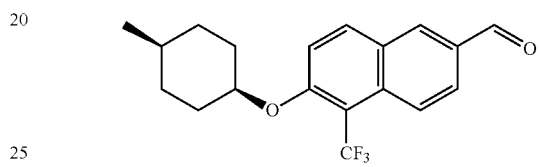

The title compound was prepared according to the method described for compound (1.5) from trans-4-methylcyclohexan-1-ol. 1H NMR (400 MHz, CDCl3) δ: 10.11 (s, 1H), 8.31 (d, J=8.8 Hz, 1H), 8.26 (d, J=1.2 Hz, 1H), 8.07 (d, J=9.2 Hz, 1H), 7.98 (dd, J=1.6 Hz, 9.2 Hz, 1H), 7.37 (d, J=9.2 Hz, 1H), 4.84 (s, 1H), 2.09-2.06 (m, 2H), 1.68-1.62 (m, 2H), 1.54-1.43 (m, 5H), 0.96 (d, J=5.2 Hz, 3H); ESI-MS (M+H)+: 336.9

Step 2: 2-(4-((6-((cis-4-Methylcyclohexyl)oxy)-5-(trifluoromethyl)naphthalen-2-yl)methyl)morpholin-2-yl)acetic acid

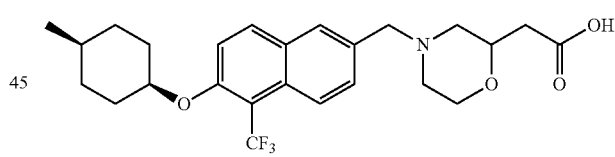

To a mixture of 6-((cis-4-methylcyclohexyl)oxy)-5-(trifluoromethyl)-2-naphthaldehyde (17 mg, 0.050 mmol), methyl 2-(morpholin-2-yl)acetate hydrochloride (16 mg, 0.080 mmol) and sodium triacetoxyborohydride (17 mg, 0.080 mmol) in THF (0.6 mL) was added acetic acid (5.7 μL, 0.10 mmol). The reaction mixture was heated with microwave irritation at 100° C. for 20 min. To the above mixture was added MeOH (0.4 mL) and 3 M of NaOH in water (0.20 mL, 0.60 mmol). The mixture was heated with microwave irritation at 100° C. for 10 min. Neutralized with 1NHCl, and purified by HPLC (TFA method) to get a white powder after lyophilization (24 mg, yield 81%). 1H NMR (300 MHz, METHANOL-d4) δ 8.29 (d, J=9.06 Hz, 1H), 8.15 (d, J=9.44 Hz, 1H), 8.06 (d, J=1.89 Hz, 1H), 7.68 (dd, J=2.27, 9.06 Hz, 1H), 7.60 (d, J=9.06 Hz, 1H), 4.96 (br. s., 1H), 4.54 (s, 2H), 4.11 (dd, J=3.59, 13.41 Hz, 2H), 3.81 (t, J=12.09 Hz, 1H), 3.51-3.63 (m, 1H), 3.38-3.48 (m, 1H), 3.16-3.29 (m, 1H), 3.01-3.14 (m, 1H), 2.59 (d, J=6.42 Hz, 2H), 2.00-2.15 (m, 2H), 1.65-1.78 (m, 2H), 1.36-1.59 (m, 5H), 0.97 (d, J=5.67 Hz, 3H); LCMS m/z 466.2 [M+H]+

Example 9

2-(1-((6-((cis-4-methylcyclohexyl)oxy)-5-(trifluoromethyl)naphthalen-2-yl)methyl)piperidin-3-yl)acetic acid

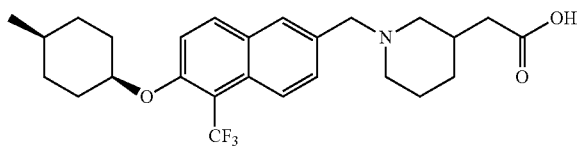 [SMILES: C[C@H]1CC[C@@H](Oc2ccc3cc(CN4CCCC(CC(=O)O)C4)ccc3c2C(F)(F)F)CC1]

To a mixture of 6-((cis-4-methylcyclohexyl)oxy)-5-(trifluoromethyl)-2-naphthaldehyde (17 mg, 0.050 mmol), 2-(piperidin-3-yl)acetic acid hydrochloride (14 mg, 0.080 mmol) and sodium triacetoxyborohydride (17 mg, 0.080 mmol) in THF (0.6 mL) was added acetic acid (5.7 µL, 0.10 mmol). The reaction mixture was heated with microwave irritation at 100° C. for 20 min. The crude mixture was diluted with MeOH/DMSO and purified by HPLC (TFA method) to get an off-white powder after lyophilization (14 mg, yield 48%). $^1$H NMR (400 MHz, DMSO-d$_6$) δ 8.22 (d, J=9.29 Hz, 1H), 8.14 (d, J=7.78 Hz, 1H), 8.08 (s, 1H), 7.62-7.80 (m, 2H), 5.02 (br. s., 1H), 4.45 (d, J=4.27 Hz, 2H), 3.41 (t, J=11.29 Hz, 2H), 2.62-2.94 (m, 2H), 2.18-2.30 (m, 2H), 2.12 (br. s., 1H), 1.57-2.01 (m, 7H), 1.48 (d, J=10.04 Hz, 3H), 1.24-1.38 (m, 2H), 1.04-1.21 (m, 1H), 0.90 (d, J=6.27 Hz, 3H); LCMS m/z 464.3 [M+H]+

Example 10

2-((3R)-1-(1-(6-((cis-4-Methylcyclohexyl)oxy)-5-(trifluoromethyl)naphthalen-2-yl)propyl)piperidin-3-yl)acetic acid

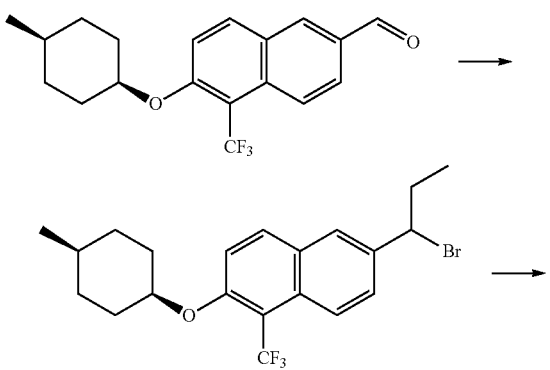

Step 1: 1-(6-((cis-4-Methylcyclohexyl)oxy)-5-(trifluoromethyl)naphthalen-2-yl)propan-1-ol

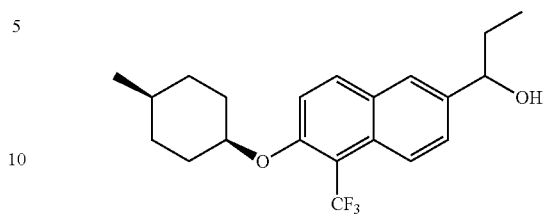

To a solution of 6-((cis-4-methylcyclohexyl)oxy)-5-(trifluoromethyl)-2-naphthaldehyde (336 mg, 1.00 mmol) in dry THF (5 mL, 60 mmol) at −78° C. (acetone/dry ice bath) under N$_2$ was added a solution of 3M EtMgBr in Et$_2$O (0.5 mL, 1.5 mmol). After stirred at −78° C. for 30 min, it was switched to an ice-cold bath, and stirred at 0° C. for 1.5 h. The reaction was quenched with satd.NH$_4$Cl, extracted with EtOAc. The organic phase was dried, filtered and concentrated. The residue was purified by flash chromatography on silica gel column to provide the title alcohol as a colorless oil (235 mg, yield 64%). $^1$H NMR (300 MHz, METHANOL-d$_4$) δ 8.13 (d, J=7.55 Hz, 1H), 8.03 (d, J=9.06 Hz, 1H), 7.80 (d, J=1.51 Hz, 1H), 7.57 (dd, J=1.89, 9.06 Hz, 1H), 7.46 (d, J=9.44 Hz, 1H), 4.70 (t, J=6.61 Hz, 1H), 1.99-2.17 (m, 2H), 1.78-1.92 (m, 2H), 1.60-1.76 (m, 2H), 1.40-1.58 (m, 5H), 0.88-1.02 (m, 6H); LCMS m/z 349.1 [M+H−H$_2$O]+

Step 2: 6-(1-Bromopropyl)-2-((cis-4-methylcyclohexyl)oxy)-1-(trifluoromethyl)naphthalene

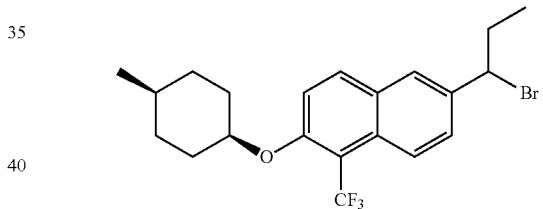

To a solution of 1-[6-(cis-4-methyl-cyclohexyloxy)-5-trifluoromethyl-naphthalen-2-yl]-propan-1-ol (220 mg, 0.600 mmol) in THF under N$_2$ was added 1 M of PBr$_3$ in Methylene chloride at room temperature. The reaction mixture was stirred at rt for 5 minutes, and then partitioned between EtOAc and water. The organic phase was dried, filtered and concentrated to get the bromide intermediate as a colorless oil (284 mg, yield>100%). The oil product was dissolved in DMF (6 mL) to make 0.1M solution, and used as such for next step directly. LCMS m/z 349.1 [M+H−HBr]+

Step 3: Ethyl 2-((3R)-1-(1-(6-((cis-4-methylcyclohexyl)oxy)-5-(trifluoromethyl)naphthalen-2-yl)propyl)piperidin-3-yl)acetate

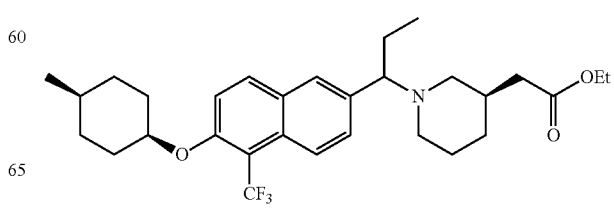

To a solution of 0.1M 6-(1-bromopropyl)-2-((cis-4-methylcyclohexyl)oxy)-1-(trifluoromethyl)naphthalene in DMF (1 mL, 0.1 mmol) was added (R)-ethyl 2-(piperidin-3-yl)acetate HCl salt (27 mg, 0.13 mmol) and K$_2$CO$_3$ (21 mg, 0.15 mmol). The reaction mixture was stirred at rt overnight. The crude sample (after filtration) was purified by HPLC (TFA method) to get the TFA salt as a colorless oil (45 mg, yield 71%). LCMS m/z 520.3 [M+H]$^+$ Step 4: 2-((3R)-1-(1-(6-(((cis-4-methylcyclohexyl)oxy)-5-(trifluoromethyl)naphthalen-2-yl)propyl)piperidin-3-yl)acetic acid

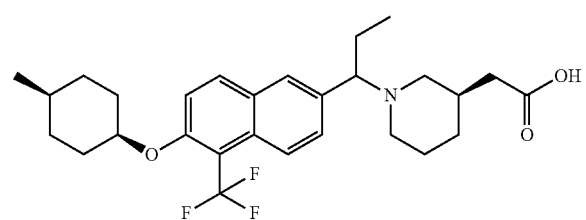 [SMILES: CCC(c1ccc2c(C(F)(F)F)c(O[C@H]3CC[C@@H](C)CC3)ccc2c1)N1CCC[C@H](CC(=O)O)C1]

To a solution of ethyl 2-((3R)-1-(1-(6-(((cis-4-methylcyclohexyl)oxy)-5-(trifluoromethyl)naphthalen-2-yl)propyl)piperidin-3-yl)acetate TFA salt (45 mg, 0.071 mmol) in THF (0.5 mL) and MeOH (0.5 mL) was added 3N NaOH (0.5 mL). The reaction mixture was heated at 55° C. for 1 h, and adjusted pH~5 by adding 1N HCl. The mixture was purified by HPLC (TFA method) to get the desired acid as a white solid. $^1$H NMR (400 MHz, METHANOL-d4) δ 8.30 (d, J=8.53 Hz, 1H), 8.15 (d, J=9.29 Hz, 1H), 8.02 (s, 1H), 7.65 (d, J=9.29 Hz, 1H), 7.59 (d, J=9.29 Hz, 1H), 4.95 (br. s., 1H), 4.39 (dd, J=3.89, 10.92 Hz, 1H), 3.68-3.89 (m, 1H), 3.38-3.57 (m, 1H), 2.69-2.84 (m, 1H), 2.51-2.66 (m, 1H), 2.16-2.43 (m, 5H), 1.81-2.12 (m, 5H), 1.70 (t, J=13.18 Hz, 2H), 1.37-1.60 (m, 5H), 1.08-1.26 (m, 1H), 0.96 (d, J=5.52 Hz, 3H), 0.82 (t, J=7.28 Hz, 3H); LCMS m/z 492.3 [M+H]$^+$ Example 11

1-(Carboxy(6-(((cis-4-methylcyclohexyl)oxy)-5-(trifluoromethyl)naphthalen-2-yl)methyl)piperidine-4-carboxylic acid

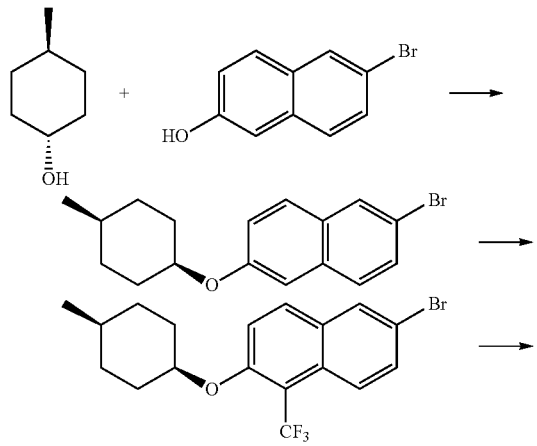

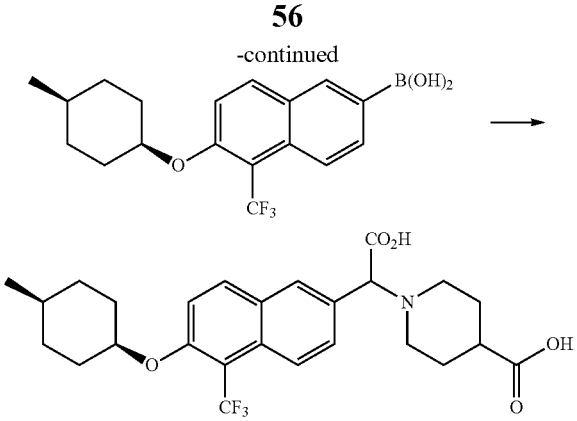

Step 1: 2-bromo-6-((cis-4-methylcyclohexyl)oxy)naphthalene (11.1)

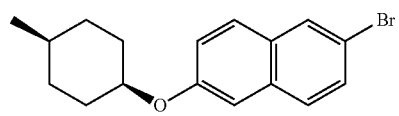 [SMILES: C[C@H]1CC[C@@H](Oc2ccc3cc(Br)ccc3c2)CC1]

To a mixture of trans-4-methylcyclohexan-1-ol (20.5 g, 179.6 mmol, 1.2 eq) and 6-bromonaphthalen-2-ol (33.1 g, 149.8 mmol) in THF (300 mL) was added PPh$_3$ (62.8 g, 239.5 mmol, 1.6 eq), followed by DIAD (48.4 g, 239.5 mmol, 1.6 eq) dropwise. The mixture was stirred at rt for 24 h and concentrated. The residue was diluted with EtOAc (300 mL), washed with water (100 mL) and brine (100 mL). The organic layer was dried over anhydrous Na$_2$SO$_4$ and evaporated. The residue was purified by column chromatography on silica gel (Petroleum ether/EtOAc=20/1) to give 2-bromo-6-((cis-4-methylcyclohexyl)oxy)naphthalene (4.1) as a white solid (35.5 g, yield: 75%).

Step 2: 6-Bromo-2-((cis-4-methylcyclohexyl)oxy)-1-(trifluoromethyl)naphthalene (11.2)

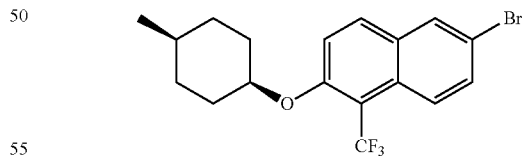

The title compound was prepared according to the procedure for 5-(trifluoromethyl)-6-(((1s,4s)-4-(trifluoromethyl)cyclohexyl)oxy)-2-naphthaldehyde (1.5) from 2-bromo-6-((cis-4-methylcyclohexyl)oxy)naphthalene (11.1). $^1$H NMR (400 MHz, DMSO-d$_6$) δ: 8.27 (s, 1H), 8.16 (d, J=9.2 Hz, 1H), 7.97 (d, J=9.2 Hz, 1H), 7.73 (d, J=9.2 Hz, 1H), 7.66 (d, J=9.2 Hz, 1H), 4.98 (s, 1H), 1.93-1.89 (m, 2H), 1.65-1.58 (m, 2H), 1.48-1.45 (m, 3H), 1.30-1.27 (m, 2H), 0.88 (d, J=6.0 Hz, 3H).

Step 3: (6-((cis-4-Methylcyclohexyl)oxy)-5-(trifluoromethyl)naphthalen-2-yl)boronic acid (11.3)

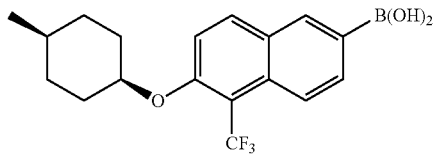 [SMILES: C[C@H]1CC[C@@H](Oc2ccc3cc(B(O)O)ccc3c2C(F)(F)F)CC1]

To a solution of 6-bromo-2-(cis-4-methyl-cyclohexyloxy)-1-trifluoromethyl-naphthalene (11.2) (774 mg, 2.00 mmol) in THF (4 mL) at −78° C. was added 2.5 M of n-Butyllithium in hexane (0.96 mL, 2.4 mmol) drop-wise under N$_2$. The reaction mixture was stirred at −78° C. for 30 min. Triisopropyl borate (0.69 mL, 3.0 mmol) was added, and stirred at −78° C. for 1 h. The reaction was quenched with 1N HCl, and extracted with EtOAc. The organic phase was washed with brine, dried over MgSO$_4$, filtered and concentrated. The residue was purified by flash chromatography on silica gel column, eluted with EtOAc/MeOH/AcOH (100:10:1) to get the desired boronic acid as a white solid (234 mg, yield 33%). $^1$H NMR (300 MHz, METHANOL-d$_4$) δ 8.00-8.19 (m, 3H), 7.76 (dd, J=1.13, 8.69 Hz, 1H), 7.45 (d, J=9.06 Hz, 1H), 4.89 (br, s, 1H), 1.91-2.15 (m, 2H), 1.59-1.79 (m, 2H), 1.38-1.57 (m, 5H), 0.96 (d, J=5.29 Hz, 3H); LCMS m/z 353.1 [M+H]$^+$

Step 4: 2-(4-(Methoxycarbonyl)piperidin-1-yl)-2-(6-((cis-4-methylcyclohexyl)oxy)-5-(trifluoromethyl)naphthalen-2-yl)acetic acid (11.3)

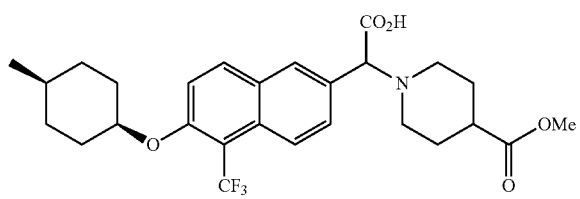 [SMILES: COC(=O)C1CCN(C(C(=O)O)c2ccc3c(C(F)(F)F)c(O[C@H]4CC[C@@H](C)CC4)ccc3c2)CC1]

To a suspension of (6-((cis-4-methylcyclohexyl)oxy)-5-(trifluoromethyl)naphthalen-2-yl)boronic acid (54 mg, 0.15 mmol) in 1,1,1,3,3,3-hexafluoropropan-2-ol (1.5 mL) was added piperidine-4-carboxylic acid methyl ester (33 mg, 0.23 mmol), followed by glyoxalic acid hydrate (17 mg, 0.18 mmol). The suspension turned to a clear solution after 2 h at room temperature. The mixture was purified by HPLC (TFA method) to provide the desired ester as a white powder after lyophilization (89 mg, yield 93%). $^1$H NMR (300 MHz, METHANOL-d$_4$) δ 8.26 (d, J=8.31 Hz, 1H), 8.02-8.16 (m, 2H), 7.67 (dd, J=2.08, 9.25 Hz, 1H), 7.58 (d, J=9.44 Hz, 1H), 5.02 (s, 1H), 4.94 (br. s., 1H), 3.70 (s, 3H), 3.03-3.23 (m, 4H), 2.63-2.75 (m, 1H), 1.94-2.26 (m, 6H), 1.70 (t, J=13.22 Hz, 2H), 1.35-1.59 (m, 5H), 0.95 (d, J=5.29 Hz, 3H); LCMS m/z 508.0 [M+H]$^+$

Step 5: 1-(Carboxy(6-((cis-4-methylcyclohexyl)oxy)-5-(trifluoromethyl)naphthalen-2-yl)methyl)piperidine-4-carboxylic acid

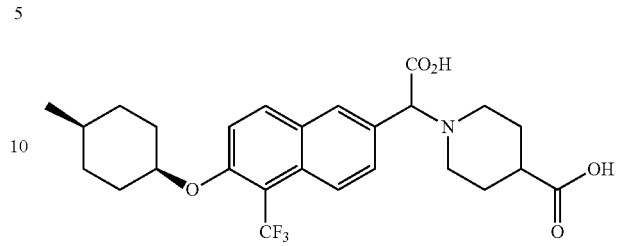

To a solution of above ester (65 mg, 0.10 mmol) in MeOH (0.6 mL) and THF (0.6 mL) was added 3 M of NaOH in water (0.15 mL, 0.45 mmol). The mixture was heated at 55° C. for 1 h. The reaction mixture was neutralized with 1N HCl, and purified by HPLC (TFA method) to collect desired acid as a white powder after lyophilization (61 mg, yield 96%). $^1$H NMR (300 MHz, METHANOL-d$_4$) δ 8.28 (d, J=7.93 Hz, 1H), 8.13 (d, J=9.06 Hz, 1H), 8.08 (d, J=1.89 Hz, 1H), 7.66 (dd, J=2.08, 9.25 Hz, 1H), 7.60 (d, J=9.44 Hz, 1H), 5.16 (s, 1H), 4.95 (br. s., 1H), 3.05-3.26 (m, 4H), 2.65 (br. s., 1H), 1.95-2.32 (m, 6H), 1.70 (t, J=13.03 Hz, 2H), 1.35-1.60 (m, 5H), 0.95 (d, J=5.29 Hz, 3H); LCMS m/z 494.0 [M+H]$^+$

Example 12

1-(2,2,2-Trifluoro-1-(6-((cis-4-methylcyclohexyl)oxy)-5-(trifluoromethyl)naphthalen-2-yl)ethyl)piperidine-4-carboxylic acid

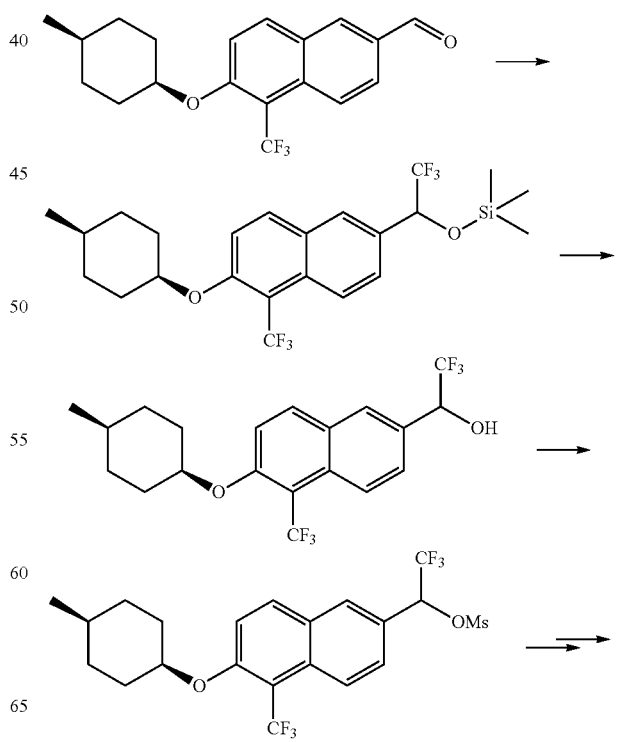

-continued

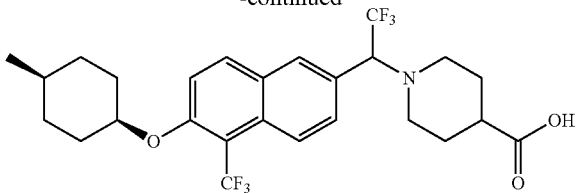

Step 1: Trimethyl(2,2,2-trifluoro-1-(6-((cis-4-methylcyclohexyl)oxy)-5-(trifluoromethyl)naphthalen-2-yl)ethoxy)silane

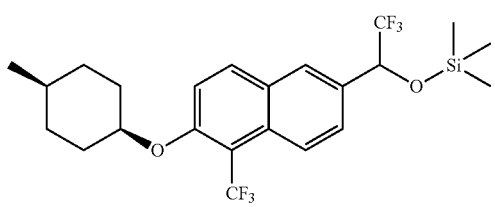

To a mixture of 6-((cis-4-methylcyclohexyl)oxy)-5-(trifluoromethyl)-2-naphthaldehyde (168 mg, 0.500 mmol), (trifluoromethyl)trimethylsilane (220 uL, 1.5 mmol) in DMF (1 mL) was added 1,3-bis(1-adamantyl)imidazole-2-ylidene (4 mg, 0.012 mmol). The reaction mixture was stirred at rt overnight. It was partitioned between EtOAc and water. The organic phase was washed with brine, dried over MgSO$_4$, filtered and concentrated. The residue was purified by flash chromatography on silica gel column, eluted with EtOAc in heptane (2-5%) to collect desired intermediate as a colorless oil (172 mg, yield 72%). $^1$H NMR (300 MHz, METHANOL-d$_4$) δ 8.17 (d, J=9.06 Hz, 1H), 8.08 (d, J=9.44 Hz, 1H), 7.97 (s, 1H), 7.66 (d, J=9.06 Hz, 1H), 7.51 (d, J=9.44 Hz, 1H), 5.31 (q, J=6.67 Hz, 1H), 4.91 (br. s., 2H), 1.98-2.13 (m, 2H), 1.62-1.79 (m, 2H), 1.37-1.60 (m, 5H), 0.96 (d, J=5.29 Hz, 3H), 0.13 (s, 9H)

Step 2: 2,2,2-Trifluoro-1-(6-((cis-4-methylcyclohexyl)oxy)-5-(trifluoromethyl)naphthalen-2-yl)ethanol

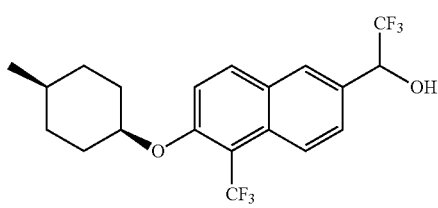 [SMILES: C[C@H]1CC[C@@H](Oc2ccc3cc(C(O)C(F)(F)F)ccc3c2C(F)(F)F)CC1]

The above intermediate was dissolved in DMF (0.5 mL), and added 2N HCl (0.5 mL). The mixture was stirred at rt for 1 h, and then partitioned between EtOAc and water. The organic phase was washed with brine, dried over MgSO$_4$, filtered and concentrated to get the desired alcohol as an oil (148 mg, yield 100%). $^1$H NMR (400 MHz, METHANOL-d$_4$) δ 8.17 (d, J=8.28 Hz, 1H), 8.08 (d, J=9.29 Hz, 1H), 7.98 (s, 1H), 7.67 (d, J=9.04 Hz, 1H), 7.50 (d, J=9.29 Hz, 1H), 5.18 (q, J=7.19 Hz, 1H), 4.90 (br. s., 1H), 1.98-2.12 (m, 2H), 1.69 (t, J=12.93 Hz, 2H), 1.37-1.59 (m, 5H), 0.96 (d, J=5.52 Hz, 3H)

Step 3: 2,2,2-Trifluoro-1-(6-((cis-4-methylcyclohexyl)oxy)-5-(trifluoromethyl)naphthalen-2-yl)ethyl methanesulfonate

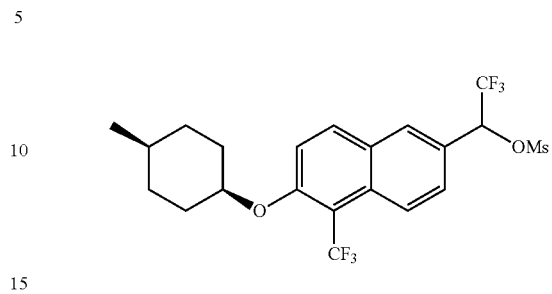

To a solution of 2,2,2-trifluoro-1-(6-((cis-4-methylcyclohexyl)oxy)-5-(trifluoromethyl)naphthalen-2-yl)ethanol (142 mg, 0.349 mmol) and N,N-diisopropylethylamine (182 uL, 1.05 mmol) in dichloromethane (2 mL) was added methanesulfonyl chloride (54 uL, 0.70 mmol) drop-wise. The solution was stirred at rt for 45 min. The mixture was diluted with dichloromethane and washed with sodium bicarbonate aq. solution and water, dried over MgSO$_4$, filtered, and concentrated to get the desired ester as a pale brown oil (171 mg, yield 100%). $^1$H NMR (300 MHz, METHANOL-d$_4$) δ 8.28 (d, J=8.69 Hz, 1H), 8.06-8.21 (m, 2H), 7.72 (d, J=8.69 Hz, 1H), 7.58 (d, J=9.44 Hz, 1H), 6.29 (q, J=6.67 Hz, 1H), 4.95 (br. s., 1H), 3.09 (s, 3H), 2.01-2.14 (m, 2H), 1.72 (t, J=13.03 Hz, 2H), 1.39-1.61 (m, 5H), 0.98 (d, J=5.67 Hz, 3H)

Step 4: Methyl 1-(2,2,2-trifluoro-1-(6-((cis-4-methylcyclohexyl)oxy)-5-(trifluoromethyl)naphthalen-2-yl)ethyl)piperidine-4-carboxylate

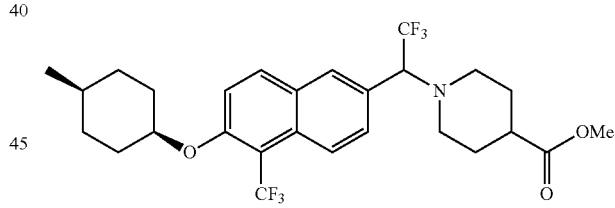

To a mixture of 2,2,2-trifluoro-1-(6-((cis-4-methylcyclohexyl)oxy)-5-(trifluoromethyl)naphthalen-2-yl)ethyl methanesulfonate (42 mg, 0.087 mmol) and piperidine-4-carboxylic acid methyl ester (19 mg, 0.13 mmol) in MeCN (0.6 mL) was added triethylamine (36 uL, 0.26 mmol). The reaction mixture was heated with microwave irritation at 130° C. for a total of 6 hour. The mixture was filtered and purified by HPLC (TFA method) to collect the desired ester as an oil (13 mg, yield 23%). $^1$H NMR (300 MHz, METHANOL-d$_4$) δ 8.16-8.25 (m, 1H), 8.09 (d, J=9.44 Hz, 1H), 7.92 (s, 1H), 7.62 (dd, J=1.70, 9.25 Hz, 1H), 7.53 (d, J=9.44 Hz, 1H), 4.91 (br. s., 1H), 4.68 (q, J=8.94 Hz, 1H), 3.64 (s, 3H), 3.14 (dd, J=3.78, 11.33 Hz, 2H), 2.54-2.69 (m, 1H), 2.25-2.50 (m, 2H), 1.99-2.13 (m, 2H), 1.86-1.98 (m, 2H), 1.61-1.85 (m, 4H), 1.38-1.59 (m, 5H), 0.96 (d, J=5.67 Hz, 3H); LCMS m/z 532.0 [M+H]$^+$

Step 5: 1-(2,2,2-Trifluoro-1-(6-((cis-4-methylcyclohexyl)oxy)-5-(trifluoromethyl)naphthalen-2-yl)ethyl)piperidine-4-carboxylic acid

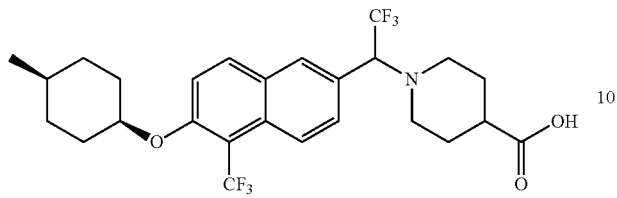

To a solution of above ester (13 mg, 0.020 mmol) in MeOH (0.6 mL) and THF (0.6 mL, 7 mmol) was added 3 M of Sodium hydroxide in Water (0.1 mL). The mixture was heated with at 50° C. for 1 h. It was neutralized with 1N HCl, and purified by HPLC (TFA method) to collect the desired acid as a white powder after lyophilization (9.8 mg, yield 77%). $^1$H NMR (400 MHz, METHANOL-$d_4$) δ 8.20 (d, J=8.28 Hz, 1H), 8.10 (d, J=9.29 Hz, 1H), 7.94 (s, 1H), 7.62 (d, J=8.03 Hz, 1H), 7.53 (d, J=9.29 Hz, 1H), 4.91 (br. s., 1H), 4.71 (q, J=8.28 Hz, 1H), 3.06-3.21 (m, 2H), 2.59-2.74 (m, 1H), 2.38-2.53 (m, 1H), 2.22-2.34 (m, 1H), 2.01-2.12 (m, 2H), 1.88-1.99 (m, 2H), 1.63-1.86 (m, 4H), 1.39-1.58 (m, 5H), 0.96 (d, J=5.52 Hz, 3H); LCMS m/z 518.0 [M+H]$^+$

Example 13

1-((5-(Difluoromethyl)-6-((cis-4-methylcyclohexyl)oxy)naphthalen-2-yl)methyl)piperidine-4-carboxylic acid

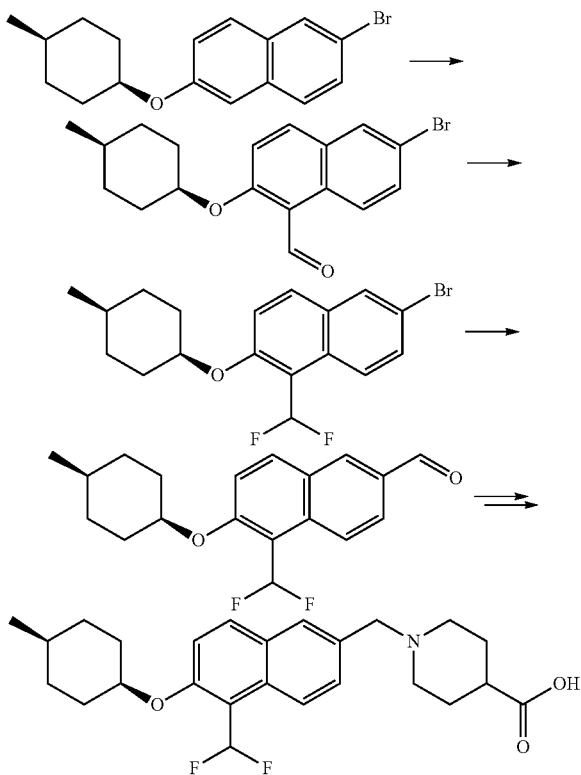

Step 1: 6-bromo-2-((cis-4-methylcyclohexyl)oxy)-1-naphthaldehyde (13.1)

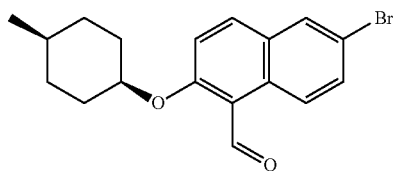 [SMILES: C[C@H]1CC[C@@H](Oc2ccc3cc(Br)ccc3c2C=O)CC1]

To a solution of 2-bromo-6-((cis-4-methylcyclohexyl)oxy)naphthalene (11.1) (35.5 g, 111.6 mmol) in $CH_2Cl_2$ (350 mL) was added a solution of $TiCl_4$ (31.5 g, 167.5 mmol, 1.5 eq) and dichloro(methoxy)methane (14.0 g, 122.8 mmol, 1.1 eq) in $CH_2Cl_2$ (700 mL) at 0° C. After addition, the mixture was stirred at rt for 12 h. 1N HCl (200 mL) was added and the mixture was extracted with $CH_2Cl_2$ (500 mL×2). The organic layers were dried over $Na_2SO_4$, filtered and concentrated to give 6-bromo-2-((cis-4-methylcyclohexyl)oxy)-1-naphthaldehyde as a light yellow solid (38.0 g, yield: 98%), which was used to the next step without further purification.

Step 2: 6-bromo-1-(difluoromethyl)-2-((cis-4-methylcyclohexyl)oxy)naphthalene (13.2)

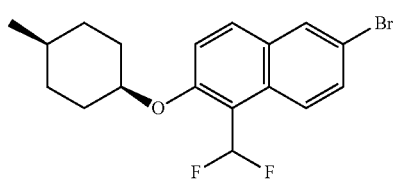 [SMILES: C[C@H]1CC[C@@H](Oc2ccc3cc(Br)ccc3c2C(F)F)CC1]

To a solution of 6-bromo-2-((cis-4-methylcyclohexyl)oxy)-1-naphthaldehyde (12.1) (38.0 g, 109.83 mmol) in DCE (200 mL) was added DAST (106.1 g, 658.98 mmol, 6.0 eq) at rt. The mixture was stirred at 80° C. for 24 h and cooled down. Water (300 mL) was added and the mixture was extracted with $CH_2Cl_2$ (200 mL×2). The combined organic layers were washed with sat. aq. $NaHCO_3$ (200 mL), dried over $Na_2SO_4$, filtered and concentrated. The residue was washed with heptane to give 6-bromo-1-(difluoromethyl)-2-((cis-4-methylcyclohexyl)oxy)naphthalene (13.2) as a white solid (38.0 g, yield: 95%). $^1$H NMR (400 MHz, CDCl$_3$) δ: 8.24 (d, J=9.2 Hz, 1H), 7.93 (d, J=2.0 Hz, 1H), 7.77 (d, J=9.2 Hz, 1H), 7.58 (dd, J=2.0 Hz, 9.2 Hz, 1H), 7.56 (t, J=54.8 Hz, 1H), 7.24 (d, J=9.2 Hz, 1H), 4.72-4.70 (m, 1H), 2.04-2.00 (m, 2H), 1.63-1.54 (m, 5H), 1.35 (m, 2H), 0.96 (d, J=6.4 Hz, 3H).

Step 3: 5-(difluoromethyl)-6-((cis-4-methylcyclohexyl)oxy)-2-naphthaldehyde (13.3)

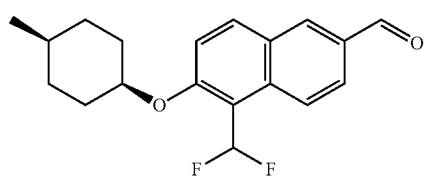 [SMILES: C[C@H]1CC[C@@H](Oc2ccc3cc(C=O)ccc3c2C(F)F)CC1]

To a solution of 6-bromo-1-(difluoromethyl)-2-((cis-4-methylcyclohexyl)oxy)naphthalene (13.2) (17 g, 46.19 mmol) in THF (130 mL) was added ″BuLi (33 mL, 1.6 M, 55.43 mmol, 1.2 eq) dropwise at −78° C. After addition, the mixture was stirred at −78° C. for 30 min. DMF (6.74 g, 92.38 mmol, 2.0 eq) was added to the mixture and stirring continued for 2 hours −78° C. and the reaction was quenched with water (200 mL) and extracted with CH$_2$Cl$_2$ (200 mL×2). The combined organic layers were washed with water (200 mL×2), brine (200 mL×2) and concentrated. The residue was washed with heptane to give 5-(difluoromethyl)-6-((cis-4-methylcyclohexyl)oxy)-2-naphthaldehyde (13.3) as a white solid (12.5 g, yield: 85%). $^1$H NMR (400 MHz, CDCl$_3$) δ: 10.12 (s, 1H), 8.46 (d, J=8.8 Hz, 1H), 8.27 (d, J=1.6 Hz, 1H), 8.03 (d, J=9.2 Hz, 1H), 7.99 (dd, J=2.0 Hz, 8.8 Hz, 1H), 7.59 (t, J=54.8 Hz, 1H), 7.32 (d, J=8.8 Hz, 1H), 4.80-4.78 (m, 1H), 2.07-2.03 (m, 2H), 1.67-1.55 (m, 5H) 1.37-1.33 (m, 2H) 0.97 (d, J=6.4 Hz, 3H). ESI-MS (M+H)$^+$: 319.1.

Step 4: 1-((5-(Difluoromethyl)-6-((cis-4-methylcyclohexyl)oxy)naphthalen-2-yl)methyl)piperidine-4-carboxylic acid

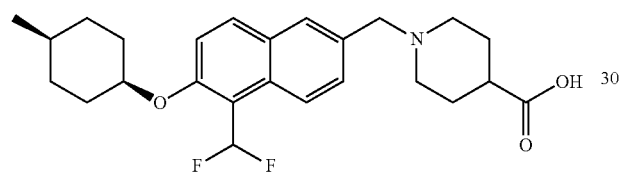

To a solution of 5-(difluoromethyl)-6-((cis-4-methylcyclohexyl)oxy)-2-naphthaldehyde (25 mg, 0.080 mmol), piperidine-4-carboxylic acid methyl ester (16 mg, 0.11 mmol) in THF (0.8 mL) was added sodium triacetoxyborohydride (25 mg, 0.12 mmol), followed by acetic acid (6.8 μL, 0.12 mmol). The reaction mixture was heated with microwave irritation at 100° C. for 20 min. To the above mixture was added MeOH (0.4 mL) and 3 M of NaOH in water (0.3 mL). It was heated with microwave irritation at 100° C. for 10 min, and then neutralized with 1NHCl, and purified by HPLC (TFA method) to collect the desired acid as a white powder after lyophilization (32 mg, yield 73%). $^1$H NMR (400 MHz, METHANOL-d$_4$) δ 8.40 (d, J=8.78 Hz, 1H), 8.06 (d, J=9.04 Hz, 1H), 8.01 (s, 1H), 7.41-7.78 (m, 3H), 4.87-4.92 (m, 1H), 4.46 (s, 2H), 3.39-3.65 (m, 2H), 3.02-3.26 (m, 2H), 2.55-2.74 (m, 1H), 1.77-2.39 (m, 6H), 1.71 (t, J=13.30 Hz, 2H), 1.48-1.63 (m, 3H), 1.25-1.43 (m, 2H), 0.98 (d, J=5.77 Hz, 3H); LCMS m/z 432.0 [M+H]$^+$ Example 14

2-((R)-1-(((5-(trifluoromethyl)-6-(cis-4-(trifluoromethyl)cyclohexyl)oxy)quinolin-2-yl)methyl)piperidin-3-yl)acetic acid

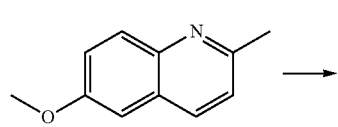

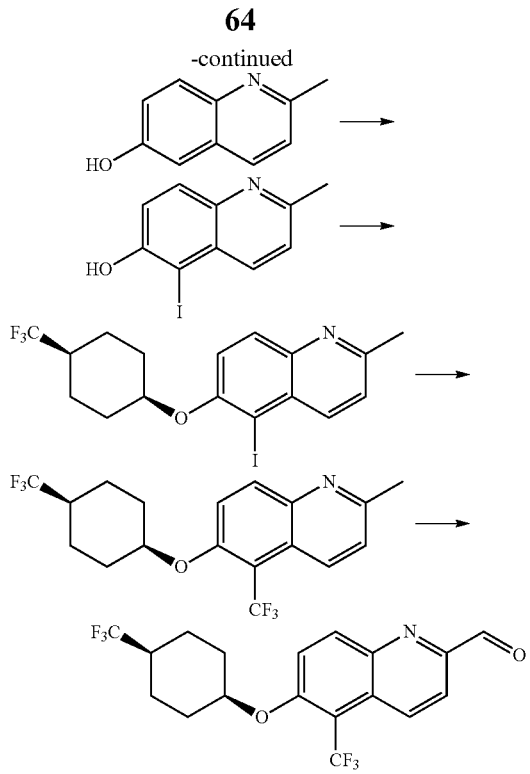

Step 1: 2-Methylquinolin-6-ol (14.1)

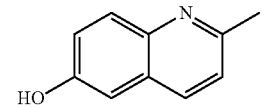

To a solution of 6-methoxy-2-methylquinoline (prepared according to the procedure described in reference: Kitamura et al, J. Syn. Org. Chem. 2003 (15), 2415, which is incorporated by reference in its entirety) (10 g, 57.5 mmol) in 150 mL of dichloromethane was dropwise added a solution of BBr$_3$ (43.1 g, 172.5 mmol) in dichloromethane (100 mL) at −78° C. The mixture was allowed to warm to RT and stirred at RT for 16 h. The reaction was carefully quenched with methanol at 0° C. and the mixture was diluted with saturated aqueous sodium bicarbonate. The aqueous mixture was extracted with ethyl acetate (3×). The combined organics were dried, filtered, and concentrated to give the title compound as a yellow solid (7.2 g). $^1$H NMR (CDCl$_3$, 300 MHz) δ: 7.87-7.81 (m, 2H), 7.20-7.08 (m, 3H), 2.65 (s, 3H).

Step 2: 5-Iodo-2-methylquinolin-6-ol (14.2)

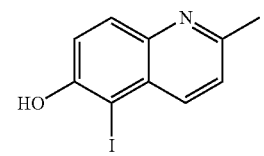

To a solution of 2-methylquinolin-6-ol (14.1) (4.1 g, 27.3 mmol) in dichloromethane (200 mL) was added N-iodosuccinamide (9.2 g, 40.9 mmol) and trifluoroacetic acid (1.9 g, 8.2 mmol). The mixture was stirred at room temperature for 16 h. The mixture was basified with ammonia to pH=7.5, and washed with 100 mL of water. The organic layer was dried and concentrated. The crude was purified by column chromatography on silica gel (petroleum ether/ethyl acetate 8/1) to give the title compound as a yellow solid (4.5 g). $^1$H NMR (DMSO-d6, 300 MHz) δ: 10.76 (s, 1H), 8.16 (d, J=8.7 Hz, 1H), 7.80 (d, J=9.0 Hz, 1H), 7.41 (d, J=9.0 Hz, 1H), 7.40 (d, J=8.7 Hz, 1H), 2.62 (s, 3H).

Step 3: 5-Iodo-2-methyl-6-((cis-4-(trifluoromethyl) cyclohexyl)oxy)quinoline (14.3)

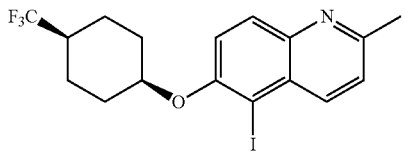 [SMILES: Cc1ccc2c(I)c(O[C@H]3CC[C@@H](C(F)(F)F)CC3)ccc2n1]

The mixture of 5-iodo-2-methylquinolin-6-ol (14.2) (8.0 g, 28 mmol), trans-4-(tert-butyl)cyclohexyl methanesulfonate (6.9 g, 28 mmol, 1.0 eq) and cesium carbonate (9.2 g, 28 mmol) in tert-butanol (100 mL) was heated at 90° C. for 6 h. The mixture was cooled down and filtered. The filtrate was concentrated and the residue was purified by column chromatography on silica gel (petroleum ether/ethyl acetate 20/1) to give the title compound as a white solid (4.9 g). $^1$H NMR (400 MHz, CDCl$_3$) δ: 8.32 (d, J=8.8 Hz, 1H), 7.98 (d, J=8.8 Hz, 1H), 7.36 (d, J=9.2 Hz, 1H), 7.31 (d, J=8.4 Hz, 1H), 4.86 (s, 1H), 2.74 (s, 3H), 2.23-2.19 (m, 2H), 2.17-2.01 (m, 3H), 1.81-1.78 (m, 2H), 1.63-1.57 (m, 2H); ESI-MS (M+H)$^+$: 436.1.

Step 4: 2-Methyl-5-(trifluoromethyl)-6-((cis-4-(trifluoromethyl)cyclohexyl)oxy)quinoline (14.4)

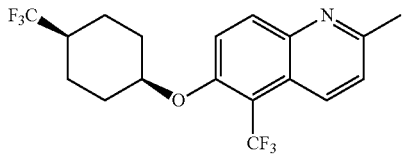 [SMILES: Cc1ccc2c(C(F)(F)F)c(O[C@H]3CC[C@@H](C(F)(F)F)CC3)ccc2n1]

The title compound was synthesized using the same procedure described for compound 1.5 from 5-iodo-2-methyl-6-((cis-4-(trifluoromethyl)cyclohexyl)oxy)quinoline (14.3) to give the title compound as a white solid (40% yield). $^1$H NMR (400 MHz, CDCl$_3$) δ: 8.45 (d, J=8.4 Hz, 1H), 8.17 (d, J=9.2 Hz, 1H), 7.48 (d, J=9.2 Hz, 1H), 7.37 (d, J=8.4 Hz, 1H), 4.86 (s, 1H), 2.73 (s, 3H), 2.25-2.21 (m, 2H), 2.14-2.11 (m, 1H), 1.89-1.78 (m, 4H), 1.68-1.58 (m, 2H); ESI-MS (M+H)$^+$: 378.1.

Step 5: 5-(Trifluoromethyl)-6-((cis-4-(trifluoromethyl)cyclohexyl)oxy)quinoline-2-carbaldehyde (14.5)

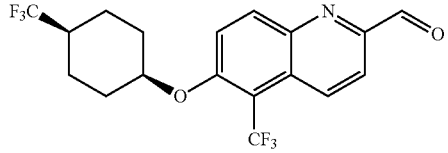 [SMILES: O=Cc1ccc2c(C(F)(F)F)c(O[C@H]3CC[C@@H](C(F)(F)F)CC3)ccc2n1]

To a solution of 2-methyl-5-(trifluoromethyl)-6-((cis-4-(trifluoromethyl)cyclohexyl)oxy)quinoline (14.4) (1 eq.) in dioxane was added SeO$_2$ (2.5 eq.). The mixture was stirred at 100° C. for 1.5 h and concentrated. The residue was purified by column chromatography on silica gel with heptane and ethyl acetate to give the title compound as a yellow solid (yield: 36%). $^1$H NMR (400 MHz, CDCl$_3$) δ: 10.18 (s, 1H), 8.73 (d, J=8.8 Hz, 1H), 8.39 (d, J=9.6 Hz, 1H), 8.08 (d, J=9.6 Hz, 1H), 7.62 (d, J=9.6 Hz, 1H), 4.96 (s, 1H), 2.28-2.24 (m, 2H), 2.19-2.10 (m, 1H), 1.93-1.81 (m, 4H), 1.73-1.65 (m, 2H); ESI-MS (M+H)$^+$: 392.0.

Step 6: 2-((R)-1-(((5-(trifluoromethyl)-6-(cis-4-(trifluoromethyl)cyclohexyl)oxy)quinolin-2-yl)methyl) piperidin-3-yl)acetic acid

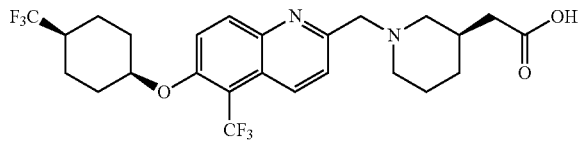 [SMILES: O=C(O)C[C@H]1CCCN(Cc2ccc3c(C(F)(F)F)c(O[C@H]4CC[C@@H](C(F)(F)F)CC4)ccc3n2)C1]

To a mixture of 5-trifluoromethyl-6-(4-trifluoromethyl-cyclohexyloxy)-quinoline-2-carbaldehyde (14.5) (80.0 mg, 0.204 mmol), (R)-ethyl 2-(piperidin-3-yl)acetate hydrochloride (70.02 mg, 0.4089 mmol) in tetrahydrofuran (2.0 mL, 25 mmol) was added sodium triacetoxyborohydride (86.66 mg, 0.4089 mmol) and acetic acid (11.62 uL, 0.2044 mmol). The reaction mixture was heated with microwave at 100° C. for 10 min. The reaction was worked up with EtOAc/water. The organic phase was then separated, dried and concentrated. The crude was then purified by HPLC to give the intermediate ester as a white powder (RT 1.50 min., MH+547.0) which was then dissolved in tetrahydrofuran (1.0 mL, 12 mmol) and methanol (1.0 mL, 25 mmol). 3.0 M of aqueous sodium hydroxide (1.0 mL, 3.0 mmol) was added. The mixture was heated in microwave at 100° C. for 10 min. The reaction was neutralized with 2M HCl. The organic layer was separated, dried, and concentrated. The crude was purified by HPLC to give the title product as a white powder (52 mg, TFA salt). LCMS: RT 1.39 min.; MH+519.0; 1H NMR (400 MHz, METHANOL-d4) d 8.68 (td, J=1.19, 8.91 Hz, 1H), 8.34 (d, J=9.54 Hz, 1H), 7.85 (d, J=9.54 Hz, 1H), 7.61 (d, J=9.29 Hz, 1H), 5.07 (br. s., 1H), 4.67 (br. s., 2H), 3.58-3.93 (m, 2H), 2.80-3.19 (m, 2H), 2.12-2.56 (m, 6H), 1.92-2.09 (m, 3H), 1.69-1.89 (m, 6H), 1.28-1.46 (m, 1H).

Example 15

2,2-dimethyl-3-(((1-(5-(trifluoromethyl)-6-(cis-4-(trifluoromethyl)cyclo-hexyl)oxy)quinolin-2-yl)ethyl)amino)cyclobutanecarboxylic acid

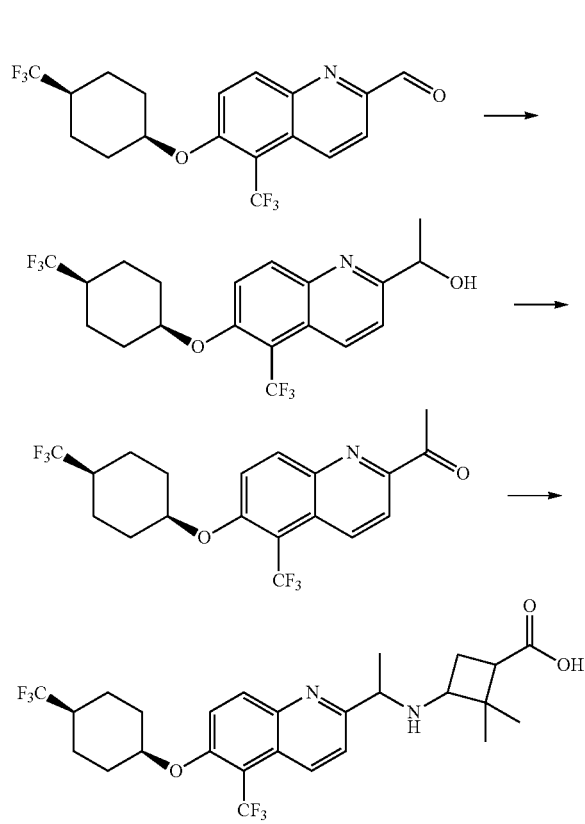

Step 1: 1-(5-(trifluoromethyl)-6-(cis-4-(trifluoromethyl)cyclohexyl)oxy)-quinolin-2-yl)ethanol (15.1)

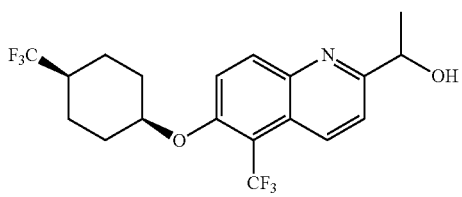 [SMILES: CC(O)c1ccc2c(C(F)(F)F)c(O[C@H]3CC[C@@H](C(F)(F)F)CC3)ccc2n1]

To a solution of 5-trifluoromethyl-6-(4-trifluoromethyl-cyclohexyloxy)-quinoline-2-carbaldehyde (2.9, 200.0 mg, 0.51 mmol) in dry tetrahydrofuran (4.0 mL, 49 mmol) at −78° C. under argon was dropwise added 1.4 M of methyl bromide in toluene/THF (solvent mixture, 75/25) (0.5476 mL, 0.7667 mmol). After stirred at −78° C. for 2 h, allowed the reaction to warm up a little before quenched with saturated ammonium chloride, extracted with ethyl acetate. The organic phase was dried, filtered and concentrated. The crude was purified by ISCO EtOAc/heptane gradient from 0/100 to 100/0) to give the title product as a colorless oil (133 mg). LC-MS: RT 1.53 min.; MH+408.0.

Step 2: 1-(5-(trifluoromethyl)-6-(cis-4-(trifluoromethyl)cyclohexyl)-oxy)quinolin-2-yl)ethanone (15.2)

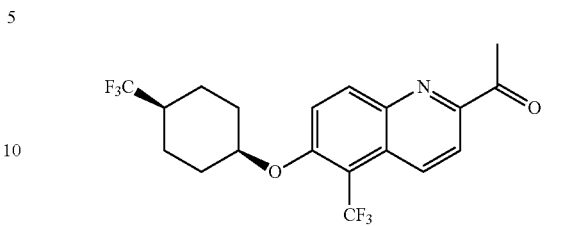

To a solution of 1-[5-Trifluoromethyl-6-(4-trifluoromethyl-cyclohexyloxy)-quinolin-2-yl]-ethanol (3.1, 0.13 g, 0.32 mmol) in acetonitrile (2.00 mL, 38.3 mmol) was added Dess-Martin periodinane (0.271 g, 0.638 mmol). After stirred at RT overnight, the reaction was diluted with ethyl acetate, washed with aqueous Na$_2$S$_2$O$_3$/NaHCO3 (1:1), followed by water, and brine. The organic phase was dried, filtered and concentrated to give the desired product as a white powder (127 mg) which was used in the next step without further purifications. LC-MS: RT 2.16 min.; MH+405.9;

Step 3: 2,2-dimethyl-3-((1-(5-(trifluoromethyl)-6-(cis-4-(trifluoromethyl)cyclo-hexyl)oxy)quinolin-2-yl)ethyl)amino)cyclobutanecarboxylic acid

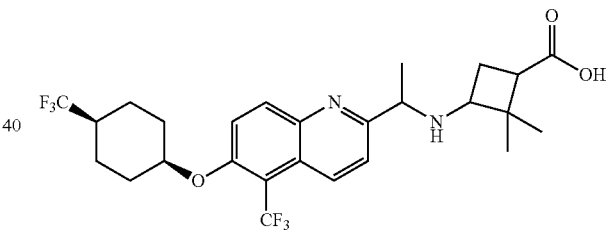

To a mixture of 1-[5-trifluoromethyl-6-(4-trifluoromethyl-cyclohexyloxy)-quinolin-2-yl]-ethanone (5.11, 40.0 mg, 0.10 mmol) and 3-Amino-2,2-dimethyl-cyclobutanecarboxylic acid (28.3 mg, 0.1974 mmol) in methanol (0.5 mL, 10 mmol) and 1,2-dichloroethane (0.5 mL, 6 mmol) was added titanium tetraisopropoxide (33.66 mg, 0.1184 mmol), and the reaction was heated in microwave at 100° C. for 20 min. Cooled down, sodium triacetoxyborohydride (41.8 mg, 0.20 mmol) was then added. The reaction was stirred at RT for 1 h. The reaction was then diluted with ethyl acetate, washed with brine, dried over MgSO4 and concentrated. The crude was purified by HPLC to give the title product as a white powder (8 mg, TFA salt). LCMS: RT 1.50 min.; MH+533.1; 1H NMR (400 MHz, METHANOL-d4) δ 8.69 (d, J=9.04 Hz, 1H), 8.34 (d, J=9.29 Hz, 1H), 7.86 (d, J=9.54 Hz, 1H), 7.65 (d, J=9.29 Hz, 1H), 5.03-5.12 (m, 1H), 4.72 (d, J=7.03 Hz, 1H), 3.54-3.63 (m, 1H), 2.61-2.72 (m, 1H), 2.11-2.39 (m, 4H), 1.91-2.06 (m, 1H), 1.66-1.88 (m, 10H), 1.27-1.39 (m, 6H).

Example 16

2,2-dimethyl-3-((1-(6-(cis-4-methylcyclohexyl)oxy)-5-(trifluoromethyl)naphthalen-2-yl)cyclopropyl)amino)cyclobutanecarboxylic acid

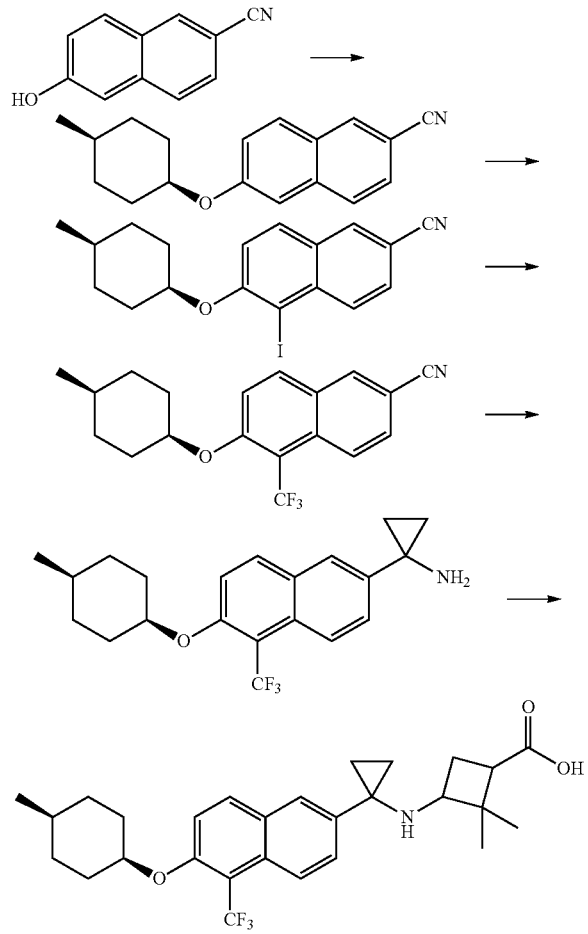

Step 1: 6-hydroxy-2-naphthonitrile (16.1)

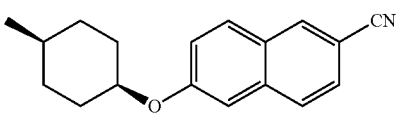 [SMILES: C[C@H]1CC[C@@H](Oc2ccc3cc(C#N)ccc3c2)CC1]

To a solution of 6-hydroxy-naphthalene-2-carbonitrile (5.0 g, 30 mmol) in N,N-dimethylformamide (50 mL) was added cesium carbonate (19.2 g, 59.1 mmol) at rt. Trans-4-methylcyclohexyl methanesulfonate (11.4 g, 59 mmol) was then added in two portions (the second portion was added after heating for 5 h). The reaction mixture was heated at 90° C. overnight. The reaction mixture was diluted with ethyl acetate, washed with aqueous ammonium chloride, brine and water. The organic phase was separate, dried over sulfate, filtered and concentrated. The crude was purified by column chromatography (ethyl acetate/heptane from 0/100 to 30/70) followed by crystallization from cold methanol to give the desired product as a white crystalline solid (6.81 g). LCMS: RT 2.22 min; MH+266.1; 1H NMR (400 MHz, CHLOROFORM-d) δ 8.14 (s, 1H), 7.78 (dd, J=8.78, 18.57 Hz, 2H), 7.56 (dd, J=1.51, 8.53 Hz, 1H), 7.25-7.32 (m, 1H), 7.18 (d, J=2.01 Hz, 1H), 4.72 (br. s., 1H), 2.02-2.18 (m, 2H), 1.34-1.75 (m, 7H), 0.99 (d, J=5.77 Hz, 3H).

Step 2: 5-iodo-6-(cis-4-methylcyclohexyl)oxy)-2-naphthonitrile (16.2)

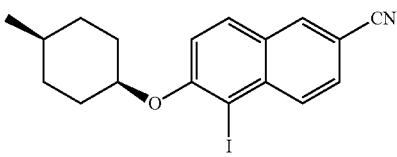 [SMILES: C[C@H]1CC[C@@H](Oc2ccc3cc(C#N)ccc3c2I)CC1]

To a solution of 6-hydroxy-2-naphthonitrile (5.1) (6.70 g, 25.2 mmol) in methylene chloride (150 mL) was added N-iodosuccinimide (6.82 g, 30.3 mmol) and zirconium tetrachloride (1.18 g, 5.05 mmol) under argon. The reaction mixture was stirred at room temperature under argon for 1 h, HPLC showed complete conversion. The reaction was diluted with methylene chloride, washed with aqueous sodium thiosulfate, aqueous sodium bicarbonate, and water. The organic phase was then dried over sulfate, concentrated. The crude was then re-crystallized from cold methanol to give the title compound as a light yellow powder (9.13 g). LCMS: RT 2.39 min.; MH+392.0; $^1$H NMR (400 MHz, CHLOROFORM-d) δ 8.23 (d, J=8.78 Hz, 1H), 8.11 (br. s., 1H), 7.83 (d, J=9.04 Hz, 1H), 7.63 (d, J=8.78 Hz, 1H), 7.22-7.32 (m, 1H), 4.87 (br. s., 1H), 2.07 (d, J=6.02 Hz, 2H), 1.44-1.73 (m, 7H), 0.92-1.08 (m, 3H).

Step 3: 6-(cis-4-methylcyclohexyl)oxy)-5-(trifluoromethyl)-2-naphthonitrile (16.3)

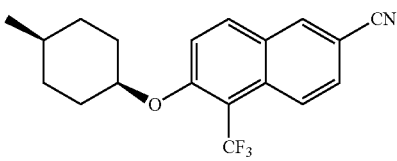 [SMILES: C[C@H]1CC[C@@H](Oc2ccc3cc(C#N)ccc3c2C(F)(F)F)CC1]

A solution of 5-iodo-6-(cis-4-methylcyclohexyl)oxy)-2-naphthonitrile (6.2) (9.0 g, 23 mmol), hexamethylphosphoramide (19.2 mL, 109 mmol) in N,N-dimethylformamide (100 mL) was degassed with argon. To this was added copper(I) iodide (7.48 g, 39.3 mmol) and methyl fluorosulphonyldifluoroacetate (14.3 mL, 109 mmol) and the reaction was stirred at 90° C. under an atmosphere of argon for 2 h. LCMS showed complete conversion (RT=2.32 min, MH+334.1). The reaction mixture was diluted with ethyl acetate, filtered off the solid, and the filtrate was washed with brine, and water. The organic layer was then separated, dried, concentrated. The crude was re-crystallized from cold methanol to give the product as a white powder (6.4 g). LCMS: RT 2.31 min; MH+334.1: $^1$H NMR (400 MHz, METHANOL-d$_4$) δ 8.37 (d, J=1.76 Hz, 1H), 8.25-8.30 (m, 1H), 8.18 (d, J=9.54 Hz, 1H), 7.74 (dd, J=1.88, 9.16 Hz, 1H), 7.64 (d, J=9.29 Hz, 1H), 4.98 (t, J=2.76 Hz, 1H), 1.98-2.12 (m, 2H), 1.64-1.78 (m, 2H), 1.34-1.60 (m, 5H), 0.96 (d, J=6.02 Hz, 3H); 19F NMR (376 MHz, METHANOL-d4) d ppm −53.72 (s, 3 F).

Step 4: 1-(6-(cis-4-methylcyclohexyl)oxy)-5-(trifluoromethyl)naphthalen-2-yl)-cyclopropanamine (16.4)

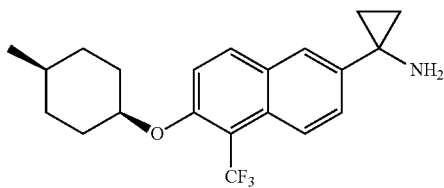 [SMILES: C[C@H]1CC[C@@H](Oc2ccc3cc(C4(N)CC4)ccc3c2C(F)(F)F)CC1]

According to the procedure described in the article in JOC, 2003, 68, 7133, by Philippe Bertus and Jan Szymoniak, which is incorporated by reference in its entirety. A solution of 6-(cis-4-methylcyclohexyl)oxy)-5-(trifluoromethyl)-2-naphthonitrile (5.3) (1.00 g, 3.00 mmol) and titanium tetraisopropoxide (1.0 mL, 3.3 mmol) in ether (15.0 mL) was cooled to −70° C. To this was added 3.0 M of ethyl bromide in ether (2.2 mL, 6.6 mmol) over 5 min. and the reaction was stirred at −78° C. for 10 min., then warmed to RT over 1.5 h. Boron trifluoride etherate (0.8 mL, 6.00 mmol) was then added over 5 min., the reaction was then stirred at RT for another 1.5 h. 1.0 M of hydrogen chloride in water (9.0 mL, 9.0 mmol) and ether (25.0 mL) were added to the reaction mixture, and the whole was poured into aqueous 10% sodium hydroxide solution (30 ml). The product was extracted with ether (2×50 ml). The organic layer was then separated, dried over sodium sulfate, concentrated. The crude was purified by column (ISCO ethyl acetate/heptane gradient 10/90 to 100/0) to give the product as yellow oil (0.55 g) (solidified upon standing). LCMS: RT 1.53 min; MH+364.2 (major fragment —NH2, mass 347); $^1$H NMR (400 MHz, CHLOROFORM-d) δ 8.15 (d, J=8.03 Hz, 1H), 7.87 (d, J=9.04 Hz, 1H), 7.74 (d, J=1.76 Hz, 1H), 7.39 (dd, J=2.13, 9.16 Hz, 1H), 7.28 (s, 1H), 4.74 (br. s., 1H), 2.05 (d, J=15.56 Hz, 2H), 1.55-1.68 (m, 2H), 1.49 (br. s., 5H), 1.04-1.19 (m, 4H), 0.95 (d, J=4.77 Hz, 3H).

Step 5: 2,2-dimethyl-3-((1-(6-(cis-4-methylcyclohexyl)oxy)-5-(trifluoromethyl)naphthalen-2-yl)cyclopropyl)amino)cyclobutanecarboxylic acid

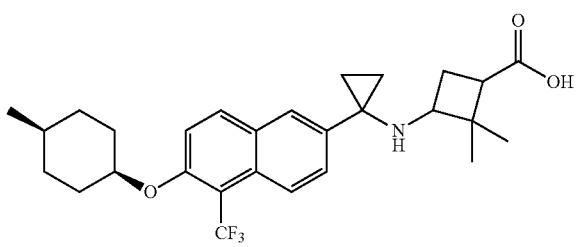 [SMILES: CC1(C)C(NC2(c3ccc4c(C(F)(F)F)c(O[C@H]5CC[C@@H](C)CC5)ccc4c3)CC2)CC1C(=O)O]

To a mixture of 2,2-Dimethyl-3-oxo-cyclobutanecarboxylic acid methyl ester (52 mg, 0.33 mmol) and 1-(6-(cis-4-methylcyclohexyl)oxy)-5-(trifluoromethyl)naphthalen-2-yl)-cyclopropanamine (5.4) (80 mg, 0.22 mmol) in tetrahydrofuran (2 mL) was added acetic acid (25 uL, 0.44 mmol), sodium triacetoxyborohydride (93 mg, 0.44 mmol) and titanium tetraisopropoxide (0.13 mL, 0.44 mmol), and the reaction was heated in microwave at 100° C. for 20 min. LCMS showed formation of desired ester intermediate (RT 1.72 min, MH+504.3). Worked up with ethyl acetate and brine, the organic phase was dried over magnesium sulfate and concentrated. The crude was purified by HPLC to give the ester intermediate as a white powder. The ester was then dissolved in tetrahydrofuran (1.0 mL) and methanol (1.0 mL), treated with 3.0 M of sodium hydroxide in water (1.0 mL), heated in microwave at 100° C. for 10 min., acidified with 2N HCl, the organic phase was dried and concentrated. The crude was purified by HPLC to give the title compound as a white powder (12 mg). LCMS: RT 1.60 min.; MH+490.3; $^1$H NMR (400 MHz, METHANOL-d$_4$) δ 8.26 (d, J=8.78 Hz, 1H), 8.07-8.17 (m, 2H), 7.78 (dd, J=2.01, 9.04 Hz, 1H), 7.58 (d, J=9.29 Hz, 1H), 4.94 (br. s., 1H), 3.56 (dd, J=7.91, 9.66 Hz, 1H), 2.57-2.70 (m, 1H), 1.96-2.12 (m, 3H), 1.81-1.95 (m, 1H), 1.70 (t, J=13.18 Hz, 2H), 1.34-1.60 (m, 9H), 1.13 (d, J=15.31 Hz, 6H), 0.96 (d, J=5.52 Hz, 3H).

Example 17

4-Acetamido-4-(5-(trifluoromethyl)-6-(cis-4-(trifluoromethyl)cyclo-hexyl)oxy)naphthalen-2-yl)pentanoic acid

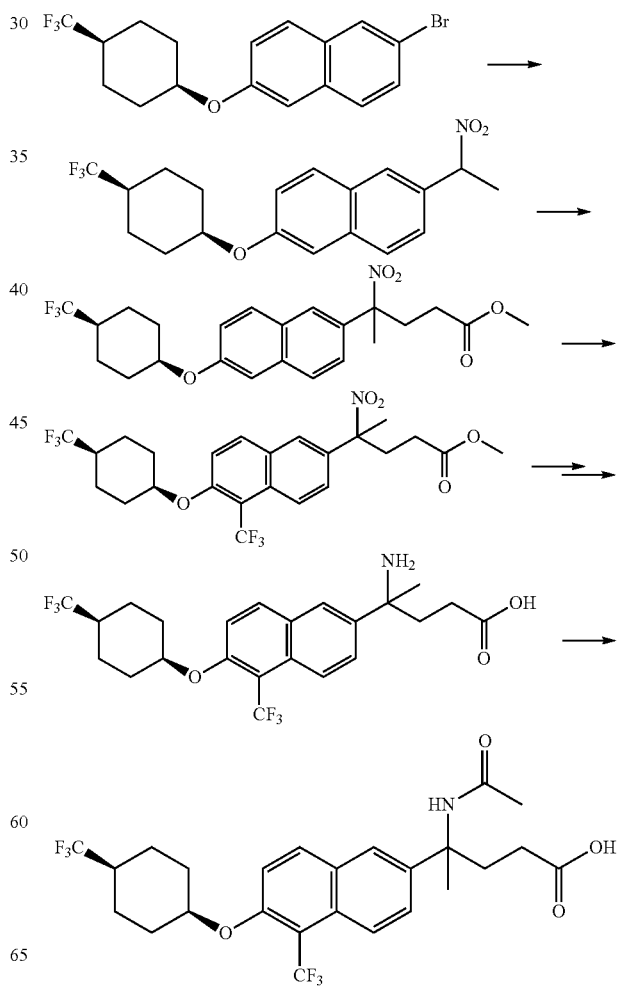

Step 1: 2-Bromo-6-(cis-4-(trifluoromethyl)cyclohexyl)oxy)naphthalene (17.1)

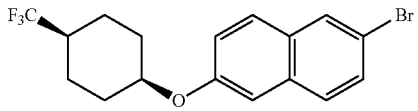 [SMILES: FC(F)(F)[C@H]1CC[C@@H](Oc2ccc3cc(Br)ccc3c2)CC1]

A mixture of 6-bromonaphthalen-2-ol (5.0 g, 22 mmol), 4-trifluoromethyl-cyclohexanol (4.52 g, 26.9 mmol) and triphenylphosphine (7.05 g, 26.9 mmol) in toluene (50 mL) was heated to reflux. When all the starting material dissolved, diisopropyl azodicarboxylate (5.3 mL, 26.9 mmol) was added slowly (keep refluxing smoothly). Keep heating at reflux (heating temp. 125° C.) overnight. The solvent was then evaporated under vacuo. The residue was dissolved in a mixture of ethyl acetate and heptane (30:70), washed with brine. The organic layer was then dried and concentrated. The white solid formed was then filtered off. The filtrate was then concentrated and loaded on silica gel, purified on ISCO column chromatography using 0-10% ethyl acetate in heptane as eluent to give the cis-isomer 17.1 (1.77 g, identified by NMR) and the trans-isomer (1.28 g). For cis-isomer: LCMS RT 2.36 min; MH+373.10; $^1$H NMR (400 MHz, CHLOROFORM-d) δ 7.92 (s, 1H), 7.68 (d, J=8.78 Hz, 1H), 7.55-7.61 (m, 1H), 7.47-7.53 (m, 1H), 7.20 (dd, J=2.26, 9.04 Hz, 1H), 7.13 (d, J=1.76 Hz, 1H), 4.73 (br. s., 1H), 2.01-2.33 (m, 3H), 1.72-1.92 (m, 4H), 1.56-1.67 (m, 2H). For trans-isomer: LCMS RT 2.33 min.; MH+373.00; $^1$H NMR (400 MHz, CHLOROFORM-d) δ 7.92 (s, 1H), 7.66 (d, J=8.78 Hz, 1H), 7.55-7.61 (m, 1H), 7.47-7.54 (m, 1H), 7.09-7.17 (m, 2H), 4.26-4.41 (m, 1H), 2.36 (br. s., 2H), 2.10 (d, J=7.28 Hz, 3H), 1.44-1.54 (m, 4H).

Step 2: 2-(1-Nitroethyl)-6-(cis-4-(trifluoromethyl)cyclohexyl)oxy)naphthalene (17.2)

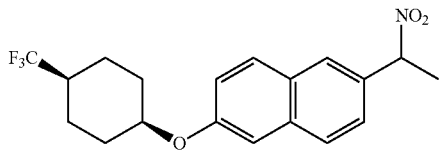 [SMILES: CC(c1ccc2cc(O[C@H]3CC[C@@H](C(F)(F)F)CC3)ccc2c1)[N+](=O)[O-]]

According to the procedure described in reference: Vogl, Erasmus M.; Buchwald, Stephen L. *J. Org. Chem.*, 2002, 67, 106, which is incorporated by reference in its entirety, a mixture of 2-bromo-6-(cis-4-(trifluoromethyl)cyclohexyl)oxy)naphthalene (17.1) (1.50 g, 4.0 mmol), tris(dibenzylideneacetone)dipalladium(0) (360 mg, 0.4 mmol) and 2-(di-t-butylphosphino)-2'-methylbiphenyl (0.51 g, 1.6 mmol), cesium carbonate (1.56 g, 4.8 mmol) 1,2-dimethoxyethane (30 mL) was degassed with argon. The reaction was stirred under argon and nitroethane (0.6 mL, 8.0 mmol) was added. The mixture was then stirred vigorously and heated at 50° C. for 3 h. The reaction mixture was quenched with aqueous ammonium chloride, diluted with ethyl acetate. The solid formed was filtered off. The filtrate was washed with brine, dried over magnesium sulfate, filtered and evaporated. The residue was purified by ISCO column chromatography (0-30% ethyl acetate/heptane), followed by crystallization from methanol to give the title compound as a white powder (0.59 g). LCMS: RT 2.13 min, MH+368.1; $^1$H NMR (400 MHz, CHLOROFORM-d) δ 7.85 (s, 1H), 7.77 (dd, J=8.91, 18.20 Hz, 2H), 7.53 (dd, J=1.63, 8.66 Hz, 1H), 7.23 (dd, J=2.38, 8.91 Hz, 1H), 7.17 (d, J=2.01 Hz, 1H), 5.76 (q, J=6.94 Hz, 1H), 4.67-4.82 (m, 1H), 2.25 (d, J=14.81 Hz, 2H), 2.07-2.20 (m, 1H), 1.99 (d, J=6.78 Hz, 3H), 1.74-1.91 (m, 4H), 1.56-1.69 (m, 2H).

Step 3: Methyl 4-nitro-4-(6-(cis-4-(trifluoromethyl)cyclohexyl)oxy)naphthalen-2-yl)pentanoate (17.3)

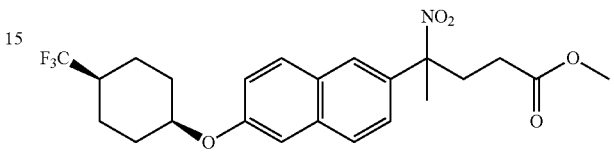

To a mixture of potassium carbonate (370 mg, 2.68 mmol), tetrabutylammonium hydrogen sulfate (50 mg, 0.15 mmol) and N,N-dimethylformamide (10 mL) was added 2-(1-nitroethyl)-6-(cis-4-(trifluoromethyl)cyclohexyl)oxy) naphthalene (17.2) (0.78 g, 2.1 mmol). The mixture was stirred at RT, and methyl acrylate (0.24 mL, 2.66 mmol) was added. The reaction was then stirred at RT overnight. Ethyl acetate was added and the solution was washed with saturated ammonium chloride, then brine. The organics were dried over magnesium sulfate, filtered, concentrated. The residue was purified by ISCO column chromatography (0-30% ethyl acetate in heptane) to give the title compound as a colorless thick oil (0.81 g). LCMS: RT 2.15 min.; MH+454 not seen, observed 407.20 (M-NO2) and 476.20 (M+Na). $^1$H NMR (400 MHz, CHLOROFORM-d) δ 7.78 (dd, J=3.51, 5.27 Hz, 2H), 7.72 (d, J=8.78 Hz, 1H), 7.40 (dd, J=2.01, 8.78 Hz, 1H), 7.23 (dd, J=2.38, 8.91 Hz, 1H), 7.15 (d, J=2.01 Hz, 1H), 4.69-4.80 (m, 1H), 3.66 (s, 3H), 2.70-2.95 (m, 2H), 2.20-2.38 (m, 4H), 2.13 (ddd, J=3.51, 7.34, 11.48 Hz, 1H), 2.06 (s, 3H), 1.72-1.91 (m, 4H), 1.59-1.67 (m, 2H).

4: Methyl 4-(5-iodo-6-(cis-4-(trifluoromethyl)cyclohexyl)oxy)naphthalen-2-yl)-4-nitropentanoate (17.4)

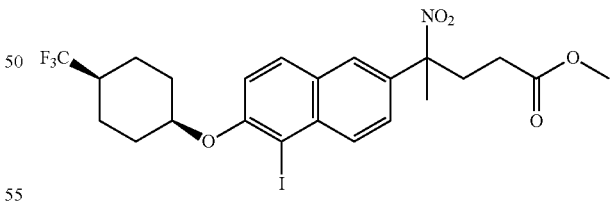

To a solution of methyl 4-nitro-4-(6-(cis-4-(trifluoromethyl)cyclohexyl)oxy)naph-thalen-2-yl)pentanoate (17.3) (0.80 g, 1.8 mmol) in methylene chloride (20 mL) was added N-iodosuccinimide (600 mg, 2.7 mmol) and zirconium tetrachloride (61.7 mg, 0.27 mmol) under argon. The reaction mixture was stirred at room temperature under argon for 5 h. The solid was then filtered off, and the filtrate was concentrated and purified by ISCO column chromatography using 0-50% ethyl acetate in heptane as eluent to give the title compound as light yellow oil (0.73 g). HPLC: RT 2.25 min.; LCMS: RT 2.27 min.; MH+580 not observed. Only see 533.1 (M-NO2) and 602.10 (M+23). ¹H NMR (400 MHz, CHLOROFORM-d) δ 8.18 (d, J=9.04 Hz, 1H), 7.81 (d, J=9.04 Hz, 1H), 7.74 (d, J=2.01 Hz, 1H), 7.49 (dd, J=2.01, 9.04 Hz, 1H), 7.21 (d, J=9.04 Hz, 1H), 4.89 (br. s., 1H), 3.58-3.74 (m, 3H), 2.68-2.97 (m, 2H), 2.33 (t, J=8.16 Hz, 2H), 2.06-2.26 (m, 8H), 1.80 (d, J=10.79 Hz, 2H), 1.56-1.67 (m, 2H).

Step 5: Methyl 4-nitro-4-(5-(trifluoromethyl)-6-(cis-4-(trifluoromethyl)cyclo-hexyl)oxy)naphthalen-2-yl)pentanoate (17.5)

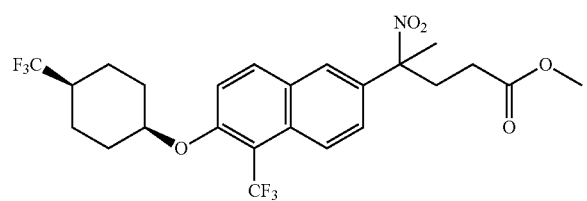 [SMILES: COC(=O)CCC(C)(c1ccc2c(C(F)(F)F)c(O[C@H]3CC[C@@H](C(F)(F)F)CC3)ccc2c1)[N+](=O)[O-]]

A solution of methyl 4-(5-iodo-6-(cis-4-(trifluoromethyl)cyclohexyl)oxy)naphtha-len-2-yl)-4-nitropentanoate (17.4) (0.72 g, 1.2 mmol), hexamethylphosphoramide (1.1 mL, 6.21 mmol) in N,N-dimethylformamide (6.0 mL) was degassed with argon. To this was added copper(I) iodide (0.425 g, 2.23 mmol) and methyl fluorosulphonyldifluoroacetate (0.82 mL, 6.21 mmol), and the reaction was stirred at 80° C. under an atmosphere of argon for 18 hours. The reaction was diluted with ethyl acetate. The solid was filtered off. The filtrate was washed with water (5×). The organic layer was then dried, concentrated. The crude was purified by silica gel chromatography (ISCO) using 0-60% ethyl acetate in heptane as eluent to give the title compound as a light yellow thick oil (0.54 g). LCMS: RT 2.21 min; MH+ not seen, only showing 475.2 (M-NO2), 544.2 (M+Na). ¹H NMR (400 MHz, CHLOROFORM-d) δ 8.26 (d, J=9.29 Hz, 1H), 7.97 (d, J=9.29 Hz, 1H), 7.79 (d, J=2.01 Hz, 1H), 7.53 (dd, J=2.13, 9.41 Hz, 1H), 7.33 (d, J=9.04 Hz, 1H), 4.87 (br. s., 1H), 3.67 (s, 3H), 2.69-2.95 (m, 2H), 2.34 (t, J=8.03 Hz, 2H), 2.22 (d, J=14.81 Hz, 2H), 2.13 (dtd, J=4.02, 8.06, 16.00 Hz, 2H), 1.74-1.96 (m, 4H), 1.58-1.70 (m, 2H).

Step 6: 4-nitro-4-(5-(trifluoromethyl)-6-(cis-4-(trifluoromethyl)cyclohexyl)oxy)naphthalen-2-yl)pentanoic acid (17.6)

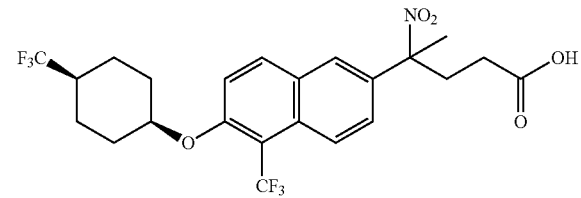 [SMILES: CC(CCC(=O)O)(c1ccc2c(C(F)(F)F)c(O[C@H]3CC[C@@H](C(F)(F)F)CC3)ccc2c1)[N+](=O)[O-]]

To a solution of methyl 4-nitro-4-(5-(trifluoromethyl)-6-(cis-4-(trifluoromethyl)cyclohexyl)oxy)naphthalen-2-yl)pentanoate (7.5) (0.54 g, 1.0 mmol) in methanol (4.0 mL) and tetrahydrofuran (4.0 mL) was added 2 M of lithium hydroxide, monohydrate in Water (4.0 mL, 8.0 mmol). The mixture was stirred at RT for 1 h. The mixture was concentrated under vacuum. The resulting product was diluted in methylene chloride and washed with 1N HCl. The combined organic phases were dried over sodium sulfate, filtered and concentrated to give the title compound as light yellow thick oil (0.58 g) which was used in the next step without further purifications. LCMS: RT 2.01 min.; MH+ not seen. Only showing 461.2 (M-NO2). ¹H NMR (400 MHz, CHLOROFORM-d) δ 8.27 (d, J=9.04 Hz, 1H), 7.97 (d, J=9.29 Hz, 1H), 7.78 (d, J=2.01 Hz, 1H), 7.52 (dd, J=2.13, 9.41 Hz, 1H), 7.33 (d, J=9.29 Hz, 1H), 4.87 (br. s., 1H), 2.70-2.95 (m, 2H), 2.32-2.47 (m, 2H), 1.99-2.29 (m, 6H), 1.73-1.96 (m, 4H), 1.56-1.70 (m, 2H).

Step 7: 4-Amino-4-(5-(trifluoromethyl)-6-(cis-4-(trifluoromethyl)cyclohexyl)oxy)naphthalen-2-yl)pentanoic acid (17.7)

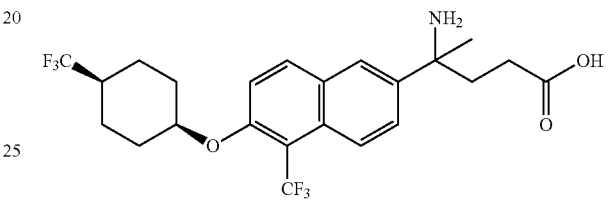

To a solution of 4-nitro-4-(5-(trifluoromethyl)-6-(cis-4-(trifluoromethyl)cyclohexyl)oxy)naphthalen-2-yl)pentanoic acid (17.6) (0.36 g, 0.71 mmol) in acetic acid (5.0 mL, 88 mmol) at RT was added zinc (0.618 g, 9.45 mmol). The mixture was stirred at room temperature overnight. The mixture was diluted with ethyl acetate, filtered off the solid, and filtrate was concentrated to dryness under reduced pressure. The crude was purified by preparative HPLC to give the title compound as a white powder (206 mg). LCMS: RT 1.36 min, MH+478.20, also showing 461.10 (M-NH2). ¹H NMR (400 MHz, DMSO-d₆) δ 8.49-8.68 (m, 2H), 8.23 (d, J=9.29 Hz, 1H), 8.14 (d, J=8.03 Hz, 1H), 8.05 (d, J=1.76 Hz, 1H), 7.78 (dd, J=2.01, 9.29 Hz, 1H), 7.71 (d, J=9.54 Hz, 1H), 5.11 (br. s., 1H), 2.44 (d, J=8.28 Hz, 1H), 2.21-2.34 (m, 2H), 1.94-2.19 (m, 4H), 1.55-1.80 (m, 9H).

Step 8: 4-Acetamido-4-(5-(trifluoromethyl)-6-(cis-4-(trifluoromethyl)cyclo-hexyl)oxy)naphthalen-2-yl)pentanoic acid

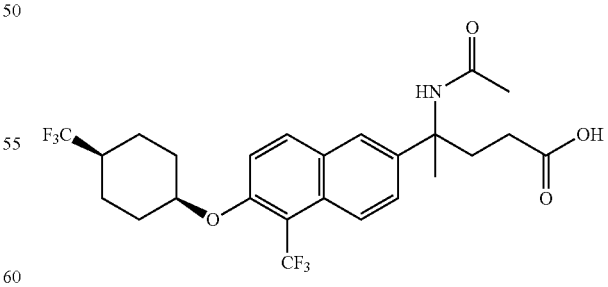

To a solution of 4-amino-4-(5-(trifluoromethyl)-6-(cis-4-(trifluoromethyl)cyclo-hexyl)oxy)naphthalen-2-yl) pentanoic acid (17.7) (80 mg, 0.2 mmol) in methylene chloride (1.6 mL) was dropwise added acetyl chloride (14.3 uL, 0.20 mmol) at 0° C. The solution was stirred from 0° C. to RT over 20 min. The mixture was diluted with methylene chloride and washed successively with citric acid (5% in water), sodium bicarbonate aqueous solution and water, dried over magnesium sulfate, filtered, concentrated. The crude was purified by HPLC to give the title compound as a white powder (5.5 mg). LCMS RT 1.74 min; MH+520.20; $^1$H NMR (400 MHz, DICHLOROMETHANE-d$_2$) δ 8.17 (d, J=8.28 Hz, 1H), 7.98 (d, J=9.29 Hz, 1H), 7.72 (d, J=1.76 Hz, 1H), 7.53 (dd, J=2.01, 9.29 Hz, 1H), 7.32 (d, J=9.29 Hz, 1H), 6.65 (s, 1H), 4.87 (br. s., 1H), 2.10-2.48 (m, 7H), 2.05 (s, 3H), 1.71-1.92 (m, 7H), 1.56-1.70 (m, 2H).

Example 18

(3-(6-((3,5-dichlorobenzyl)oxy)-5-(trifluoromethyl)-2-naphthamido)propyl)phosphonic acid

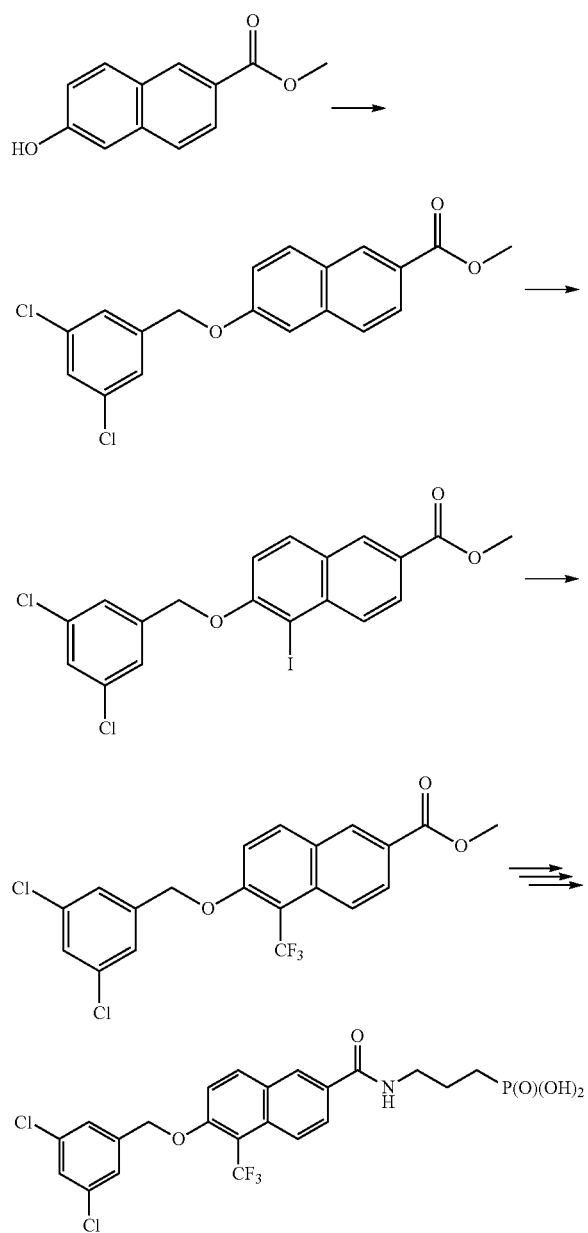

Step 1: Methyl 6-((3,5-dichlorobenzyl)oxy)-2-naphthoate (18.1)

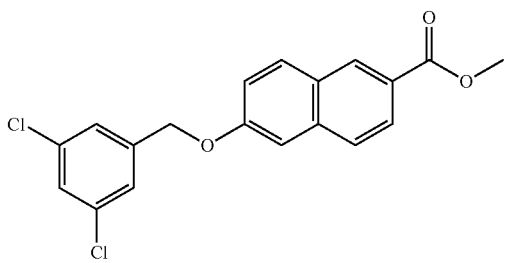 [SMILES: COC(=O)c1ccc2cc(OCc3cc(Cl)cc(Cl)c3)ccc2c1]

Potassium carbonate (3.28 g, 23.7 mmol) was added to a solution of 6-hydroxy-naphthalene-2-carboxylic acid methyl ester (2.00 g, 9.89 mmol) in N,N-dimethyl-formamide (25 mL), followed by 1,3-dichloro-5-chloromethyl-benzene (2.51 g, 12.8 mmol). Stirred at 50° C. for 1 h. Cooled to rt and diluted with ethyl acetate and washed with water (5×). The organics were dried and concentrated. The white solid was then washed with ethyl acetate and dried to give the title compound as a white powder (1.74 g). LCMS: RT 2.27 min; MH+361. $^1$H NMR (300 MHz, CHLOROFORM-d) δ 8.51-8.59 (m, 1H), 8.05 (dd, J=1.51, 8.69 Hz, 1H), 7.90 (d, J=8.69 Hz, 1H), 7.76 (d, J=8.31 Hz, 1H), 7.39 (d, J=1.89 Hz, 2H), 7.33-7.37 (m, 1H), 7.30 (d, J=2.64 Hz, 1H), 7.20 (d, J=2.27 Hz, 1H), 5.16 (s, 2H), 3.93-4.03 (m, 3H).

Step 2: Methyl 6-((3,5-dichlorobenzyl)oxy)-5-iodo-2-naphthoate (18.2)

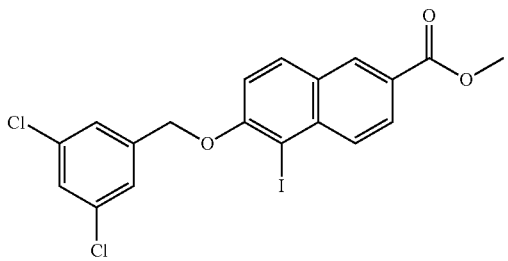 [SMILES: COC(=O)c1ccc2c(I)c(OCc3cc(Cl)cc(Cl)c3)ccc2c1]

The title compound was prepared according to the procedure described for 5-iodo-6-(cis-4-(trifluoromethyl)cyclohexyl)oxy)-2-naphthaldehyde (1.4) as a white solid in 94% yield. $^1$H NMR (300 MHz, CHLOROFORM-d) δ 8.52 (d, J=1.51 Hz, 1H), 8.19-8.26 (m, 1H), 8.09-8.16 (m, 1H), 7.94 (d, J=9.06 Hz, 1H), 7.49 (d, J=1.89 Hz, 2H), 7.36 (t, J=1.89 Hz, 1H), 7.22 (d, J=9.06 Hz, 1H), 5.28 (s, 2H), 4.00 (s, 3H).

Step 3: Methyl 6-((3,5-dichlorobenzyl)oxy)-5-(trifluoromethyl)-2-naphthoate (18.3)

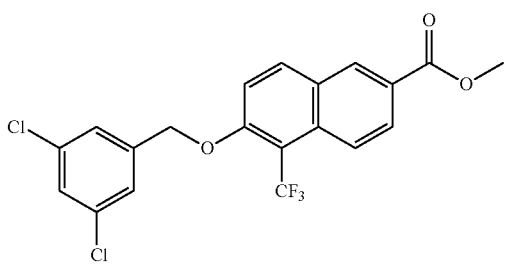 [SMILES: COC(=O)c1ccc2c(C(F)(F)F)c(OCc3cc(Cl)cc(Cl)c3)ccc2c1]

The title compound was prepared according to the procedure described for 5-(trifluoromethyl)-6-((cis-4-(trifluoromethyl)cyclohexyl)oxy)-2-naphthaldehyde (1.5) as a white solid in 92% yield. LCMS: RT 2.37 min, MH+429. $^1$H NMR (400 MHz, CHLOROFORM-d) δ 8.57 (d, J=1.51 Hz, 1H), 8.31 (d, J=9.04 Hz, 1H), 8.15 (dd, J=1.76, 9.29 Hz, 1H), 8.10 (d, J=9.04 Hz, 1H), 7.32-7.41 (m, 4H), 5.26 (s, 2H), 3.96-4.04 (m, 3H).

Step 4: (3-(6-((3,5-dichlorobenzyl)oxy)-5-(trifluoromethyl)-2-naphthamido)propyl)phosphonic acid

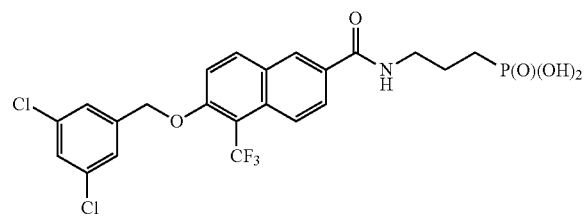

To a solution of methyl 6-((3,5-dichlorobenzyl)oxy)-5-(trifluoromethyl)-2-naphthoate (18.3) (0.50 g, 1.2 mmol) in methanol (5.0 mL) and tetrahydrofuran (25 mL) was added 1 M of lithium hydroxide in water (9.0 mL, 9.0 mmol). The mixture was stirred at RT for 2 h. LCMS showed no starting material left. The mixture was concentrated under vacuum. The resulting product was diluted in ethyl acetate and washed with 1N HCl. The combined organic phases were concentrated. The solid formed was washed with cold methanol to give the corresponding carboxylic acid as a white solid (0.46 g) which was used in the next step without further purifications. $^1$H NMR (400 MHz, DMSO-d$_6$) δ 8.68 (d, J=1.51 Hz, 1H), 8.49 (d, J=9.29 Hz, 1H), 8.16-8.23 (m, 1H), 8.08-8.15 (m, 1H), 7.77 (d, J=9.29 Hz, 1H), 7.63 (d, J=1.76 Hz, 1H), 7.56 (d, J=1.76 Hz, 2H), 5.49 (s, 2H).

A solution of the above 6-((3,5-dichlorobenzyl)oxy)-5-(trifluoromethyl)-2-naphthoic acid (80.0 mg, 0.19 mmol) in N,N-dimethylformamide (5 mL) was stirred at RT for 15 min. N,N-Diisopropylethylamine (0.0671 mL, 0.000385 mol) and N,N,N',N'-Tetramethyl-O-(7-azabenzotriazol-1-yl) uronium Hexafluorophosphate (102 mg, 0.000270 mol) were then added and the solution stirred for another hour. (3-Amino-propyl)-phosphonic acid diethyl ester (37.6 mg, 0.19 mmol) was then added, and the reaction was stirred at RT for 2 h. Diluted with ethyl acetate, washed with brine (2×), and then water (3×). The organic layer was separated, dried and concentrated to give an orange crystal (101 mg) which was used in the next step without further purifications. LCMS: RT 2.00 min, MH+592. 1H NMR (400 MHz, CHLOROFORM-d) δ 8.42 (d, J=1.51 Hz, 1H), 8.32 (d, J=8.03 Hz, 1H), 8.10 (d, J=9.04 Hz, 1H), 8.02 (dd, J=1.88, 9.16 Hz, 1H), 7.53 (s, 1H), 7.39 (s, 2H), 7.31-7.37 (m, 2H), 5.25 (s, 2H), 4.12 (dsxt, J=3.01, 7.33 Hz, 4H), 3.65 (q, J=6.02 Hz, 2H), 1.96-2.10 (m, 2H), 1.85-1.96 (m, 2H), 1.33 (t, J=7.03 Hz, 6H).

To a solution of the above diethyl(3-(6-((3,5-dichlorobenzyl)oxy)-5-(trifluoromethyl)-2-naphthamido)propyl)phosphonate (100 mg, 0.17 mmol) in acetonitrile (9 mL) was added bromotrimethylsilane (0.50 mL, 3.8 mmol). The reaction mixture was stirred at 50° C. for 1 h. The reaction was diluted with ethyl acetate and washed with water and concentrated. The crude was purified by HPLC to give the title compound as a white powder (41.9 mg). LCMS: RT 1.91, MH+536. $^1$H NMR (400 MHz, DMSO-d6) δ 8.77 (t, J=1.00 Hz, 1H), 8.52 (d, J=1.25 Hz, 1H), 8.36 (d, J=9.29 Hz, 1H), 8.13 (d, J=1.00 Hz, 1H), 8.07 (t, J=1.00 Hz, 1H), 7.73 (d, J=9.29 Hz, 1H), 7.62 (d, J=2.01 Hz, 1H), 7.55 (d, J=1.76 Hz, 2H), 5.46 (s, 2H), 3.36-3.42 (m, 2H), 1.70-1.83 (m, 2H), 1.53-1.65 (m, 2H).

Example 19

(3-(5-(trifluoromethyl)-6-((cis-4-(trifluoromethyl)cyclohexyl)oxy)-2-naphthamido)propyl)phosphonic acid

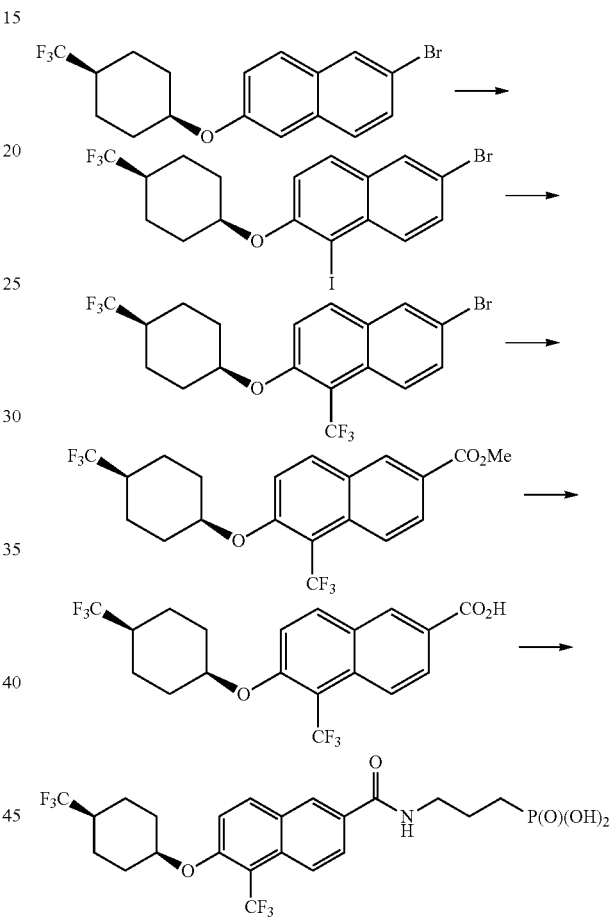

Step 1: 6-bromo-1-iodo-2-((cis-4-(trifluoromethyl)cyclohexyl)oxy)naphthalene (19.1)

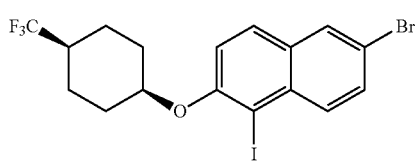 [SMILES: FC(F)(F)[C@H]1CC[C@@H](Oc2ccc3cc(Br)ccc3c2I)CC1]

Into a solution of 2-bromo-6-((cis-4-(trifluoromethyl)cyclohexyl)oxy)naphthalene (3.00 g, 8.04 mmol, 1.0 eq) and NIS (1.99 g, 8.85 mmol, 1.1 eq) in CH$_3$CN (50 mL) was added TFA (90 mg, 0.80 mmol, 0.1 eq). The mixture was stirred at rt overnight. The solvent was removed by reduced pressure and the residue dissolved in EtOAc (100 mL). The solvent was washed with water (100 mL), dried over Na₂SO₄ and concentrated. The residue was purified by column chromatography on silica gel (Petroleum ether/EtOAc=9/1) to give the title compound as a yellow solid (3.6 g, yield: 90%). $^1$H NMR (400 MHz, CDCl$_3$) δ: 8.03 (d, T=9.2 Hz, 1H), 7.88 (s, 1H), 7.68 (d, T=8.8 Hz, 1H), 7.56 (dd, T=2.0 Hz, 9.2 Hz, 1H), 7.13 (d, T=9.2 Hz, 1H), 4.84 (s, 1H), 2.21-2.00 (m, 5H), 1.80-1.77 (m, 2H), 1.62-1.55 (m, 2H).

Step 2: 6-bromo-1-(trifluoromethyl)-2-((cis-4-(trifluoromethyl)cyclohexyl)oxy)naphthalene (19.2)

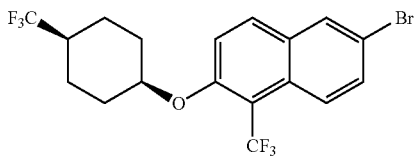 [SMILES: FC(F)(F)c1c(O[C@H]2CC[C@@H](C(F)(F)F)CC2)ccc2cc(Br)ccc12]

To a mixture of 6-bromo-1-iodo-2-((cis-4-(trifluoromethyl)cyclohexyl)oxy)naphthalene (19.1) (3.00 g, 6.04 mmol), CuI (2.87 g, 15.10 mmol, 2.5 eq) and DIPEA (7.79 g, 60.40 mmol, 10.0 eq) in DMF (50 mL) was added FSO₂CF₂CO₂CH₃ (11.59 g, 60.40 mmol, 10.0 eq). The mixture stirred at 85° C. for 16 h and cooled down. The mixture was diluted with water (200 mL) and extracted with EtOAc (100 mL×2). The combined organic layers were washed with water (200 mL) and brine (200 mL). The solvent was removed and the residue was purified by column chromatography on silica gel (Petroleum ether/EtOAc=9/1) to give the title compound as a yellow solid (2.4 g, yield: 91%).

Step 3: Methyl 5-(trifluoromethyl)-6-((cis-4-(trifluoromethyl)cyclohexyl)oxy)-2-naphthoate (12.3)

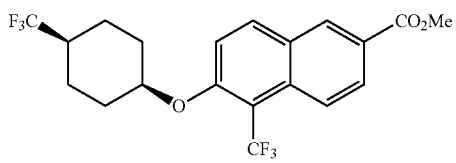 [SMILES: COC(=O)c1ccc2c(C(F)(F)F)c(O[C@H]3CC[C@@H](C(F)(F)F)CC3)ccc2c1]

Into an autoclave was added a solution of 6-bromo-1-(trifluoromethyl)-2-((cis-4-(trifluoromethyl)cyclohexyl) oxy)naphthalene (19.2) (1.32 g, 3.0 mmol) in MeOH (50 mL), followed by PdCl₂(dppf) (245 mg, 0.3 mmol, 0.1 eq) and TEA (1.26 mL, 9.0 mmol, 3.0 eq). The mixture was stirred at 100° C. for 4 h under CO (15 atm). The mixture was cooled down and concentrated. The crude product was purified by column chromatography on silica gel (Petroleum ether/EtOAc=4/1) to give the title compound as a yellow solid (750 mg, yield: 62%). $^1$H NMR (400 MHz, CDCl$_3$) δ 8.53 (d, J=1.6 Hz, 1H), 8.26 (d, J=9.6 Hz, 1H), 8.10 (dd, J=2.0 Hz, J=9.2 Hz, 1H), 8.05 (d, J=9.6 Hz, 1H), 7.32 (d, J=9.2 Hz, 1H), 4.88 (s, 1H), 3.98 (s, 3H), 2.24-2.20 (m, 2H), 2.14-2.10 (m, 1H), 1.90-1.77 (m, 4H), 1.68-1.56 (m, 2H); ESI-MS (M+H)$^+$: 421.1.

Step 4: 5-(trifluoromethyl)-6-((cis-4-(trifluoromethyl)cyclohexyl)oxy)-2-naphthoic acid (19.4)

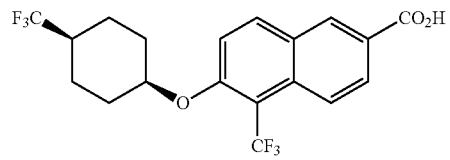 [SMILES: O=C(O)c1ccc2c(C(F)(F)F)c(O[C@H]3CC[C@@H](C(F)(F)F)CC3)ccc2c1]

To a mixture of methyl 5-(trifluoromethyl)-6-((cis-4-(trifluoromethyl)cyclohexyl)oxy)-2-naphthoate (19.3) (750 mg, 1.78 mmol) in MeOH (10 mL) was added NaOH (214 mg, 5.36 mmol, 3.0 eq). The mixture was stirred at 70° C. for 2 h. Then the mixture was cooled to rt and concentrated. The residue was suspended in 3 mL of water and acidified to pH=6 with 1N HCl. The white solid was collected by filtration and dried to give the title compound (660 mg, yield: 90%). $^1$H NMR (400 MHz, CD$_3$OD) δ 8.57 (d, J=1.6 Hz, 1H), 8.20-8.18 (m, 2H), 8.10 (dd, J=1.6 Hz, J=9.2 Hz, 1H), 7.55 (d, J=9.2 Hz, 1H), 5.02 (s, 1H), 2.30-2.21 (m, 1H), 2.19-2.15 (m, 2H), 1.81-1.70 (m, 6H); ESI-MS (M+H)$^+$: 407.1.

Step 5: (3-(5-(trifluoromethyl)-6-((cis-4-(trifluoromethyl)cyclohexyl)oxy)-2-naphthamido)propyl)phosphonic acid

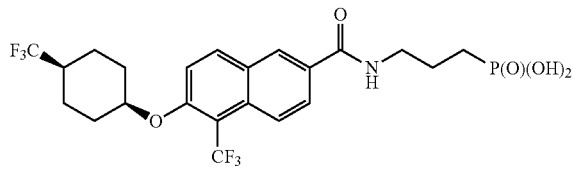

The title compound was prepared using similar method as described for Example 18 from 5-(trifluoromethyl)-6-((cis-4-(trifluoromethyl)cyclohexyl)oxy)-2-naphthoic acid (19.4) and (3-amino-propyl)-phosphonic acid diethyl ester. 1H NMR (400 MHz, DMSO-d$_6$) δ 8.74 (t, J=5.6 Hz, 1H), 8.50 (d, J=1.6 Hz, 1H), 8.29 (d, J=9.2 Hz, 1H), 8.11-8.03 (m, 2H), 7.71 (d, J=9.2 Hz, 1H), 5.12 (s, 1H), 3.38-3.33 (m, 2H), 2.50-2.43 (m, 1H), 2.08-2.04 (m, 2H), 1.79-1.55 (m, 10H); ESI-MS (M+H)$^+$: 526.1

Example 20

1-((5-cyano-6-((cis-4-(trifluoromethyl)cyclohexyl) oxy)naphthalen-2-yl)methyl)piperidine-4-carboxylic acid

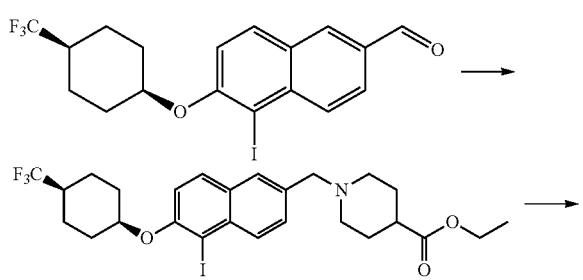

-continued

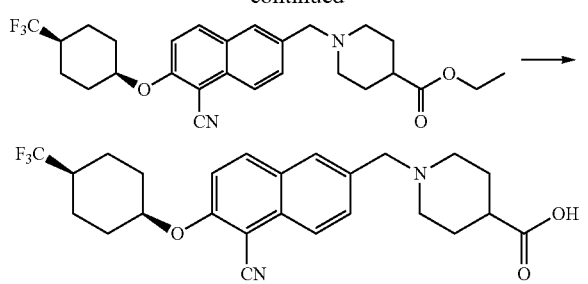

Step 1: Ethyl 1-((5-iodo-6-((cis-4-(trifluoromethyl)cyclohexyl)oxy)naphthalen-2-yl)methyl)piperidine-4-carboxylate (20.1)

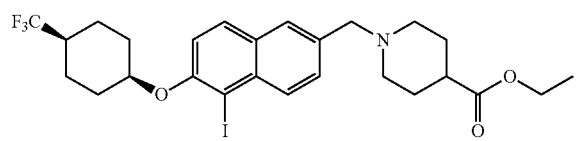

The title compound was prepared according to the procedure described Methyl 1-((5-(trifluoromethyl)-6-((cis-4-(trifluoromethyl)cyclohexyl)-oxy)naphthalen-2-yl)methyl)piperidine-4-carboxylate (2.1) from compound 1.4 and ethyl piperidine-4-carboxylate. ESI-MS (M+H)$^+$: 590.1.

Step 2: Ethyl 1-((5-cyano-6-((cis-4-(trifluoromethyl)cyclohexyl)oxy)naphthalen-2-yl)methyl)piperidine-4-carboxylate (20.2)

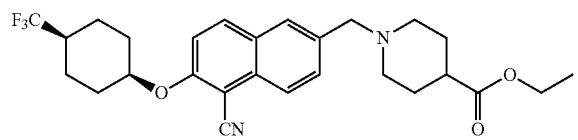 [SMILES: CCOC(=O)C1CCN(Cc2ccc3c(C#N)c(O[C@H]4CC[C@@H](C(F)(F)F)CC4)ccc3c2)CC1]

A mixture of ethyl 1-((5-iodo-6-((cis-4-(trifluoromethyl)cyclohexyl)oxy)naphthalen-2-yl)methyl)piperidine-4-carboxylate (20.1) (600 mg, 1.02 mmol, 1.0 eq), Pd(dppf)Cl$_2$ (83 mg, 0.10 mmol, 0.1 eq) and Zn(CN)$_2$ (238 mg, 2.04 mmol, 2.0 eq) in DMF (4 mL) was stirred at 120° C. for 16 h under N$_2$ atmosphere. The mixture was diluted with water (50 mL) and extracted with DCM (50 mL×2). The combined organic layers were washed with water (100 mL×2), dried over Na$_2$SO$_4$, filtrate and concentrated. The crude product was purified by column chromatography on silica gel (DCM/methanol=20/1) to give ethyl 1-((5-cyano-6-((cis-4-(trifluoromethyl)cyclohexyl)oxy)naphthalen-2-yl)methyl)piperidine-4-carboxylate as a yellow oil (209 mg, yield: 42%). $^1$H NMR (400 MHz, CDCl$_3$) δ: 8.07 (d, J=8.4 Hz, 1H), 7.96 (d, J=9.2 Hz, 1H), 7.74 (s, 1H), 7.65 (dd, J=2.0 Hz, 8.8 Hz, 1H), 7.23 (d, J=9.6 Hz, 1H), 4.88 (s, 1H), 4.16 (q, J=6.8 Hz, 2H), 3.63 (s, 2H), 2.88-2.85 (m, 2H), 2.25-2.22 (m, 2H), 2.13-1.80 (m, 10H), 1.68-1.62 (m, 4H), 1.26 (t, J=6.8 Hz, 3H); ESI-MS (M+H)$^+$: 489.1.

Step 3: 1-((5-cyano-6-((cis-4-(trifluoromethyl)cyclohexyl)oxy)naphthalen-2-yl)methyl)piperidine-4-carboxylic acid

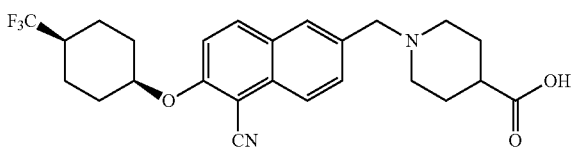 [SMILES: N#Cc1c(O[C@H]2CC[C@@H](C(F)(F)F)CC2)ccc2cc(CN3CCC(C(=O)O)CC3)ccc12]

The title compound was prepared according to the procedure described for Example 2. $^1$H NMR (400 MHz, DMSO-d$_6$) δ: 12.52 (br s, 1H), 8.31 (d, J=8.4 Hz, 1H), 8.14 (s, 1H), 8.02 (d, J=8.0 Hz, 1H), 7.83 (d, J=8.0 Hz, 1H), 7.75 (d, J=9.6 Hz, 1H), 5.16 (s, 1H), 4.45 (s, 2H), 3.45-3.42 (m, 3H), 3.02-2.96 (m, 2H), 2.51-2.49 (m, 1H), 2.11-1.88 (m, 4H), 1.79-1.66 (m, 8H); ESI-MS (M+H)$^+$: 461.2.

Example 21

1-((5-(difluoromethyl)-6-((cis-4-(trifluoromethyl)cyclohexyl)oxy)naphthalen-2-yl)methyl)piperidine-4-carboxylic acid

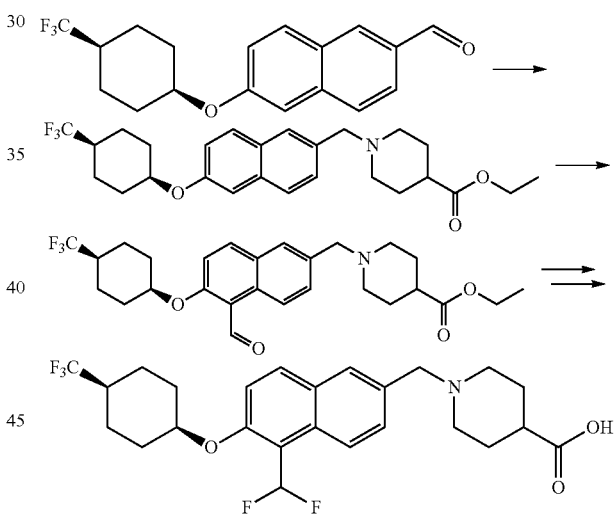

Step 1: Ethyl 1-((6-((cis-4-(trifluoromethyl)cyclohexyl)oxy)naphthalen-2-yl)methyl)piperidine-4-carboxylate (21.1)

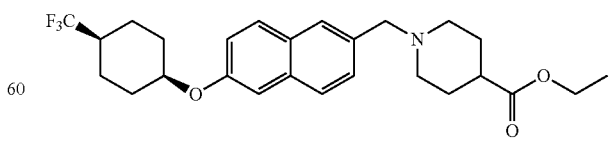

A mixture of 6-((cis-4-(trifluoromethyl)cyclohexyl)oxy)-2-naphthaldehyde (1.2) (1.0 g, 3.1 mmol, 1.0 eq), AcOH (0.2 g, 3.7 mmol, 1.2 eq) and ethyl piperidine-4-carboxylate (0.6 g, 3.7 mmol, 1.2 eq) in CH$_2$Cl$_2$ (20 mL) was stirred at rt for 30 min. NaBH(AcO)₃ (1.3 g, 6.2 mmol, 2.0 eq) was added to the mixture and the mixture was stirred at rt for 6 h. After the reaction completed, the mixture was diluted with water (100 mL) and extracted with CH₂Cl₂ (100 mL×2). The organic layers were washed with water (200 mL×2), brine (200 mL×2), dried over Na₂SO₄, filtered and concentrated. The residue was purified by column chromatography on silica gel (Petroleum ether/EtOAc=10/1) to give the title compound as a colorless oil (1.2 g, yield: 83%). ¹H NMR (400 MHz, CDCl₃) δ: 7.76-7.74 (m, 2H), 7.71 (d, J=8.8 Hz, 1H), 7.57 (d, J=8.0 Hz, 1H), 7.20 (dd, J=2.0 Hz, 8.8 Hz, 1H), 7.15 (d, J=2.0 Hz, 1H), 4.74-4.72 (m, 1H), 4.12 (q, J=6.8 Hz, 2H), 3.88 (s, 2H), 3.03-3.00 (m, 2H), 2.47-2.42 (m, 3H), 2.26-2.22 (m, 2H), 2.13-1.96 (m, 5H), 1.85-1.78 (m, 4H), 1.75-1.56 (m, 2H), 1.25 (t, J=6.8 Hz, 3H); ESI-MS (M+H)⁺: 464.2.

Step 2: Ethyl 1-((5-formyl-6-((cis-4-(trifluoromethyl)cyclohexyl)oxy)naphthalen-2-yl)methyl)piperidine-4-carboxylate (21.2)

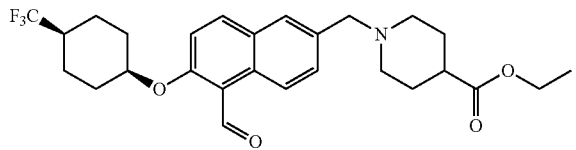 [SMILES: CCOC(=O)C1CCN(Cc2ccc3c(C=O)c(O[C@H]4CC[C@@H](C(F)(F)F)CC4)ccc3c2)CC1]

To a solution of ethyl 1-((6-((cis-4-(trifluoromethyl)cyclohexyl)oxy)naphthalen-2-yl)methyl)piperidine-4-carboxylate (21.1) (2.5 g, 5.38 mmol, 1.0 eq) in CH₂Cl₂ (10 ml) was added a solution of TiCl₄ (2.2 g, 11.29 mmol, 2.1 eq) and dichloro(methoxy)methane (0.7 g, 5.92 mmol, 1.1 eq) in CH₂Cl₂ (20 mL) at 0° C. After addition, the mixture was stirred at r.t. for 12 h. 1N HCl (30 mL) was added and the mixture was extracted with CH₂Cl₂ (50 mL×2). The organic layers was dried over Na₂SO₄, filtered and concentrated. The residue was purified by column chromatography on silica gel (PE/EA=10:1) to give the desired product as a white solid (1.7 g, yield: 66%). ESI-MS (M+H)⁺: 492.1.

Step 3: 1-((5-(difluoromethyl)-6-((cis-4-(trifluoromethyl)cyclohexyl)oxy)naphthalen-2-yl)methyl)piperidine-4-carboxylic acid

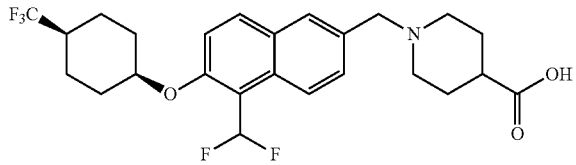 [SMILES: O=C(O)C1CCN(Cc2ccc3c(C(F)F)c(O[C@H]4CC[C@@H](C(F)(F)F)CC4)ccc3c2)CC1]

To a solution of ethyl 1-((5-formyl-6-((cis-4-(trifluoromethyl)cyclohexyl)oxy)naphthalen-2-yl)methyl)piperidine-4-carboxylate (21.2) (300 mg, 0.61 mmol, 1.0 eq) in CH₂Cl₂ (30 mL) was added DAST (147 mg, 0.92 mmol, 1.5 eq) at rt. The mixture was stirred at 50° C. for 10 h and cooled down. Water (50 mL) was added and the mixture was extracted with CH₂Cl₂ (50 mL×2). The combined organic layers were washed with sat. aq. NaHCO₃ (100 mL), dried over Na₂SO₄ and concentrated. The residue was purified by column chromatography on silica gel (PE/EA=10:1) to give ethyl 1-((5-(difluoromethyl)-6-((cis-4-(trifluoromethyl)cyclohexyl)oxy)naphthalen-2-yl)methyl)piperidine-4-carboxylate as a yellow solid (270 mg, yield: 81%). ¹H NMR (400 MHz, CDCl₃) δ: 8.33 (d, J=8.8 Hz, 1H), 7.88 (d, J=9.2 Hz, 1H), 7.71 (s, 1H), 7.68 (t, J=54.8 Hz, 1H), 7.54 (dd, J=1.6 Hz, 8.8 Hz, 1H), 7.21 (d, J=9.6 Hz, 1H), 4.77 (s, 1H), 4.16 (q, J=7.2 Hz, 2H), 3.64 (s, 2H), 2.91-2.89 (m, 2H), 2.30-2.08 (m, 5H), 1.88-1.58 (m, 11H), 1.26 (t, J=6.8 Hz, 3H); ESI-MS (M+H)⁺: 514.3.

The above product was hydrolyzed using similar method described for Example 2 to give the title compound (110 mg, yield: 92%). ¹H NMR (400 MHz, DMSO-d₆) δ: 12.54 (br s, 1H), 8.25 (d, J=8.8 Hz, 1H), 8.14-8.12 (m, 2H), 7.83 (d, J=8.4 Hz, 1H), 7.64 (t, J=54.0 Hz, 1H), 7.63 (d, J=8.8 Hz, 1H), 5.04 (s, 1H), 4.45 (s, 2H), 3.41-3.38 (m, 3H), 2.97-2.95 (m, 2H), 2.46-2.44 (m, 1H), 2.06-1.72 (m, 6H), 1.64-1.56 (m, 6H); ESI-MS (M+H)⁺: 486.1.

Example 22

1-((5-(trifluoromethyl)-6-((cis-4-(trifluoromethyl)cyclohexyl)amino)naphthalen-2-yl)methyl)piperidine-4-carboxylic acid

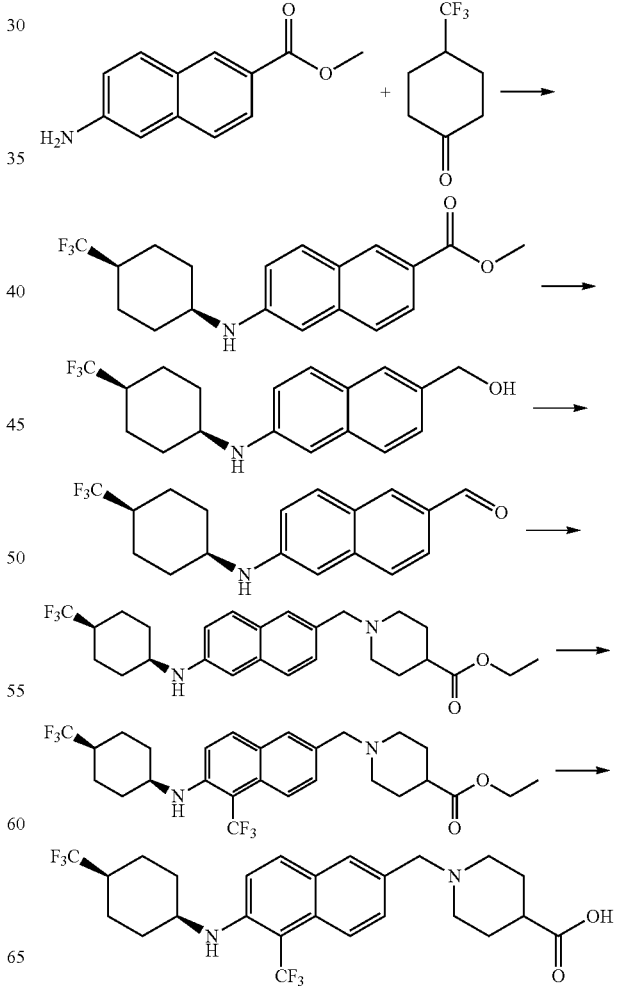

Step 1: Methyl 6-((cis-4-(trifluoromethyl)cyclohexyl)amino)-2-naphthoate (22.1)

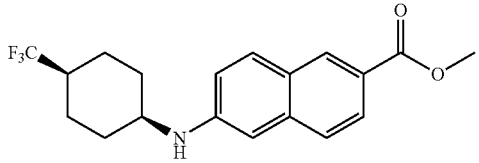 [SMILES: COC(=O)c1ccc2cc(N[C@H]3CC[C@@H](C(F)(F)F)CC3)ccc2c1]

To a solution of methyl 6-amino-2-naphthoate (1.2 g, 6.0 mmol, 1.0 eq) and 4-(trifluoromethyl)cyclohexanone (2.0 g, 12.0 mmol, 2.0 eq) in DCM (20 mL) were added NaBH(OAc)$_3$ (2.6 mg, 12.0 mmol, 2.0 eq) and HOAc (360 mg, 6.0 mmol, 1.0 eq). The mixture was stirred at rt for 16 h and washed with sat. aq. NaHCO$_3$ (30 mL). The aqueous layer was extracted with EtOAc (30 mL×2). The combined organic layers were combined and concentrated. The residue was washed with MeOH to give the title compound as a yellow solid (700 mg, yield: 30%) with cis isomer only. $^1$H NMR (400 MHz, CDCl$_3$) δ 8.42 (s, 1H), 7.93 (dd, J=1.6 Hz, 9.2 Hz, 1H), 7.72 (d, J=9.2 Hz, 1H), 7.59 (d, J=8.0 Hz, 1H), 6.92 (d, J=8.0 Hz, 1H), 6.78 (s, 1H), 3.94 (s, 3H), 3.83 (s, 1H), 2.22-2.05 (m, 3H), 1.85-1.60 (m, 6H); ESI-MS (M+H)$^+$: 352.2.

Step 2: (6-((cis-4-(trifluoromethyl)cyclohexyl)amino)naphthalen-2-yl)methanol (22.2)

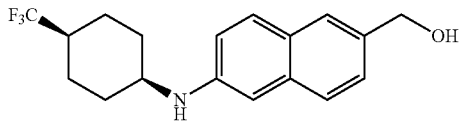 [SMILES: OCc1ccc2cc(N[C@H]3CC[C@@H](C(F)(F)F)CC3)ccc2c1]

To a solution of methyl 6-((cis-4-(trifluoromethyl)cyclohexyl)amino)-2-naphthoate (22.1) (200 mg, 0.6 mmol, 1.0 eq) in THF (anhydrous, 2 mL) was added LiAlH$_4$ (120 mg, 3.0 mmol, 5.0 eq) portionwise at 0° C. The mixture was stirred at 0° C. for 2 h and quenched with Na$_2$SO$_4$·10H$_2$O. The mixture was filtered and the filtrate was concentrated to give the desired product as a yellow oil, which was used for next step without further purification (160 mg, yield: 80%). ESI-MS (M+H)$^+$: 324.2.

Step 3: 6-((cis-4-(trifluoromethyl)cyclohexyl)amino)-2-naphthaldehyde (22.3)

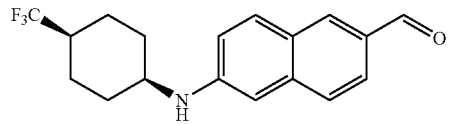 [SMILES: O=Cc1ccc2cc(N[C@H]3CC[C@@H](C(F)(F)F)CC3)ccc2c1]

A mixture of (6-((cis-4-(trifluoromethyl)cyclohexyl)amino)naphthalen-2-yl)methanol (22.2) (160 mg, 0.5 mmol, 1.0 eq) and MnO$_2$ (440 mg, 5.0 mmol, 10.0 eq) in DCM (5 mL) was stirred at rt for 16 h. The mixture was filtered and the filtrate was concentrated to give the desired product as a yellow oil, which was used for next step without further purification (130 mg, yield: 80%). ESI-MS (M+H)$^+$: 322.2.

Step 4: Ethyl 1-((6-((cis-4-(trifluoromethyl)cyclohexyl)amino)naphthalen-2-yl)methyl)piperidine-4-carboxylate (22.4)

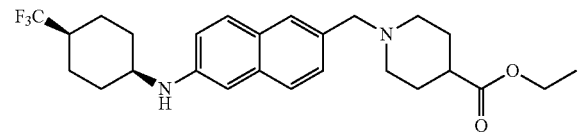 [SMILES: CCOC(=O)C1CCN(Cc2ccc3cc(N[C@H]4CC[C@@H](C(F)(F)F)CC4)ccc3c2)CC1]

To a solution of 6-((cis-4-(trifluoromethyl)cyclohexyl)amino)-2-naphthaldehyde (22.3) (100 mg, 0.3 mmol) in DCM (20 mL) were added ethyl piperidine-4-carboxylate (59 mg, 0.37 mmol, 1.2 eq) and HOAc (2.0 mg, 0.03 mmol, 0.1 eq). The mixture was stirred at rt for 10 min, then NaBH(OAc)$_3$ (127 mg, 0.6 mmol, 2.0 eq) was added. The reaction mixture was stirred at rt for 16 h. Saturated solution of NaHCO$_3$ (15 mL) was added. The mixture was stirred for 30 min. After separation, the organic layer was dried over Na$_2$SO$_4$. The solvent was removed and the residue was purified by column chromatography on silica gel (petroleum/ethyl acetate=2/1) to give the desired product as a brown oil (70 mg, yield: 49%). $^1$H NMR (400 MHz, CDCl$_3$) δ 7.65 (d, J=8.0 Hz, 1H), 7.61 (d, J=8.8 Hz, 2H), 7.34-7.29 (m, 1H), 6.99-6.96 (m, 1H), 6.86 (s, 1H), 4.28-4.24 (m, 2H), 4.19-4.09 (m, 2H), 3.79 (s, 1H), 3.67-3.64 (m, 1H), 3.48-3.44 (m, 1H), 2.92-2.90 (m, 1H), 2.64-2.60 (m, 1H), 2.40-2.31 (m, 1H), 2.22-2.02 (m, 6H), 1.85-1.65 (m, 7H), 1.23 (t, J=7.2 Hz, 3H); ESI-MS (M+H)$^+$: 463.2.

Step 5: Ethyl 1-((5-(trifluoromethyl)-6-((cis-4-(trifluoromethyl)cyclohexyl)amino)naphthalen-2-yl)methyl)piperidine-4-carboxylate (22.5)

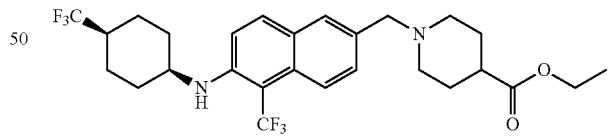

A mixture of ethyl 1-((6-((cis-4-(trifluoromethyl)cyclohexyl)amino)naphthalen-2-yl)methyl)piperidine-4-carboxylate (22.4) (200 mg, 0.4 mmol, 1.0 eq) and 3,3-Dimethyl-1-(trifluoromethyl)-1,2-benziodoxole (CAS#887144-97-0) (200 mg, 0.6 mmol, 1.5 eq) in MeCN (2 mL) was heated at 80° C. for 16 h in a sealed tube. The mixture was cooled to rt and diluted with H$_2$O (10 mL). The mixture was extracted with DCM (10 mL×3). The combined organic layers were dried and concentrated to give the desired product as a yellow oil, which was used to next step without further purification (230 mg, yield: 80%). ESI-MS (M+H)$^+$: 531.3.

Step 6: 1-((5-(trifluoromethyl)-6-((cis-4-(trifluoromethyl)cyclohexyl)amino)naphthalen-2-yl)methyl)piperidine-4-carboxylic acid

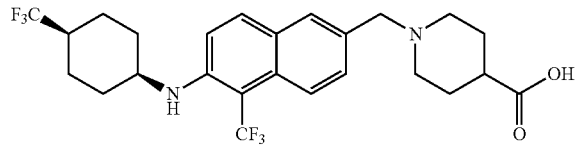 [SMILES: O=C(O)C1CCN(Cc2ccc3c(C(F)(F)F)c(N[C@H]4CC[C@@H](C(F)(F)F)CC4)ccc3c2)CC1]

The above ester was hydrolyzed using similar method as described for Example 2 to give the title acid as a white solid, 15 mg, Y: 20%, purified by pre-HPLC (MeOH and $H_2O$ with 0.02% $NH_4HCO_3$ as mobile phase). $^1H$ NMR (400 MHz, $CD_3OD$) δ: 7.88 (d, J=8.8 Hz, 1H), 7.81 (d, J=8.8 Hz, 1H), 7.73 (s, 1H), 7.42 (d, J=8.8 Hz, 1H), 7.81 (d, J=9.6 Hz, 1H), 4.10 (s, 2H), 3.93 (s, 1H), 3.24-3.22 (m, 1H), 2.79-2.74 (m, 2H), 2.24-2.14 (m, 2H), 1.92-1.65 (m, 11H), 1.52-1.41 (m, 2H); ESI-MS (M+H)$^+$: 503.1.

Example 23

6-((5-(trifluoromethyl)-6-((cis)-4-(trifluoromethyl)cyclohexyloxy)-2-naphthamido)methyl)nicotinic acid The title compound was prepared according to the method of Example 19. $^1H$ NMR (400 MHz, DMSO-$d_6$) δ: 13.35 (br s, 1H), 9.38 (t, J=5.6 Hz, 1H), 9.02 (d, J=1.6 Hz, 1H), 8.60 (s, 1H), 8.32 (d, J=9.2 Hz, 1H), 8.25 (dd, J=2.4 Hz, 8.4 Hz, 1H), 8.14-8.12 (m, 2H), 7.72 (d, J=9.6 Hz, 1H), 7.49 (d, J=8.4 Hz, 1H), 5.13 (s, 1H), 4.69 (d, J=5.6 Hz, 2H), 2.46-2.41 (m, 1H), 2.08-2.05 (m, 2H), 1.76-1.62 (m, 6H). ESI-MS (M+H)$^+$: 541.2

Example 24

(R)-1-((5-(trifluoromethyl)-6-((cis)-4-(trifluoromethyl)cyclohexyloxy)naphthalen-2-yl)methyl)piperidine-3-carboxylic acid The title compound was prepared according to the method of Example 2. $^1H$ NMR (400 MHz, $CD_3OD$) d: 8.17 (d, J=8.8 Hz, 1H), 8.05 (d, J=9.2 Hz, 1H), 7.97 (d, J=1.2 Hz, 1H), 7.59 (dd, J=1.6 Hz, 8.8 Hz, 1H), 7.49 (d, J=9.2 Hz, 1H), 4.92 (s, 1H), 4.46-4.36 (m, 2H), 3.57-2.79 (m, 5H), 2.20-2.06 (m, 4H), 1.88-1.49 (m, 9H). ESI-MS (M+H)$^+$: 504.2

Example 25

(trans)-4-(((5-(trifluoromethyl)-6-((cis)-4-(trifluoromethyl)cyclohexyloxy)naphthalen-2-yl)methylamino)methyl)cyclohexanecarboxylic acid The title compound was prepared according to the method of Example 2. $^1H$ NMR (400 MHz, $CD_3OD$) d: 8.16 (d, J=8.8 Hz, 1H), 8.04 (d, J=9.6 Hz, 1H), 7.93 (s, 1H), 7.57 (dd, J=1.6 Hz, 9.2 Hz, 1H), 7.49 (d, J=9.2 Hz, 1H), 4.92 (s, 1H), 4.26 (s, 2H), 2.86 (d, J=6.8 Hz, 2H), 2.19-2.06 (m, 4H), 1.96-1.94 (m, 2H), 1.82-1.61 (m, 9H), 1.39-1.30 (m, 2H), 1.06-0.99 (m, 2H). ESI-MS (M+H)$^+$: 532.2

Example 26

(S)-1-((5-(trifluoromethyl)-6-((cis)-4-(trifluoromethyl)cyclohexyloxy)naphthalen-2-yl)methyl)piperidine-3-carboxylic acid The title compound was prepared according to the method of Example 2. $^1H$ NMR (400 MHz, $CD_3OD$) δ 8.29 (d, J=8.4 Hz, 1H), 8.16 (d, J=9.2 Hz, 1H), 8.07 (d, J=1.6 Hz, 1H), 7.70 (d, J=8.8 Hz, 1H), 7.61 (d, J=9.2 Hz, 1H), 5.04 (s, 1H), 4.57-4.47 (m, 2H), 3.72-3.38 (m, 2H), 3.25-2.88 (m, 3H), 2.31-2.17 (m, 4H), 2.00-1.62 (m, 9H). ESI-MS (M+H)$^+$: 504.2

Example 27

2-(1-((5-(trifluoromethyl)-6-((cis)-4-(trifluoromethyl)cyclohexyloxy)naphthalen-2-yl)methyl)piperidin-2-yl)acetic acid The title compound was prepared according to the method of Example 2. $^1H$ NMR (400 MHz, $CDCl_3$) d: 8.03 (d, J=7.6 Hz, 1H), 7.76 (d, J=9.2 Hz, 1H), 7.60 (s, 1H), 7.38 (d, J=8.8 Hz, 1H), 7.08 (d, J=9.2 Hz, 1H), 4.68 (s, 1H), 4.06-4.03 (m, 1H), 3.53-3.48 (m, 1H), 2.97 (m, 1H), 2.69-2.51 (m, 3H), 2.09-2.02 (m, 4H), 1.83-1.68 (m, 5H), 1.54-1.49 (m, 4H), 1.37-1.26 (m, 3H). ESI-MS (M+H)$^+$: 518.2

Example 28

(trans)-4-((methyl((5-(trifluoromethyl)-6-((cis)-4-(trifluoromethyl)cyclohexyloxy)naphthalen-2-yl)methyl)amino)methyl)cyclohexanecarboxylic acid The title compound was prepared according to the method of Example 2. $^1H$ NMR (400 MHz, $CD_3OD$) d: 8.30 (d, J=8.8 Hz, 1H), 8.18 (d, J=9.6 Hz, 1H), 8.08 (s, 1H), 7.67 (dd, J=1.6 Hz, 9.2 Hz, 1H), 7.62 (d, J=9.2 Hz, 1H), 5.05 (s, 1H), 4.62-4.41 (m, 2H), 3.10-3.05 (m, 2H), 2.90 (s, 3H), 2.29-2.17 (m, 4H), 2.06-2.04 (m, 2H), 1.92-1.90 (m, 3H), 1.85-1.72 (m, 6H), 1.50 (m, 2H), 1.14-1.01 (m, 2H). ESI-MS (M+H)$^+$: 546.2

Example 29

1-((5-(trifluoromethyl)-6-((cis)-4-(trifluoromethyl)cyclohexyloxy)naphthalen-2-yl)methyl)piperidine-2-carboxylic acid The title compound was prepared according to the method of Example 2. $^1H$ NMR (400 MHz, $CD_3OD$) d: 8.09 (d, J=9.2 Hz, 1H), 8.04 (d, J=9.2 Hz, 1H), 7.84 (s, 1H), 7.68 (dd, J=2.0 Hz, 9.2 Hz, 1H), 7.44 (d, J=9.2 Hz, 1H), 4.95 (s, 1H), 4.14-4.12 (m, 1H), 3.41-3.37 (m, 1H), 2.90-2.87 (m, 1H), 2.78-2.75 (m, 1H), 2.30-2.15 (m, 3H), 2.02-1.89 (m, 2H), 1.86-1.68 (m, 8H), 1.56-1.52 (m, 2H), 1.32-1.22 (m, 1H). ESI-MS (M+H)$^+$: 504.2

Example 30

4-methyl-1-((5-(trifluoromethyl)-6-((cis)-4-(trifluoromethyl)cyclohexyloxy)naphthalen-2-yl)methyl)piperidine-4-carboxylic acid The title compound was prepared according to the method of Example 2. $^1H$ NMR (400 MHz, $CD_3OD$) d: 8.28 (d, J=9.2 Hz, 1H), 8.16 (d, J=9.2 Hz, 1H), 8.05 (d, J=0.8 Hz, 1H), 7.66 (dd, J=2.0 Hz, 9.2 Hz, 1H), 7.61 (d, J=9.2 Hz, 1H), 5.04 (s, 1H), 4.48 (s, 2H), 3.49-3.44 (m, 2H), 3.14-3.11 (m, 2H), 2.34-2.17 (m, 5H), 1.85-1.69 (m, 8H), 1.29 (s, 3H). ESI-MS (M+H)+: 517.9

Example 31

1-(5-(trifluoromethyl)-6-((cis)-4-(trifluoromethyl)cyclohexyloxy)-2-naphthoyl)azepane-4-carboxylic acid The title compound was prepared according to the method of Example 19. $^1$H NMR (400 MHz, CD$_3$OD) δ: 8.15 (d, J=8.4 Hz, 1H), 8.06 (d, J=8.8 Hz, 1H), 7.87 (s, 1H), 7.51-7.46 (m, 2H), 4.92 (s, 1H), 3.88-3.33 (m, 4H), 2.52-2.50 (m, 1H), 2.18-2.09 (m, 3H), 1.99-1.85 (m, 3H), 1.78-1.61 (m, 9H). ESI-MS (M+H)+: 532.1

Example 32

2-(4-((5-(difluoromethyl)-6-((cis)-4-(trifluoromethyl)cyclohexyloxy)naphthalen-2-yl)methyl)morpholin-2-yl)acetic acid The title compound was prepared according to the method of Example 21. $^1$H NMR (400 MHz, DMSO-d$_6$) δ: 12.49 (br s, 1H), 8.28 (d, J=8.4 Hz, 1H), 8.17 (d, J=8.8 Hz, 1H), 8.07 (s, 1H), 7.78 (t, J=54.8 Hz, 1H), 7.71 (d, J=8.8 Hz, 1H), 7.66 (d, J=9.6 Hz, 1H), 5.05 (s, 1H), 4.51 (s, 2H), 4.00 (d, J=7.2 Hz, 2H), 3.72-3.70 (m, 1H), 3.34-3.01 (m, 4H), 2.58-2.54 (m, 1H), 2.46-2.33 (m, 2H), 2.05-2.02 (m, 2H), 1.75-1.72 (m, 4H), 1.62-1.56 (m, 2H). ESI-MS (M+H)+: 502.2

Example 33

3-((5-(difluoromethyl)-6-((cis)-4-(trifluoromethyl)cyclohexyloxy)naphthalen-2-yl)methylamino)-2,2-dimethylcyclobutanecarboxylic acid The title compound was prepared according to the method of Example 21. $^1$H NMR (400 MHz, DMSO-d$_6$) δ: 8.18 (d, J=8.4 Hz, 1H), 8.09 (d, J=8.8 Hz, 1H), 7.94 (s, 1H), 7.67 (d, J=8.8 Hz, 1H), 7.61 (t, J=54.8 Hz, 1H), 7.57 (d, J=9.6 Hz, 1H), 5.00 (s, 1H), 3.96 (s, 2H), 3.04-2.98 (m, 1H), 2.47-2.41 (m, 2H), 2.06-1.92 (m, 4H), 1.74-1.63 (m, 4H), 1.60-1.57 (m, 2H), 1.20 (s, 3H), 1.03 (s, 3H). ESI-MS (M+H)+: 500.1

Example 34

(trans)-4-(((5-(difluoromethyl)-6-((cis)-4-(trifluoromethyl)cyclohexyloxy)naphthalen-2-yl)methylamino)methyl)cyclohexanecarboxylic acid The title compound was prepared according to the method of Example 21. $^1$H NMR (400 MHz, DMSO-d$_6$) δ: 8.18 (d, J=8.8 Hz, 1H), 8.09 (d, J=9.2 Hz, 1H), 7.96 (s, 1H), 7.68 (d, J=8.8 Hz, 1H), 7.61 (t, J=54.0 Hz, 1H), 7.58 (d, J=9.6 Hz, 1H), 5.00 (s, 1H), 4.04 (s, 2H), 2.56 (d, J=5.6 Hz, 2H), 2.47-2.42 (m, 1H), 2.14-2.03 (m, 3H), 1.90-1.82 (m, 4H), 1.74-1.68 (m, 4H), 1.65-1.54 (m, 3H), 1.33-1.23 (m, 2H), 0.97-0.88 (m, 2H). ESI-MS (M+H)+: 514.1

Example 35

4-hydroxy-1-((5-(trifluoromethyl)-6-((cis)-4-(trifluoromethyl)cyclohexyloxy)naphthalen-2-yl)methyl)piperidine-3-carboxylic acid The title compound was prepared according to the method of Example 2. $^1$H NMR (400 MHz, CD$_3$OD) δ: 8.22 (d, J=8.8 Hz, 1H), 8.10 (d, J=7.2 Hz, 1H), 8.04 (d, J=3.6 Hz, 1H), 7.65 (d, J=8.8 Hz, 1H), 7.54 (d, J=9.2 Hz, 1H), 4.97 (s, 1H), 4.56-4.46 (m, 2H), 4.42-4.35 (m, 1H), 3.50-3.37 (m, 2H), 3.30-3.27 (m, 2H), 2.95-2.81 (m, 1H), 2.26-2.20 (m, 1H), 2.14-2.06 (m, 3H), 1.96-1.88 (m, 1H), 1.82-1.65 (m, 6H). ESI-MS (M+H)+: 520.2

Example 36

2,2-dimethyl-3-(1-(6-((cis)-4-methylcyclohexyloxy)-5-(trifluoromethyl)naphthalen-2-yl)propylamino)cyclobutanecarboxylic acid The title compound was prepared according to the method of Example 10. $^1$H NMR (400 MHz, CD$_3$OD) δ: 8.30 (t, J=8.4 Hz, 1H), 8.13 (dd, J=3.2 Hz, 9.6 Hz, 1H), 7.99 (d, J=6.8 Hz, 1H), 7.67-7.64 (m, 1H), 7.59 (d, J=6.8 Hz, 1H), 4.95 (s, 1H), 4.29-4.23 (m, 1H), 3.44-3.40 (m, 0.5H), 3.20-3.16 (m, 0.5H), 2.68-2.64 (m, 0.5H), 2.58-2.54 (m, 0.5H), 2.46-2.19 (m, 2H), 2.16-1.93 (m, 3H), 1.74-1.67 (m, 2H), 1.55-1.43 (m, 6H), 1.34 (s, 1.7H), 1.28 (d, J=6.4 Hz, 3H), 1.15 (s, 1.3H), 0.96 (d, J=6.0 Hz, 3H), 0.83-0.79 (m, 3H). ESI-MS (M+H)+: 492.3

Example 37

2,2-dimethyl-3-(1-(5-(trifluoromethyl)-6-((cis)-4-(trifluoromethyl)cyclohexyloxy)naphthalen-2-yl)ethylamino)cyclobutanecarboxylic acid

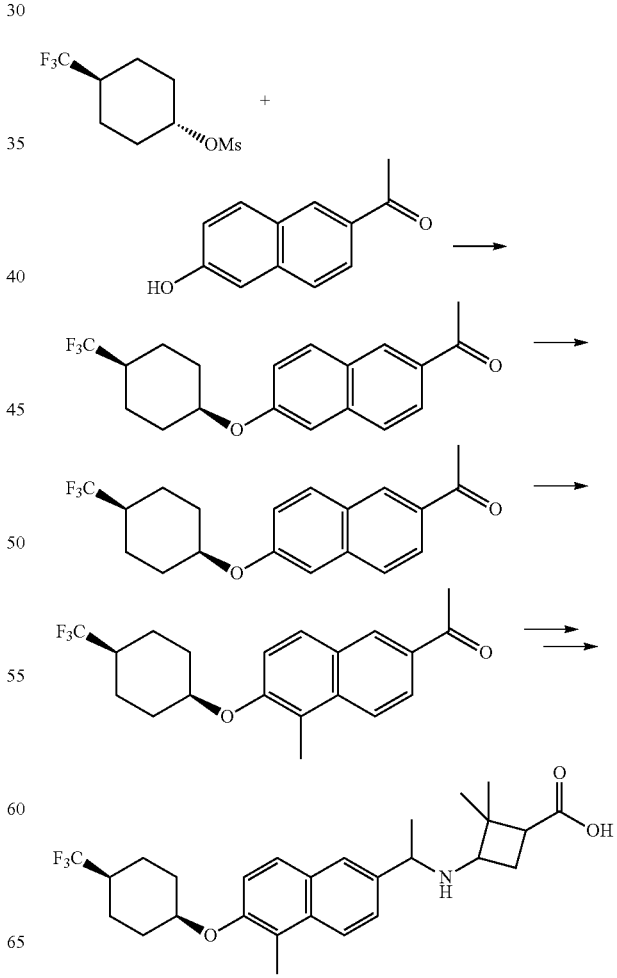

Step 1: 1-(6-((cis-4-(trifluoromethyl)cyclohexyl)oxy)naphthalen-2-yl)ethanone

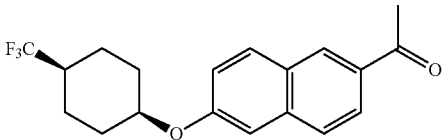 [SMILES: CC(=O)c1ccc2cc(O[C@H]3CC[C@@H](C(F)(F)F)CC3)ccc2c1]

To a solution of trans-4-(trifluoromethyl)cyclohexyl methanesulfonate (2.2 g, 9.0 mmol) and 1-(6-hydroxynaphthalen-2-yl)ethanone (1.7 g, 7.0 mmol, 0.8 eq) in t-BuOH (40 mL) was added $Cs_2CO_3$ (4.4 g, 13.0 mmol, 1.5 eq). The mixture was stirred at 90° C. for 16 h and cooled down to room temperature. The mixture was diluted with water (100 mL) and extracted with EtOAc (100 mL×2). The combined organic layers were dried over $Na_2SO_4$ and concentrated. The residue was purified by column chromatography on silica gel (Petroleum ether/EtOAc=15/1) to give 1-(6-((cis-4-(trifluoromethyl)cyclohexyl)oxy)naphthalen-2-yl)ethanone as a white solid (1.7 g, yield: 55%). ESI-MS $(M+H)^+$: 337.2.

Step 2: 1-(5-iodo-6-((cis-4-(trifluoromethyl)cyclohexyl)oxy)naphthalen-2-yl)ethanone

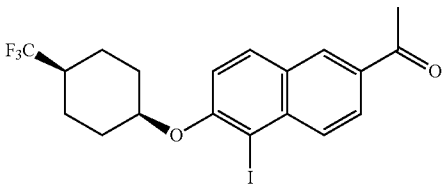 [SMILES: CC(=O)c1ccc2c(I)c(O[C@H]3CC[C@@H](C(F)(F)F)CC3)ccc2c1]

To a solution of 1-(6-((cis-4-(trifluoromethyl)cyclohexyl)oxy)naphthalen-2-yl)ethanone (1.70 g, 5.0 mmol) in MeCN (15 mL) was added NIS (1.35 g, 6.0 mmol, 1.2 eq), followed by TFA (57 mg, 0.5 mmol, 0.1 eq). The mixture was stirred at rt for 16 h. The reaction mixture was concentrated. The residue was purified by column chromatography on silica gel (Petroleum ether/EtOAc=10/1) to give 1-(5-iodo-6-((cis-4-(trifluoromethyl)cyclohexyl)oxy)naphthalen-2-yl)ethanone as a white solid (2.1 g, yield: 90%). $^1$H NMR (400 MHz, $CDCl_3$) δ 8.28 (s, 1H), 8.11 (d, J=8.4 Hz, 1H), 7.98 (d, J=8.8 Hz, 1H), 7.84 (d, J=8.4 Hz, 1H), 7.14 (d, J=9.2 Hz, 1H), 4.84 (s, 1H), 2.95 (s, 3H), 2.16-1.94 (m, 5H), 1.75-1.72 (m, 2H), 1.58-1.51 (m, 2H); ESI-MS $(M+H)^+$: 463.1.

Step 3: 1-(5-(trifluoromethyl)-6-((cis-4-(trifluoromethyl)cyclohexyl)oxy)naphthalen-2-yl)ethanone

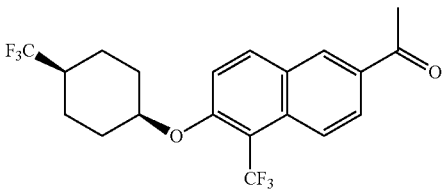 [SMILES: CC(=O)c1ccc2c(C(F)(F)F)c(O[C@H]3CC[C@@H](C(F)(F)F)CC3)ccc2c1]

To a solution of 1-(5-iodo-6-((cis-4-(trifluoromethyl)cyclohexyl)oxy)naphthalen-2-yl)ethanone (2.1 g, 4.5 mmol) in DMF (20 mL) was added CuI (2.1 g, 11.3 mmol, 2.5 eq), $FSO_2CF_2COOCH_3$ (8.6 g, 45.0 mmol, 10.0 eq) and HMPA (8.1 g, 45.0 mmol, 10.0 eq). The mixture was stirred at 80° C. for 16 h under $N_2$ atmosphere. The reaction mixture was cooled to rt and diluted with water (60 mL). The mixture was extracted with EtOAc (60 mL×3). The combined organic layers were dried and concentrated. The crude product was purified by column chromatography on silica gel (Petroleum ether/EtOAc 10/1) to give 1-(5-(trifluoromethyl)-6-((cis-4-(trifluoromethyl)cyclohexyl)oxy)naphthalen-2-yl)ethanone as a white solid (1.6 g, yield: 85%). $^1$H NMR (400 MHz, $CDCl_3$) δ 8.33 (d, J=1.6 Hz, 1H), 8.20 (d, J=8.4 Hz, 1H), 8.02-7.99 (m, 2H), 7.28 (s, 1H), 4.83 (s, 1H), 2.95 (s, 3H), 2.10-2.01 (m, 3H), 1.85-1.70 (m, 4H), 1.62-1.53 (m, 2H); ESI-MS $(M+H)^+$: 405.2.

Step 4: 2,2-dimethyl-3-(1-(5-(trifluoromethyl)-6-((cis)-4-(trifluoromethyl)cyclohexyloxy)naphthalen-2-yl)ethylamino)cyclobutanecarboxylic acid

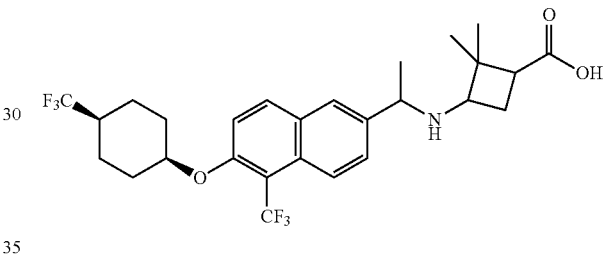

To a solution of 1-(5-(trifluoromethyl)-6-((cis-4-(trifluoromethyl)cyclohexyl)oxy)naphthalen-2-yl)ethanone (100 mg, 0.24 mmol) in 2 mL of DCE, methyl 3-amino-2,2-dimethylcyclobutanecarboxylate (44 mg, 0.28 mmol, 1.1 eq) was added $Ti\{OCH(CH_3)_2\}_4$ (160 mg, 0.48 mmol, 2.0 eq). The reaction was microwaved at 100° C. for 2 h before it was cooled down to room temperature. It was then added $NaBH(OAc)_3$ (102 mg, 0.48 mmol, 2.0 eq) to the mixture and stirred at rt for 16 h. Diluted with sat. aq. $NaHCO_3$ (10 mL) and extracted with DCM (10 mL×3). The combined organic layers were dried over $Na_2SO_4$ and concentrated. The residue was purified by reversed HPLC (MeCN/$H_2O$-0.05% TFA) to give a mixture of both methyl ester (ESI-MS $(M+H)^+$: 545.9) and isopropyl ester ($[M+H]^+$=573.9). as a colorless oil (50 mg, yield: 37%). The above mixture (50 mg, 0.09 mmol) was dissolved in MeOH/$H_2O$ (5 mL, 1:1) and added NaOH (11 mg, 0.27 mmol, 3.0 eq). The mixture was stirred at 65° C. for 16 h. The solvent was removed by reduced pressure and the residue was suspended in water (1 mL). The mixture was acidified with 1N HCl to pH 6 and purified by reversed HPLC (MeCN/$H_2O$-0.05% TFA) to give the desired product as a white solid (30 mg, yield: 60%). $^1$H NMR (400 MHz, $CD_3OD$) δ 8.22-8.18 (m, 1H), 8.05 (d, J=9.2 Hz, 1H), 7.94-7.92 (m, 1H), 7.62-7.56 (m, 1H), 7.50 (d, J=9.2 Hz, 1H), 4.92 (s, 1H), 4.48-4.41 (m, 1H), 3.37-3.32 (m, 0.7H), 3.17-3.12 (m, 0.3H), 2.60-2.56 (m, 0.3H), 2.51-2.46 (m, 0.7H), 2.32-2.25 (m, 0.3H), 2.24-2.06 (m, 3H), 1.93-1.85 (m, 0.7H), 1.78-1.61 (m, 9H), 1.49-1.43 (m, 0.7H), 1.33-1.32 (m, 0.3H), 1.24 (s, 2.1H), 1.12-1.09 (m, 3.9H); ESI-MS $(M+H)^+$: 531.9.

Example 38

3-(cyclopropyl(6-((cis)-4-methylcyclohexyloxy)-5-(trifluoromethyl)naphthalen-2-yl)methylamino)-2,2-dimethylcyclobutanecarboxylic acid The title compound was prepared according to the method of Example 10. $^1$H NMR (400 MHz, CD$_3$OD) δ: 8.27 (d, J=9.2 Hz, 1H), 8.12 (d, J=9.2 Hz, 1H), 7.99 (s, 1H), 7.74-7.69 (m, 1H), 7.55 (d, J=8.8 Hz, 1H), 4.93 (s, 1H), 3.79-3.71 (m, 1H), 3.52-3.44 (m, 1H), 2.71-2.56 (m, 1H), 2.47-2.35 (m, 1H), 2.13-2.02 (m, 2H), 1.71-1.49 (m, 9H), 1.39-1.19 (m, 6H), 0.95-0.93 (m, 1H), 0.94 (d, J=4.8 Hz, 3H), 0.78-0.75 (m, 1H), 0.66-0.64 (m, 1H), 0.37-0.34 (m, 1H). ESI-MS (M+H)$^+$: 504.3

Example 39

2,2-dimethyl-3-(2-methyl-1-(5-(trifluoromethyl)-6-((cis)-4-(trifluoromethyl)cyclohexyloxy)naphthalen-2-yl)propylamino)cyclobutanecarboxylic acid The title compound was prepared according to the method of Example 10. $^1$H NMR (400 MHz, CD$_3$OD) δ: 8.28 (d, J=8.8 Hz, 1H), 8.15 (d, J=9.6 Hz, 1H), 7.96 (d, J=1.6 Hz, 1H), 7.61-7.59 (m, 2H), 5.03 (s, 1H), 4.24-4.17 (m, 1H), 3.17 (t, J=8.0 Hz, 1H), 2.63-2.52 (m, 2H), 2.47-2.39 (m, 1H), 2.32-2.26 (m, 2H), 2.20-2.16 (m, 2H), 1.84-1.71 (m, 6H), 1.32-1.28 (m, 3H), 1.22-1.18 (m, 3H), 1.14 (d, J=6.8 Hz, 3H), 0.93 (d, J=6.8 Hz, 3H). ESI-MS (M+H)$^+$: 560.2

Example 40

2,2-dimethyl-3-(3-methyl-1-(5-(trifluoromethyl)-6-((cis)-4-(trifluoromethyl)cyclohexyloxy)naphthalen-2-yl)butylamino)cyclobutanecarboxylic acid The title compound was prepared according to the method of Example 10. $^1$H NMR (400 MHz, CD$_3$OD) δ: 8.34-8.27 (m, 1H), 8.19-8.13 (m, 1H), 8.07-7.98 (m, 1H), 7.72-7.64 (m, 1H), 7.62-7.56 (m, 1H), 5.03 (s, 1H), 4.52-4.34 (m, 1H), 3.48-3.44 (m, 0.3H), 3.20-3.16 (m, 0.7H), 2.67-2.36 (m, 7H), 2.23-1.75 (m, 8H), 1.42 (s, 3H), 1.14 (s, 3H), 1.00 (d, J=6.4 Hz, 3H), 0.87 (d, J=6.4 Hz, 3H). ESI-MS (M+H)$^+$: 574.2

Example 41

4-(1-((5-(trifluoromethyl)-6-((cis)-4-(trifluoromethyl)cyclohexyloxy)naphthalen-2-yl)methylamino)ethyl)cyclohexanecarboxylic acid The title compound was prepared according to the method of Example 2. $^1$H NMR (400 MHz, CD$_3$OD) δ: 8.17 (d, J=8.4 Hz, 1H), 8.04 (d, J=9.2 Hz, 1H), 7.96 (s, 1H), 7.59 (dd, J=1.6 Hz, 9.2 Hz, 1H), 7.49 (d, J=9.6 Hz, 1H), 4.92 (s, 1H), 4.30 (AB, 2H), 3.18-3.15 (m, 1H), 2.21-1.98 (m, 6H), 1.77-1.61 (m, 9H), 1.51-1.11 (m, 4H), 1.26 (d, J=6.8 Hz, 3H); ESI-MS (M+H)$^+$: 545.9.

Example 42

3-(cyclohexyl(6-((cis)-4-methylcyclohexyloxy)-5-(trifluoromethyl)naphthalen-2-yl)methylamino)-2,2-dimethylcyclobutanecarboxylic acid The title compound was prepared according to the method of Example 10. $^1$H NMR (400 MHz, CD$_3$OD) δ: 8.25 (d, J=9.2 Hz, 1H), 8.11 (d, J=9.6 Hz, 1H), 7.95-7.93 (m, 1H), 7.62-7.58 (m, 1H), 7.55 (d, J=9.2 Hz, 1H), 4.93 (s, 1H), 4.21-4.16 (m, 1H), 3.12 (t, J=8.0 Hz, 1H), 2.58 (t, J=8.0 Hz, 1H), 2.45-2.38 (m, 1H), 2.29-2.17 (m, 2H), 2.04-1.98 (m, 3H), 1.83-1.80 (m, 1H), 1.70-1.56 (m, 5H), 1.51-1.35 (m, 7H), 1.29 (s, 3H), 1.17 (s, 3H), 1.11-0.96 (m, 3H), 0.93 (d, J=4.8 Hz, 3H). ESI-MS (M+H)$^+$: 546.3

Example 43

3-(cyclohexyl(5-(trifluoromethyl)-6-((cis)-4-(trifluoromethyl)cyclohexyloxy)naphthalen-2-yl)methylamino)-2,2-dimethylcyclobutanecarboxylic acid The title compound was prepared according to the method of Example 10. $^1$H NMR (400 MHz, CD$_3$OD) δ: 8.28 (d, J=9.2 Hz, 1H), 8.15 (d, J=9.2 Hz, 1H), 7.97-7.95 (m, 1H), 7.63-7.58 (m, 2H), 5.02 (s, 1H), 4.24-4.19 (m, 1H), 3.22-3.18 (m, 1H), 2.63-2.59 (m, 1H), 2.51-2.41 (m, 1H), 2.29-2.16 (m, 5H), 1.99-1.96 (m, 1H), 1.87-1.58 (m, 10H), 1.43-1.28 (m, 2H), 1.22-1.18 (s, 3H), 1.18 (s, 3H), 1.08-0.92 (m, 3H). ESI-MS (M+H)$^+$: 600.3

Example 44

3-(cyclopropyl(5-(trifluoromethyl)-6-((cis)-4-(trifluoromethyl)cyclohexyloxy)naphthalen-2-yl)methylamino)-2,2-dimethylcyclobutanecarboxylic acid The title compound was prepared according to the method of Example 10. $^1$H NMR (400 MHz, CD$_3$OD) δ: 8.29 (d, J=8.8 Hz, 1H), 8.15 (d, J=9.6 Hz, 1H), 8.00-7.98 (m, 1H), 7.75-7.70 (m, 1H), 7.61 (d, J=9.6 Hz, 1H), 5.03 (s, 1H), 3.79-3.70 (m, 1H), 3.49-3.44 (m, 1H), 2.91-2.71 (m, 1H), 2.43-2.38 (m, 2H), 2.30-2.25 (m, 1H), 2.20-2.17 (m, 2H), 1.85-1.69 (m, 6H), 1.61-1.53 (m, 1H), 1.32-1.22 (m, 6H), 1.01-0.98 (m, 1H), 0.81-0.75 (m, 1H), 0.70-0.63 (m, 1H), 0.39-0.30 (m, 1H). ESI-MS (M+H)$^+$: 558.3

Example 45

1-(1-(5-trifluoromethyl-6-(cis-4-methylcyclohexyloxy)naphthalene-2-yl)ethyl)-piperidine-4-carboxylic acid The title compound was prepared according to the method of Example 10. $^1$H NMR (300 MHz, DMSO-d$_6$) δ 9.38 (br. s., 1H), 8.17-8.27 (m, 1H), 8.07-8.17 (m, 2H), 7.75 (d, J=9.06 Hz, 1H), 7.64-7.73 (m, 1H), 5.02 (br. s., 1H), 4.57-4.82 (m, 1H), 3.70 (d, J=11.71 Hz, 1H), 3.33 (d, J=12.09 Hz, 1H), 2.68-2.95 (m, 2H), 2.38-2.56 (m, 1H), 1.86-2.15 (m, 4H), 1.55-1.86 (m, 4H), 1.72 (d, J=10.95 Hz, 3H), 1.38-1.55 (m, 3H), 1.17-1.39 (m, 2H), 0.90 (d, J=6.04 Hz, 3H); LCMS m/z 464.2 [M+H]$^+$

Example 46

1-((5-trifluoromethyl-6-(cis-4-methylcyclohexyloxy)naphthalene-2-yl)methyl)-pyrrolidine-3-acetic acid The title compound was prepared according to the method of Example 9. $^1$H NMR (400 MHz, METHANOL-d$_4$) d 8.26 (d, J=8.53 Hz, 1H), 8.12 (d, J=9.29 Hz, 1H), 8.03 (d, J=1.26 Hz, 1H), 7.65 (dd, J=1.76, 9.04 Hz, 1H), 7.58 (d, J=9.29 Hz, 1H), 4.94 (br. s., 1H), 4.53 (s, 2H), 2.15-3.35 (m, 9H), 2.01-2.11 (m, 2H), 1.64-1.77 (m, 2H), 1.36-1.58 (m, 5H), 0.96 (d, J=5.52 Hz, 3H); LCMS m/z 450.2 [M+H]$^+$ Example 47

1-((5-trifluoromethyl-6-(cis-4-methylcyclohexyloxy) naphthalene-2-yl)methyl)-azetidine-3-acetic acid The title compound was prepared according to the method of Example 9. $^1$H NMR (400 MHz, METHANOL-d$_4$) d 8.20-8.29 (m, 1H), 8.09-8.16 (m, 1H), 7.94-8.04 (m, 1H), 7.52-7.65 (m, 2H), 4.91-4.98 (m, 1H), 4.44-4.62 (m, 2H), 3.90-4.40 (m, 4H), 3.14-3.25 (m, 1H), 2.65-2.81 (m, 1H), 1.98-2.11 (m, 2H), 1.62-1.77 (m, 2H), 1.35-1.59 (m, 5H), 0.96 (d, J=5.77 Hz, 3H); LCMS m/z 436.2 [M+H]$^+$ Example 48

1-((5-trifluoromethyl-6-(cis-4-methylcyclohexyloxy) naphthalene-2-yl)methyl)-azepane-3-carboxylic acid The title compound was prepared according to the method of Example 9. $^1$H NMR (400 MHz, METHANOL-d$_4$) d 8.27 (d, J=8.53 Hz, 1H), 8.14 (d, J=9.29 Hz, 1H), 8.05 (d, J=1.51 Hz, 1H), 7.67 (dd, J=1.76, 9.04 Hz, 1H), 7.59 (d, J=9.54 Hz, 1H), 4.95 (br. s., 1H), 4.52 (s, 2H), 3.11-3.72 (m, 4H), 2.78 (br. s., 1H), 1.78-2.40 (m, 8H), 1.71 (t, J=13.18 Hz, 2H), 1.38-1.60 (m, 5H), 0.97 (d, J=5.77 Hz, 3H); LCMS m/z 464.3 [M+H]$^+$ Example 49

2-((3R)-1-((6-((cis-4-Methylcyclohexyl)oxy)-5-(trifluoromethyl)naphthalen-2-yl)methyl)piperidin-3-yl) acetic acid The title compound was prepared according to the method of Example 9. $^1$H NMR (400 MHz, METHANOL-d$_4$) d 8.28 (d, J=8.53 Hz, 1H), 8.15 (d, J=9.29 Hz, 1H), 8.05 (s, 1H), 7.66 (dd, J=1.51, 9.04 Hz, 1H), 7.60 (d, J=9.29 Hz, 1H), 4.96 (br. s., 1H), 4.47 (s, 2H), 3.45-3.68 (m, 2H), 2.89-3.05 (m, 1H), 2.72-2.87 (m, 1H), 2.18-2.49 (m, 3H), 1.89-2.12 (m, 4H), 1.66-1.86 (m, 3H), 1.41-1.60 (m, 5H), 1.19-1.38 (m, 1H), 0.98 (d, J=5.77 Hz, 3H); LCMS m/z 464.2 [M+H]$^+$ Example 50

1-(1-(6-((cis-4-Methylcyclohexyl)oxy)-5-(trifluoromethyl)naphthalen-2-yl)propyl)piperidine-4-carboxylic acid The title compound was prepared according to the method of Example 10. $^1$H NMR (400 MHz, METHANOL-d$_4$) d 8.29 (d, J=9.04 Hz, 1H), 8.14 (d, J=9.29 Hz, 1H), 8.00 (s, 1H), 7.63 (d, J=9.29 Hz, 1H), 7.59 (d, J=9.29 Hz, 1H), 4.94 (br. s., 1H), 4.38 (dd, J=4.14, 10.92 Hz, 1H), 3.43-3.89 (m, 2H), 2.77-2.99 (m, 2H), 2.43-2.57 (m, 1H), 2.14-2.40 (m, 4H), 2.00-2.10 (m, 2H), 1.75-1.99 (m, 2H), 1.69 (t, J=13.18 Hz, 2H), 1.36-1.59 (m, 5H), 0.95 (d, J=5.52 Hz, 3H), 0.82 (t, J=7.15 Hz, 3H); LCMS m/z 478.3 [M+H]$^+$ Example 51

2-((3R)-1-(1-(6-((cis-4-Methylcyclohexyl)oxy)-5-(trifluoromethyl)naphthalen-2-yl)ethyl)piperidin-3-yl)acetic acid The title compound was prepared according to the method of Example 10. $^1$H NMR (400 MHz, METHANOL-d$_4$) d 8.28 (d, J=8.53 Hz, 1H), 8.14 (d, J=9.29 Hz, 1H), 8.03 (s, 1H), 7.67 (dd, J=1.76, 9.29 Hz, 1H), 7.58 (d, J=9.29 Hz, 1H), 4.94 (br. s., 1H), 4.64 (q, J=6.86 Hz, 1H), 3.67-3.89 (m, 1H), 3.36-3.52 (m, 1H), 2.52-2.94 (m, 2H), 1.05-2.47 (m, 19H), 0.96 (d, J=5.77 Hz, 3H); LCMS m/z 478.3 [M+H]$^+$ Example 52

2-((3S)-1-(1-(6-((cis-4-Methylcyclohexyl)oxy)-5-(trifluoromethyl)naphthalen-2-yl)propyl)piperidin-3-yl)acetic acid The title compound was prepared according to the method of Example 10. $^1$H NMR (400 MHz, METHANOL-d$_4$) d 8.30 (d, J=8.53 Hz, 1H), 8.14 (d, J=9.29 Hz, 1H), 8.02 (s, 1H), 7.65 (d, J=9.04 Hz, 1H), 7.59 (d, J=9.29 Hz, 1H), 4.95 (br. s., 1H), 4.30-4.45 (m, 1H), 3.70-3.92 (m, 1H), 3.38-3.57 (m, 1H), 2.68-2.84 (m, 1H), 2.59 (dt, J=6.27, 11.55 Hz, 1H), 2.12-2.43 (m, 5H), 2.00-2.11 (m, 2H), 1.63-1.99 (m, 5H), 1.37-1.59 (m, 5H), 1.05-1.26 (m, 1H), 0.96 (d, J=5.77 Hz, 3H), 0.72 (t, J=7.28 Hz, 3H); LCMS m/z 492.1 [M+H]$^+$ Example 53

2-((3R)-1-(1-(6-((cis-4-Methylcyclohexyl)oxy)-5-(difluoromethyl)naphthalen-2-yl)ethyl)piperidin-3-yl)acetic acid The title compound was prepared according to the method of Example 13. $^1$H NMR (400 MHz, METHANOL-d$_4$) d 8.41 (d, J=8.78 Hz, 1H), 8.06 (d, J=9.04 Hz, 1H), 8.00 (s, 1H), 7.36-7.78 (m, 3H), 4.88 (br. s., 1H), 4.54-4.69 (m, 1H), 3.69-3.89 (m, 1H), 3.34-3.51 (m, 1H), 2.52-2.92 (m, 2H), 2.15-2.39 (m, 3H), 1.98-2.10 (m, 2H), 1.77-1.95 (m, 5H), 1.65-1.76 (m, 2H), 1.47-1.62 (m, 3H), 1.27-1.43 (m, 2H), 1.10-1.25 (m, 1H), 0.98 (d, J=6.27 Hz, 3H); LCMS m/z 460.1 [M+H]$^+$ Example 54

2-((3S)-1-(1-(6-((cis-4-Methylcyclohexyl)oxy)-5-(difluoromethyl)naphthalen-2-yl)ethyl)piperidin-3-yl)acetic acid The title compound was prepared according to the method of Example 13. $^1$H NMR (400 MHz, METHANOL-d$_4$)$^1$H NMR (400 MHz, METHANOL-d$_4$) d 8.41 (d, J=8.78 Hz, 1H), 8.06 (d, J=9.04 Hz, 1H), 8.00 (s, 1H), 7.36-7.76 (m, 3H), 4.89-4.92 (m, 1H), 4.55-4.69 (m, 1H), 3.35-3.88 (m, 2H), 2.49-2.94 (m, 2H), 2.12-2.40 (m, 3H), 1.98-2.09 (m, 2H), 1.77-1.96 (m, 5H), 1.65-1.76 (m, 2H), 1.47-1.63 (m, 3H), 1.27-1.43 (m, 2H), 1.09-1.24 (m, 1H), 0.98 (d, J=6.02 Hz, 3H); LCMS m/z 460.1 [M+H]$^+$ Example 55

1-(1-(6-((cis-4-Methylcyclohexyl)oxy)-5-(difluoromethyl)naphthalen-2-yl)ethyl)piperidine-4-carboxylic acid The title compound was prepared according to the method of Example 13. $^1$H NMR (400 MHz, METHANOL-d$_4$) d 8.41 (d, J=9.04 Hz, 1H), 8.06 (d, J=9.29 Hz, 1H), 8.00 (s, 1H), 7.41-7.77 (m, 3H), 4.88-4.92 (m, 1H), 4.63 (q, J=6.69 Hz, 1H), 3.38-3.91 (m, 2H), 2.76-3.07 (m, 2H), 2.54 (t, J=12.30 Hz, 1H), 1.76-2.31 (m, 9H), 1.65-1.74 (m, 2H), 1.47-1.63 (m, 3H), 1.23-1.42 (m, 2H), 0.98 (d, J=6.02 Hz, 3H); LCMS m/z 446.1 [M+H]+

Example 56

2-((3R)-1-((6-((cis-4-Methylcyclohexyl)oxy)-5-(difluoromethyl)naphthalen-2-yl)methyl)piperidin-3-yl)acetic acid The title compound was prepared according to the method of Example 13. $^1$H NMR (400 MHz, METHANOL-d$_4$) d 8.39 (d, J=8.78 Hz, 1H), 8.06 (d, J=9.04 Hz, 1H), 8.01 (s, 1H), 7.41-7.77 (m, 3H), 4.87-4.92 (m, 1H), 4.45 (s, 2H), 3.45-3.67 (m, 2H), 2.72-3.03 (m, 2H), 2.15-2.44 (m, 3H), 1.87-2.09 (m, 4H), 1.65-1.85 (m, 3H), 1.47-1.63 (m, 3H), 1.19-1.42 (m, 3H), 0.98 (d, J=6.02 Hz, 3H); LCMS m/z 446.1 [M+H]+

Example 57

2-((3R)-1-(1-(6-((cis-4-Methylcyclohexyl)oxy)-5-(difluoromethyl)naphthalen-2-yl)propyl)piperidin-3-yl)acetic acid The title compound was prepared according to the method of Example 13. $^1$H NMR (400 MHz, METHANOL-d$_4$) d 8.43 (d, J=9.04 Hz, 1H), 8.07 (d, J=9.04 Hz, 1H), 7.99 (s, 1H), 7.41-7.77 (m, 3H), 4.89 (br. s., 1H), 4.29-4.43 (m, 1H), 3.38-3.90 (m, 2H), 2.68-2.84 (m, 1H), 2.59 (dt, J=5.52, 11.67 Hz, 1H), 2.16-2.42 (m, 5H), 1.65-2.09 (m, 7H), 1.48-1.64 (m, 3H), 1.27-1.42 (m, 2H), 1.07-1.24 (m, 1H), 0.98 (d, J=6.02 Hz, 3H), 0.82 (t, J=7.28 Hz, 3H); LCMS m/z 474.1 [M+H]+

Example 58

1-(1-(6-((cis-4-Methylcyclohexyl)oxy)-5-(difluoromethyl)naphthalen-2-yl)propyl)piperidine-4-carboxylic acid The title compound was prepared according to the method of Example 13. $^1$H NMR (400 MHz, METHANOL-d$_4$) d 8.43 (d, J=8.78 Hz, 1H), 8.07 (d, J=9.29 Hz, 1H), 7.99 (s, 1H), 7.41-7.77 (m, 3H), 4.89 (br. s., 1H), 4.32-4.48 (m, 1H), 3.43-3.91 (m, 2H), 2.78-3.02 (m, 2H), 2.43-2.58 (m, 1H), 2.14-2.41 (m, 4H), 1.77-2.12 (m, 4H), 1.71 (t, J=13.55 Hz, 2H), 1.50-1.62 (m, 3H), 1.27-1.42 (m, 2H), 0.98 (d, J=6.27 Hz, 3H), 0.83 (t, J=7.28 Hz, 3H); LCMS m/z 460.1 [M+H]+

Example 59

2-((3R)-1-((S)-1-(6-((cis-4-Methylcyclohexyl)oxy)-5-(trifluoromethyl)naphthalen-2-yl)propyl)piperidin-3-yl)acetic acid The title compound was prepared according to the method of Example 10. $^1$H NMR (400 MHz, METHANOL-d$_4$) d 8.29 (d, J=8.53 Hz, 1H), 8.14 (d, J=9.29 Hz, 1H), 8.02 (d, J=1.00 Hz, 1H), 7.65 (dd, J=1.63, 9.16 Hz, 1H), 7.58 (d, J=9.54 Hz, 1H), 4.94 (br. s., 1H), 4.38 (dd, J=4.02, 11.29 Hz, 1H), 3.82 (d, J=11.55 Hz, 1H), 3.43 (d, J=12.05 Hz, 1H), 2.74 (dt, J=2.76, 12.67 Hz, 1H), 2.60 (t, J=11.67 Hz, 1H), 2.22-2.43 (m, 5H), 1.63-2.11 (m, 7H), 1.37-1.59 (m, 5H), 1.06-1.26 (m, 1H), 0.96 (d, J=5.77 Hz, 3H), 0.82 (t, J=7.28 Hz, 3H); LCMS m/z 492.1 [M+H]+

Example 60

2-((3R)-1-((R)-1-(6-((cis-4-Methylcyclohexyl)oxy)-5-(trifluoromethyl)naphthalen-2-yl)propyl)piperidin-3-yl)acetic acid The title compound was prepared according to the method of Example 10. $^1$H NMR (400 MHz, METHANOL-d$_4$) d 8.29 (d, J=8.53 Hz, 1H), 8.14 (d, J=9.29 Hz, 1H), 8.02 (d, J=1.25 Hz, 1H), 7.65 (dd, J=1.63, 9.16 Hz, 1H), 7.58 (d, J=9.29 Hz, 1H), 4.95 (br. s., 1H), 4.38 (dd, J=4.27, 11.29 Hz, 1H), 3.76 (d, J=11.80 Hz, 1H), 3.51 (d, J=11.55 Hz, 1H), 2.77 (dt, J=3.01, 12.67 Hz, 1H), 2.58 (t, J=11.67 Hz, 1H), 2.16-2.42 (m, 5H), 1.63-2.12 (m, 7H), 1.35-1.59 (m, 5H), 1.06-1.27 (m, 1H), 0.96 (d, J=5.52 Hz, 3H), 0.82 (t, J=7.28 Hz, 3H); LCMS m/z 492.1 [M+H]+

Example 61

1-((S)-1-(6-((cis-4-Methylcyclohexyl)oxy)-5-(difluoromethyl)naphthalen-2-yl)ethyl)piperidine-4-carboxylic acid The title compound was prepared according to the method of Example 13. $^1$H NMR (400 MHz, METHANOL-d$_4$) d 8.41 (d, J=9.04 Hz, 1H), 8.06 (d, J=9.29 Hz, 1H), 8.00 (s, 1H), 7.41-7.77 (m, 3H), 4.88-4.92 (m, 1H), 4.63 (q, J=6.69 Hz, 1H), 3.38-3.91 (m, 2H), 2.76-3.07 (m, 2H), 2.54 (t, J=12.30 Hz, 1H), 1.76-2.31 (m, 9H), 1.65-1.74 (m, 2H), 1.47-1.63 (m, 3H), 1.23-1.42 (m, 2H), 0.98 (d, J=6.02 Hz, 3H); LCMS m/z 446.1 [M+H]+

Example 62

2-(1-((5-(trifluoromethyl)-6-(4-cis-(trifluoromethyl)cyclohexyloxy)naphthalene-2-yl)methyl)azetidine-3-yl)acetic acid The title compound was prepared according to the method of Example 2. $^1$H NMR (300 MHz, MeOH-d$_4$) δ 8.26 (d, J=7.55 Hz, 1H), 8.14 (d, J=9.44 Hz, 1H), 7.97-8.09 (m, 1H), 7.53-7.72 (m, 2H), 5.02 (br. s., 1H), 4.54 (d, J=17.00 Hz, 2H), 3.92-4.41 (m, 3H), 3.25 (d, J=13.22 Hz, 1H), 2.75 (d, J=7.55 Hz, 2H), 2.07-2.40 (m, 3H), 1.62-1.97 (m, 6H); ESI-MS (M+H)+: 490.2

Example 63

3-(((5-(trifluoromethyl)-6-(cis-4-(trifluoromethyl)cyclohexyloxy)naphthalene-2-yl)methyl)amino)propylphosphonic acid The title compound was prepared according to the method of Example 2. 1H NMR (400 MHz, DMSO-d6) δ 8.21 (d, J=9.29 Hz, 1H), 8.13 (d, J=7.53 Hz, 1H), 8.06 (d, J=1.26 Hz, 1H), 7.66-7.75 (m, 2H), 5.11 (br. s., 1H), 4.30 (s, 2H), 3.06 (t, J=7.03 Hz, 2H), 2.45 (d, J=8.78 Hz, 2H), 2.05 (d, J=12.80 Hz, 2H), 1.54-1.93 (m, 10H); ESI-MS (M+H)+: 514.1

Example 64

1-((5-(trifluoromethyl)-6-((cis-4-(trifluoromethyl)cyclohexyl)oxy)-naphthalen-2-yl)methyl)pyrrolidine-3-acetic acid The title compound was prepared according to the method of Example 2. 1H NMR (400 MHz, DMSO-d6) δ 8.23 (d, J=9.29 Hz, 1H), 8.07-8.18 (m, 2H), 7.67-7.79 (m, 2H), 5.12 (br. s., 1H), 4.52 (d, J=5.27 Hz, 2H), 3.07-3.61 (m, 5H), 2.71-2.99 (m, 1H), 2.43 (d, J=7.53 Hz, 2H), 1.96-2.30 (m, 3H), 1.43-1.85 (m, 7H); ESI-MS (M+H)$^+$: 504.2

Example 65

1-((5-(trifluoromethyl)-6-((cis-4-(trifluoromethyl) cyclohexyl)oxy)-naphthalen-2-yl)methyl)piperidine-4-acetic acid The title compound was prepared according to the method of Example 2. 1H NMR (400 MHz, DMSO-d6) δ 9.47 (br. s., 1H), 8.23 (d, J=9.29 Hz, 1H), 8.05-8.19 (m, 2H), 7.72 (d, J=9.04 Hz, 2H), 5.13 (br. s., 1H), 4.35-4.58 (m, 2H), 3.40 (d, J=11.55 Hz, 2H), 2.92-3.09 (m, 2H), 2.36-2.47 (m, 1H), 2.19 (d, J=6.53 Hz, 2H), 2.04 (d, J=13.30 Hz, 2H), 1.55-1.96 (m, 9H), 1.39 (q, J=12.13 Hz, 2H); ESI-MS (M+H)$^+$: 518.2

Example 66

1-((5-(trifluoromethyl)-6-((cis-4-(trifluoromethyl) cyclohexyl)oxy)-naphthalen-2-yl)methyl)aminocyclopentane-3-carboxylic acid The title compound was prepared according to the method of Example 2. 1H NMR (400 MHz, DMSO-d6) δ 9.09 (br. s., 2H), 8.22 (d, J=9.29 Hz, 1H), 8.06-8.17 (m, 2H), 7.64-7.79 (m, 2H), 5.11 (br. s., 1H), 4.31 (br. s., 2H), 3.46-3.65 (m, 1H), 2.72-2.88 (m, 1H), 2.26-2.47 (m, 2H), 2.05 (d, J=13.55 Hz, 3H), 1.53-1.97 (m, 10H); ESI-MS (M+H)$^+$: 504.2

Example 67

1-((5-(trifluoromethyl)-6-((cis-4-(trifluoromethyl) cyclohexyl)oxy)-naphthalen-2-yl)methyl)piperidine-3-acetic acid The title compound was prepared according to the method of Example 2. 1H NMR (400 MHz, DMSO-d6) δ 8.24 (d, J=9.29 Hz, 1H), 8.06-8.18 (m, 2H), 7.67-7.79 (m, 2H), 5.12 (br. s., 1H), 4.44 (br. s., 2H), 2.61-2.95 (m, 2H), 2.00-2.27 (m, 5H), 1.51-1.91 (m, 10H), 1.06-1.26 (m, 1H); ESI-MS (M+H)$^+$: 518.2

Example 68

(4-((5-(trifluoromethyl)-6-(cis-4-(trifluoromethyl) cyclohexyloxy)naphthalene-2-yl)methyl)aminophenyl)methylphosphonic acid The title compound was prepared according to the method of Example 2. 1H NMR (400 MHz, DMSO-d6) δ 8.13 (d, J=9.29 Hz, 1H), 8.03 (dd, J=2.26, 9.04 Hz, 1H), 7.91 (s, 1H), 7.55-7.67 (m, 2H), 6.94 (dd, J=2.13, 8.41 Hz, 2H), 6.57 (d, J=8.03 Hz, 2H), 5.05 (br. s., 1H), 4.40 (s, 2H), 2.69-2.81 (m, 2H), 2.42 (d, J=8.53 Hz, 1H), 1.96-2.10 (m, 2H), 1.56-1.77 (m, 6H); ESI-MS (M+H)$^+$: 562.2

Example 69

6-(((((5-(trifluoromethyl)-6-((cis)-4-(trifluoromethyl) cyclohexyloxy)naphthalene-2-yl)methyl)amino) methyl)nicotinic acid The title compound was prepared according to the method of Example 2. 1H NMR (400 MHz, DMSO-d6) δ 9.68 (br. s., 2H), 9.11 (d, J=1.51 Hz, 1H), 8.33 (dd, J=2.13, 8.16 Hz, 1H), 8.21 (d, J=9.29 Hz, 1H), 8.06-8.16 (m, 2H), 7.77 (dd, J=1.76, 9.04 Hz, 1H), 7.69 (d, J=9.29 Hz, 1H), 7.62 (d, J=8.03 Hz, 1H), 5.11 (br. s., 1H), 4.43 (d, J=19.33 Hz, 4H), 2.37-2.47 (m, 1H), 1.96-2.14 (m, 2H), 1.52-1.81 (m, 6H); ESI-MS (M+H)$^+$: 527.2

Example 70 cis-4-(((5-(trifluoromethyl)-6-((cis)-4-(trifluoromethyl)cyclohexyloxy)naphthalene-2-yl)methyl) amino)cyclohexane-1-carboxylic acid The title compound was prepared according to the method of Example 2. 1H NMR (400 MHz, DMSO-d6) δ 8.85 (br. s., 2H), 8.21 (d, J=9.29 Hz, 1H), 8.05-8.15 (m, 2H), 7.64-7.77 (m, 2H), 5.10 (br. s., 1H), 4.31 (t, J=5.40 Hz, 2H), 3.13 (br. s., 1H), 2.58 (d, J=3.76 Hz, 1H), 2.34-2.46 (m, 1H), 1.87-2.16 (m, 6H), 1.41-1.82 (m, 10H); ESI-MS (M+H)$^+$: 518.2

Example 71

(S)-1-((5-(trifluoromethyl)-6-((cis)-4-(trifluoromethyl)cyclohexyloxy)naphthalene-2-yl)methyl)pyrrolidine-3-acetic acid The title compound was prepared according to the method of Example 2. 1H NMR (400 MHz, METHANOL-d4) d 8.28 (d, J=8.78 Hz, 1H), 8.15 (d, J=9.29 Hz, 1H), 8.05 (s, 1H), 7.54-7.72 (m, 2H), 5.03 (br. s., 1H), 4.54 (s, 2H), 3.38-3.85 (m, 4H), 2.78-3.08 (m, 1H), 2.58 (br. s., 2H), 2.09-2.45 (m, 4H), 1.66-1.88 (m, 7H); ESI-MS (M+H)$^+$: 504.2

Example 72

(R)-1-((5-(trifluoromethyl)-6-((cis)-4-(trifluoromethyl)cyclohexyloxy)naphthalene-2-yl)methyl)pyrrolidine-3-acetic acid The title compound was prepared according to the method of Example 2. 1H NMR (400 MHz, METHANOL-d4) d 8.24-8.33 (m, 1H), 8.15 (d, J=9.54 Hz, 1H), 8.05 (d, J=1.76 Hz, 1H), 7.67 (dd, J=2.01, 9.04 Hz, 1H), 7.60 (d, J=9.29 Hz, 1H), 5.03 (br. s., 1H), 4.54 (s, 2H), 3.36-3.83 (m, 4H), 3.01 (br. s., 1H), 2.47-2.80 (m, 3H), 2.12-2.36 (m, 4H), 1.67-2.00 (m, 6H); ESI-MS (M+H)$^+$: 504.2

Example 73

3-((4-((5-(trifluoromethyl)-6-(cis-4-(trifluoromethyl) cyclohexyloxy)naphthalene-2-yl)methyl)amino)cyclohexyl)propionic acid The title compound was prepared according to the method of Example 2. 1H NMR (400 MHz, METHANOL-d4) d 8.26 (d, J=8.78 Hz, 1H), 8.13 (d, J=9.04 Hz, 1H), 8.00-8.06 (m, 1H), 7.63-7.71 (m, 1H), 7.58 (d, J=9.29 Hz, 1H), 5.02 (br. s., 1H), 4.31-4.47 (m, 2H), 3.10-3.28 (m, 1H), 2.07-2.40 (m, 6H), 1.95 (dd, J=4.02, 13.05 Hz, 2H), 1.00-1.89 (m, 14H); ESI-MS (M+H)$^+$: 546.3

Example 74

1-((5-(trifluoromethyl)-6-((cis-4-(trifluoromethyl)cyclohexyl)oxy)-naphthalen-2-yl)methyl)-3-methyl-piperidine-4-carboxylic acid The title compound was prepared according to the method of Example 2. 1H NMR (400 MHz, METHANOL-d4) d 8.28 (d, J=8.78 Hz, 1H), 8.16 (d, J=9.29 Hz, 1H), 8.07 (s, 1H), 7.68 (d, J=9.04 Hz, 1H), 7.60 (d, J=9.29 Hz, 1H), 5.03 (br. s., 1H), 4.42-4.59 (m, 2H), 3.37-3.65 (m, 2H), 3.00-3.27 (m, 1H), 2.78 (br. s., 1H), 2.66 (s, 1H), 1.97-2.38 (m, 6H), 1.66-1.90 (m, 6H), 0.99-1.15 (m, 3H) ESI-MS (M+H)$^+$: 518.2

Example 75

5-((((5-(trifluoromethyl)-6-((cis-4-(trifluoromethyl)cyclohexyl)oxy)-naphthalen-2-yl)methyl)amino)methyl)pyridine-2-carboxylic acid The title compound was prepared according to the method of Example 2. 1H NMR (400 MHz, METHANOL-d4) d ppm 1.66-1.89 (m, 6 H) 2.11-2.34 (m, 3 H) 4.41-4.54 (m, 4 H) 5.02 (br. s., 1 H) 7.59 (d, J=9.29 Hz, 1 H) 7.68 (dd, J=9.04, 1.76 Hz, 1 H) 8.04 (d, J=1.25 Hz, 1 H) 8.14 (d, J=9.04 Hz, 2 H) 8.20-8.30 (m, 2 H) 8.78 (s, 1 H); ESI-MS (M+H)$^+$: 527.2

Example 76

1-((5-(trifluoromethyl)-6-((cis-4-(trifluoromethyl)cyclohexyl)oxy)-naphthalen-2-yl)methyl)azepane-4-carboxylic acid The title compound was prepared according to the method of Example 2. 1H NMR (400 MHz, METHANOL-d4) d 8.28 (d, J=8.53 Hz, 1H), 8.15 (d, J=9.29 Hz, 1H), 8.06 (d, J=1.51 Hz, 1H), 7.68 (dd, J=1.88, 9.16 Hz, 1H), 7.60 (d, J=9.54 Hz, 1H), 5.03 (br. s., 1H), 4.52 (s, 2H), 3.37-3.67 (m, 3H), 3.10-3.27 (m, 1H), 2.77 (br. s., 1H), 1.65-2.40 (m, 15H); ESI-MS (M+H)$^+$: 518.2

Example 77

4-((5-(trifluoromethyl)-6-((cis-4-(trifluoromethyl)cyclohexyl)oxy)-naphthalen-2-yl)methyl)morpholine-2-carboxylic acid The title compound was prepared according to the method of Example 2. 1H NMR (400 MHz, METHANOL-d4) d 8.29 (d, J=8.78 Hz, 1H), 8.16 (d, J=9.29 Hz, 1H), 8.07 (d, J=1.25 Hz, 1H), 7.68 (dd, J=2.01, 9.04 Hz, 1H), 7.61 (d, J=9.54 Hz, 1H), 5.03 (br. s., 1H), 4.53 (s, 2H), 4.09 (dd, J=3.39, 13.18 Hz, 2H), 3.81 (t, J=12.30 Hz, 1H), 3.55 (d, J=12.30 Hz, 1H), 3.42 (d, J=12.30 Hz, 1H), 3.22 (dt, J=3.64, 12.36 Hz, 1H), 3.07 (t, J=11.67 Hz, 1H), 2.57 (d, J=6.27 Hz, 2H), 2.08-2.38 (m, 3H), 1.64-1.89 (m, 6H); ESI-MS (M+H)$^+$: 520.2

Example 78

1-((5-(trifluoromethyl)-6-((cis-4-(trifluoromethyl)cyclohexyl)oxy)-naphthalen-2-yl)methyl)-3-aminopyrrolidine-3-carboxylic acid The title compound was prepared according to the method of Example 2. 1H NMR (400 MHz, METHANOL-d4) d 8.24 (d, J=8.28 Hz, 1H), 8.11 (d, J=9.29 Hz, 1H), 8.04 (d, J=1.00 Hz, 1H), 7.70 (dd, J=1.88, 9.16 Hz, 1H), 7.57 (d, J=9.29 Hz, 1H), 5.01 (br. s., 1H), 4.41-4.55 (m, 2H), 3.56-3.78 (m, 2H), 3.39-3.53 (m, 2H), 2.64-2.78 (m, 1H), 2.08-2.41 (m, 4H), 1.66-1.90 (m, 6H); ESI-MS (M+H)$^+$: 505.2

Example 79

N-methyl-cis-4-((((5-(trifluoromethyl)-6-(cis-4-(trifluoromethyl)cyclohexyloxy)naphthalene-2-yl)methyl)amino)cyclohexane-1-carboxylic acid The title compound was prepared according to the method of Example 2. 1H NMR (400 MHz, METHANOL-d4) d 8.28 (d, J=8.78 Hz, 1H), 8.16 (d, J=9.29 Hz, 1H), 8.06 (d, J=1.51 Hz, 1H), 7.55-7.70 (m, 2H), 5.03 (br. s., 1H), 4.65 (d, J=13.05 Hz, 1H), 4.33 (d, J=12.80 Hz, 1H), 3.34-3.45 (m, 1H), 2.68-2.83 (m, 4H), 2.00-2.46 (m, 7H), 1.59-1.91 (m, 10H); ESI-MS (M+H)$^+$: 532.2

Example 80

2-((R)-1-((2-(cis-4-(trifluoromethyl)cyclohexyloxy)-1-(trifluoromethyl)naphthalen-6-yl)methyl)piperidin-3-yl)acetic acid The title compound was prepared according to the method of Example 2. 1H NMR (400 MHz, METHANOL-d4) d 8.28 (d, J=8.53 Hz, 1H), 8.16 (d, J=9.29 Hz, 1H), 8.05 (s, 1H), 7.56-7.72 (m, 2H), 5.03 (br. s., 1H), 4.46 (s, 2H), 3.45-3.67 (m, 2H), 2.90-3.05 (m, 1H), 2.80 (t, J=12.05 Hz, 1H), 2.07-2.45 (m, 6H), 1.66-2.05 (m, 10H), 1.19-1.37 (m, 1H); ESI-MS (M+H)$^+$: 518.2

Example 81

1-((5-(trifluoromethyl)-6-(cis-4-(trifluoromethyl)cyclohexyloxy)naphthalene-2-yl)methyl)-5-hydroxypiperidine-3-carboxylic acid The title compound was prepared according to the method of Example 2. 1H NMR (400 MHz, METHANOL-d4) d 8.14-8.24 (m, 1H), 7.92-8.02 (m, 1H), 7.55-7.67 (m, 1H), 7.50 (d, J=9.29 Hz, 1H), 4.93 (br. s., 1H), 4.00-4.61 (m, 4H), 3.28-3.73 (m, 2H), 2.70-3.17 (m, 3H), 1.97-2.42 (m, 4H), 1.56-1.79 (m, 6H); ESI-MS (M+H)$^+$: 520.2

Example 82

2-((S)-4-((2-(cis-4-(trifluoromethyl)cyclohexyloxy)-1-(trifluoromethyl)naphthalen-6-yl)methyl)morpholin-2-yl)acetic acid The title compound was prepared according to the method of Example 2. 1H NMR (400 MHz, METHANOL-d4) d 8.29 (d, J=8.53 Hz, 1H), 8.16 (d, J=9.29 Hz, 1H), 8.07 (d, J=1.26 Hz, 1H), 7.68 (dd, J=1.88, 9.16 Hz, 1H), 7.61 (d, J=9.29 Hz, 1H), 5.03 (br. s., 1H), 4.53 (s, 2H), 4.10 (dd, J=3.26, 13.05 Hz, 2H), 3.80 (t, J=12.30 Hz, 1H), 3.55 (d, J=12.30 Hz, 1H), 3.42 (d, J=12.55 Hz, 1H), 3.02-3.27 (m, 2H), 2.58 (d, J=6.27 Hz, 2H), 2.10-2.38 (m, 3H), 1.66-1.90 (m, 6H); ESI-MS (M+H)$^+$: 520.2

Example 83

3-(1-((2-(cis-4-(trifluoromethyl)cyclohexyloxy)-1-(trifluoromethyl)naphthalen-6-yl)methyl)piperidine-4-yl)propionic acid The title compound was prepared according to the method of Example 2. 1H NMR (400 MHz, METHANOL-d4) d 8.28 (d, J=8.53 Hz, 1H), 8.15 (d, J=9.29 Hz, 1H), 8.04 (s, 1H), 7.55-7.70 (m, 2H), 5.03 (br. s., 1H), 4.44 (s, 2H), 3.53 (d, J=12.30 Hz, 2H), 3.04 (t, J=12.05 Hz, 2H), 2.09-2.45 (m, 5H), 1.95-2.06 (m, 2H), 1.52-1.90 (m, 9H), 1.32-1.49 (m, 2H); ESI-MS (M+H)$^+$: 532.2

Example 84

2-((R)-1-((2-(cis-4-(ethyl)cyclohexyloxy)-1-(trifluoromethyl)naphthalen-6-yl)methyl)piperidin-3-yl)acetic acid The title compound was prepared according to the method of Example 2. 1H NMR (400 MHz, METHANOL-d4) d 8.26 (d, J=8.53 Hz, 1H), 8.13 (d, J=9.29 Hz, 1H), 8.03 (s, 1H), 7.65 (dd, J=1.63, 9.16 Hz, 1H), 7.57 (d, J=9.29 Hz, 1H), 4.95 (br. s., 1H), 3.44-3.66 (m, 2H), 2.95 (d, J=2.01 Hz, 1H), 2.79 (s, 1H), 2.15-2.44 (m, 3H), 1.53-2.13 (m, 10H), 1.20-1.52 (m, 7H), 0.93 (t, J=7.15 Hz, 3H); ESI-MS (M+H)$^+$: 478.1

Example 85

2,2-dimethyl-3-((((S)-1-(5-(trifluoromethyl)-6-(cis-4-(trifluoromethyl)cyclo-hexyl)oxy)naphthalene-2-yl)ethyl)amino)cyclobutanecarboxylic acid The title compound was prepared by chiral separation of the compound of Example 37. 1H NMR (400 MHz, METHANOL-d4) d 8.22 (d, J=8.53 Hz, 1H), 8.10 (d, J=9.29 Hz, 1H), 7.89 (s, 1H), 7.63 (dd, J=1.88, 9.16 Hz, 1H), 7.54 (d, J=9.29 Hz, 1H), 5.00 (br. s., 1H), 4.33 (d, J=6.53 Hz, 1H), 2.91 (t, J=7.40 Hz, 1H), 2.38-2.48 (m, 1H), 2.10-2.36 (m, 5H), 1.52-1.93 (m, 9H), 1.29 (s, 1H), 1.06-1.20 (m, 6H); ESI-MS (M+H)$^+$: 532.0

Example 86

2,2-dimethyl-3-((((R)-1-(5-(trifluoromethyl)-6-(cis-4-(trifluoromethyl)cyclo-hexyl)oxy)naphthalene-2-yl)ethyl)amino)cyclobutanecarboxylic acid The title compound was prepared by chiral separation of the compound of Example 37. 1H NMR (400 MHz, METHANOL-d4) d 8.29 (d, J=8.53 Hz, 1H), 8.15 (d, J=9.29 Hz, 1H), 8.02 (d, J=1.76 Hz, 1H), 7.70 (dd, J=1.88, 9.16 Hz, 1H), 7.60 (d, J=9.29 Hz, 1H), 5.02 (br. s., 1H), 4.55 (q, J=6.78 Hz, 1H), 3.44 (dd, J=7.78, 9.79 Hz, 1H), 2.59 (dd, J=7.78, 10.29 Hz, 1H), 2.11-2.37 (m, 3H), 1.91-2.07 (m, 1H), 1.67-1.88 (m, 10H), 1.58 (td, J=7.78, 11.80 Hz, 1H), 1.34 (s, 3H), 1.22 (s, 3H); ESI-MS (M+H)$^+$: 532.0

Example 87

2,2-dimethyl-3-((((5-(trifluoromethyl)-6-(cis-4-(trifluoromethyl)cyclo-hexyl)oxy)quinolin-2-yl)methyl)amino)cyclobutanecarboxylic acid The title compound was prepared according to the method of Example 14. 1H NMR (400 MHz, METHANOL-d4) d 8.66 (d, J=9.04 Hz, 1H), 8.24-8.41 (m, 1H), 7.84 (d, J=9.54 Hz, 1H), 7.60 (d, J=9.04 Hz, 1H), 5.07 (br. s., 1H), 4.44-4.63 (m, 2H), 3.67 (t, J=8.91 Hz, 1H), 2.75-2.84 (m, 1H), 2.06-2.53 (m, 5H), 1.68-1.92 (m, 6H), 1.39-1.53 (m, 3H), 1.31 (s, 3H); ESI-MS (M+H)$^+$: 519.0

Example 88

2-((S)-1-(((5-(trifluoromethyl)-6-(cis-4-(trifluoromethyl)cyclohexyl)oxy)quinolin-2-yl)methyl)piperidin-3-yl)acetic acid The title compound was prepared according to the method of Example 14. 1H NMR (400 MHz, METHANOL-d4) d 8.68 (td, J=1.25, 8.78 Hz, 1H), 8.34 (d, J=9.54 Hz, 1H), 7.85 (d, J=9.29 Hz, 1H), 7.61 (d, J=9.04 Hz, 1H), 5.07 (br. s., 1H), 4.67 (br. s., 2H), 3.59-3.92 (m, 2H), 2.82-3.20 (m, 2H), 2.11-2.58 (m, 6H), 1.90-2.09 (m, 3H), 1.68-1.88 (m, 6H), 1.37 (br. s., 1H); ESI-MS (M+H)$^+$: 519.0

Example 89

2-((S)-1-(1-(2-(cis-4-(trifluoromethyl)cyclohexyloxy)-1-(trifluoromethyl)naphthalen-6-yl)propyl)piperidin-3-yl)acetic acid The title compound was prepared according to the method of Example 7. 1H NMR (400 MHz, METHANOL-d4) d 8.32 (d, J=8.53 Hz, 1H), 8.17 (d, J=9.29 Hz, 1H), 8.03 (s, 1H), 7.64 (dd, J=8.91, 19.70 Hz, 2H), 5.04 (br. s., 1H), 4.32-4.46 (m, 1H), 3.70-3.90 (m, 1H), 3.39-3.57 (m, 1H), 2.69-2.84 (m, 1H), 2.60 (dt, J=6.02, 11.55 Hz, 1H), 2.08-2.44 (m, 8H), 1.66-2.04 (m, 9H), 1.08-1.24 (m, 1H), 0.82 (t, J=7.28 Hz, 3H); ESI-MS (M+H)$^+$: 546.0

Example 90

2,2-dimethyl-3-(1-(6-((cis)-4-methylcyclohexyloxy)-5-(trifluoromethyl)naphthalen-2-yl)-3-methylbutylamino)cyclobutanecarboxylic acid The title compound was prepared according to the method of Example 10. 1H NMR (400 MHz, CD3OD) δ: 8.31-8.27 (m, 1H), 8.14 (dd, J=2.4 Hz, 9.2 Hz, 1H), 8.05 (d, J=7.8 Hz, 1H), 7.72-7.66 (m, 1H), 7.56 (d, J=9.2 Hz, 1H), 4.92 (s, 1H), 4.45-4.33 (m, 1H), 3.48-3.43 (m, 0.5H), 3.18-3.14 (m, 0.5H), 2.65-2.32 (m, 2H), 2.16-2.08 (m, 1H), 2.05-2.02 (m, 2H), 1.99-1.87 (m, 2H), 1.70-1.64 (m, 2H), 1.52-1.39 (m, 6H), 1.30-1.18 (m, 4H), 1.13 (s, 2H), 0.98-0.93 (m, 6H), 0.88-0.86 (m, 3H); ESI-MS (M+H)+: 520.2

Example 91

2-((3R)-1-((S)-1-(6-((cis-4-Methylcyclohexyl)oxy)-5-(difluoromethyl)naphthalen-2-yl)ethyl)piperidin-3-yl)acetic acid The title compound was prepared according to the method of Example 13. $^1$H NMR (300 MHz, METHANOL-d$_4$) d 8.41 (d, J=8.69 Hz, 1H), 7.94-8.14 (m, 2H), 7.33-7.81 (m, 3H), 4.88 (br. s., 1H), 4.62 (q, J=6.80 Hz, 1H), 3.34-3.88 (m, 2H), 2.58-2.84 (m, 2H), 2.19-2.43 (m, 3H), 1.79-2.12 (m, 7H), 1.46-1.77 (m, 5H), 1.07-1.45 (m, 3H), 0.98 (d, J=6.04 Hz, 3H); LCMS m/z 460.1 [M+H]+

Example 92

2-((3R)-1-((R)-1-(6-((cis-4-Methylcyclohexyl)oxy)-5-(difluoromethyl)naphthalen-2-yl)ethyl)piperidin-3-yl)acetic acid The title compound was prepared according to the method of Example 13. $^1$H NMR (300 MHz, METHANOL-$d_4$) d 8.41 (d, J=9.06 Hz, 1H), 8.06 (d, J=9.44 Hz, 1H), 8.00 (d, J=1.51 Hz, 1H), 7.34-7.82 (m, 3H), 4.88 (br. s., 1H), 4.63 (q, J=7.05 Hz, 1H), 3.40-3.83 (m, 2H), 2.77-2.96 (m, 1H), 2.59 (t, J=11.52 Hz, 1H), 1.46-2.38 (m, 15H), 1.09-1.45 (m, 3H), 0.98 (d, J=6.04 Hz, 3H); LCMS m/z 460.1 [M+H]$^+$

Example 93

2-((3R)-1-((S)-1-(6-((cis-4-Methylcyclohexyl)oxy)-5-(difluoromethyl)naphthalen-2-yl)propyl)piperidin-3-yl)acetic acid The title compound was prepared according to the method of Example 13. $^1$H NMR (300 MHz, METHANOL-$d_4$) d 8.43 (d, J=9.06 Hz, 1H), 8.07 (d, J=9.06 Hz, 1H), 7.99 (d, J=1.51 Hz, 1H), 7.36-7.82 (m, 3H), 4.89 (br. s., 1H), 4.36 (dd, J=4.53, 10.95 Hz, 1H), 3.83 (d, J=11.71 Hz, 1H), 3.42 (d, J=12.46 Hz, 1H), 2.74 (dt, J=2.83, 12.56 Hz, 1H), 2.60 (t, J=11.71 Hz, 1H), 2.19-2.43 (m, 5H), 1.46-2.12 (m, 10H), 1.25-1.44 (m, 2H), 1.06-1.23 (m, 1H), 0.98 (d, J=6.04 Hz, 3H), 0.82 (t, J=7.37 Hz, 3H); LCMS m/z 474.1 [M+H]$^+$

Example 94

2-((3R)-1-((R)-1-(6-((cis-4-Methylcyclohexyl)oxy)-5-(difluoromethyl)naphthalen-2-yl)propyl)piperidin-3-yl)acetic acid The title compound was prepared according to the method of Example 13. $^1$H NMR (300 MHz, METHANOL-$d_4$) d 8.42 (d, J=9.06 Hz, 1H), 8.07 (d, J=9.06 Hz, 1H), 7.99 (d, J=1.51 Hz, 1H), 7.35-7.81 (m, 3H), 4.37 (dd, J=4.53, 11.33 Hz, 1H), 3.76 (d, J=11.71 Hz, 1H), 3.45-3.57 (m, 1H), 2.69-2.86 (m, 1H), 2.59 (t, J=11.71 Hz, 1H), 2.13-2.46 (m, 5H), 1.45-2.11 (m, 10H), 1.25-1.45 (m, 2H), 1.05-1.24 (m, 1H), 0.98 (d, J=6.04 Hz, 3H), 0.82 (t, J=7.18 Hz, 3H); LCMS m/z 474.1 [M+H]$^+$

Example 95

2-((3R)-1-((S)-1-(6-((cis-4-Methylcyclohexyl)oxy)-5-(trifluoromethyl)naphthalen-2-yl)ethyl)piperidin-3-yl)acetic acid The title compound was prepared according to the method of Example 13. $^1$H NMR (300 MHz, METHANOL-$d_4$) d 8.25 (d, J=7.93 Hz, 1H), 8.12 (d, J=9.06 Hz, 1H), 7.99 (d, J=1.51 Hz, 1H), 7.66 (dd, J=1.89, 9.06 Hz, 1H), 7.56 (d, J=9.44 Hz, 1H), 4.93 (br. s., 1H), 4.51 (q, J=6.80 Hz, 1H), 3.21-3.65 (m, 2H), 2.55-2.78 (m, 2H), 1.97-2.36 (m, 5H), 1.62-1.96 (m, 7H), 1.37-1.60 (m, 5H), 1.30 (t, J=7.37 Hz, 2H), 0.95 (d, J=5.67 Hz, 3H); LCMS m/z 478.1 [M+H]$^+$

Example 96

2-((3R)-1-((R)-1-(6-((cis-4-Methylcyclohexyl)oxy)-5-(trifluoromethyl)naphthalen-2-yl)ethyl)piperidin-3-yl)acetic acid The title compound was prepared according to the method of Example 13. $^1$H NMR (300 MHz, METHANOL-$d_4$) d 8.25 (d, J=7.93 Hz, 1H), 8.12 (d, J=9.06 Hz, 1H), 7.99 (d, J=1.51 Hz, 1H), 7.66 (dd, J=1.89, 9.06 Hz, 1H), 7.56 (d, J=9.44 Hz, 1H), 4.93 (br. s., 1H), 4.51 (q, J=6.80 Hz, 1H), 3.21-3.65 (m, 2H), 2.55-2.78 (m, 2H), 1.97-2.36 (m, 5H), 1.62-1.96 (m, 7H), 1.37-1.60 (m, 5H), 1.30 (t, J=7.37 Hz, 2H), 0.95 (d, J=5.67 Hz, 3H); LCMS m/z 478.1 [M+H]$^+$

Example 97

1-((5-(Difluoromethyl)-6-((cis-4-methylcyclohexyl)oxy)naphthalen-2-yl)methyl)azetidine-3-acetic acid The title compound was prepared according to the method of Example 13. $^1$H NMR (300 MHz, METHANOL-$d_4$) d 8.37 (d, J=8.69 Hz, 1H), 8.04 (d, J=9.06 Hz, 1H), 7.97 (br. s., 1H), 7.33-7.81 (m, 3H), 4.43-4.62 (m, 2H), 3.88-4.36 (m, 4H), 3.10-3.28 (m, 1H), 2.75 (d, J=7.18 Hz, 2H), 1.96-2.11 (m, 2H), 1.45-1.79 (m, 5H), 1.23-1.43 (m, 2H), 0.98 (d, J=6.04 Hz, 3H); LCMS m/z 418.0.1 [M+H]+

Example 98

1-(1-(5-(Difluoromethyl)-6-((cis-4-methylcyclohexyl)oxy)naphthalen-2-yl)ethyl)azetidine-3-acetic acid The title compound was prepared according to the method of Example 13. $^1$H NMR (400 MHz, METHANOL-$d_4$) d 8.42 (d, J=8.78 Hz, 1H), 8.07 (d, J=9.29 Hz, 1H), 7.97 (s, 1H), 7.42-7.78 (m, 3H), 4.90 (br. s., 1H), 4.55-4.77 (m, 1H), 4.38-4.53 (m, 1H), 4.05-4.28 (m, 1H), 3.85-3.99 (m, 1H), 3.59-3.83 (m, 1H), 3.05-3.27 (m, 1H), 2.64-2.85 (m, 2H), 1.99-2.14 (m, 2H), 1.49-1.81 (m, 8H), 1.26-1.46 (m, 2H); 1.00 (d, J=6.27 Hz, 3H); LCMS m/z 432.0 [M+H]+

Example 99

1-(1-(5-(Difluoromethyl)-6-((cis-4-methylcyclohexyl)oxy)naphthalen-2-yl)propyl)azetidine-3-acetic acid The title compound was prepared according to the method of Example 13. $^1$H NMR (300 MHz, METHANOL-$d_4$) d 8.43 (d, J=8.69 Hz, 1H), 8.07 (d, J=9.06 Hz, 1H), 7.94 (s, 1H), 7.37-7.81 (m, 3H), 4.90 (br. s., 1H), 4.27-4.59 (m, 2H), 4.16 (t, J=9.63 Hz, 1H), 3.63-3.91 (m, 2H), 3.08-3.25 (m, 1H), 2.66-2.79 (m, 2H), 1.85-2.23 (m, 4H), 1.48-1.80 (m, 5H), 1.27-1.45 (m, 2H), 1.00 (d, J=6.04 Hz, 3H), 0.85 (t, J=7.18 Hz, 3H); LCMS m/z 446.1 [M+H]+

Example 100

2-((S)-1-((S)-1-(2-(cis-4-methylcyclohexyloxy)-1-(difluoromethyl)naphthalen-6-yl)ethyl)piperidin-3-yl)acetic acid The title compound was prepared according to the method of Example 13. $^1$H NMR (400 MHz, METHANOL-$d_4$) d 8.41 (d, J=8.78 Hz, 1H), 8.06 (d, J=9.29 Hz, 1H), 8.00 (d, J=1.25 Hz, 1H), 7.36-7.76 (m, 3H), 4.89 (br. s., 1H), 4.62 (q, J=7.03 Hz, 1H), 3.82 (d, J=11.80 Hz, 1H), 3.34-3.42 (m, 1H), 2.61-2.82 (m, 2H), 1.99-2.40 (m, 5H), 1.77-1.98 (m, 5H), 1.47-1.76 (m, 5H), 1.26-1.43 (m, 2H), 1.09-1.26 (m, 1H), 0.98 (d, J=6.02 Hz, 3H); LCMS m/z 460.1 [M+H]+

Example 101

2-((R)-1-((S)-1-(2-(cis-4-methylcyclohexyloxy)-1-(difluoromethyl)naphthalen-6-yl)ethyl)piperidin-3-yl)acetic acid The title compound was prepared according to the method of Example 13. $^1$H NMR (400 MHz, METHANOL-d$_4$) d 8.41 (d, J=9.04 Hz, 1H), 8.06 (d, J=9.04 Hz, 1H), 8.00 (s, 1H), 7.37-7.79 (m, 3H), 4.89 (br. s., 1H), 4.63 (q, J=6.78 Hz, 1H), 3.42-3.80 (m, 2H), 2.77-2.93 (m, 1H), 2.59 (t, J=11.80 Hz, 1H), 1.96-2.35 (m, 5H), 1.77-1.95 (m, 5H), 1.71 (t, J=13.30 Hz, 2H), 1.48-1.63 (m, 3H), 1.29-1.43 (m, 2H), 1.11-1.25 (m, 1H), 0.98 (d, J=6.27 Hz, 3H); LCMS m/z 460.1 [M+H]+

Example 102

(S)-2-((R)-1-((5-(trifluoromethyl)-6-((cis-4-(trifluoromethyl)cyclohexyl)oxy)naphthalen-2-yl)methyl)piperidin-3-yl)propanoic acid

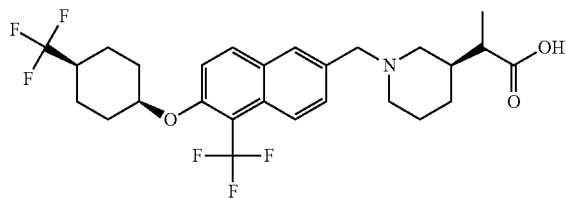 [SMILES: CC(C(=O)O)[C@H]1CCCN(Cc2ccc3c(C(F)(F)F)c(O[C@H]4CC[C@@H](C(F)(F)F)CC4)ccc3c2)C1]

The target compound was prepared according to the method of Example 2 to give a white solid (35 mg, yield: 45%). $^1$H NMR (400 MHz, CD3OD, a mixture of diastereomers) δ: 8.22 (d, J=8.8 Hz, 1H), 8.13 (d, J=9.2 Hz, 1H), 8.00 (s, 1H), 7.66 (d, J=9.2 Hz, 1H), 7.57 (d, J=9.2 Hz, 1H), 5.02 (s, 1H), 4.24 (s, 2H), 3.33-3.30 (m, 2H), 2.73-2.60 (m, 2H), 2.29-2.16 (m, 4H), 1.95-1.72 (m, 11H), 1.13 (d, J=6.8 Hz, 2H), 1.09 (d, J=7.2 Hz, 1H); ESI-MS (M+H)+: 532.2.

Example 103

2-((R)-1-((R)-1-(5-(trifluoromethyl)-6-((cis-4-(trifluoromethyl)cyclohexyl)oxy)naphthalen-2-yl)propyl)piperidin-3-yl)acetic acid and 2-((R)-1-((S)-1-(5-(trifluoromethyl)-6-((cis-4-(trifluoromethyl)cyclohexyl)oxy)naphthalen-2-yl)propyl)piperidin-3-yl)acetic acid

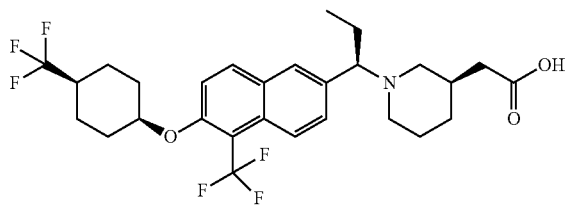

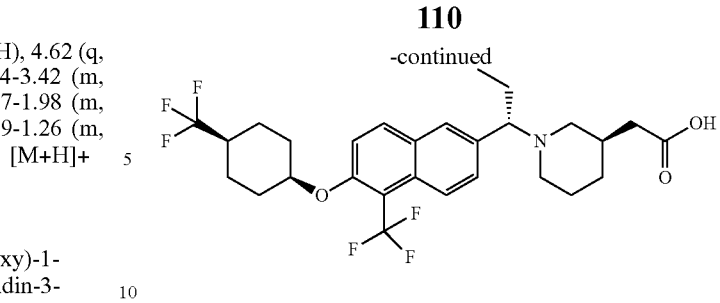

((R)-1-{1-[5-Trifluoromethyl-6-(4-trifluoromethyl-cyclohexyloxy)-naphthalen-2-yl]-propyl}-piperidin-3-yl)-acetic acid ethyl ester (440 mg, 0.77 mmol) (prepared according to Example 7) was separated with the chiral methods: IC(2×15 cm), 10% ethanol (0.1% DEA)/CO2, 100 bar; 60 ml/min., 220 nM.; ini vol: 0.5 mL, 11 mg/mL methanol. Two isomers were obtained after the chiral separation. Peak#1 (230 mg, chiral HPLC: RT 1.26 min.; purity>99% based on HPLC, ee>99%), ESI-MS (M+H)+: 574.1. Peak#2 (227 mg, chiral HPLC: RT 1.41 min.; purity>99% based on HPLC, ee>98%), ESI-MS (M+H)+: MH+574.1; The two fractions were used in the standard hydrolysis step to give two enantiomers:

Enantiomer 1 (from Peak 1), white powder (156 m, 74%). $^1$H NMR (400 MHz, METHANOL-d4) d 8.31 (d, J=7.78 Hz, 1H), 8.18 (d, J=9.29 Hz, 1H), 8.06 (d, J=1.76 Hz, 1H), 7.69 (dd, J=2.01, 9.03 Hz, 1H), 7.61 (d, J=9.29 Hz, 1H), 5.04 (br. s., 1H), 4.41 (br. s., 1H), 3.68-3.86 (m, 1H), 3.45-3.58 (m, 1H), 2.48-2.86 (m, 2H), 2.10-2.43 (m, 8H), 1.65-2.06 (m, 9H), 1.18 (br. s., 1H), 0.81 (t, J=7.28 Hz, 3H); ESI-MS (M+H)+: 546.3.

Enantiomer 2 (from Peak 2), white powder (132 mg, 63%). $^1$H NMR (400 MHz, METHANOL-d4) d 8.31 (d, J=7.78 Hz, 1H), 8.18 (d, J=9.29 Hz, 1H), 8.06 (d, J=1.76 Hz, 1H), 7.68 (dd, J=2.01, 9.29 Hz, 1H), 7.61 (d, J=9.29 Hz, 1H), 5.04 (br. s., 1H), 4.40 (d, J=6.53 Hz, 1H), 3.84 (d, J=11.29 Hz, 1H), 3.43 (d, J=12.05 Hz, 1H), 2.53-2.86 (m, 2H), 2.07-2.45 (m, 8H), 1.67-2.00 (m, 9H), 1.16 (d, J=11.04 Hz, 1H), 0.82 (t, J=7.15 Hz, 3H); ESI-MS (M+H)+: 546.3.

Example 103

Activity measurements

ATX (Autotaxin) is a 125 KDa glycoprotein with lysophospholipase D (LPLD) activity that generates the bioactive lipid lysophosphatidic acid (LPA) from lysophosphatidylcholine (LPC). The ATX biochemical assay utilizes a FRET (fluorescence resonance energy transfer) technology platform. The fluorescence signal of FRET substrate FS-3 is quenched due to intra-molecular FRET of a fluorophore to a non-fluorescing quencher (Ferguson, C. G., et al., Org Lett. 2006 May 11; 8(10): 2023-2026, which is incorporated by reference in its entirety). ATX catalyzes the hydrolysis of the substrate which separates the dabsyl quencher from the fluorescein reporter, which becomes fluorescent. The reaction is monitored by a SpectraMax M5 (Molecular Devices, Sunnyvale, Calif.) with at excitation wavelength 485 nm and emission wavelength 535 nm.

Reagents

Fatty acid free-BSA (Sigma A8806): 10 mg/mL in H$_2$O, stored at 4° C.

2×ATX assay buffer: 100 mM Tris, 280 mM NaCl, 10 mM KCl, 2 mM CaCl$_2$, 2 mM MgCl$_2$, pH 7.4.

Human ATX protein: expressed and purified in house. Stored at −80° C.

Substrate FS-3 (Echelon, L-2000): 100 µg in 77.74.L H$_2$O (1 mM stock), stored at −20° C.

384-well flat bottom plates—Corning #3575.

Assay

Compound dilution—All compounds were provided at 10 mM in 100% DMSO. In the first well, 2 µL of 10 mM compound was added to 78 µL of DMSO (1:40 dilution). In subsequent wells 3-fold dilution (total 10 dilutions) were performed.

1×ATX assay buffer was made up with a final concentration of 1 mg/mL fatty acid free-BSA using 2×ATX assay buffer, 10 mg/ml fatty acid free-BSA and ddH$_2$O.

ATX protein was diluted with 1×ATX assay buffer to a concentration of 1.32 µg/mL (1.32×). 38 µL was added per well to the assay plate. The final concentration of ATX in the reaction as 1.0 µg/mL.

2 µL per well of compounds was transferred to provide the desired concentration. The plate was centrifuged, then incubated at room temperature for 30 minutes on the shaker.

FS-3 was diluted with 1×ATX assay buffer to a concentration of FS-3 of 10 µM (5×). Then, 10 µL was added per well to the assay plate. The final concentration of FS-3 in the reaction was 2 µM. The plate was centrifuged. The plate was kept shaking at room temperature for 2 hours. Because FS-3 substrate is light sensitive, plates were kept covered and protected from light.

Fluorescence was measured using SpectraMax M5 (excitation at 485 nm/emission at 538 nm, top read).

The compounds of examples 6, 7, 10, 13, 18, 19, 37, 44, 49, 51, 52, 53, 54, 55, 56, 57, 58, 59, 60, 63, 68, 84, 86, 89, 91, 92, 93, 94, 95, 96, 97, 98, 99, 100, 101, and 103 had an IC$_{50}$ of no greater than 100 nM.

The compounds of examples 5, 9, 14, 15, 21, 22, 25, 26, 27, 34, 38, 39, 40, 61, 62, 64, 65, 67, 69, 75, 80, 81, 82, and 102 had an IC$_{50}$ of no greater than 250 nM.

The compounds of examples 1, 2, 3b, 4, 8, 11, 12, 23, 24, 28, 29, 30, 31, 32, 33, 35, 36, 41, 42, 43, 45, 46, 47, 48, 50, 66, 70, 71, 73, 74, 76, 77, 78, 79, 83, 85, 87, 88, and 90 had an IC$_{50}$ of no greater than 500 nM.

OPC Differentiation Assay

Enriched populations of oligodendrocytes were grown from post-natal day 2 (P2) female Sprague Dawley rats. The forebrain was dissected out and placed in Hank's buffered saline solution (HBSS; Invitrogen, Grand Island, N.Y.). The tissue was cut into 1 mm fragments and incubated at 37° C. for 15 minutes in 0.01% trypsin and 10 µg/mL DNase. Dissociated cells were plated on poly-L-lysine-coated T75 tissue culture flasks and grown at 37° C. for 10 days in Dulbecco's modified Eagle's medium (DMEM) with 20% fetal calf serum (Invitrogen). A2B5$^+$ OPCs were collected by shaking the flask overnight at 200 rpm and 37° C., resulting in a 95% pure population.

For the differentiation assay, 2 µM and 20 µM antagonist or the same concentrations of vehicle (DMSO) were applied to OPCs cultured in CNTF/T3 containing media. After a 3-day incubation, cells were lysed in 80 µL lysis buffer (50 mM HEPES [4-(2-hydroxyethyl)-1-piperazineethanesulfonic acid], pH 7.5, 150 mM NaCl, 1.5 mM MgCl$_2$, 1 mM ethylene glycol tetraacetic acid [EGTA], 1% Triton X-100 and 10% glycerol) for 30 minutes at 4° C. After centrifugation at 14,000 g for 15 minutes, the supernatants were boiled in Laemmli sample buffer, subjected to 4-20% SDS-PAGE, and analyzed by Western blotting with anti-MBP, anti-myelin-associated glycoprotein (MAG), or anti-beta actin antibodies. The secondary antibodies used were anti-mouse IgG-HRP (horseradish peroxidase) and anti-rabbit IgG-HRP respectively.

DRG-OPC Myelination Assay

Embryonic neocortical neurons are dissected from embryonic day 18 (E18) Sprague Dawley rats, and then plated on poly-D-lysine (100 µg/mL)-coated cover slips and grown in neurobasal medium supplemented with B27 (Invitrogen) for one week. A2B5$^+$ OPCs are prepared as described above and then added into the cultured neocortical neurons. One day later, different concentrations of an ATX inhibitor and control reagents are applied into the co-cultures. Fresh media containing the different concentrations of an ATX inhibitor or control compounds are supplied every three days. After ten days, co-cultures are subjected to sodium dodecyl sulfate polyacrylamide gel electrophoresis (SDS-PAGE)/Western blot analyses to quantify MAG, MBP, and MOG.

Remyelination Assay in Brain Slice Culture

Approximately three to four consecutive 300 µm slices are taken from the junction of the corpus callosum to the hippocampus in post-natal, day 17 Sprague Dawley rats (Charles River, Willmington, Mass.). Slices are cultured in basal DMEM supplemented with 25% horse serum for three days, before being treated with 6 mg/mL LPC (Sigma L-4129) for a further three days. The medium is then changed, and slices incubated with medium containing an ATX inhibitor or vehicle control for a final period of three days, after which myelination is visualized by black gold staining (Millipore, Bedford, Mass.) following the manufacture's protocol. Images are acquired using a Leica M420 microscope (Bannockburn, Ill.) and the staining intensity of corpus callosum is analyzed using Metamorph software (Molecular Devices, Downingtown, Pa.). Three or four brain slices are used for each treatment group.

Lysolecithin Demyelination Model

Adult Sprague Dawley rats (220-260 g) are anesthetized by intraperitoneal injection of a cocktail, consisting of Ketamine (35 mg/kg), Xylazine (6 mg/kg) and Acepromazine (1 mg/kg). The back of the animal is shaved from the lower thoracic to the lumbar region, subsequently sanitized with 70% isopropanol, Betadine Scrub solution, and 70% isopropanol again. The animal is then placed onto stereotaxic frame.

After ensuring an adequate anesthetic level, the skin is incised along the midline over the thoracic region. The dorsal fascia is incised and the paraspinal muscles separated from the spinous processes of the thoracic vertebrae T-9 through T-11. The T-10 vertebra is demolished, and the lamina removed with micro-rongeurs. Once the dorsal spinal cord region is exposed, a microcapillary glass needle is inserted into the dorsal column to a depth of 0.6 mm. The demyelinating reagent, 1.5 µL of 1% Lysolecithin (LPC, Sigma# L1381) in saline is injected with the infusion rate of 2 nL/sec controlled by a micro-pump (World Precision Instrument #micro4). Once the injection is completed, the needle is placed for additional 1 min before removal. The paraspinal muscles and the lumbar fascia are closed with suture (#5, silk). The skin incision is closed with wound clips. Animals are allowed to recover from the anesthesia and are observed in the humidified incubator.

Buprenorphine (0.05 mg/kg) is administrated subcutaneously (s.c.) twice a day for additional two days following operation.

Three days following the primary surgery, treatments with an ATX inhibitor (30 pmol), LPA (30 pmol) or control (0.1% DMSO in saline) are injected at the primary injection region in a volume of 1.5 µL with the same infusion speed as indicated above. Nine days following the primary surgery, the animals are anesthetized and perfused trans-cardially with heparin (10 iu/mL) in saline followed by 4% PFA in PBS. The spinal cords are removed and post fixed in PFA overnight. Then the cords are cut into 100 µM thickness longitudinally and then 1% loxuol fast blue is stained and histological evaluation for remyelination and repair is assessed under microscope.

For systemic treatment, the animals are administered once daily intraperitoneally with either an ATX inhibitor (10 mg/kg) or control (15% HPCD (hydroxypropyl-β-cyclodextrin)) 2 days following the primary surgery. Nine days after the primary surgery, animals are sacrificed and the spinal cords were processed as indicated above.

CFA Inflammatory Pain Model

In the CFA (complete Freund's adjuvant) model, adult male SD (250-300 g) rats are anesthetized with isoflurane inhalation (4.5% induction/2.0% maintenance). Heat-killed M. Tuberculosis H37 RA (non-viable) suspended at a concentration of 1.0 mg/ml in incomplete Freund's adjuvant is used (Chondrex Inc., catalog#7008). At day 0, intradermal injection (i.d.) of 100 µl of CFA (1:1 oil/saline) is slowly perfused into the right footpad of the rats. At day 1, baseline tactile allodynia test are conducted: rats that develop sensitive painful response are enrolled to the study. At day 2, rats are orally dosed once with either vehicle or ATX inhibitor, then at 2 hrs, 4 hrs, 6 hrs and 24 hrs after dosage, all rats are tested for mechanical allodynia response.

Tactile allodynia is tested as follows. A rat is placed in an elevated Plexiglas observation chamber (approximately 4"×6"×10") having a wire grid (1 cm² spacing) mesh floor under polycarbonate cages. The rat is left to acclimate to the experimental conditions for 20 minutes before testing begins. After the rat is calm, tactile allodynia is assessed using a series of von Frey filaments ranging from 2.04-28.84 g (Stoelting, Wood Dale, Ill.). Graded pressure is presented to a localized area on the plantar surface of the paw via the use of Von Frey hairs (monofilaments which are calibrated to bend at a known pressure). A response to the VonFrey hair is recorded as the rat withdrawing the tested paw and is usually followed by lifting and licking. A series of filaments are used to determine the threshold response using the established "Up-Down" method. Each paw is tested 4-6 times repeatedly with 1-2 seconds (modified from Seltzer et al., 1991) in between each probe to accurately assess the behavior. A sharp lifting of the paw is scored as a positive response.

Rat Model of Neuropathic Pain

Chronic Constriction Injury (CCI) Surgery: In the CCI model (Bennett and Xie, *Pain,* 1989, which is incorporated by reference in its entirety), adult male SD (250-275 g) rats are anesthetized with isoflurane inhalation (4.5% induction/2.0% maintenance). The surgery is performed under aseptic conditions and involves exposing the sciatic nerve at the mid-thigh level. Ocular lubricant is used as needed to prevent corneal drying. After shaving and disinfecting the skin (betadine followed by 70% ethanol), a small incision is made just caudal to the biceps femoris. Care is taken to not disturb the sciatic nerve. The nerve is slightly elevated, and 4 loose ligatures of 4-0 chromic gut suture are inserted under the nerve, and then are loosely tied around it. The sutures constrict the nerve but do not strangle it. Prior to inserting the chromic gut, it is rinsed twice in sterile saline. The incision is closed with wound clips, and rats are allowed to recover from anesthesia on a circulating water heating pad before being returned to their home cages. In the sham controls the skin is opened, and the sciatic nerve is identified and elevated, but no sutures are tied around the nerve. All rats are screened for pain response around post-surgery day 7 and only rats with sensitive pain response are enrolled to the study.

Animals are orally dosed twice/day for 3 times/week with either vehicle or ATX inhibitor post-surgery at days 10, 12, 14, 17, 19 and 21, and animals are also tested at the same schedule for three types of neuropathic pain: thermal hyperalgesia, tactile allodynia and incapacitance.

(1) Plantar thermal hyperalgesia: Rats are tested for hyperalgesia using a plantar device (Ugo Basile Inc., Cat.#37370). After acclimation to the testing room, rats are placed on an elevated glass floor beneath inverted clear plastic cages, and a radiant heat source beneath the glass is aimed at the mid-plantar surface of the hindpaw after they have ceased all exploratory behavior. The onset of light activates a timer, which is terminated by a hindpaw withdrawal response. A cutoff time of 30 seconds is used to avoid tissue damage in the absence of a response. The average withdrawal latency value of three trials from the ipsilateral hindpaw is measured with at least 5-10 minutes between each trial to avoid any tissue damage.

(2) Tactile allodynia is tested as described above.

(3) Incapacitance: The incapacitance test measures the weight the rat places on each of its hindpaws. The rat is placed in a small, clear Plexiglas box (6" long×3" wide×4" tall). The box is tilted up and opens in the front. The rat is placed in the box so that its hindpaws are at the back (lower) portion of the box, and the forepaws are at the front (raised) part of the box. The rat's head is at the opening in the front of the box. The box is placed on a divided scale such that each of the rat's hindpaws is on one of the two weighing pans of the scale. The weight that the rat placed on each hindpaw is then measured. The procedure is rapid (about 10 sec) and does not cause the animal any pain.

Other embodiments are within the scope of the following claims.

What is claimed is:

1. A compound represented by formula (I):

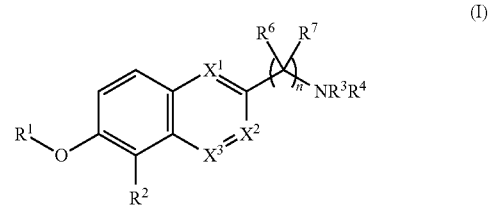

(I)

or a pharmaceutically acceptable salt thereof, wherein:
$X^1$, $X^2$, and $X^3$ are CH; or one of $X^1$, $X^2$, or $X^3$ is N and the other two are CH;
$R^1$ is

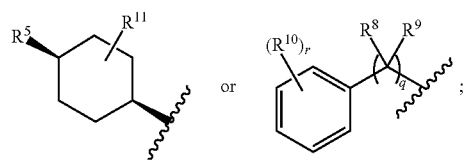

$R^2$ is a $C_{1-4}$haloalkyl or cyano;
$R^3$ is $-L^1-J-L^2-R^{12}$; and $R^4$ is hydrogen or a $C_{1-6}$alkyl; or
$R^3$ and $R^4$ together with the nitrogen to which they are attached are a 3- to 8-membered heterocyclyl which is substituted with -L²-R¹², and is optionally substituted with a halo, hydroxyl, amino, or a C₁₋₆alkyl;
R⁵ is a halo, a C₁₋₆alkyl or a C₁₋₆haloalkyl;
R⁶ and R⁷ are each independently hydrogen or C₁₋₆alkyl; or R⁶ and R⁷ together with the carbon to which they are attached are —C(=O)—, a C₃₋₈spirocycloalkyl, or a 3- to 8-membered spiroheterocyclalkyl;
R⁸ and R⁹ are each independently hydrogen or a C₁₋₆alkyl; or R⁸ and R⁹ taken together with the carbon to which are attached are —C(=O)—;
R¹⁰, for each occurrence, is halo;
R¹¹ is hydrogen, halo, or C₁₋₄alkyl;
R¹² is —COOR¹³ or —P(O)(OR¹³)₂;
each R¹³, independently, is H, C₁₋₄alkyl, aryl, or aryl-C₁₋₄-alkyl;
J is a C₁₋₆alkylene, a C₃₋₈cycloalkylene, a 3- to 8-membered divalent monocyclic heterocyclyl, a phenylene, or a 5- to 6-membered heteroarylene, wherein J is optionally substituted with one or two substituents independently selected from a halo and a C₁₋₆alkyl;
L¹ and L² are each independently, a C₁₋₃alkylene or a direct bond;
n is 1, 2 or 3;
q is 1 or 2; and
r is 0, 1, or 2.

2. A compound represented by formula (Ia):

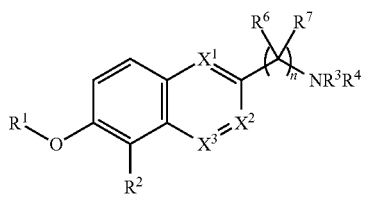

or a pharmaceutically acceptable salt thereof, wherein:
X¹, X², and X³ are CH; or one of X¹, X², or X³ is N and the other two are CH;
R¹ is

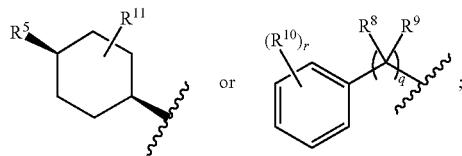

R² is a C₁₋₄haloalkyl or cyano;
R³ is -L¹-J-L²-R¹²; and R⁴ is hydrogen or a C₁₋₆alkyl; or R³ and R⁴ together with the nitrogen to which they are attached is a 3- to 8-membered heterocyclyl which is substituted with -L²-R¹², and is optionally substituted with a halo, hydroxyl, amino, or a C₁₋₆alkyl;
R⁵ is a halo, a C₁₋₆alkyl or a C₁₋₆haloalkyl;
R⁶ and R⁷ are each independently hydrogen, C₁₋₆alkyl, a C₁₋₆haloalkyl, C₃₋₇cycloalkyl, or COOH; or R⁶ and R⁷ together with the carbon to which they are attached is —C(=O)—, a C₃₋₈spirocycloalkyl, or a 3- to 8-membered spiroheterocyclalkyl;
R⁸ and R⁹ are each independently hydrogen or a C₁₋₆alkyl; or R⁸ and R⁹ taken together with the carbon to which they are attached is —C(=O)—;
R¹⁰, for each occurrence, is halo;
R¹¹ is hydrogen, halo, or C₁₋₄alkyl;
R¹² is —COOR¹³, —P(O)(OR¹³)₂, or tetrazolyl;
Each R¹³, independently, is H, C₁₋₄alkyl, aryl, or aryl-C₁₋₄-alkyl;
J is a C₁₋₆alkylene, a C₃₋₈cycloalkylene, a 3- to 8-membered divalent monocyclic heterocyclyl, a phenylene, or a 5- to 6-membered heteroarylene, wherein J is optionally substituted with one or two substituents independently selected from a halo and a C₁₋₆alkyl;
L¹ and L² are each independently, a C₁₋₃alkylene or a direct bond;
n is 1, 2 or 3;
q is 1 or 2; and
r is 0, 1, or 2.

3. The compound according to claim 1, or a pharmaceutically acceptable salt thereof, wherein n is 1, and R⁶ and R⁷ together with the carbon to which they are attached are —C(=O)—.

4. The compound according to claim 1, or a pharmaceutically acceptable salt thereof, wherein n is 1 and R⁶ and R⁷ are both hydrogen.

5. The compound according to claim 2, or a pharmaceutically acceptable salt thereof, wherein n is 1 and R⁶ is H and R⁷ is methyl, trifluoromethyl, ethyl, isopropyl, isobutyl, or cyclopropyl.

6. The compound according to claim 5, wherein R¹² is —COOH.

7. The compound according to claim 1, or a pharmaceutically acceptable salt thereof, wherein
L¹ is a direct bond;
J is a C₁₋₆alkylene or a phenylene, wherein J is optionally substituted with one or two substituents independently selected from a halo and a C₁₋₆alkyl;
L² is a C₁₋₃alkylene; and
R¹² is —P(O)(OR¹³)₂.

8. The compound according to claim 1, or a pharmaceutically acceptable salt thereof, wherein
R³ and R⁴ together with the nitrogen to which they are attached are a 4- to 7-membered heterocyclyl which is substituted with -L²-R¹², and is optionally substituted with a halo, hydroxyl, amino, or a C₁₋₆alkyl;
L² is a direct bond or —CH₂—; and
R¹² is —COOR¹³.

9. The compound according to claim 1, or a pharmaceutically acceptable salt thereof, wherein R² is —CHF₂ or —CF₃.

10. The compound according to claim 1, or a pharmaceutically acceptable salt thereof, wherein R¹ is

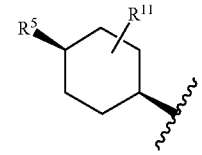

wherein R⁵ is a halo, a C₁alkyl, or a C₁haloalkyl.

11. The compound according to claim 1, or a pharmaceutically acceptable salt thereof, wherein R¹ is

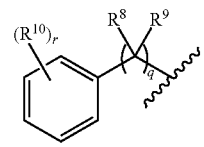

wherein q is 1, R⁸ and R⁹ are each independently H, and each R¹⁰ is independently H or a halo.

12. The compound of claim 2 selected from the group consisting of:

2,2-dimethyl-3-(((5-(trifluoromethyl)-6-((cis-4-(trifluoromethyl)cyclo-hexyl)oxy)naphthalen-2-yl)methyl)amino)cyclobutanecarboxylic acid;

1-((5-(trifluoromethyl)-6-((cis-4-(trifluoromethyl)cyclohexyl)oxy)-naphthalen-2-yl)methyl)piperidine-4-carboxylic acid;

3-(((5-(trifluoromethyl)-6-((cis-4-(trifluoromethyl)cyclohexyl)oxy)-naphthalen-2-yl)methyl)amino)cyclopentanecarboxylic acid;

(R)-2-(1-(((6-((4,4-difluorocyclohexyl)oxy)-5-(trifluoromethyl)naphthalen-2-yl)methyl)piperidin-3-yl)acetic acid;

4-(2H-tetrazol-5-yl)-1-((5-(trifluoromethyl)-6-((cis-4-(trifluoromethyl)cyclohexyl)oxy)naphthalen-2-yl)methyl)piperidine;

2-((3R)-1-(1-(6-((cis-4-ethylcyclohexyl)oxy)-5-(trifluoromethyl)naphthalen-2-yl)ethyl)piperidin-3-yl)acetic acid;

2-((3R)-1-(1-(6-((cis-4-ethylcyclohexyl)oxy)-5-(trifluoromethyl)naphthalen-2-yl)propyl)piperidin-3-yl)acetic acid;

2-(4-((6-((cis-4-Methylcyclohexyl)oxy)-5-(trifluoromethyl)naphthalen-2-yl)methyl)morpholin-2-yl)acetic acid;

2-(1-((6-((cis-4-methylcyclohexyl)oxy)-5-(trifluoromethyl)naphthalen-2-yl)methyl)piperidin-3-yl)acetic acid;

2-((3R)-1-(1-(6-((cis-4-Methylcyclohexyl)oxy)-5-(trifluoromethyl)naphthalen-2-yl)propyl)piperidin-3-yl)acetic acid;

1-(Carboxy(6-((cis-4-methylcyclohexyl)oxy)-5-(trifluoromethyl)naphthalen-2-yl)methyl)piperidine-4-carboxylic acid;

1-(2,2,2-Trifluoro-1-(6-((cis-4-methylcyclohexyl)oxy)-5-(trifluoromethyl)naphthalen-2-yl)ethyl)piperidine-4-carboxylic acid;

1-((5-(Difluoromethyl)-6-((cis-4-methylcyclohexyl)oxy)naphthalen-2-yl)methyl)piperidine-4-carboxylic acid;

2-((R)-1-(((5-(trifluoromethyl)-6-(cis-4-(trifluoromethyl)cyclohexyl)oxy)quinolin-2-yl)methyl)piperidin-3-yl)acetic acid; and 2,2-dimethyl-3-(((1-(5-(trifluoromethyl)-6-(cis-4-(trifluoromethyl)cyclo-hexyl)oxy)quinolin-2-yl)ethyl)amino)cyclobutanecarboxylic acid; 2,2-dimethyl-3-((1-(6-(cis-4-methylcyclohexyl)oxy)-5-(trifluoromethyl) naphthalen-2-yl)cyclopropyl)amino)cyclobutanecarboxylic acid;

4-Acetamido-4-(5-(trifluoromethyl)-6-(cis-4-(trifluoromethyl)cyclo-hexyl)oxy)naphthalen-2-yl)pentanoic acid;

(3-(6-((3,5-dichlorobenzyl)oxy)-5-(trifluoromethyl)-2-naphthamido)propyl) phosphonic acid;

(3-(5-(trifluoromethyl)-6-((cis-4-(trifluoromethyl)cyclohexyl)oxy)-2-naphthamido)propyl)phosphonic acid;

1-((5-cyano-6-((cis-4-(trifluoromethyl)cyclohexyl)oxy)naphthalen-2-yl)methyl)piperidine-4-carboxylic acid;

1-((5-(difluoromethyl)-6-((cis-4-(trifluoromethyl)cyclohexyl)oxy)naphthalen-2-yl)methyl)piperidine-4-carboxylic acid;

1-((5-(trifluoromethyl)-6-((cis-4-(trifluoromethyl)cyclohexyl)amino)naphthalen-2-yl)methyl)piperidine-4-carboxylic acid;

6-((5-(trifluoromethyl)-6-((cis)-4-(trifluoromethyl)cyclohexyloxy)-2-naphthamido)methyl)nicotinic acid;

(R)-1-((5-(trifluoromethyl)-6-((cis)-4-(trifluoromethyl)cyclohexyloxy)naphthalen-2-yl)methyl)piperidine-3-carboxylic acid;

(trans)-4-(((5-(trifluoromethyl)-6-((cis)-4-(trifluoromethyl)cyclohexyloxy)naphthalen-2-yl)methylamino)methyl)cyclohexanecarboxylic acid;

(S)-1-((5-(trifluoromethyl)-6-((cis)-4-(trifluoromethyl)cyclohexyloxy)naphthalen-2-yl)methyl)piperidine-3-carboxylic acid;

2-(1-((5-(trifluoromethyl)-6-((cis)-4-(trifluoromethyl)cyclohexyloxy)naphthalen-2-yl)methyl)piperidin-2-yl)acetic acid;

(trans)-4-((methyl((5-(trifluoromethyl)-6-((cis)-4-(trifluoromethyl)cyclohexyloxy)naphthalen-2-yl)methyl)amino)methyl)cyclohexanecarboxylic acid;

1-((5-(trifluoromethyl)-6-((cis)-4-(trifluoromethyl)cyclohexyloxy)naphthalen-2-yl)methyl)piperidine-2-carboxylic acid;

4-methyl-1 -((5-(trifluoromethyl)-6-((cis)-4-(trifluoromethyl)cyclohexyloxy)naphthalen-2-yl)methyl)piperidine-4-carboxylic acid;

1-(5-(trifluoromethyl)-6-((cis)-4-(trifluoromethyl)cyclohexyloxy)-2-naphthoyl)azepane-4-carboxylic acid;

2-(4-((5-(difluoromethyl)-6-((cis)-4-(trifluoromethyl)cyclohexyloxy)naphthalen-2-yl)methyl)morpholin-2-yl)acetic acid;

3-((5-(difluoromethyl)-6-((cis)-4-(trifluoromethyl)cyclohexyloxy)naphthalen-2-yl)methylamino)-2,2-dimethylcyclobutanecarboxylic acid;

(trans)-4-(((5-(difluoromethyl)-6-((cis)-4-(trifluoromethyl)cyclohexyloxy)naphthalen-2-yl)methylamino)methyl)cyclohexanecarboxylic acid;

4-hydroxy-1-((5-(trifluoromethyl)-6-((cis)-4-(trifluoromethyl)cyclohexyloxy)naphthalen-2-yl)methyl)piperidine-3-carboxylic acid;

2,2-dimethyl-3-(1-(6-((cis)-4-methylcyclohexyloxy)-5-(trifluoromethyl)naphthalen-2-yl)propylamino)cyclobutanecarboxylic acid;

2,2-dimethyl-3-(1-(5-(trifluoromethyl)-6-((cis)-4-(trifluoromethyl)cyclohexyloxy)naphthalen-2-yl)ethylamino)cyclobutanecarboxylic acid;

3-cyclopropyl(6-((cis)-4-methylcyclohexyloxy)-5-(trifluoromethyl)naphthalen-2-yl)methylamino)-2,2-dimethylcyclobutanecarboxylic acid;

2,2-dimethyl-3-(2-methyl-1-(5-(trifluoromethyl)-6-((cis)-4-(trifluoromethyl)cyclohexyloxy)naphthalen-2-yl)propylamino)cyclobutanecarboxylic acid;

2,2-dimethyl-3-(3-methyl-1-(5-(trifluoromethyl)-6-((cis)-4-(trifluoromethyl)cyclohexyloxy)naphthalen-2-yl)butylamino)cyclobutanecarboxylic acid;

4-(1-((5-(trifluoromethyl)-6-((cis)-4-(trifluoromethyl)cyclohexyloxy)naphthalen-2-yl)methylamino)ethyl)cyclohexanecarboxylic acid;

3-cyclohexyl(6-((cis)-4-methylcyclohexyloxy)-5-(trifluoromethyl)naphthalen-2-yl)methylamino)-2,2-dimethylcyclobutanecarboxylic acid;

3-cyclohexyl(5-(trifluoromethyl)-6-((cis)-4-(trifluoromethyl)cyclohexyloxy)naphthalen-2-yl)methylamino)-2,2-dimethylcyclobutanecarboxylic acid;

3-cyclopropyl(5-(trifluoromethyl)-6-((cis)-4-(trifluoromethyl)cyclohexyloxy)naphthalen-2-yl)methylamino)-2,2-dimethylcyclobutanecarboxylic acid;

1-(1-(5-(trifluoromethyl-6-(cis-4-methylcyclohexyloxy)naphthalene-2-yl)ethyl)-piperidine-4-carboxylic acid;

1-((5-trifluoromethyl-6-(cis-4-methylcyclohexyloxy)naphthalene-2-yl)methyl)-pyrrolidine-3-acetic acid;

1-((5-trifluoromethyl-6-(cis-4-methylcyclohexyloxy)
naphthalene-2-yl)methyl)-azetidine-3-acetic acid;

1-((5-trifluoromethyl-6-(cis-4-methylcyclohexyloxy)
naphthalene-2-yl)methyl)-azepane-3-carboxylic acid;

2-((3R)-1-((6-(((cis-4-Methylcyclohexyl)oxy)-5-(trifluoromethyl)naphthalen-2-yl)methyl)piperidin-3-yl)acetic acid;

1-(1-(6-((cis-4-Methylcyclohexyl)oxy)-5-(trifluoromethyl)naphthalen-2-yl)propyl)piperidine-4-carboxylic acid;

2-((3R)-1-(1-(6-((cis-4-Methylcyclohexyl)oxy)-5-(trifluoromethyl)naphthalen-2-yl)ethyl)piperidin-3-yl)acetic acid;

2-((3S)-1-(1-(6-((cis-4-Methylcyclohexyl)oxy)-5-(trifluoromethyl)naphthalen-2-yl)propyl)piperidin-3-yl)acetic acid;

2-((3R)-1-(1-(6-((cis-4-Methylcyclohexyl)oxy)-5-(difluoromethyl)naphthalen-2-yl)ethyl)piperidin-3-yl)acetic acid;

2-((3S)-1-(1-(6-((cis-4-Methylcyclohexyl)oxy)-5-(difluoromethyl)naphthalen-2-yl)ethyl)piperidin-3-yl)acetic acid;

1-(1-(6-((cis-4-Methylcyclohexyl)oxy)-5-(difluoromethyl)naphthalen-2-yl)ethyl)piperidine-4-carboxylic acid;

2-((3R)-1-((6-(((cis-4-Methylcyclohexyl)oxy)-5-(difluoromethyl)naphthalen-2-yl)methyl)piperidin-3-yl)acetic acid;

2-((3R)-1-(1-(6-((cis-4-Methylcyclohexyl)oxy)-5-(difluoromethyl)naphthalen-2-yl)propyl)piperidin-3-yl)acetic acid;

1-(1-(6-((cis-4-Methylcyclohexyl)oxy)-5-(difluoromethyl)naphthalen-2-yl)propyl)piperidine-4-carboxylic acid;

2-((3R)-1-((S)-1-(6-((cis-4-Methylcyclohexyl)oxy)-5-(trifluoromethyl)naphthalen-2-yl)propyl)piperidin-3-yl)acetic acid;

2-((3R)-1-((R)-1-(6-((cis-4-Methylcyclohexyl)oxy)-5-(trifluoromethyl)naphthalen-2-yl)propyl)piperidin-3-yl)acetic acid;

1-((S)-1-(6-((cis-4-Methylcyclohexyl)oxy)-5-(difluoromethyl)naphthalen-2-yl)ethyl)piperidine-4-carboxylic acid;

2-(1-((5-(trifluoromethyl)-6-(4-cis-(trifluoromethyl)cyclohexyloxy)naphthalene-2-yl)methyl)azetidine-3-yl)acetic acid;

3-(((5-(trifluoromethyl)-6-(cis-4-(trifluoromethyl)cyclohexyloxy)naphthalene-2-yl)methyl)amino)propylphosphonic acid;

1-((5-(trifluoromethyl)-6-((cis-4-(trifluoromethyl)cyclohexyl)oxy)-naphthalen-2-yl)methyl)pyrrolidine-3-acetic acid;

1-((5-(trifluoromethyl)-6-((cis-4-(trifluoromethyl)cyclohexyl)oxy)-naphthalen-2-yl)methyl)piperidine-4-acetic acid;

1-((5-(trifluoromethyl)-6-((cis-4-(trifluoromethyl)cyclohexyl)oxy)-naphthalen-2-yl)methyl)aminocyclopentane-3-carboxylic acid;

1-((5-(trifluoromethyl)-6-((cis-4-(trifluoromethyl)cyclohexyl)oxy)-naphthalen-2-yl)methyl)piperidine-3-acetic acid;

(4-((5-(trifluoromethyl)-6-(cis-4-(trifluoromethyl)cyclohexyloxy)naphthalene-2-yl)methyl)aminophenyl)methylphosphonic acid;

6-((((5-(trifluoromethyl)-6-((cis)-4-(trifluoromethyl)cyclohexyloxy)naphthalene-2-yl)methyl)amino)methyl)nicotinic acid;

cis-4-(((5-(trifluoromethyl)-6-((cis)-4-(trifluoromethyl)cyclohexyloxy)naphthalene-2-yl)methyl)amino)cyclohexane-1-carboxylic acid;

(S)-1-((5-(trifluoromethyl)-6-((cis)-4-(trifluoromethyl)cyclohexyloxy)naphthalene-2-yl)methyl)pyrrolidine-3-acetic acid;

(R)-1-((5-(trifluoromethyl)-6-((cis)-4-(trifluoromethyl)cyclohexyloxy)naphthalene-2-yl)methyl)pyrrolidine-3-acetic acid;

3-((4-((5-(trifluoromethyl)-6-(cis-4-(trifluoromethyl)cyclohexyloxy)naphthalene-2-yl)methyl)amino)cyclohexyl)propionic acid;

1-((5-(trifluoromethyl)-6-((cis-4-(trifluoromethyl)cyclohexyl)oxy)-naphthalen-2-yl)methyl)-3-methylpiperidine-4-carboxylic acid;

5-((((5-(trifluoromethyl)-6-((cis-4-(trifluoromethyl)cyclohexyl)oxy)-naphthalen-2-yl)methyl)amino)methyl)pyridine-2-carboxylic acid;

1-((5-(trifluoromethyl)-6-((cis-4-(trifluoromethyl)cyclohexyl)oxy)-naphthalen-2-yl)methyl)azepane-4-carboxylic acid;

4-((5-(trifluoromethyl)-6-((cis-4-(trifluoromethyl)cyclohexyl)oxy)-naphthalen-2-yl)methyl)morpholine-2-carboxylic acid;

1-((5-(trifluoromethyl)-6-((cis-4-(trifluoromethyl)cyclohexyl)oxy)-naphthalen-2-yl)methyl)-3-aminopyrrolidine-3-carboxylic acid;

N-methyl-cis-4-(((5-(trifluoromethyl)-6-(cis-4-(trifluoromethyl)cyclohexyloxy)naphthalene-2-yl)methyl)amino)cyclohexane-1-carboxylic acid;

2-((R)-1-((2-(cis-4-(trifluoromethyl)cyclohexyloxy)-1-(trifluoromethyl)naphthalen-6-yl)methyl)piperidin-3-yl)acetic acid;

1-((5-(trifluoromethyl)-6-(cis-4-(trifluoromethyl)cyclohexyloxy)naphthalene-2-yl)methyl)-5-hydroxypiperidine-3-carboxylic acid;

2-((S)-4-((2-(cis-4-(trifluoromethyl)cyclohexyloxy)-1-(trifluoromethyl)naphthalen-6-yl)methyl)morpholin-2-yl)acetic acid;

3-(1-((2-(cis-4-(trifluoromethyl)cyclohexyloxy)-1-(trifluoromethyl)naphthalen-6-yl)methyl)piperidine-4-yl)propionic acid;

2-((R)-1-((2-(cis-4-(ethyl)cyclohexyloxy)-1-(trifluoromethyl)naphthalen-6-yl)methyl)piperidin-3-yl)acetic acid;

2,2-dimethyl-3-((((S)-1-(5-(trifluoromethyl)-6-(cis-4-(trifluoromethyl)cyclo-hexyl)oxy)naphthalen-2-yl)ethyl)amino)cyclobutanecarboxylic acid;

2,2-dimethyl-3-((((R)-1-(5-(trifluoromethyl)-6-(cis-4-(trifluoromethyl)cyclo-hexyl)oxy)naphthalene-2-yl)ethyl)amino)cyclobutanecarboxylic acid;

2,2-dimethyl-3-((((5-(trifluoromethyl)-6-(cis-4-(trifluoromethyl)cyclo-hexyl)oxy)quinolin-2-yl)methyl)amino)cyclobutanecarboxylic acid;

2-((S)-1-(((5-(trifluoromethyl)-6-(cis-4-(trifluoromethyl)cyclohexyl)oxy)quinolin-2-yl)methyl)piperidin-3-yl)acetic acid;

2-((S)-1-(1-(2-(cis-4-(trifluoromethyl)cyclohexyloxy)-1-(trifluoromethyl)naphthalen-6-yl)propyl)piperidin-3-yl)acetic acid;

2,2-dimethyl-3-(1-(6-((cis)-4-methylcyclohexyloxy)-5-(trifluoromethyl)naphthalen-2-yl)-3-methylbutylamino)cyclobutanecarboxylic acid;

2-((3R)-1-((S)-1-(6-((cis-4-Methylcyclohexyl)oxy)-5-(difluoromethyl)naphthalen-2-yl)ethyl)piperidin-3-yl)acetic acid;

2-((3R)-1-((R)-1-(6-((cis-4-Methylcyclohexyl)oxy)-5-(difluoromethyl)naphthalen-2-yl)ethyl)piperidin-3-yl)acetic acid;
2-((3R)-1-((S)-1-(6-((cis-4-Methylcyclohexyl)oxy)-5-(difluoromethyl)naphthalen-2-yl)propyl)piperidin-3-yl)acetic acid;
2-((3R)-1-((R)-1-(6-((cis-4-Methylcyclohexyl)oxy)-5-(difluoromethyl)naphthalen-2-yl)propyl)piperidin-3-yl)acetic acid;
2-((3R)-1-((S)-1-(6-((cis-4-Methylcyclohexyl)oxy)-5-(trifluoromethyl)naphthalen-2-yl)ethyl)piperidin-3-yl)acetic acid;
2-((3R)-1-((R)-1-(6-((cis-4-Methylcyclohexyl)oxy)-5-(trifluoromethyl)naphthalen-2-yl)ethyl)piperidin-3-yl)acetic acid;
1-((5-(Difluoromethyl)-6-((cis-4-methylcyclohexyl)oxy)naphthalen-2-yl)methyl)azetidine-3-acetic acid;
1-(1-(5-(Difluoromethyl)-6-((cis-4-methylcyclohexyl)oxy)naphthalen-2-yl)ethyl)azetidine-3-acetic acid;
1-(1-(5-(Difluoromethyl)-6-((cis-4-methylcyclohexyl)oxy)naphthalen-2-yl)propyl)azetidine-3-acetic acid;
2-((S)-1-((S)-1-(2-(cis-4-methylcyclohexyloxy)-1-(difluoromethyl)naphthalen-6-yl)ethyl)piperidin-3-yl)acetic acid;
2-((R)-1-((S)-1-(2-(cis-4-methylcyclohexyloxy)-1-(difluoromethyl)naphthalen-6-yl)ethyl)piperidin-3-yl)acetic acid;
(S)-2-((R)-1-((5-(trifluoromethyl)-6-((cis-4-(trifluoromethyl)cyclohexyl)oxy) naphthalen-2-yl)methyl)piperidin-3-yl)propanoic acid;
2-((R)-1-((R)-1-(5-(trifluoromethyl)-6-((cis-4-(trifluoromethyl) cyclohexyl)oxy)naphthalen-2-yl)propyl)piperidin-3-yl)acetic acid; and
2-((R)-1-((S)-1-(5-(trifluoromethyl)-6-((cis-4-(trifluoromethyl)cyclohexyl)oxy)naphthalen-2-yl)propyl) piperidin-3-yl)acetic acid,
or a pharmaceutically acceptable salt thereof.

13. A pharmaceutical composition comprising a pharmaceutically acceptable carrier or excipient and the compound of claim 1, or a pharmaceutically acceptable salt thereof.

14. A method of treating, or reducing chronic pain in a mammal comprising administering to said mammal an effective amount of the compound of claim 1, or a pharmaceutically acceptable salt thereof.

15. The method of claim 14, wherein the chronic pain is inflammatory pain.

16. The method of claim 14, wherein the chronic pain is neuropathic pain.

17. The pharmaceutical composition of claim 13, wherein n is 1 and $R^6$ and $R^7$ are both hydrogen.

18. The pharmaceutical composition of claim 13, wherein:
$R^3$ and $R^4$ together with the nitrogen to which they are attached are a 4- to 7-membered heterocyclyl which is substituted with -$L^2$-$R^{12}$, and is optionally substituted with a halo, hydroxyl, amino, or a $C_{1-6}$alkyl;
$L^2$ is a direct bond or —$CH_2$—; and
$R^{12}$ is —$COOR^{13}$.

19. The pharmaceutical composition of claim 13, wherein $R^1$ is

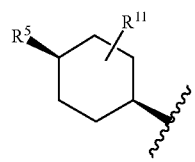

wherein $R^5$ is a halo, a $C_1$alkyl, or a $C_1$haloalkyl.

20. The pharmaceutical composition of claim 13, wherein the compound is selected from the group consisting of:
2,2-dimethyl-3-(((5-(trifluoromethyl)-6-((cis-4-(trifluoromethyl)cyclo-hexyl)oxy)naphthalen-2-yl)methyl)amino)cyclobutanecarboxylic acid;
1-((5-(trifluoromethyl)-6-((cis-4-(trifluoromethyl)cyclohexyl)oxy)-naphthalen-2-yl)methyl)piperidine-4-carboxylic acid;
3-(((5-(trifluoromethyl)-6-((cis-4-(trifluoromethyl)cyclohexyl)oxy)-naphthalen-2-yl)methyl)amino)cyclopentanecarboxylic acid;
(R)-2-(1-((6-((4,4-difluorocyclohexyl)oxy)-5-(trifluoromethyl)naphthalen-2-yl)methyl)piperidin-3-yl)acetic acid;
4-(2H-tetrazol-5-yl)-1-((5-(trifluoromethyl)-6-((cis-4-(trifluoromethyl)cyclohexyl)oxy)naphthalen-2-yl)methyl)piperidine;
2-((3R)-1-(1-(6-((cis-4-ethylcyclohexyl)oxy)-5-(trifluoromethyl)naphthalen-2-yl)ethyl)piperidin-3-yl)acetic acid;
2-((3R)-1-(1-(6-((cis-4-ethylcyclohexyl)oxy)-5-(trifluoromethyl)naphthalen-2-yl)propyl)piperidin-3-yl)acetic acid;
2-(4-((6-((cis-4-Methylcyclohexyl)oxy)-5-(trifluoromethyl)naphthalen-2-yl)methyl)morpholin-2-yl)acetic acid;
2-(1-((6-((cis-4-methylcyclohexyl)oxy)-5-(trifluoromethyl)naphthalen-2-yl)methyl)piperidin-3-yl)acetic acid;
2-((3R)-1-(1-(6-((cis-4-Methylcyclohexyl)oxy)-5-(trifluoromethyl)naphthalen-2-yl)propyl)piperidin-3-yl)acetic acid;
1-(Carboxy(6-((cis-4-methylcyclohexyl)oxy)-5-(trifluoromethyl)naphthalen-2-yl)methyl)piperidine-4-carboxylic acid;
1-(2,2,2-Trifluoro-1-(6-((cis-4-methylcyclohexyl)oxy)-5-(trifluoromethyl)naphthalen-2-yl)ethyl)piperidine-4-carboxylic acid;
1-((5-(Difluoromethyl)-6-((cis-4-methylcyclohexyl)oxy)naphthalen-2-yl)methyl)piperidine-4-carboxylic acid;
2-((R)-1-(((5-(trifluoromethyl)-6-(cis-4-(trifluoromethyl)cyclohexyl)oxy)quinolin-2-yl)methyl)piperidin-3-yl)acetic acid; and
2,2-dimethyl-3-(((1-(5-(trifluoromethyl)-6-(cis-4-(trifluoromethyl)cyclo-hexyl)oxy)quinolin-2-yl)ethyl)amino)cyclobutanecarboxylic acid;
2,2-dimethyl-3-((1-(6-(cis-4-methylcyclohexyl)oxy)-5-(trifluoromethyl) naphthalen-2-yl)cyclopropyl)amino)cyclobutanecarboxylic acid;
4-Acetamido-4-(5-(trifluoromethyl)-6-(cis-4-(trifluoromethyl)cyclo-hexyl)oxy)naphthalen-2-yl)pentanoic acid;
(3-(6-((3,5-dichlorobenzyl)oxy)-5-(trifluoromethyl)-2-naphthamido)propyl) phosphonic acid;
(3-(5-(trifluoromethyl)-6-((cis-4-(trifluoromethyl)cyclohexyl)oxy)-2-naphthamido)propyl)phosphonic acid;
1-((5-cyano-6-((cis-4-(trifluoromethyl)cyclohexyl)oxy)naphthalen-2-yl)methyl)piperidine-4-carboxylic acid;
1-((5-(difluoromethyl)-6-((cis-4-(trifluoromethyl)cyclohexyl)oxy)naphthalen-2-yl)methyl)piperidine-4-carboxylic acid;
1-((5-(trifluoromethyl)-6-((cis-4-(trifluoromethyl)cyclohexyl)amino)naphthalen-2-yl)methyl)piperidine-4-carboxylic acid;
6-((5-(trifluoromethyl)-6-((cis)-4-(trifluoromethyl)cyclohexyloxy)-2-naphthamido)methyl)nicotinic acid;

(R)-1-((5-(trifluoromethyl)-6-((cis)-4-(trifluoromethyl) cyclohexyloxy)naphthalen-2-yl)methyl)piperidine-3-carboxylic acid;
(trans)-4-(((5-(trifluoromethyl)-6-((cis)-4-(trifluoromethyl)cyclohexyloxy)naphthalen-2-yl)methylamino) methyl)cyclohexanecarboxylic acid;
(S)-1-((5-(trifluoromethyl)-6-((cis)-4-(trifluoromethyl) cyclohexyloxy)naphthalen-2-yl)methyl)piperidine-3-carboxylic acid;
2-(1-((5-(trifluoromethyl)-6-((cis)-4-(trifluoromethyl)cyclohexyloxy)naphthalen-2-yl)methyl)piperidin-2-yl) acetic acid;
(trans)-4-((methyl((5-(trifluoromethyl)-6-((cis)-4-(trifluoromethyl)cyclohexyloxy)naphthalen-2-yl)methyl) amino)methyl)cyclohexanecarboxylic acid;
1-((5-(trifluoromethyl)-6-((cis)-4-(trifluoromethyl)cyclohexyloxy)naphthalen-2-yl)methyl)piperidine-2-carboxylic acid;
4-methyl-1-((5-(trifluoromethyl)-6-((cis)-4-(trifluoromethyl)cyclohexyloxy)naphthalen-2-yl)methyl)piperidine-4-carboxylic acid;
1-(5-(trifluoromethyl)-6-((cis)-4-(trifluoromethyl)cyclohexyloxy)-2-naphthoyl)azepane-4-carboxylic acid;
2-(4-((5-(difluoromethyl)-6-((cis)-4-(trifluoromethyl)cyclohexyloxy)naphthalen-2-yl)methyl)morpholin-2-yl) acetic acid;
3-((5-(difluoromethyl)-6-((cis)-4-(trifluoromethyl)cyclohexyloxy)naphthalen-2-yl)methylamino)-2,2-dimethylcyclobutanecarboxylic acid;
(trans)-4-(((5-(difluoromethyl)-6-((cis)-4-(trifluoromethyl)cyclohexyloxy)naphthalen-2-yl)methylamino) methyl)cyclohexanecarboxylic acid;
4-hydroxy-1-((5-(trifluoromethyl)-6-((cis)-4-(trifluoromethyl)cyclohexyloxy)naphthalen-2-yl)methyl)piperidine-3-carboxylic acid;
2,2-dimethyl-3-(1-(6-((cis)-4-methylcyclohexyloxy)-5-(trifluoromethyl)naphthalen-2-yl)propylamino)cyclobutanecarboxylic acid;
2,2-dimethyl-3-(1-(5-(trifluoromethyl)-6-((cis)-4-(trifluoromethyl)cyclohexyloxy)naphthalen-2-yl)ethylamino)cyclobutanecarboxylic acid;
3-(cyclopropyl(6-((cis)-4-methylcyclohexyloxy)-5-(trifluoromethyl)naphthalen-2-yl)methylamino)-2,2-dimethylcyclobutanecarboxylic acid;
2,2-dimethyl-3-(2-methyl-1-(5-(trifluoromethyl)-6-((cis)-4-(trifluoromethyl)cyclohexyloxy)naphthalen-2-yl) propylamino)cyclobutanecarboxylic acid;
2,2-dimethyl-3-(3-methyl-1-(5-(trifluoromethyl)-6-((cis)-4-(trifluoromethyl)cyclohexyloxy)naphthalen-2-yl)butylamino)cyclobutanecarboxylic acid;
4-(1-((5-(trifluoromethyl)-6-((cis)-4-(trifluoromethyl)cyclohexyloxy)naphthalen-2-yl)methylamino)ethyl)cyclohexanecarboxylic acid;
3-(cyclohexyl(6-((cis)-4-methylcyclohexyloxy)-5-(trifluoromethyl)naphthalen-2-yl)methylamino)-2,2-dimethylcyclobutanecarboxylic acid;
3-(cyclohexyl(5-(trifluoromethyl)-6-((cis)-4-(trifluoromethyl)cyclohexyloxy)naphthalen-2-yl)methylamino)-2,2-dimethylcyclobutanecarboxylic acid;
3-(cyclopropyl(5-(trifluoromethyl)-6-((cis)-4-(trifluoromethyl)cyclohexyloxy)naphthalen-2-yl)methylamino)-2,2-dimethylcyclobutanecarboxylic acid;
1-(1-(5-trifluoromethyl-6-(cis-4-methylcyclohexyloxy) naphthalene-2-yl)ethyl)-piperidine-4-carboxylic acid;
1-((5-trifluoromethyl-6-(cis-4-methylcyclohexyloxy) naphthalene-2-yl)methyl)-pyrrolidine-3-acetic acid;
1-((5-trifluoromethyl-6-(cis-4-methylcyclohexyloxy) naphthalene-2-yl)methyl)-azetidine-3-acetic acid;
1-((5-trifluoromethyl-6-(cis-4-methylcyclohexyloxy) naphthalene-2-yl)methyl)-azepane-3-carboxylic acid;
2-((3R)-1-((6-((cis-4-Methylcyclohexyl)oxy)-5-(trifluoromethyl)naphthalen-2-yl)methyl)piperidin-3-yl)acetic acid;
1-(1-(6-((cis-4-Methylcyclohexyl)oxy)-5-(trifluoromethyl)naphthalen-2-yl)propyl)piperidine-4-carboxylic acid;
2-((3R)-1-(1-(6-((cis-4-Methylcyclohexyl)oxy)-5-(trifluoromethyl)naphthalen-2-yl)ethyl)piperidin-3-yl)acetic acid;
2-((3S)-1-(1-(6-((cis-4-Methylcyclohexyl)oxy)-5-(trifluoromethyl)naphthalen-2-yl)propyl)piperidin-3-yl) acetic acid;
2-((3R)-1-(1-(6-((cis-4-Methylcyclohexyl)oxy)-5-(difluoromethyl)naphthalen-2-yl)ethyl)piperidin-3-yl)acetic acid;
2-((3S)-1-(1-(6-((cis-4-Methylcyclohexyl)oxy)-5-(difluoromethyl)naphthalen-2-yl)ethyl)piperidin-3-yl)acetic acid;
1-(1-(6-((cis-4-Methylcyclohexyl)oxy)-5-(difluoromethyl)naphthalen-2-yl)ethyl)piperidine-4-carboxylic acid;
2-((3R)-1-((6-((cis-4-Methylcyclohexyl)oxy)-5-(difluoromethyl)naphthalen-2-yl)methyl)piperidin-3-yl)acetic acid;
2-((3R)-1-(1-(6-((cis-4-Methylcyclohexyl)oxy)-5-(difluoromethyl)naphthalen-2-yl)propyl)piperidin-3-yl) acetic acid;
1-(1-(6-((cis-4-Methylcyclohexyl)oxy)-5-(difluoromethyl)naphthalen-2-yl)propyl)piperidine-4-carboxylic acid;
2-((3R)-1-((S)-1-(6-((cis-4-Methylcyclohexyl)oxy)-5-(trifluoromethyl)naphthalen-2-yl)propyl)piperidin-3-yl)acetic acid;
2-((3R)-1-((R)-1-(6-((cis-4-Methylcyclohexyl)oxy)-5-(trifluoromethyl)naphthalen-2-yl)propyl)piperidin-3-yl)acetic acid;
1-((S)-1-(6-((cis-4-Methylcyclohexyl)oxy)-5-(difluoromethyl)naphthalen-2-yl)ethyl)piperidine-4-carboxylic acid;
2-(1-((5-(trifluoromethyl)-6-(4-cis-(trifluoromethyl)cyclohexyloxy)naphthalene-2-yl)methyl)azetidine-3-yl) acetic acid;
3-(((5-(trifluoromethyl)-6-(cis-4-(trifluoromethyl)cyclohexyloxy)naphthalene-2-yl)methyl)amino)propylphosphonic acid;
1-((5-(trifluoromethyl)-6-((cis)-4-(trifluoromethyl)cyclohexyl)oxy) -naphthalen-2-yl)methyl)pyrrolidine-3-acetic acid;
1-((5-(trifluoromethyl)-6-((cis)-4-(trifluoromethyl)cyclohexyl)oxy)-naphthalen-2-yl)methyl)piperidine-4- acetic acid;
1-((5-(trifluoromethyl)-6-((cis)-4-(trifluoromethyl)cyclohexyl)oxy)-naphthalen-2-yl)methyl)aminocyclopentane-3-carboxylic acid;
1-((5-(trifluoromethyl)-6-((cis)-4-(trifluoromethyl)cyclohexyl)oxy)-naphthalen-2-yl)methyl)piperidine-3-acetic acid;
(4-((5-(trifluoromethyl)-6-(cis-4-(trifluoromethyl)cyclohexyloxy)naphthalene-2-yl)methyl)aminophenyl) methylphosphonic acid;
6-(((((5-(trifluoromethyl)-6-((cis)-4-(trifluoromethyl)cyclohexyloxy)naphthalene-2-yl)methyl)amino)methyl) nicotinic acid;

cis-4-(((5-(trifluoromethyl)-6-((cis)-4-(trifluoromethyl)cyclohexyloxy)naphthalene-2-yl)methyl)amino)cyclohexane-1-carboxylic acid;
(S)-1-((5-(trifluoromethyl)-6-((cis)-4-(trifluoromethyl)cyclohexyloxy)naphthalene-2-yl)methyl)pyrrolidine-3-acetic acid;
(R)-1-((5-(trifluoromethyl)-6-((cis)-4-(trifluoromethyl)cyclohexyloxy)naphthalene-2-yl)methyl)pyrrolidine-3-acetic acid;
3-((4-((5-(trifluoromethyl)-6-(cis-4-(trifluoromethyl)cyclohexyloxy)naphthalene-2-yl)methyl)amino)cyclohexyl)propionic acid;
1-((5-(trifluoromethyl)-6-((cis-4-(trifluoromethyl)cyclohexyl)oxy)-naphthalen-2-yl)methyl)-3-methylpiperidine-4-carboxylic acid;
5-(((((5-(trifluoromethyl)-6-((cis-4-(trifluoromethyl)cyclohexyl)oxy)-naphthalen-2-yl)methyl)amino)methyl)pyridine-2-carboxylic acid;
1-((5-(trifluoromethyl)-6-((cis-4-(trifluoromethyl)cyclohexyl)oxy)-naphthalen-2-yl)methyl)azepane-4-carboxylic acid;
4-((5-(trifluoromethyl)-6-((cis-4-(trifluoromethyl)cyclohexyl)oxy)-naphthalen-2-yl)methyl)morpholine-2-carboxylic acid;
1-((5-(trifluoromethyl)-6-((cis-4-(trifluoromethyl)cyclohexyl)oxy)-naphthalen-2-yl)methyl)-3-aminopyrrolidine-3-carboxylic acid;
N-methyl-cis-4-(((5-(trifluoromethyl)-6-(cis-4-(trifluoromethyl)cyclohexyloxy)naphthalene-2-yl)methyl)amino)cyclohexane-1-carboxylic acid;
2-((R)-1-((2-(cis-4-(trifluoromethyl)cyclohexyloxy)-1-(trifluoromethyl)naphthalen-6-yl)methyl)piperidin-3-yl)acetic acid;
1-((5-(trifluoromethyl)-6-(cis-4-(trifluoromethyl)cyclohexyloxy)naphthalene-2-yl)methyl)-5-hydroxypiperidine-3-carboxylic acid;
2-((S)-4-((2-(cis-4-(trifluoromethyl)cyclohexyloxy)-1-(trifluoromethyl)naphthalen-6-yl)methyl)morpholin-2-yl)acetic acid;
3-(1-((2-(cis-4-(trifluoromethyl)cyclohexyloxy)-1-(trifluoromethyl)naphthalen-6-yl)methyl)piperidine-4-yl)propionic acid;
2-((R)-1-((2-(cis-4-(ethyl)cyclohexyloxy)-1-(trifluoromethyl)naphthalen-6-yl)methyl)piperidin-3-yl)acetic acid;
2,2-dimethyl-3-((((S)-1-(5-(trifluoromethyl)-6-(cis-4-(trifluoromethyl)cyclo-hexyl)oxy)naphthalene-2-yl)ethyl)amino)cyclobutanecarboxylic acid;
2,2-dimethyl-3-((((R)-1-(5-(trifluoromethyl)-6-(cis-4-(trifluoromethyl)cyclo-hexyl)oxy)naphthalene-2-yl)ethyl)amino)cyclobutanecarboxylic acid;
2,2-dimethyl-3-((((5-(trifluoromethyl)-6-(cis-4-(trifluoromethyl)cyclo-hexyl)oxy)quinolin-2-yl)methyl)amino)cyclobutanecarboxylic acid;
2-((S)-1-(((5-(trifluoromethyl)-6-(cis-4-(trifluoromethyl)cyclohexyl)oxy)quinolin-2-yl)methyl)piperidin-3-yl)acetic acid;
2-((S)-1-(1-(2-(cis-4-(trifluoromethyl)cyclohexyloxy)-1-(trifluoromethyl)naphthalen-6-yl)propyl)piperidin-3-yl)acetic acid;
2,2-dimethyl-3-(1-(6-((cis)-4-methylcyclohexyloxy)-5-(trifluoromethyl)naphthalen-2-yl)-3-methylbutylamino)cyclobutanecarboxylic acid;
2-((3R)-1-((S)-1-(6-((cis-4-Methylcyclohexyl)oxy)-5-(difluoromethyl)naphthalen-2-yl)ethyl)piperidin-3-yl)acetic acid;
2-((3R)-1-((R)-1-(6-((cis-4-Methylcyclohexyl)oxy)-5-(difluoromethyl)naphthalen-2-yl)ethyl)piperidin-3-yl)acetic acid;
2-((3R)-1-((S)-1-(6-((cis-4-Methylcyclohexyl)oxy)-5-(difluoromethyl)naphthalen-2-yl)propyl)piperidin-3-yl)acetic acid;
2-((3R)-1-((R)-1-(6-((cis-4-Methylcyclohexyl)oxy)-5-(difluoromethyl)naphthalen-2-yl)propyl)piperidin-3-yl)acetic acid;
2-((3R)-1-((S)-1-(6-((cis-4-Methylcyclohexyl)oxy)-5-(trifluoromethyl)naphthalen-2-yl)ethyl)piperidin-3-yl)acetic acid;
2-((3R)-1-((R)-1-(6-((cis-4-Methylcyclohexyl)oxy)-5-(trifluoromethyl)naphthalen-2-yl)ethyl)piperidin-3-yl)acetic acid;
1-((5-(Difluoromethyl)-6-((cis-4-methylcyclohexyl)oxy)naphthalen-2-yl)methyl)azetidine-3-acetic acid;
1-(1-(5-(Difluoromethyl)-6-((cis-4-methylcyclohexyl)oxy)naphthalen-2-yl)ethyl)azetidine-3-acetic acid;
1-(1-(5-(Difluoromethyl)-6-((cis-4-methylcyclohexyl)oxy)naphthalen-2-yl)propyl)azetidine-3-acetic acid;
2-((S)-1-((S)-1-(2-(cis-4-methylcyclohexyloxy)-1-(difluoromethyl)naphthalen-6-yl)ethyl)piperidin-3-yl)acetic acid;
2-((R)-1-((S)-1-(2-(cis-4-methylcyclohexyloxy)-1-(difluoromethyl)naphthalen-6-yl)ethyl)piperidin-3-yl)acetic acid;
(S)-2-((R)-1-((5-(trifluoromethyl)-6-((cis-4-(trifluoromethyl)cyclohexyl)oxy) naphthalen-2-yl)methyl)piperidin-3-yl)propanoic acid;
2-((R)-1-((R)-1-(5-(trifluoromethyl)-6-((cis-4-(trifluoromethyl) cyclohexyl)oxy)naphthalen-2-yl)propyl)piperidin-3-yl)acetic acid; and
2-((R)-1-((S)-1-(5-(trifluoromethyl)-6-((cis-4-(trifluoromethyl)cyclohexyl)oxy)naphthalen-2-yl)propyl) piperidin-3-yl)acetic acid,
or a pharmaceutically acceptable salt thereof.

21. The method of claim 14, wherein n is 1 and $R^6$ and $R^7$ are both hydrogen.

22. The method of claim 14, wherein:
$R^3$ and $R^4$ together with the nitrogen to which they are attached are a 4- to 7-membered heterocyclyl which is substituted with $-L^2-R^{12}$, and is optionally substituted with a halo, hydroxyl, amino, or a $C_{1-6}$alkyl;
$L^2$ is a direct bond or $-CH_2-$; and
$R^{12}$ is $-COOR^{13}$.

23. The method of claim 14, wherein $R^1$ is

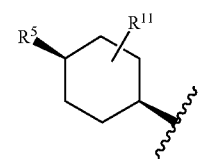

wherein $R^5$ is a halo, a $C_1$alkyl, or a $C_1$haloalkyl.

24. The method of claim 14, wherein the compound is selected from the group consisting of:
2,2-dimethyl-3-(((5-(trifluoromethyl)-6-((cis-4-(trifluoromethyl)cyclo-hexyl)oxy)naphthalen-2-yl)methyl)amino)cyclobutanecarboxylic acid;
1-((5-(trifluoromethyl)-6-((cis-4-(trifluoromethyl)cyclohexyl)oxy)-naphthalen-2-yl)methyl)piperidine-4-carboxylic acid;

3-(((5-(trifluoromethyl)-6-((cis-4-(trifluoromethyl)cyclohexyl)oxy)-naphthalen-2-yl)methyl)amino)cyclopentanecarboxylic acid;

(R)-2-(1-(((6-((4,4-difluorocyclohexyl)oxy)-5-(trifluoromethyl)naphthalen-2-yl)methyl)piperidin-3-yl)acetic acid;

4-(2H-tetrazol-5-yl)-1-((5-(trifluoromethyl)-6-((cis-4-(trifluoromethyl)cyclohexyl)oxy)naphthalen-2-yl)methyl)piperidine;

2-((3R)-1-(1-(6-((cis-4-ethylcyclohexyl)oxy)-5-(trifluoromethyl)naphthalen-2-yl)ethyl)piperidin-3-yl)acetic acid;

2-((3R)-1-(1-(6-((cis-4-ethylcyclohexyl)oxy)-5-(trifluoromethyl)naphthalen-2-yl)propyl)piperidin-3-yl)acetic acid;

2-(4-((6-((cis-4-Methylcyclohexyl)oxy)-5-(trifluoromethyl)naphthalen-2-yl)methyl)morpholin-2-yl)acetic acid;

2-(1-((6-((cis-4-methylcyclohexyl)oxy)-5-(trifluoromethyl)naphthalen-2-yl)methyl)piperidin-3-yl)acetic acid;

2-((3R)-1-(1-(6-((cis-4-Methylcyclohexyl)oxy)-5-(trifluoromethyl)naphthalen-2-yl)propyl)piperidin-3-yl)acetic acid;

1-(Carboxy(6-((cis-4-methylcyclohexyl)oxy)-5-(trifluoromethyl)naphthalen-2-yl)methyl)piperidine-4-carboxylic acid;

1-(2,2,2-Trifluoro-1-(6-((cis-4-methylcyclohexyl)oxy)-5-(trifluoromethyl)naphthalen-2-yl)ethyl)piperidine-4-carboxylic acid;

1-((5-(Difluoromethyl)-6-((cis-4-methylcyclohexyl)oxy)naphthalen-2-yl)methyl)piperidine-4-carboxylic acid;

2-((R)-1-(((5-(trifluoromethyl)-6-(cis-4-(trifluoromethyl)cyclohexyl)oxy)quinolin-2-yl)methyl)piperidin-3-yl)acetic acid; and 2,2-dimethyl-3-(((1-(5-(trifluoromethyl)-6-(cis-4-(trifluoromethyl)cyclo-hexyl)oxy)quinolin-2-yl)ethyl)amino)cyclobutanecarboxylic acid;

2,2-dimethyl-3-((1-(6-(cis-4-methylcyclohexyl)oxy)-5-(trifluoromethyl) naphthalen-2-yl)cyclopropyl)amino)cyclobutanecarboxylic acid;

4-Acetamido-4-(5-(trifluoromethyl)-6-(cis-4-(trifluoromethyl)cyclo-hexyl)oxy)naphthalen-2-yl)pentanoic acid;

(3-(6-((3,5-dichlorobenzyl)oxy)-5-(trifluoromethyl)-2-naphthamido)propyl) phosphonic acid;

(3-(5-(trifluoromethyl)-6-((cis-4-(trifluoromethyl)cyclohexyl)oxy)-2-naphthamido)propyl)phosphonic acid;

1-((5-cyano-6-((cis-4-(trifluoromethyl)cyclohexyl)oxy)naphthalen-2-yl)methyl)piperidine-4-carboxylic acid;

1-((5-(difluoromethyl)-6-((cis-4-(trifluoromethyl)cyclohexyl)oxy)naphthalen-2-yl)methyl)piperidine-4-carboxylic acid;

1-((5-(trifluoromethyl)-6-((cis-4-(trifluoromethyl)cyclohexyl)amino)naphthalen-2-yl)methyl)piperidine-4-carboxylic acid;

6-((5-(trifluoromethyl)-6-((cis)-4-(trifluoromethyl)cyclohexyloxy)-2-naphthamido)methyl)nicotinic acid;

(R)-1-((5-(trifluoromethyl)-6-((cis)-4-(trifluoromethyl)cyclohexyloxy)naphthalen-2-yl)methyl)piperidine-3-carboxylic acid;

(trans)-4-(((5-(trifluoromethyl)-6-((cis)-4-(trifluoromethyl)cyclohexyloxy)naphthalen-2-yl)methylamino)methyl)cyclohexanecarboxylic acid;

(S)-1-((5-(trifluoromethyl)-6-((cis)-4-(trifluoromethyl)cyclohexyloxy)naphthalen-2-yl)methyl)piperidine-3-carboxylic acid;

2-(1-((5-(trifluoromethyl)-6-((cis)-4-(trifluoromethyl)cyclohexyloxy)naphthalen-2-yl)methyl)piperidin-2-yl)acetic acid;

(trans)-4-((methyl((5-(trifluoromethyl)-6-((cis)-4-(trifluoromethyl)cyclohexyloxy)naphthalen-2-yl)methyl)amino)methyl)cyclohexanecarboxylic acid;

1-((5-(trifluoromethyl)-6-((cis)-4-(trifluoromethyl)cyclohexyloxy)naphthalen-2-yl)methyl)piperidine-2-carboxylic acid;

4-methyl-1-((5-(trifluoromethyl)-6-((cis)-4-(trifluoromethyl)cyclohexyloxy)naphthalen-2-yl)methyl)piperidine-4-carboxylic acid;

1-(5-(trifluoromethyl)-6-((cis)-4-(trifluoromethyl)cyclohexyloxy)-2-naphthoyl)azepane-4-carboxylic acid;

2-(4-((5-(difluoromethyl)-6-((cis)-4-(trifluoromethyl)cyclohexyloxy)naphthalen-2-yl)methyl)morpholin-2-yl)acetic acid;

3-((5-(difluoromethyl)-6-((cis)-4-(trifluoromethyl)cyclohexyloxy)naphthalen-2-yl)methylamino)-2,2-dimethylcyclobutanecarboxylic acid;

(trans)-4-(((5-(difluoromethyl)-6-((cis)-4-(trifluoromethyl)cyclohexyloxy)naphthalen-2-yl)methylamino)methyl)cyclohexanecarboxylic acid;

4-hydroxy-1-((5-(trifluoromethyl)-6-((cis)-4-(trifluoromethyl)cyclohexyloxy)naphthalen-2-yl)methyl)piperidine-3-carboxylic acid;

2,2-dimethyl-3-(1-(6-((cis)-4-methylcyclohexyloxy)-5-(trifluoromethyl)naphthalen-2-yl)propylamino)cyclobutanecarboxylic acid;

2,2-dimethyl-3-(1-(5-(trifluoromethyl)-6-((cis)-4-(trifluoromethyl)cyclohexyloxy)naphthalen-2-yl)ethylamino)cyclobutanecarboxylic acid;

3-(cyclopropyl(6-((cis)-4-methylcyclohexyloxy)-5-(trifluoromethyl)naphthalen-2-yl)methylamino)-2,2-dimethylcyclobutanecarboxylic acid;

2,2-dimethyl-3-(2-methyl-1-(5-(trifluoromethyl)-6-((cis)-4-(trifluoromethyl)cyclohexyloxy)naphthalen-2-yl)propylamino)cyclobutanecarboxylic acid;

2,2-dimethyl-3-(3-methyl-1-(5-(trifluoromethyl)-6-((cis)-4-(trifluoromethyl)cyclohexyloxy)naphthalen-2-yl)butylamino)cyclobutanecarboxylic acid;

4-(1-((5-(trifluoromethyl)-6-((cis)-4-(trifluoromethyl)cyclohexyloxy)naphthalen-2-yl)methylamino)ethyl)cyclohexanecarboxylic acid;

3-(cyclohexyl(6-((cis)-4-methylcyclohexyloxy)-5-(trifluoromethyl)naphthalen-2-yl)methylamino)-2,2-dimethylcyclobutanecarboxylic acid;

3-(cyclohexyl(5-(trifluoromethyl)-6-((cis)-4-(trifluoromethyl)cyclohexyloxy)naphthalen-2-yl)methylamino)-2,2-dimethylcyclobutanecarboxylic acid;

3-(cyclopropyl(5-(trifluoromethyl)-6-((cis)-4-(trifluoromethyl)cyclohexyloxy)naphthalen-2-yl)methylamino)-2,2-dimethylcyclobutanecarboxylic acid;

1-(1-(5-trifluoromethyl-6-(cis-4-methylcyclohexyloxy)naphthalene-2-yl)ethyl)-piperidine-4-carboxylic acid;

1-((5-trifluoromethyl-6-(cis-4-methylcyclohexyloxy)naphthalene-2-yl)methyl)-pyrrolidine-3-acetic acid;

1-((5-trifluoromethyl-6-(cis-4-methylcyclohexyloxy)naphthalene-2-yl)methyl)-azetidine-3-acetic acid;

1-((5-trifluoromethyl-6-(cis-4-methylcyclohexyloxy)naphthalene-2-yl)methyl)-azepane-3-carboxylic acid;

2-((3R)-1-((6-((cis-4-Methylcyclohexyl)oxy)-5-(trifluoromethyl)naphthalen-2-yl)methyl)piperidin-3-yl)acetic acid;

1-(1-(6-((cis-4-Methylcyclohexyl)oxy)-5-(trifluoromethyl)naphthalen-2-yl)propyl)piperidine-4-carboxylic acid;

2-((3R)-1-(1-(6-((cis-4-Methylcyclohexyl)oxy)-5-(trifluoromethyl)naphthalen-2-yl)ethyl)piperidin-3-yl)acetic acid;
2-((3S)-1-(1-(6-((cis-4-Methylcyclohexyl)oxy)-5-(trifluoromethyl)naphthalen-2-yl)propyl)piperidin-3-yl)acetic acid;
2-((3R)-1-(1-(6-((cis-4-Methylcyclohexyl)oxy)-5-(difluoromethyl)naphthalen-2-yl)ethyl)piperidin-3-yl)acetic acid;
2-((3S)-1-(1-(6-((cis-4-Methylcyclohexyl)oxy)-5-(difluoromethyl)naphthalen-2-yl)ethyl)piperidin-3-yl)acetic acid;
1-(1-(6-((cis-4-Methylcyclohexyl)oxy)-5-(difluoromethyl)naphthalen-2-yl)ethyl)piperidine-4-carboxylic acid;
2-((3R)-1-((6-((cis-4-Methylcyclohexyl)oxy)-5-(difluoromethyl)naphthalen-2-yl)methyl)piperidin-3-yl)acetic acid;
2-((3R)-1-(1-(6-((cis-4-Methylcyclohexyl)oxy)-5-(difluoromethyl)naphthalen-2-yl)propyl)piperidin-3-yl)acetic acid;
1-(1-(6-((cis-4-Methylcyclohexyl)oxy)-5-(difluoromethyl)naphthalen-2-yl)propyl)piperidine-4-carboxylic acid;
2-((3R)-1-((S)-1-(6-((cis-4-Methylcyclohexyl)oxy)-5-(trifluoromethyl)naphthalen-2-yl)propyl)piperidin-3-yl)acetic acid;
2-((3R)-1-((R)-1-(6-((cis-4-Methylcyclohexyl)oxy)-5-(trifluoromethyl)naphthalen-2-yl)propyl)piperidin-3-yl)acetic acid;
1-((S)-1-(6-((cis-4-Methylcyclohexyl)oxy)-5-(difluoromethyl)naphthalen-2-yl)ethyl)piperidine-4-carboxylic acid;
2-(1-((5-(trifluoromethyl)-6-(4-cis-(trifluoromethyl)cyclohexyloxy)naphthalene-2-yl)methyl)azetidine-3-yl)acetic acid;
3-(((5-(trifluoromethyl)-6-(cis-4-(trifluoromethyl)cyclohexyloxy)naphthalene-2-yl)methyl)amino)propylphosphonic acid;
1-(5-(trifluoromethyl)-6-((cis-4-(trifluoromethyl)cyclohexyl)oxy)-naphthalen-2-yl)methyl)pyrrolidine-3-acetic acid;
1-((5-(trifluoromethyl)-6-((cis-4-(trifluoromethyl)cyclohexyl)oxy)-naphthalen-2-yl)methyl)piperidine-4-acetic acid;
1-((5-(trifluoromethyl)-6-((cis-4-(trifluoromethyl)cyclohexyl)oxy)-naphthalen-2-yl)methyl)aminocyclopentane-3-carboxylic acid;
1-((5-(trifluoromethyl)-6-((cis-4-(trifluoromethyl)cyclohexyl)oxy)-naphthalen-2-yl)methyl)piperidine-3-acetic acid;
(4-((5-(trifluoromethyl)-6-(cis-4-(trifluoromethyl)cyclohexyloxy)naphthalene-2-yl)methyl)aminophenyl)methylphosphonic acid;
6-((((5-(trifluoromethyl)-6-((cis)-4-(trifluoromethyl)cyclohexyloxy)naphthalene-2-yl)methyl)amino)methyl)nicotinic acid;
cis-4-(((5-(trifluoromethyl)-6-((cis)-4-(trifluoromethyl)cyclohexyloxy)naphthalene-2-yl)methyl)amino)cyclohexane-1-carboxylic acid;
(S)-1-((5-(trifluoromethyl)-6-((cis)-4-(trifluoromethyl)cyclohexyloxy)naphthalene-2-yl)methyl)pyrrolidine-3-acetic acid;
(R)-1-((5-(trifluoromethyl)-6-((cis)-4-(trifluoromethyl)cyclohexyloxy)naphthalene-2-yl)methyl)pyrrolidine-3-acetic acid;
3-((4-((5-(trifluoromethyl)-6-(cis-4-(trifluoromethyl)cyclohexyloxy)naphthalene-2-yl)methyl)amino)cyclohexyl)propionic acid;
1-((5-(trifluoromethyl)-6-((cis-4-(trifluoromethyl)cyclohexyl)oxy)-naphthalen-2-yl)methyl)-3-methylpiperidine-4-carboxylic acid;
5-((((5-(trifluoromethyl)-6-((cis-4-(trifluoromethyl)cyclohexyl)oxy)-naphthalen-2-yl)methyl)amino)methyl)pyridine-2-carboxylic acid;
1-((5-(trifluoromethyl)-6-((cis-4-(trifluoromethyl)cyclohexyl)oxy)-naphthalen-2-yl)methyl)azepane-4-carboxylic acid;
4-((5-(trifluoromethyl)-6-((cis-4-(trifluoromethyl)cyclohexyl)oxy)-naphthalen-2-yl)methyl)morpholine-2-carboxylic acid;
1-((5-(trifluoromethyl)-6-((cis-4-(trifluoromethyl)cyclohexyl)oxy)-naphthalen-2-yl)methyl)-3-aminopyrrolidine-3-carboxylic acid;
N-methyl-cis-4-(((5-(trifluoromethyl)-6-(cis-4-(trifluoromethyl)cyclohexyloxy)naphthalene-2-yl)methyl)amino)cyclohexane-l-carboxylic acid;
2-((R)-1-((2-(cis-4-(trifluoromethyl)cyclohexyloxy)-1-(trifluoromethyl)naphthalen-6-yl)methyl)piperidin-3-yl)acetic acid;
1-((5-(trifluoromethyl)-6-(cis-4-(trifluoromethyl)cyclohexyloxy)naphthalene-2-yl)methyl)-5-hydroxypiperidine-3-carboxylic acid;
2-((S)-4-((2-(cis-4-(trifluoromethyl)cyclohexyloxy)-1-(trifluoromethyl)naphthalen-6-yl)methyl)morpholin-2-yl)acetic acid;
3-(1-((2-(cis-4-(trifluoromethyl)cyclohexyloxy)-1-(trifluoromethyl)naphthalen-6-yl)methyl)piperidine-4-yl)propionic acid;
2-((R)-1-((2-(cis-4-(ethyl)cyclohexyloxy)-1-(trifluoromethyl)naphthalen-6-yl)methyl)piperidin-3-yl)acetic acid;
2,2-dimethyl-3-((((S)-1-(5-(trifluoromethyl)-6-(cis-4-(trifluoromethyl)cyclo-hexyl)oxy)naphthalen-2-yl)ethyl)amino)cyclobutanecarboxylic acid;
2,2-dimethyl-3-((((R)-1-(5-(trifluoromethyl)-6-(cis-4-(trifluoromethyl)cyclo-hexyl)oxy)naphthalen-2-yl)ethyl)amino)cyclobutanecarboxylic acid;
2,2-dimethyl-3-((((5-(trifluoromethyl)-6-(cis-4-(trifluoromethyl)cyclo-hexyl)oxy)quinolin-2-yl)methyl)amino)cyclobutanecarboxylic acid;
2-((S)-1-(((5-(trifluoromethyl)-6-(cis-4-(trifluoromethyl)cyclohexyl)oxy)quinolin-2-yl)methyl)piperidin-3-yl)acetic acid;
2-((S)-1-(1-(2-(cis-4-(trifluoromethyl)cyclohexyloxy)-1-(trifluoromethyl)naphthalen-6-yl)propyl)piperidin-3-yl)acetic acid;
2,2-dimethyl-3-(1-(6-((cis)-4-methylcyclohexyloxy)-5-(trifluoromethyl)naphthalen-2-yl)-3-methylbutylamino)cyclobutanecarboxylic acid;
2-((3R)-1-((S)-1-(6-((cis-4-Methylcyclohexyl)oxy)-5-(difluoromethyl)naphthalen-2-yl)ethyl)piperidin-3-yl)acetic acid;
2-((3R)-1-((R)-1-(6-((cis-4-Methylcyclohexyl)oxy)-5-(difluoromethyl)naphthalen-2-yl)ethyl)piperidin-3-yl)acetic acid;
2-((3R)-1-((S)-1-(6-((cis-4-Methylcyclohexyl)oxy)-5-(difluoromethyl)naphthalen-2-yl)propyl)piperidin-3-yl)acetic acid;
2-((3R)-1-((R)-1-(6-((cis-4-Methylcyclohexyl)oxy)-5-(difluoromethyl)naphthalen-2-yl)propyl)piperidin-3-yl)acetic acid;

2-((3R)-1-((S)-1-(6-((cis-4-Methylcyclohexyl)oxy)-5-(trifluoromethyl)naphthalen-2-yl)ethyl)piperidin-3-yl) acetic acid;

2-((3R)-1-((R)-1-(6-((cis-4-Methylcyclohexyl)oxy)-5-(trifluoromethyl)naphthalen-2-yl)ethyl)piperidin-3-yl) acetic acid;

1-((5-(Difluoromethyl)-6-((cis-4-methylcyclohexyl)oxy) naphthalen-2-yl)methyl)azetidine-3-acetic acid;

1-(1-(5-(Difluoromethyl)-6-((cis-4-methylcyclohexyl) oxy)naphthalen-2-yl)ethyl)azetidine-3-acetic acid;

1-(1-(5-(Difluoromethyl)-6-((cis-4-methylcyclohexyl) oxy)naphthalen-2-yl)propyl)azetidine-3-acetic acid;

2-((S)-1-((S)-1-(2-(cis-4-methylcyclohexyloxy)-1-(difluoromethyl)naphthalen-6-yl)ethyl)piperidin-3-yl)acetic acid;

2-((R)-1-((S)-1-(2-(cis-4-methylcyclohexyloxy)-1-(difluoromethyl)naphthalen-6-yl)ethyl)piperidin-3-yl)acetic acid;

(S)-2-((R)-1-((5-(trifluoromethyl)-6-((cis-4-(trifluoromethyl)cyclohexyl)oxy) naphthalen-2-yl)methyl)piperidin-3-yl)propanoic acid;

2-((R)-1-((R)-1-(5-(trifluoromethyl)-6-((cis-4-(trifluoromethyl) cyclohexyl)oxy)naphthalen-2-yl)propyl)piperidin-3-yl)acetic acid; and 2-((R)-1-((S)-1-(5-(trifluoromethyl)-6-((cis-4-(trifluoromethyl)cyclohexyl)oxy)naphthalen-2-yl)propyl) piperidin-3-yl)acetic acid, or a pharmaceutically acceptable salt thereof.

* * * * *